(12) United States Patent
Pastor Fernández et al.

(10) Patent No.: US 9,682,991 B2
(45) Date of Patent: Jun. 20, 2017

(54) TRICYCLIC COMPOUNDS FOR USE AS KINASE INHIBITORS

(75) Inventors: Joaquín Pastor Fernández, Madrid (ES); Francisco Javier Ramos Lima, Madrid (ES); Ana Isabel Hernandez Higueras, Madrid (ES); Sonia Martínez González, Madrid (ES); Jose Ignacio Martín Hernando, Madrid (ES); Carl-Gustave Pierre Saluste, Madrid (ES); Esther Gonzalez Cantalapiedra, Madrid (ES); Carmen Blanco Aparicio, Madrid (ES); Antonio Rodríguez Hergueta, Madrid (ES); Ana Maria Garcia Collazo, Madrid (ES); Antonio Salgado Serrano, Madrid (ES); Beatriz Noya Marino, Madrid (ES)

(73) Assignee: FUNDACIÓN CENTRO NACIONAL DE INVESTIGACIONES ONCOLOGICAS CARLOS III (ES)

( * ) Notice: Subject to any disclaimer, the term of this patent is extended or adjusted under 35 U.S.C. 154(b) by 681 days.

(21) Appl. No.: 13/519,872

(22) PCT Filed: Dec. 31, 2010

(86) PCT No.: PCT/GB2010/002348
§ 371 (c)(1),
(2), (4) Date: Nov. 5, 2012

(87) PCT Pub. No.: WO2011/080510
PCT Pub. Date: Jul. 7, 2011

(65) Prior Publication Data
US 2013/0065881 A1    Mar. 14, 2013

(30) Foreign Application Priority Data
Dec. 31, 2009   (EP) .................................. 09380202

(51) Int. Cl.
*C07D 491/14*    (2006.01)
*C07D 487/14*    (2006.01)

(52) U.S. Cl.
CPC ......... *C07D 491/14* (2013.01); *C07D 487/14* (2013.01)

(58) Field of Classification Search
None
See application file for complete search history.

(56) References Cited

U.S. PATENT DOCUMENTS

| 4,814,470 | A | 3/1989 | Colin et al. |
| 5,011,835 | A | 4/1991 | Peet et al. |
| 5,438,072 | A | 8/1995 | Bobee et al. |
| 5,698,582 | A | 12/1997 | Bastart et al. |
| 5,714,512 | A | 2/1998 | Bastart et al. |
| 5,750,561 | A | 5/1998 | Bastart et al. |
| 6,713,485 | B2 | 3/2004 | Carter et al. |
| 6,727,256 | B1 | 4/2004 | Carter et al. |
| 6,933,299 | B1 | 8/2005 | Cockerill et al. |
| 6,960,614 | B2 | 11/2005 | Barrett et al. |
| 6,972,298 | B2 | 12/2005 | Baragi et al. |
| 7,084,147 | B2 | 8/2006 | Cockerill et al. |
| 7,109,333 | B2 | 9/2006 | Carter et al. |
| 7,141,576 | B2 | 11/2006 | Lackey et al. |
| 7,157,466 | B2 | 1/2007 | McClure et al. |
| 7,872,003 | B2 | 1/2011 | Shuttleworth et al. |
| 2003/0078277 | A1 | 4/2003 | Hibi et al. |
| 2004/0102360 | A1 | 5/2004 | Barnett et al. |

(Continued)

FOREIGN PATENT DOCUMENTS

| EP | 0 029 130 | 12/1985 |
| EP | 0 085 840 | 10/1986 |

(Continued)

OTHER PUBLICATIONS

Cos et al. Structure-Activity Relationship and Classification of Flavonoids as Inhibitors of Xanthine Oxidase and Superoxide Scavengers, J. Nat. Prod., 61:71-76, 1998.*
Siddiqui et al., The Presence of Substituents on the Aryl Moiety of the Aryl Phosphoramidate Derivative of d4T Enhances Anti-HIV Efficacy in Cell Culture: A Structure-Activity Relationship, J. Med. Chem., 42, 393-399, 1999.*
Hwang et al. Tetrahedron Letters, 2005, vol. 46, No. 17, pp. 3107-3110.*
Plotkin, Michael, et al., "A Practical Approach to Highly Functionalized Benzodihydrofurans," Tetrahedron Letters, 2000, 41, pp. 2269-2273.
Qian, Kevin, et al., "Structural Basis of Constitutive Activity and a Qunique Nucleotide Binding Mode of Human Pim-1 Kinase," J. Biol. Chem., 2005, vol. 280, No. 7, pp. 6130-6137.
Ringel, Israel, et al., "Studies with RP 56976 (Taxotere): A Semisynthetic Analogue of Taxol," J. Natl. Cancer Inst., 1991, vol. 83, No. 4, pp. 288-291.
Roh, Meejeon, et al., "Overexpression of the Oncogenic Kinase Pim-1 Leads to Genomic Instability," Cancer Res., 2003, 63, pp. 8079-8084.
Russell, Michael G.N. et al., "Discovery of Functionally Selective 7,8,9,10-Tetrahydro-7,10-ethano-1,2,4-triazolo [3,4-a]Phthalazines as GABAA Receptor Agonists at the a3 Subunit," J. Med. Chem., 2005, 48, pp. 1367-1383.

(Continued)

*Primary Examiner* — James D Anderson
(74) *Attorney, Agent, or Firm* — McCarter & English, LLP; Steven G. Davis; Wei Song

(57) ABSTRACT

There is provided compounds of formula (I), wherein $R^1$, $R^2$, $R^3$ and $R^4$ have meanings given in the description (and which compounds are optionally substituted as indicated in the description), and pharmaceutically-acceptable esters, amides, solvates or salts thereof, which compounds are useful in the treatment of diseases in which inhibition of a protein or lipid kinase (e.g. a PIM family kinase, such as PIM-1, PIM-2 and/or PIM-3) is desired and/or required, and particularly in the treatment of cancer or a proliferative disease. There is also provided combinations comprising the compounds of formula (I).

(I)

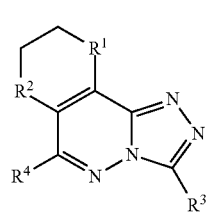

12 Claims, No Drawings

(56) References Cited

U.S. PATENT DOCUMENTS

| | | |
|---|---|---|
| 2004/0147478 A1 | 7/2004 | Merriman |
| 2005/0085550 A1 | 4/2005 | Macikenas et al. |
| 2007/0167453 A1 | 7/2007 | Takahashi et al. |
| 2010/0190804 A1 | 7/2010 | Combs et al. |

FOREIGN PATENT DOCUMENTS

| | | |
|---|---|---|
| EP | 0 104 506 | 11/1986 |
| EP | 0 253 738 | 1/1990 |
| EP | 0 548 923 | 7/1998 |
| EP | 0 620 224 | 7/1998 |
| EP | 0 562 439 | 6/1999 |
| GB | 2 345 443 | 7/2000 |
| JP | 53-021197 | 2/1978 |
| JP | 2002-501067 A | 1/2002 |
| JP | 2006501271 A | 1/2006 |
| JP | 2011500823 A | 1/2011 |
| WO | 98/04559 | 2/1998 |
| WO | 98/04560 | 2/1998 |
| WO | 99/06404 | 2/1999 |
| WO | 99/25353 | 5/1999 |
| WO | 9937645 A1 | 7/1999 |
| WO | WO-99/67245 A1 | 12/1999 |
| WO | 02/083064 | 10/2002 |
| WO | 02/083140 | 10/2002 |
| WO | WO-03/062236 A1 | 7/2003 |
| WO | 03/084473 | 10/2003 |
| WO | 2004026881 A1 | 4/2004 |
| WO | WO-2004/058769 A2 | 7/2004 |
| WO | WO-2005/005426 A1 | 1/2005 |
| WO | 2005/041971 | 5/2005 |
| WO | WO-2005/094830 A1 | 10/2005 |
| WO | 2006/024640 | 3/2006 |
| WO | WO-2006/046031 A1 | 5/2006 |
| WO | 2006/072612 | 7/2006 |
| WO | 2006/072615 | 7/2006 |
| WO | WO-2006/084015 A2 | 8/2006 |
| WO | WO-2007/129161 A2 | 11/2007 |
| WO | WO-2008/032157 A2 | 3/2008 |
| WO | 2008/109104 | 9/2008 |
| WO | 2008/130951 A1 | 10/2008 |
| WO | WO-2009/036082 A2 | 3/2009 |
| WO | 2009/040552 | 4/2009 |
| WO | 2009/055418 A1 | 4/2009 |
| WO | WO-2009/055730 A1 | 4/2009 |
| WO | 2009/060197 | 5/2009 |
| WO | 2009/060197 A1 | 5/2009 |
| WO | WO-2009/117277 A2 | 9/2009 |
| WO | 2010085597 A1 | 7/2010 |
| WO | 2010/108074 A2 | 9/2010 |
| WO | WO-2010/105008 A2 | 9/2010 |
| WO | WO-2010/110782 A1 | 9/2010 |
| WO | WO-2011/028540 A1 | 3/2011 |
| WO | WO-2011/054620 A1 | 5/2011 |
| WO | WO-2011/130654 A1 | 10/2011 |

OTHER PUBLICATIONS

Saris, Chris J.M., et al, "The pim-1 Oncogene Encodes Two Related Protein-Serine/Threonine Kinases by Alternative Initiation at AUG and CUG," EMBO J., 1991, vol. 10, No. 3. pp. 655-664-664.
Schlosser, Manfred, "Organometallics in Synthesis. A Manual," 2002, Wiley & Sons Ltd., Chichester, UK.
Schmidt, Thorsten, et al., "Evidence Implicating Gfi-1 and Pim-1 in pre-T-cell Differentiation Steps Associated with B-Selection," EMBO J., 1998, vol. 17, No. 18, pp. 5349-5359.
Severinsen, Rune, et al., "Versatile Strategies for the Solid Phase Synthesis of Small Heterocyclic Scaffolds: [1,3,4]-Thiadiazoles and [1,3,4]-Oxadiazoles," Tetrahedron, 2005, 61, pp. 5565-5575.
Seyden-Penne, J., "Reductions by the Alumino- and Borohydrides in Organic" 1991, VCH, NY.
Shintani, Ryo, et al. "Carbon-Carbon Bond-Forming Enantioselective Synthesis of Chiral Organosilicon Compounds by Rhodium/Chiral Diene-Catalyzed Asymmetric 1,4-Addition Reaction," Organic Letters, 2005, vol. 7, No. 21, pp. 4757-4759.
Shirogane, Takahiro, et al., "Synergistic Roles for Pim-1 and c-Myc in STAT3-Mediated Cell Cycle Progression and Antiapoptosis," Immunity, 1999, vol. 11, pp. 709-719.
Tarzia, Giorgio, et al., "6-(Alkylamino)-3-Aryl-1,2,4-Triazolo[3,4-a]Phthalazines. A New Class of Benzodiazepine Receptor Ligands," J Med. Chem., 1988, 31, pp. 1115-1123.
Tebib, Souhail, et al., "The Active Analog Approach Applied to the Pharmacophore Identification of Benzodiazepine Receptor Ligands," J. Comput. Aid. Mol. Des., 1987, 1, pp. 153-170.
Valdman, Alexander, et al., "Pim-I Expression in Prostatic Intraepithelial Neoplasia and Human Prostate Cancer," Prostate, 2004, 60, pp. 367-371.
Van Lohuizen, et al., "Predisposition to Lymphomagenesis in pim-1 Transgenic Mice; Cooperation with c-myc and N-myc in Murine Leukemia Virus-Induced Tumors," Cell, 1989, 56, pp. 673-682.
Van Lohuizen, Maarten, et al., "Identification of Cooperating Oncogenes iin Eu-myc Transgenic Mice by Provirus Tagging," Cell, 1991, 65, pp. 737-752.
Vijayan, R.S.K., et al., "Combinatorial Library Enumeration and Lead Hopping Using Comparative Interaction Fingerprint Analysis and Classical 2D QSAR Methods for Seeking Novel GABAA. alpha.3 Modulators," J. Chem. Inf. Mod., 2009, 49, pp. 2498-2511.
Vijayan, R.S.K., et al., "Structural Basis for Ligand Recognition at the Benzodiazepine Binding Site of GABAA. alpha.3 Receptor, and Pharmacophore-based Virtual Screening Approach," J. Mol. Graph. Model., 2008, 27, pp. 286-298.
Wang, Zeping et al., "Phosphorylation of the Cell Cycle Inhibitor p21 Cip1/WAF1 by Pim-1 Kinase," Biochim. Biophys. Acta, 2002, 1593, pp. 45-55.
Wang, Zeping, et al., "Pim-1 Serine/Threonine Kinase with a Role in Cell Survival, Proliferation, Differentation and Tumorigenesis," J. Vet. Sci., 2001, vol. 2, No. 3, pp. 167-179.
Wenwei Lin, et al., "Preparation of Highly Functionalized Arylmagnesium Reagents by the Addition of Magnesium Phenylselenide to Arynes," Tetrahedron Letters, 2006, 47, pp. 1941-1944.
Werber, Giuseppe, et al., "The Synthesis and Reactivity of Some 2-Amino-5-Bromo-1,3,4-Thiadiazoles and the Corresponding-1,3,4-Thiadiazolines," J. Heterocycl. Chem., 1977, 14, pp. 823-827.
Wiggins, J. Mark, et al., "A Convenient Procedure for the Reduction of Diarylmethanols with Dichlorodimethylsilane/Sodium Iodide," Synthetic Communications, 1988, vol. 18, No. 7, pp. 741-749.
Wipf, Peter, et al., "Formal Total Synthesis of (+)-Diepoxin o" J. Org. Chem., 2000, 65, pp. 6319-6337.
Binderup et al. *Bioorg. Med. Chem. Lett.* 2005, 15, 2491-2494.
Davidsen et al. *J. Med. Chem.* 1994, 37(26), 4423-4429.
Morwick et al. *Expert Opin. Ther. Pat.* 2010, 20(2), 193-212.
Abdel-Magid, Ahmed F., et al., "Reductive Amination of Aldehydes and Ketones with Sodium Triacetoxyborohydride. Studies on Direct and Indirect Reductive Amination Procedure," . J. Org. Chem., 1996, 61, pp. 3849-3862.
Abdel-Magid, Ahmed F., et al., "Reductive Amination of Aldehydes and Ketones with Weakly Basic Anilines Using Sodium Triacetoxyborohydride," Synlett, 1990, pp. 537-539.
Abignete, Enrico, et al, "Research on Heterocyclic Compounds. XXVII. Synthesis and Antiinflammatory Activity of 2-Phenylimidazo(1,2-b) Pyridazine-3-Carboxylic Acids," Il Farmaco, 1990, 45, pp. 1075-1087.
Akasaka, Hiroshi, et al., "Molecular Anatomy of BCL6 Translocations Revealed by Long-Distance Polymerase Chain reaction-Based Assays," Cancer Research, 2000, 60, pp. 2335-2341.
Bachmann, Malte, et al., "The Serine/Threonine Kinase Pim-1," Int. J. Biochem. Cell Biol., 2005, 37, pp. 726-730.
Baytel, Dorit, et al., "The Human Pim-2 Proto-Oncogene and its Testicular Expression," Biochimica et Biophysica Acta, 1998, 1442, pp. 274-285.
Bellamy, F.D., et al., "Selective Reduction of Aromatic Nitro Compounds with Stannous Chloride in Non Acidic and Non Aqueous Medium," Tetrahedron Letters, 1984, vol. 25, No. 8, pp. 839-842.

(56) References Cited

OTHER PUBLICATIONS

Bissery, Marie-Christine, et al., "Experimental Antitumor Activity of Taxotere, (RP 56976, NSC 628503), a Taxol Analogue," 1991, 51, pp. 4845-4852.
Blanco-Aparicio, Carmen, et al., "Pim 1 Kinase Inhibitor ETP-45299 Suppresses Cellular Proliferation and Synergizes with PI3K Inhibition," Cancer Letters, 2011, 300, pp. 145-153.
Boulanger, Thierry, et al., "X-ray Crystal Structures of Three Nonbenzodiazepinic Ligands for the Benzodiazepine Receptor Sites: SR95926, smw 1842, and L16317," Journal of Crystallographic and Spectroscopic Research, 1991, 21, pp. 287-295.
Branko Stanovnik, et al., "The Synthesis and Transformations of 9H-Imidazo[1,2-b]pyrazolo[4,3-d]-Pyridazine and 9H-Pyrazolo[4,3-d]-s-Triazolo[4,3-b]pyridazine Derivatives," J. Heterocyclic Chem. 1988, 25, pp. 393-398.
Breuer, Marco, et al., Very High Frequency of Lymphoma Induction by a Chemical Carcinogen in pim-ltransgenic mice, Nature, 1989, 340, pp. 61-63.
Carling, Robert W., et al., "3-Phenyl-6-(2-Pyridy) Methyloxy-1,2,4-Triazolo[3,4-a]Phthalazines and Analogues: High-Affinity, gamma.-Aminobutyric Acid-A Benzodiazepine Receptor Ligands with Alpha 2, Alpha 3, and Alpha 5- Substype Binding Selectivity Over Alpha 1," J. Med. Chem., 2004, 47, pp. 1807-1822.
Carling, Robert W., et al., "7-(1,1-Dimethylethyl)-6-(2-ethyl-2H-1,2,4,-Triazol-3-ylmethoxy)-3-(2-fluoropheynyl)-1,2,4-triazolo[4,3-13]pyridazine: A Functionally Selective y-Aminobutyric Acid (GABA) a2/a3-Subtype Selective Agonist That Exhibits Potent Anxiolytic Activity but is Not Sedating in Animal Models," J. Med. Chem. 2005, vol. 48, No. 23, pp. 7089-7092.
Cohen, Philip, et al, "The Development and Therapeutic Potential of Protein Kinase Inhibitors," Curr. Opin. Chem. Biol., 1999, 3, pp. 459-465.
Cuypers, H. Theo, et al., "Murine Leukemia Virus-Induced T-Cell Lymphomagenesis: Integration of Proviruses in a Distinct Chromosomal Region," Cell, 1984, vol. 37, pp. 141-150.
Davies, Angela M., et al., "Docetaxel in Non-Small Cell Lung Cancer: A Review," Expert. Opin. Pharmacother. 2003, 4, pp. 553-565.
Defacqz, Nathalie, et al., "Synthesis of C5-Substituted Imidazolines," Tetrahedron Letters, 2003, 44, pp. 9111-9114.
Dermer, Otis C., "Metallic Salts of Alcohols and Alcohol Analogs," Chem. Rev., 1934, 14, pp. 385-430.
Domen, J., et al., "Impaired Interleukin-3 Response in Pim-1-Deficient Bone Marrow-Derived Mast Cells," Blood, 1993, 82, pp. 1445-1452.
Durant, Francois, et al., "Physicochemical Study on the Stereoelectronic Properties of Aminophyridazines," Actual. Chim. Therapeu., 1989, 16, pp. 241-258.
El-Sherbeny, M.A., et al., "Synthesis and Cardiotonic Activity of Certain Imidazo[2,1-b]-1,3,4-Thiadiazole Derivatives," Boll. Chim. Farm., 1997, 136, pp. 253-256.
Fabio, P.F., et al., et al., "Synthesis of Carbon-14 and Deuterium Labeled 3-Nitro-6-Propoxyimidazo [1,2-B] Pyridazine—An Antiparasitic Agent," Journal of Labelled Compounds and Radiopharmaceuticals, 1978, 15, pp. 407-412.
Feldman, Jonathan D., et al., "KID-1, a Protein Kinase Induced by Depolarization in Brain," J. Biol. Chem., 1998, vol. 273, No. 26, pp. 16535-16543.
Gadad, Andanappa K., et al., Synthesis and Anti-Tubercular Activity of a Series of 2-Sulfonamido/Trifluoromethyl-6-Substituted Imidazo-[2,1-b]-1,3,4-Thiadiazole Derivatives, Bioorg. Med. Chem., 2004, 12, pp. 5651-5659.
Gadad, Andanappa K., et al., "Aberrant Somatic Hypermutation in Multiple Subtypes of AIDS-associated non-Hodgkin Lymphoma," Blood, 2003, 102, pp. 1833-1841.
Gregson, Stephen J., et al., "Linker Lenght Modulates DNA Cross-Linking Reactivity and Cytotoxic Potency of C8/C8' Ether-Linked C2-exo-Unsaturated Pyrrolo[2,1-c][1,4]benzodiazepine (PBD) Dimers," J. Med. Chem., 2004, 47, pp. 1161-1174.

Han, So-Yeop, "Recent Development of Peptide Coupling Reagents in Organic Synthesis," Tetrahedron, 2004, 60, pp. 2447-2467.
Heinz, Paul, et al., "Uber Einige Umsetzungen von 2,5-Diaminosowic 2-Amino-1,3,4-thiadiazolen mit a-Ilalogenketonen Zu Imidazo[2,1-b]-1,3,4-Thiadiazolen," Monatshefte für Chemie, 1977, 108, pp. 665-680.
Herbst, Roy S., et al., "Mode of Action of Docetaxel—a Basis for Combination with Novel Anticancer Agents," Cancer Treat. Rev., 2003, 29, pp. 407-415.
Hirano, Toshio, et al., "Roles of STAT3 in Mediating the Cell Growth, Differentiation and Survival Signals Relayed Through the IL-6 Family of Cytokine Receptors," Oncogene, 2000, 19, pp. 2548-2556.
Hwang, Jong Yeon, et al., "Solid-Phase Synthesis of [1,2,4]triazolo[3,4-a]phthalazine and tetrazolo[5,1-a] phthalazine Derivatives," Tetrahedron Lett., 2005, 46, pp. 3107-3110.
Ikemoto, Tomomi, et al., "Reactions with N-Chlorosuccinimide of Various 5-Methylimidazo[1,2-a]Pyridine Derivatives with an Electron-Withdrawing Group Substituted at the 3-Position," Heterocycles 2001, vol. 55, No. 1, pp. 99-108.
Ikemoto, Tomomi, et al., "A Practical Synthesis of the Chronic Renal Disease Agent, 4,5-Dihydro-3H-1,4,8b-triazaacenaphthylen-3-one Derivatives, Using Regioselective Chlorination of Ethyl 5-methylimidazo[1,2-a}pyridine-3-carboxylate with N-Chlorosuccininnide," Tetrahedron, 2000, 56, pp. 7915-7921.
Jacobs, Heinz, et al., "PIM1 Reconstitutes Thymus Cellularity in Interleukin 7-and Common y Chain-Mutant Mice and Permits Thymocyte Maturation in Rag-but Not CD3y-deficient Mice," JEM, 1999, 190, pp. 1059-1068.
Kobe, J., et al., "Synthesis of Pyridazie Derivatives-XV Some Electrophilic Substitutions on Imidazo[1,2-b]-Pyridazines," Tetrahedron, 1968, 24, pp. 239-245.
Koike, Naoyuki, et al., "Identification of Heterochromatin Protein 1 (HP1) as a Phosphorylation Target by Pim-1 Kinase and the Effect of Phosphorylation on the Transcriptional Repression Function of HP1," FEBS Letters, 2000, 467, pp. 17-21.
Kuwahara, Masaaki, et al., "Synthetic Studies on Condensed-Azole Derivatives. IV. Synthesis and Anti-Asthmatic Activities of w-Sulfamoylalkyloxyimidoazo[1,2-b]Pyridazines," Chem. Pharm. Bull., 1996, vol. 44, No. 1, pp. 122-131.
Lainton, Julia A., et al., "Design and Synthesis of a Diverse Morpholine Template Library," J. Comb. Chem., 2003, 5, pp. 400-407.
Lilly, Michael, et al., "The PIM-1 Serine Kinase Prolongs Survival and Inhibits Apoptosis-Related Mitochondrial Dysfunction in Part Through a bcl-2-Dependent Pathway," Oncogene, 1999, 18, pp. 4022-4031.
Link, Wolfgang, et al., "Chemical Interrogation of FOXO3a Nuclear Translocation Identifies Potent and Selective Inhibitors of Phosphoinositide 3-Kinases," J. Biol. Chem., 2009, vol. 284, No. 41, pp. 28392-28400.
Mangatal, L., et al., "Application of the Vicinal Oxyamination Reaction with Asymmetric Induction to the Hemisynthesis of Taxol and Analogues," Tetrahedron, 1989, vol. 45, No. 13, pp. 4177-4190.
Marin, Asuncion, et al., "Synthesis and Anthelmintic Activity of Carbamates Derived from Imidazo[2,1-b][1,3,4] Thiadiazole and Imidazo[2,1-b]Thiazole(*)" Farmaco, 1992, vol. 47, No. 1, pp. 63-75.
Mikkers, Harald, et al., "Mice Deficient for All PIM Kinase Display Reduced Body Size and Impaired Responses to Hematopoietic Growth Factors," Mol. Cell. Biol., 2004, vol. 24, No. 13, pp. 6104-6115.
Mochizuke, Toshihiro, et al., "Physical and Functional Interactions Between Pim-1 Kinase and Cdc25A Phosphatase," J. Biol. Chem. 1999, vol. 274, No. 26, pp. 18659-18666.
Monge Vega, A., et al., "Synthesis, Properties and Antihypertensive Activity of Some Derivatives of 11H-1,2,4-Triazolo[4',3':2,3]pyridazino[4,5-b]indole and 11H-Tetrazolo[4'5'2:2,3]Pyridazino[4,5-b]Indole," Anales de Quimica, C-Org. Bioq., 1983, 79, pp. 462-465.
Monge, A., et al. "New Thromboxane A2 Synthetase Inhibitors Having Structures Related to Pyridazino[4,5-b] Indole," Anales de la Real Academia de Farmacia, 1985, 51, pp. 485-493.

(56) References Cited

OTHER PUBLICATIONS

Monge, Antonio, et al., "A Novel Class of Cardiotonic Agents: Synthesis and Biological Evaluation of Pyridazino [4,5-13]Indoles with Cyclic AMP Phosphodiesterases Inhibiting Properties," J. Pharm. Sci., 1991, 82, pp. 526-530.
Montesinos-Rongen, Manuel, et al., "Primary Diffuse Large B-Cell Lymphomas of the Central Nervous System are Targeted by Aberrant Somatic Hypermutation," Blood, 2004, 103, pp. 1869-1875.
Pasqualucci, Laura, et al., "Hypermutation of Multiple Proto-Oncogenes in B-Cell Diffuse Large-Cell Lymphomas," Nature, 2001, vol. 412, pp. 341-346.
Deng G. et al., "Pim-2 kinase influences Tregulatory cell functions and stability by mediating Foxp3 N-terminal phosphorylation," Journal of Biology Chemistry, pp. 1-20, 2015.
Li Z. et al., "PIM1 kinase Phosphorylates the Human Transcription Factor FOXP3 at Serine 422 tp Negatively Regulate Its Activity under Inflammation," Journal of Biology Chemistry, vol. 289, No. 39, pp. 26872-26881, 2014.
Shen Y. M. et al., "Inhibition of Pim-1 Kinase Ameliorates Dextran Sodium Sulfate-Induced Colitis in Mice," Dig Dis Sci, pp. 1822-1831, 2012.
Shin Y. S. et al., "Inhibition of Pim1 Kinase Activation Attenuates Allergen-Induced Airway Hyperresponsiveness and Inflammation," American Journal of Respiratory Cell and Molecular Biology, vol. 46, pp. 488-497, 2012.
Wang M. et al., "Inhibition of Pim1 kinase prevents peanut allergy by enhancing Runx3 expression and suppressing TH2 and TH17 T-cell differentiation," J Allergy Clin Immunol, vol. 130, No. 4, pp. 932-944, 2012.
Bretonnet, A.S. et al., "NMR Screening Applied to the Fragment-Based Generation of Inhibitors of Creatine Kinase Exploiting a New Interaction Proximate to the ATP Binding Site", *J. Med. Chem.*, 2007, vol. 50, pp. 1865-1875.
Bundgaard, H., "Design of Prodrugs", 1985, Elsevier pp. 1-92.
Gaidano, G. et al., "Aberrant somatic hypermutation in multiple subtypes of AIDS-associated non-Hodgkin lymphoma", *Blood*, 2003, 102(5):1833-1841.
Greene T.W. et al., 'Protective Groups in Organic Synthesis', 1999, Wiley.
Nicolaou, K. C. et al., "Palladium-Catalyzed Cross-Coupling Reactions in Total Synthesis"., *Angew. Chem. Int. Ed.*, 2005, vol. 44, pp. 4442-4489.
Nicolaou, K. C. et al., "Metathesis Reactions in Total Synthesis," *Angew. Chem. Int. Ed.*, 2005, vol. 44, pp. 4490-4527.

\* cited by examiner

TRICYCLIC COMPOUNDS FOR USE AS KINASE INHIBITORS

FIELD OF THE INVENTION

This invention relates to novel pharmaceutically-useful compounds, which compounds are useful as inhibitors of protein or lipid kinases (such as inhibitors of a member of the PIM family kinases, e.g. PIM-1, PIM-2 or PIM-3). The invention also relates to the use of such compounds as medicaments, to the use of such compounds for in vitro, in situ and in vivo diagnosis or treatment of mammalian cells (or associated pathological conditions), to pharmaceutical compositions containing them, and to synthetic routes for their production.

BACKGROUND OF THE INVENTION

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, *Current Opinion in Chemical Biology* 1999, 3, 459-465.

PIM-1 is the protooncogene activated by murine leucemia virus (Provirus Integration site for Moloney murine leucemia virus—MoMuLV) that induces T-cell lymphoma [Cuypers, H. T., et. al. *Cell,* 1984, 37, 141-150].

The expression of the protooncogene produces a non-transmembrane serine/threonine kinase of 313 residues, including a kinase domain consisting of 253 amino acid residues. Two isoforms are known through alternative initiation (p44 and p33) [Saris, C. J. M. et al. *EMBO J.* 1991, 10, 655-664].

PIM-1, PIM-2 and PIM-3 phosphorylate protein substrates that are important in cancer neogenesis and progression. For example, PIM-1 phosphorylates inter alia p21, Bad, c-myb, Cdc 25A and eIF4B (see e.g. Quian, K. C. at al, *J. Biol. Chem.* 2005, 280(7), 6130-6137, and references cited therein).

Two PIM-1 homologs have been described [Baytel, D. Biochem. Biophys. Acta 1998, 1442, 274-285; Feldman, J. et al. *J. Biol. Chem.* 1998, 273, 16535.16543]. PIM-2 and PIM-3 are respectively 58% and 69% identical to PIM-1 at the amino acid level. PIM-1 is mainly expressed in thymus, testis, and cells of the hematopoietic system [Mikkers, H.; Nawijn, M.; Allen, J.; Brouwers, C.; Verhoeven, E.; Jonkers, J.; Berns, *Mol. Cell. Biol.* 2004, 24, 6104; Bachmann, M.; Moroy, T. *Int. J. Biochem. Cell Biol.* 2005, 37, 726-730. 6115]. PIM-1 expression is directly induced by STAT (Signal Transducers and Activators of Transcription) transcription factors, and PIM-1 expression is induced by many cytokine signalling pathways such as interleukins (IL), granulocyte-macrophage colony stimulating factor (GM-CSF), α- and γ-interferon, erythropoietin, and prolactin [Wang, Z et al. *J. Vet. Sci.* 2001, 2, 167-179].

PIM-1 has been implicated in lymphoma development. Induced expression of PIM-1 and the protooncogene c-myc synergise to increase the incidence of lymphomagenesis [Breuer, M. et al. Nature 1989, 340, 61-63; van Lohuizen M. et al. Cell, 1991, 65, 737-752]. PIM-1 functions in cytokine signalling pathways and has been shown to play a role in T cell development [Schmidt, T. et al. EMBO J. 1998, 17, 5349-5359; Jacobs, H. et al. JEM 1999, 190, 1059-1068]. Signalling through gp130, a subunit common to receptors of the IL-6 cytokine family, activates the transcription factor STAT3 and can lead to the proliferation of hematopioetic cells [Hirano, T. et al. Oncogene 2000, 19, 2548-2556]. A kinase-active PIM-1 appears to be essential for the gp130-mediated STAT3 proliferation signal. In cooperation with the c-myc PIM-1 can promote STAT3-mediated cell cycle progression and antiapoptosis [Shirogane, T. et sl., immunity, 1999, 11, 709-719]. PIM-1 also appears to be necessary for IL-3-stimulated growth in bone marrow-derived mast cells [Domen, J. et al., Blood, 1993, 82, 1445-1452] and survival of FDCP1 cells after IL-3 withdrawal [Lilly, M. et al., Oncogene, 1999, 18, 4022-4031].

Additionally, control of cell proliferation and survival by PIM-1 may be effected by means of its phosphorylation of the well-established cell cycle regulators cdc25 [Mochizuki, T. et al., J. Biol. Chem. 1999, 274, 18659-18666] and/or p21(Cip1/WAF1) [Wang Z. et al. Biochim. Biophys. Acta 2002, 1593, 45-55] or phosphorylation of heterochromatin protein 1, a molecule involved in chromatin structure and transcriptional regulation [Koike, N. et al, FEBS Lett. 2000, 467, 17-21].

Mice deficient for all three PIM genes showed an impaired response to hematopoietic growth factors and demonstrated that PIM proteins are required for efficient proliferation of peripheral T lymphocyes. In particular, it was shown that PIM function is required for efficient cell cycle induction of T cells in response to synergistic T-cell receptor and IL-2 signalling. A large number of interaction partners and substrates of PIM-1 have been identified, suggesting a pivotal role for PIM-1 in cell cycle control, proliferation, as well as in cell survival.

The oncogenic potential of this kinase has been first demonstrated in E μ PIM-1 transgenic mice in which PIM-1 over-expression is targeted to the B-cell lineage which leads to formation of B-cell tumors [van Lohuizen, M. et al.; *Cell* 1989, 56, 673-682. Subsequently PIM-1 has been reported to be over-expressed in a number of prostate cancers, erythroleukemias, and several other types of human leukemias [Roh, M. et al.; *Cancer Res.* 2003, 63, 8079-8084; Valdman, A. et al; *Prostate* 2004, 60, 367-371;

For example, chromosomal translocation of PIM-1 leads to overexpression of PIM-1 in diffuse large cell lymphoma. [Akasaka, H. et al.; *Cancer Res.* 2000, 60, 2335-2341]. Furthermore, a number of missense mutations in PIM-1 have been reported in lymphomas of the nervous system and AIDS-induced non-Hodgkins' lymphomas that probably affect PIM-1 kinase activity or stability [Pasqualucci, L. et al, *Nature* 2001, 412, 341-346; Montesinos-Rongen, M. et al., *Blood* 2004, 103, 1869-1875; Gaidano, G. et al., *Blood* 2003, 102, 1833-184]. Thus, the strong linkage between reported overexpression data and the occurrence of PIM-1 mutations in cancer suggests a dominant role of PIM-1 in tumorigenesis.

Several other protein kinases have been described in the literature, in which the activity and/or elevated activity of such protein kinases have been implicated in diseases such as cancer, in a similar manner to PIM-1, PIM-2 and PIM-3.

There is a constant need to provide alternative and/or more efficacious inhibitors of protein kinases, and particularly inhibitors of PIM-1, PIM-2 and/or PIM-3. Such modulators are expected to offer alternative and/or improved approaches for the management of medical conditions associated with activity and/or elevated activity of PIM-1, PIM-2 and/or PIM-3 protein kinases.

The listing or discussion of an apparently prior-published document in this specification should not necessarily be taken as an acknowledgement that the document is part of the state of the art or is common general knowledge.

Journal articles *J. Med. Chem.* 2005, 48, 1367-1383 by Russell et al and *J. Med. Chem.* 2005, Vol 48, No. 23, 7089 by Carling at al both disclose inter alia triazolophthalazine compounds of potential use as $GABA_A$ receptor agonists, which may be useful therefore as inter alia hypnotics (and therefore for treating sleep disorders) and muscle relaxants. However, these documents only relate to fused tricyclic compounds in which one of the cyclic moieties is bridged. Further, there is no mention that the compounds disclosed therein may be useful as kinase inhibitors.

International patent application WO 2005/041971 discloses inter alia fused tricyclic compounds that may bind to of $\alpha_2\delta$-1 sub-units of Ca channels, and may therefore be useful in the treatment of inter alia psychiatric and mood disorders. International patent applications WO 99/025353 and WO 98/04559 disclose various compounds that may act as ligands for $GABA_A$ receptors, WO 98/04560 discloses those that may act as inverse agonists of $GABA_A$ receptors, UK patent GB 2345443 discloses inter alia tricyclic compounds, which may be of use in treating premenstrual syndrome, and international patent application WO 2005/041971 discloses various tricyclic compounds for use in the treatment of bipolar diseases and the like. All of these documents only disclose fused tricyclic compounds that necessarily have oxy substituents, and do not disclose the use of those compounds as kinase inhibitors.

U.S. Pat. No. 5,011,835 discloses inter alia fused tricyclic compounds that may be useful as bronchodilators and anti-allergic agents, but does not disclose tricyclic compounds that are substituted with an aromatic substituent, nor does it mention that the compounds may be useful as kinase inhibitors.

European patents EP 0 104 506 and EP 0 029 130 both disclose inter alia tricyclic compounds that may be useful as bronchodilators, but does not disclose any that bear an aromatic substituent, nor does it disclose the potential use of those compounds as kinase inhibitors.

Journal article *J. Het. Chem.* 1988, 25(2), 393-8 by Branko et al discloses various tricyclic compounds, including those that contain an aromatic triazolopyridazine bicycle as an integral part of the tricycle. However, this journal article does not disclose that those compounds have a medical use, and further only discloses tricycles in which the 'third' ring fused to the triazolopyridazine bicycle contains an unsaturation (double bond).

European patent applications EP 0 548 923 and EP 0 562 439 disclose inter alia tricyclic compounds containing an aromatic imidazopyridazine bicyclic core or a [1,2,4]triazolo[1,5-b]pyridazine core. However, it does not disclose any tricyclic compounds containing a [1,2,4]triazolo[4,3-b]pyridazine core, nor does it mention that any of the compounds disclosed therein may be useful as kinase inhibitors.

European patent application EP 0 620 224 discloses inter alia [1,2,4]triazolo[4,3-b]pyridazines, but none in which such a bicycle is a sub-component of a fused tricyclic compound. Nor does this document disclose that the compounds therein may be useful as kinase inhibitors.

US patent application US 2003/0078277 discloses tricyclic compounds that may be useful as a corticotrophin, and therefore of use in the treatment of e.g. depression. However, this document does not primarily relate to [1,2,4]triazolo[4,3-b]pyridazines, nor does it disclose that the compounds therein may be useful as kinase inhibitors.

US patent application US 2007/0167453 discloses inter alia tricyclic compounds that may be useful as histamine-H3 receptor antagonists. However, this document does not specifically relate to [1,2,4]triazolo[4,3-b]pyridazines substituted with an amino moiety and an aromatic group. Further, this document does not mention that the compounds disclosed therein may be useful as kinase inhibitors.

International patent application WO 99/06404 discloses various fused tricyclic compounds containing a triazolopyridazine core, for use as phosphodiesterase 4 inhibitors. However, this document only relates to fused tricyclic compounds in which each of the three rings is aromatic.

International patent application WO 2008/109104 discloses various triazolopyridazines for use as Akt kinase inhibitors, but this document does not disclose any fused tricyclic compounds.

International patent applications WO 2009/060197 and WO 2009/040552 disclose various imidazopyridazine-based and imidazolothiadiazolo-based compounds, for use as certain protein kinase inhibitors. However, these documents do not mention fused tricyclic compounds containing a bicyclic aromatic triazolopyridazine core fused to a non-aromatic ring.

DISCLOSURE OF THE INVENTION

According to the invention, there is now provided a compound of formula I,

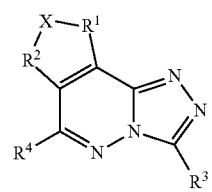

I wherein:
the $R^1$, $R^2$ and X-containing ring is non-aromatic in which:
$R^1$ and $R^2$ are independently selected from —O—, —S—, —S(O)—, —S(O)$_2$—, —C($R^6$)($R^{6a}$)— and —N($R^6$)—; and
X represents $C_2$ alkylene optionally substituted by one or more substituents selected from $E^2$;
each $R^6$ and $R^{6a}$ independently represents, on each occasion when used herein, H, —C(O)NHR$^{d1}$, —C(O)R$^{d2}$ or R$^{d3}$;
R$^{d1}$, R$^{d2}$ and R$^{d3}$ independently represent $C_{1-12}$ (e.g. $C_{1-6}$) alkyl optionally substituted by one or more substituents selected from $E^1$;
$R^3$ represents aryl optionally substituted by one or more substituents selected from $E^3$;
$R^4$ represents a fragment of formula IA,

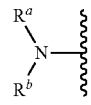

IA $R^a$ and $R^b$ independently represent H, —C(O)—$C_{1-11}$ alkyl, —S(O)$_2$—$C_{1-11}$ alkyl, $C_{1-12}$ (e.g. $C_{1-8}$) alkyl, heterocycloalkyl (which latter four groups are optionally substituted by one or more substituents selected from =O, =NOR$^{7a}$ and Q$^1$), aryl or heteroaryl (which latter two groups are optionally substituted by one or more substituents selected from Q$^2$); or $R^a$ and $R^b$ are linked together, along with the requisite nitrogen atom to which they are necessarily attached, to form a (first) 3- to 7-membered cyclic group, optionally containing one further heteroatom selected from nitrogen, sulfur and oxygen, and which ring optionally:

(a) is fused to a second ring that is either a 3- to 7-membered saturated heterocycloalkyl group containing one to four heteroatoms selected from oxygen, sulfur and nitrogen (preferably oxygen and nitrogen), a 3- to 12-membered saturated carbocyclic ring, or an unsaturated 5- to 12-membered carbocyclic or heterocyclic ring (in which the heteroatoms are preferably selected from sulfur and, especially, nitrogen and oxygen);

(b) comprises a linker group —(C(R$^x$)$_2$)$_p$— and/or —(C(R$^x$)$_2$)$_r$—O—(C(R$^x$)$_2$)$_s$— (wherein p is 1 or 2; r is 0 or 1; s is 0 or 1; and each R$^x$ independently represents hydrogen or $C_{1-6}$ alkyl), linking together any two non-adjacent atoms of the first 3- to 7-membered ring (i.e. forming a bridged structure); or (c) comprises a second ring that is either a 3- to 12-membered saturated carbocyclic ring or or a 3- to 7-membered saturated heterocycloalkyl group containing one to four heteroatoms selected from oxygen and nitrogen, and which second ring is linked together with the first ring via a single carbon atom common to both rings (i.e. forming a spiro-cycle), all of which cyclic groups, defined by the linkage of $R^a$ and $R^b$, are optionally substituted by one or more substituents selected from =O, =NOR$^{7b}$ and E$^4$;

each Q$^1$ and Q$^2$ independently represents, on each occasion when used herein:

halo, —CN, —NO$_2$, —N(R$^{10a}$)R$^{11a}$, —OR$^{10a}$, —C(=Y)—R$^{10a}$, —C(=Y)—OR$^{10a}$, —C(=Y)N(R$^{11a}$)R$^{11a}$, —C(=Y)N(R$^{10a}$)—OR$^{11a}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{11a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{11a}$)R$^{11a}$, —SC(=Y)R$^{10a}$, —S(O)$_2$R$^{10a}$, —SR$^{10a}$, —S(O)R$^{10a}$, $C_{1-12}$ alkyl, heterocycloalkyl (which latter two groups are optionally substituted by one or more substituents selected from =O, =S, =N(R$^{10a}$) and E$^5$), aryl or heteroaryl (which latter two groups are optionally substituted by one or more substituents selected from E$^6$);

R$^{7a}$ and R$^{7b}$ independently represent hydrogen or $C_{1-6}$ alkyl optionally substituted by one or more fluoro atoms;

each R$^{11c}$ independently represents, on each occasion when used herein, $C_{1-12}$ alkyl, heterocycloalkyl (which latter two groups are optionally substituted by one or more substituents selected from =O, =S, =N(R$^{20}$) and E$^7$), aryl or heteroaryl (which latter two groups are optionally substituted by one or more substituents selected from E$^8$);

each R$^{10a}$, R$^{11a}$ and R$^{12a}$ independently represent, on each occasion when used herein, hydrogen, $C_{1-12}$ alkyl, heterocycloalkyl (which latter two groups are optionally substituted by one or more substituents selected from =O, =S, =N(R$^{20}$) and E$^7$), aryl or heteroaryl (which latter two groups are optionally substituted by one or more substituents selected from E$^8$); or any relevant pair of R$^{10a}$, R$^{11a}$ and R$^{12a}$ (for example, when attached to the same atom, adjacent atom (i.e. 1,2-relationship) or to atoms that are two atoms apart, i.e. in a 1,3-relationship) may be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (e.g. double bonds), and which ring is optionally substituted by one or more substituents selected from =O, =S, =N(R$^{20}$) and E$^9$;

each E$^1$, E$^2$, E$^3$, E$^4$, E$^5$, E$^6$, E$^7$, E$^8$ and E$^9$ independently represents, on each occasion when used herein:

(i) Q$^4$;

(ii) $C_{1-2}$ alkyl optionally substituted by one or more substituents selected from =O and Q$^5$; or any two E$^1$, E$^2$, E$^3$, E$^4$, E$^5$, E$^6$, E$^7$, E$^8$ or E$^9$ groups, for example on $C_{1-12}$ alkyl groups or on aryl groups, e.g. when they are attached to the same or adjacent carbon atoms (e.g. two E$^3$ groups may be attached to adjacent carbon atoms of an aryl group, so forming a fused bicycle), may be linked together to form a 3- to 12-membered ring (in which each of the atoms of the ring may be a carbon atom or a heteroatom), optionally containing one or more (e.g. one to three) unsaturations (e.g. double bonds), and which ring is optionally substituted by one or more substituents selected from =O and J$^1$;

each Q$^4$ and Q$^5$ independently represent, on each occasion when used herein:

halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —C(=Y)N(R$^{20}$)—O—R$^{21a}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, $C_{1-6}$ alkyl, heterocycloalkyl (which latter two groups are optionally substituted by one or more substituents selected from =O and J$^2$), aryl or heteroaryl (which latter two groups are optionally substituted by one or more substituents selected from J$^3$);

each Y independently represents, on each occasion when used herein, =O, =S, =NR$^{23}$ or =N—CN;

each R$^{21a}$ independently represents, on each occasion when used herein, $C_{1-6}$ alkyl, heterocycloalkyl (which latter two groups are optionally substituted by one or more substituents selected from J$^4$ and =O), aryl or heteroaryl (which latter two groups are optionally substituted by one or more substituents selected from J$^5$);

each R$^{20}$, R$^{21}$, R$^{22}$ and R$^{23}$ independently represent, on each occasion when used herein, hydrogen, $C_{1-6}$ alkyl, heterocycloalkyl (which latter two groups are optionally substituted by one or more substituents selected from J$^4$ and =O), aryl or heteroaryl (which latter two groups are optionally substituted by one or more substituents selected from J$^5$); or any relevant pair of R$^{20}$, R$^{21}$ and R$^{22}$, may (for example, when attached to the same atom, adjacent atom (i.e. 1,2-relationship) or to atoms that are two atoms apart, i.e. in a 1,3-relationship) be linked together to form (e.g. along with the requisite nitrogen atom to which they may be attached) a 4- to 20- (e.g. 4- to 12-) membered ring, optionally containing one or more heteroatoms (for example, in addition to those that may already be present, e.g. (a) heteroatom(s) selected from oxygen, nitrogen and sulfur), optionally containing one or more unsaturations (e.g. double bonds), and which ring is optionally substituted by one or more substituents selected from $J^6$ and =O;

each $J^1$, $J^2$, $J^3$, $J^4$, $J^5$ and $J^6$ independently represents, on each occasion when used herein:

(i) $Q^7$;

(ii) $C_{1-6}$ alkyl or heterocycloalkyl, both of which are optionally substituted by one or more substituents selected from =O and $Q^8$;

each $Q^7$ and $Q^8$ independently represents, on each occasion when used herein:

halo, $-N(R^{50})R^{51}$, $-OR^{50}$, $-C(=Y^a)-R^{50}$, $-C(=Y^a)-OR^{50}$, $-C(=Y^a)N(R^{50})R^{51}$, $-N(R^{52})C(=Y^a)R^{51}$, $-NR^{52}S(O)_2R^{50}$, $-S(O)_2R^{50}$, $-SR^{50}$, $-S(O)R^{50}$ or $C_{1-6}$ alkyl optionally substituted by one or more fluoro atoms;

each $Y^a$ independently represents, on each occasion when used herein, =O, =S, =NR$^{53}$ or =N—CN;

each $R^{50}$, $R^{51}$, $R^{52}$ and $R^{53}$ independently represents, on each occasion when used herein, hydrogen or $C_{1-6}$ alkyl optionally substituted by one or more substituents selected from fluoro, $-OR^{60}$ and $-N(R^{61})R^{62}$; or any relevant pair of $R^{50}$, $R^{51}$ and $R^{52}$ may (for example when attached to the same or adjacent atoms) be linked together to form, a 3- to 8-membered ring, optionally containing one or more heteroatoms (for example, in addition to those that may already be present, heteroatoms selected from oxygen, nitrogen and sulfur), optionally containing one or more unsaturations (e.g. double bonds), and which ring is optionally substituted by one or more substituents selected from =O and $C_{1-3}$ alkyl;

$R^{60}$, $R^{61}$ and $R^{62}$ independently represent hydrogen or $C_{1-6}$ alkyl optionally substituted by one or more fluoro atoms, or a pharmaceutically acceptable ester, amide, solvate or salt thereof, which compounds, esters, amides, solvates and salts are referred to hereinafter as "the compounds of the invention".

Pharmaceutically-acceptable salts include acid addition salts and base addition salts. Such salts may be formed by conventional means, for example by reaction of a free acid or a free base form of a compound of formula I with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound of the invention in the form of a salt with another counter-ion, for example using a suitable ion exchange resin.

By "pharmaceutically acceptable ester, amide, solvate or salt thereof", we include salts of pharmaceutically acceptable esters or amides, and solvates of pharmaceutically acceptable esters, amides or salts. For instance, pharmaceutically acceptable esters and amides such as those defined herein may be mentioned, as well as pharmaceutically acceptable solvates or salts. Specific salts that may be mentioned include HCOOH and HCl salts. Oxide salts, such as N-oxides (e.g. in which there is a "$N^+$—O—" moiety present) may also be mentioned (for instance, when the nitrogen atom is an integral part of the compound of the invention).

Pharmaceutically acceptable esters and amides of the compounds of the invention are also included within the scope of the invention. Pharmaceutically acceptable esters and amides of compounds of the invention may be formed from corresponding compounds that have an appropriate group, for example an acid group, converted to the appropriate ester or amide. For example, pharmaceutically acceptable esters (of carboxylic acids of compounds of the invention) that may be mentioned include optionally substituted $C_{1-6}$ alkyl, $C_{5-10}$ aryl and/or $C_{5-10}$ aryl-$C_{1-6}$ alkyl-esters. Pharmaceutically acceptable amides (of carboxylic acids of compounds of the invention) that may be mentioned include those of the formula $-C(O)N(R^{z1})R^{z2}$, in which $R^{z1}$ and $R^{z2}$ independently represent optionally substituted $C_{1-6}$ alkyl, $C_{5-10}$ aryl, or $C_{5-10}$ aryl-$C_{1-6}$ alkylene-. Preferably, $C_{1-6}$ alkyl groups that may be mentioned in the context of such pharmaceutically acceptable esters and amides are not cyclic, e.g. linear and/or branched.

Further compounds of the invention that may be mentioned include carbamate, carboxamido or ureido derivatives, e.g. such derivatives of existing amino functional groups.

For the purposes of this invention, therefore, prodrugs of compounds of the invention are also included within the scope of the invention.

The term "prodrug" of a relevant compound of the invention includes any compound that, following oral or parenteral administration, is metabolised in vivo to form that compound in an experimentally-detectable amount, and within a predetermined time (e.g. within a dosing interval of between 6 and 24 hours (i.e. once to four times daily)). For the avoidance of doubt, the term "parenteral" administration includes all forms of administration other than oral administration.

Prodrugs of compounds of the invention may be prepared by modifying functional groups present on the compound in such a way that the modifications are cleaved, in vivo when such prodrug is administered to a mammalian subject. The modifications typically are achieved by synthesising the parent compound with a prodrug substituent. Prodrugs include compounds of the invention wherein a hydroxyl, amino, sulfhydryl, carboxy or carbonyl group in a compound of the invention is bonded to any group that may be cleaved in vivo to regenerate the free hydroxyl, amino, sulfhydryl, carboxy or carbonyl group, respectively.

Examples of prodrugs include, but are not limited to, esters and carbamates of hydroxy functional groups, esters groups of carboxyl functional groups, N-acyl derivatives and N-Mannich bases. General information on prodrugs may be found e.g. in Bundegaard, H. "Design of Prodrugs" p. 1-92, Elesevier, New York-Oxford (1985).

Compounds of the invention may contain double bonds and may thus exist as E (entgegen) and Z (zusammen) geometric isomers about each individual double bond. Positional isomers may also be embraced by the compounds of the invention. All such isomers (e.g. if a compound of the invention incorporates a double bond or a fused ring, the cis- and trans-forms, are embraced) and mixtures thereof are included within the scope of the invention (e.g. single positional isomers and mixtures of positional isomers may be included within the scope of the invention).

Compounds of the invention may also exhibit tautomerism. All tautomeric forms (or tautomers) and mixtures thereof are included within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerisations. Valence tautomers include interconversions by reorganisation of some of the bonding electrons.

Compounds of the invention may also contain one or more asymmetric carbon atoms and may therefore exhibit optical and/or diastereoisomerism. Diastereoisomers may be separated using conventional techniques, e.g. chromatography or fractional crystallisation. The various stereoisomers may be isolated by separation of a racemic or other mixture of the compounds using conventional, e.g. fractional crystallisation or HPLC, techniques. Alternatively the desired optical isomers may be made by reaction of the appropriate optically active starting materials under conditions which will not cause racemisation or epimerisation (i.e. a 'chiral pool' method), by reaction of the appropriate starting material with a 'chiral auxiliary' which can subsequently be removed at a suitable stage, by derivatisation (i.e. a resolution, including a dynamic resolution), for example with a homochiral acid followed by separation of the diastereomeric derivatives by conventional means such as chromatography, or by reaction with an appropriate chiral reagent or chiral catalyst all under conditions known to the skilled person.

All stereoisomers (including but not limited to diastereoisomers, enantiomers and atropisomers) and mixtures thereof (e.g. racemic mixtures) are included within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The present invention also embraces isotopically-labeled compounds of the present invention which are identical to those recited herein, but for the fact that one or more atoms are replaced by an atom having an atomic mass or mass number different from the atomic mass or mass number usually found in nature (or the most abundant one found in nature). All isotopes of any particular atom or element as specified herein are contemplated within the scope of the compounds of the invention. Exemplary isotopes that can be incorporated into compounds of the invention include isotopes of hydrogen, carbon, nitrogen, oxygen, phosphorus, sulfur, fluorine, chlorine and iodine, such as $^{2}H$, $^{3}H$, $^{11}C$, $^{13}C$, $^{14}C$, $^{13}N$, $^{15}O$, $^{17}O$, $^{18}O$, $^{32}P$, $^{33}P$, $^{35}S$, $^{18}F$, $^{36}Cl$, $^{123}I$, and $^{125}I$. Certain isotopically-labeled compounds of the present invention (e.g., those labeled with $^{3}H$ and $^{14}C$) are useful in compound and for substrate tissue distribution assays. Tritiated ($^{3}H$) and carbon-14 ($^{14}C$) isotopes are useful for their ease of preparation and detectability. Further, substitution with heavier isotopes such as deuterium (i.e., $^{2}H$ may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Scheme 1 and/or in the Examples herein below, by substituting an isotopically labeled reagent for a non-isotopically labeled reagent.

Unless otherwise specified, $C_{1-q}$ alkyl groups (where q is the upper limit of the range) defined herein may be straight-chain or, when there is a sufficient number (i.e. a minimum of two or three, as appropriate) of carbon atoms, be branched-chain, and/or cyclic (so forming a $C_{3-q}$-cycloalkyl group). Such cycloalkyl groups may be monocyclic or bicyclic and may further be bridged. Further, when there is a sufficient number (i.e. a minimum of four) of carbon atoms, such groups may also be part cyclic. Such alkyl groups may also be saturated or, when there is a sufficient number (i.e. a minimum of two) of carbon atoms, be unsaturated (forming, for example, a $C_{2-q}$ alkenyl or a $C_{2-q}$ alkynyl group).

Unless otherwise stated, the term $C_{2-q}$ alkylene (where q is the upper limit of the range) defined herein may be straight-chain or, when there is a sufficient number of carbon atoms, be saturated or unsaturated (so forming, for example, an alkenylene or alkynylene linker group). Such $C_{1-q}$ alkylene groups may be branched (if sufficient number of atoms), but are preferably straight-chained.

$C_{3-q}$ cycloalkyl groups (where q is the upper limit of the range) that may be specifically mentioned may be monocyclic or bicyclic alkyl groups, which cycloalkyl groups may further be bridged (so forming, for example, fused ring systems such as three fused cycloalkyl groups). Such cycloalkyl groups may be saturated or unsaturated containing one or more double bonds (forming for example a cycloalkenyl group). Substituents may be attached at any point on the cycloalkyl group. Further, where there is a sufficient number (i.e. a minimum of four) such cycloalkyl groups may also be part cyclic.

The term "halo", when used herein, preferably includes fluoro, chloro, bromo and iodo.

Heterocycloalkyl groups that may be mentioned include non-aromatic monocyclic and bicyclic heterocycloalkyl groups in which at least one (e.g. one to four) of the atoms in the ring system is other than carbon (i.e. a heteroatom), and in which the total number of atoms in the ring system is between 3 and 20 (e.g. between three and ten, e.g between 3 and 8, such as 5- to 8-). Such heterocycloalkyl groups may also be bridged. Further, such heterocycloalkyl groups may be saturated or unsaturated containing one or more double and/or triple bonds, forming for example a $C_{2-q}$ heterocycloalkenyl (where q is the upper limit of the range) group. $C_{2-q}$ heterocycloalkyl groups that may be mentioned include 7-azabicyclo[2.2.1]heptanyl, 6-azabicyclo[3.1.1]heptanyl, 6-azabicyclo[3.2.1]-octanyl, 8-azabicyclo-[3.2.1]octanyl, aziridinyl, azetidinyl, dihydropyranyl, dihydropyridyl, dihydropyrrolyl (including 2,5-dihydropyrrolyl), dioxolanyl (including 1,3-dioxolanyl), dioxanyl (including 1,3-dioxanyl and 1,4-dioxanyl), dithianyl (including 1,4-dithianyl), dithiolanyl (including 1,3-dithiolanyl), imidazolidinyl, imidazolinyl, morpholinyl, 7-oxabicyclo[2.2.1]heptanyl, 6-oxabicyclo-[3.2.1]octanyl, oxetanyl, oxiranyl, piperazinyl, piperidinyl, non-aromatic pyranyl, pyrazolidinyl, pyrrolidinonyl, pyrrolidinyl, pyrrolinyl, quinuclidinyl, sulfolanyl, 3-sulfolenyl, tetrahydropyranyl, tetrahydrofuranyl, tetrahydropyridyl (such as 1,2,3,4-tetrahydropyridyl and 1,2,3,6-tetrahydropyridyl), thietanyl, thiiranyl, thiolanyl, thiomorpholinyl, trithianyl (including 1,3,5-trithianyl), tropanyl and the like. Substituents on heterocycloalkyl groups may, where appropriate, be located on any atom in the ring system including a heteroatom. The point of attachment of heterocycloalkyl groups may be via any atom in the ring system including (where appropriate) a heteroatom (such as a nitrogen atom), or an atom on any fused carbocyclic ring that may be present as part of the ring system. Heterocycloalkyl groups may also be in the N— or S— oxidised form. Heterocycloalkyl mentioned herein may be stated to be specifically monocyclic or bicyclic.

For the avoidance of doubt, the term "bicyclic" (e.g. when employed in the context of heterocycloalkyl groups) refers to groups in which the second ring of a two-ring system is formed between two adjacent atoms of the first ring. The term "bridged" (e.g. when employed in the context of cycloalkyl or heterocycloalkyl groups) refers to monocyclic or bicyclic groups in which two non-adjacent atoms are linked by either an alkylene or heteroalkylene chain (as appropriate).

Aryl groups that may be mentioned include $C_{6-20}$, such as $C_{6-12}$ (e.g. $C_{6-10}$) aryl groups. Such groups may be monocyclic, bicyclic or tricyclic and have between 6 and 12 (e.g. 6 and 10) ring carbon atoms, in which at least one ring is aromatic. $C_{1-10}$ aryl groups include phenyl, naphthyl and the like, such as 1,2,3,4-tetrahydro-naphthyl. The point of attachment of aryl groups may be via any atom of the ring system. For example, when the aryl group is polycyclic the point of attachment may be via atom including an atom of a non-aromatic ring. However, when aryl groups are polycyclic (e.g. bicyclic or tricyclic), they are preferably linked to the rest of the molecule via an aromatic ring.

Unless otherwise specified, the term "heteroaryl" when used herein refers to an aromatic group containing one or more heteroatom(s) (e.g. one to four heteroatoms) preferably selected from N, O and S. Heteroaryl groups include those which have between 5 and 20 members (e.g. between 5 and 10) and may be monocyclic, bicyclic or tricyclic, provided that at least one of the rings is aromatic (so forming, for example, a mono-, bi-, or tricyclic heteroaromatic group). When the heteroaryl group is polycyclic the point of attachment may be via any atom including an atom of a non-aromatic ring. However, when heteroaryl groups are polycyclic (e.g. bicyclic or tricyclic), they are preferably linked to the rest of the molecule via an aromatic ring. Heteroaryl groups that may be mentioned include 3,4-dihydro-1H-isoquinolinyl, 1,3-dihydroisoindolyl, 1,3-dihydroisoindolyl (e.g. 3,4-dihydro-1H-isoquinolin-2-yl, 1,3-dihydroisoindol-2-yl, 1,3-dihydroisoindol-2-yl; i.e. heteroaryl groups that are linked via a non-aromatic ring), or, preferably, acridinyl, benzimidazolyl, benzodioxanyl, benzodioxepinyl, benzodioxolyl (including 1,3-benzodioxolyl), benzofuranyl, benzofurazanyl, benzothiadiazolyl (including 2,1,3-benzothiadiazolyl), benzothiazolyl, benzoxadiazolyl (including 2,1,3-benzoxadiazolyl), benzoxazinyl (including 3,4-dihydro-2H-1,4-benzoxazinyl), benzoxazolyl, benzomorpholinyl, benzoselenadiazolyl (including 2,1,3-benzoselenadiazolyl), benzothienyl, carbazolyl, chromanyl, cinnolinyl, furanyl, imidazolyl, imidazo[1,2-a]pyridyl, indazolyl, indolinyl, indolyl, isobenzofuranyl, isochromanyl, isoindolinyl, isoindolyl, isoquinolinyl, isothiazolyl, isothiochromanyl, isoxazolyl, naphthyridinyl (including 1,6-naphthyridinyl or, preferably, 1,5-naphthyridinyl and 1,8-naphthyridinyl), oxadiazolyl (including 1,2,3-oxadiazolyl, 1,2,4-oxadiazolyl and 1,3,4-oxadiazolyl), oxazolyl, phenazinyl, phenothiazinyl, phthalazinyl, pteridinyl, purinyl, pyranyl, pyrazinyl, pyrazolyl, pyridazinyl, pyridyl, pyrimidinyl, pyrrolyl, quinazolinyl, quinolinyl, quinolizinyl, quinoxalinyl, tetrahydroisoquinolinyl (including 1,2,3,4-tetrahydroisoquinolinyl and 5,6,7,8-tetrahydroisoquinolinyl), tetrahydroquinolinyl (including 1,2,3,4-tetrahydroquinolinyl and 5,6,7,8-tetrahydroquinolinyl), tetrazolyl, thiadiazolyl (including 1,2,3-thiadiazolyl, 1,2,4-thiadiazolyl and 1,3,4-thiadiazolyl), thiazolyl, thiochromanyl, thiophenetyl, thienyl, triazolyl (including 1,2,3-triazolyl, 1,2,4-triazolyl and 1,3,4-triazolyl) and the like. Substituents on heteroaryl groups may, where appropriate, be located on any atom in the ring system including a heteroatom. The point of attachment of heteroaryl groups may be via any atom in the ring system including (where appropriate) a heteroatom (such as a nitrogen atom), or an atom on any fused carbocyclic ring that may be present as part of the ring system. Heteroaryl groups may also be in the N— or S— oxidised form.

Heteroaryl groups mentioned herein may be stated to be specifically monocyclic or bicyclic. When heteroaryl groups are polycyclic in which there is a non-aromatic ring present, then that non-aromatic ring may be substituted by one or more =O group.

It may be specifically stated that the heteroaryl group is monocyclic or bicyclic. In the case where it is specified that the heteroaryl is bicyclic, then it may consist of a five-, six- or seven-membered monocyclic ring (e.g. a monocyclic heteroaryl ring) fused with another a five-, six- or seven-membered ring (e.g. a monocyclic aryl or heteroaryl ring).

Heteroatoms that may be mentioned include phosphorus, silicon, boron and, preferably, oxygen, nitrogen and sulfur.

For the avoidance of doubt, where it is stated herein that a group (e.g. a $C_{1-12}$ alkyl group) may be substituted by one or more substituents (e.g. selected from $E^5$), then those substituents (e.g. defined by $E^5$) are independent of one another. That is, such groups may be substituted with the same substituent (e.g. defined by $E^5$) or different substituents (defined by $E^5$).

For the avoidance of doubt, in cases in which the identity of two or more substituents in a compound of the invention may be the same, the actual identities of the respective substituents are not in any way interdependent. For example, in the situation in which there is more than one e.g. $Q^1$ or $Q^2$, or, $E^1$ to $E^9$ (such as $E^6$) substituent present, then those $Q^1$ or $Q^2$, or, $E^1$ to $E^9$ (e.g. $E^6$) substituents may be the same or different. Further, in the case where there are e.g. $Q^1$ or $Q^2$, or, $E^1$ to $E^9$ (such as $E^6$) substituents present, in which one represents —$OR^{10a}$ (or e.g. —$OR^{20}$, as appropriate) and the other represents —$C(O)_2R^{10a}$ (or e.g. —$C(O)_2R^{20}$, as appropriate), then those $R^{10a}$ or $R^{20}$ groups are not to be regarded as being interdependent. Also, when e.g. there are two —$OR^{10a}$ substituents present, then those —$OR^{10a}$ groups may be the same or different (i.e. each $R^{10a}$ group may be the same or different).

For the avoidance of doubt, when a term such as "$E^1$ to $E^9$" is employed herein, this will be understood by the skilled person to mean $E^1$, $E^2$, $E^3$, $E^4$, $E^5$, $E^6$, $E^7$, $E^8$ and $E^9$, inclusively.

All individual features (e.g. preferred features) mentioned herein may be taken in isolation or in combination with any other feature (including preferred feature) mentioned herein (hence, preferred features may be taken in conjunction with other preferred features, or independently of them).

The skilled person will appreciate that compounds of the invention that are the subject of this invention include those that are stable. That is, compounds of the invention include those that are sufficiently robust to survive isolation from e.g. a reaction mixture to a useful degree of purity.

Compounds of the invention that may be mentioned include those in which:

when $R^a$ or $R^b$ represent alkyl (e.g. $C_{1-12}$ alkyl) or heterocycloalkyl, then such groups are optionally substituted by one or more substituents selected from =O and $Q^1$;

when $R^a$ and $R^b$ are linked together to form a ring, then the/those rings formed by the linkage of $R^a$ and $R^b$ are optionally substituted by one or more substituents selected from =O and $E^4$;

each $Q^1$ and $Q^2$ independently represents, on each occasion when used herein:

halo, —CN, —NO$_2$, —N(R$^{10a}$)R$^{11a}$, —OR$^{10a}$, —C(=Y)—R$^{10a}$, —C(=Y)—OR$^{11a}$, —C(=Y)N(R$^{10a}$)R$^{11a}$, —OC(=Y)—R$^{10a}$, —OC(=Y)—OR$^{10a}$, —OC(=Y)N(R$^{10a}$)R$^{11a}$, —OS(O)$_2$OR$^{10a}$, —OP(=Y)(OR$^{10a}$)(OR$^{11a}$), —OP(OR$^{10a}$)(OR$^{11a}$), —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —SC(=Y)R$^{10a}$, —S(O)$_2$R$^{10a}$, —SR$^{10a}$, —S(O)R$^{10a}$, C$_{1-12}$ alkyl, heterocycloalkyl (which latter two groups are optionally substituted by one or more substituents selected from =O, =S, =N(R$^{10a}$) and E$^5$), aryl or heteroaryl (which latter two groups are optionally substituted by one or more substituents selected from E$^6$); and/or each Q$^4$ and Q$^5$ independently represent, on each occasion when used herein:

halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —OC(=Y)—R$^{20}$, —OC(=Y)—OR$^{20}$, —OC(=Y)N(R$^{20}$)R$^{21}$, —OS(O)$_2$OR$^{20}$, —OP(=Y)(OR$^{20}$)(OR$^{21}$), —OP(OR$^{20}$)(OR$^{21}$), —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —SC(=Y)R$^{20}$, —S(O)$_2$R$^{20}$, —SR$^{20}$, —S(O)R$^{20}$, C$_{1-6}$ alkyl, heterocycloalkyl (which latter two groups are optionally substituted by one or more substituents selected from =O and J$^2$), aryl or heteroaryl (which latter two groups are optionally substituted by one or more substituents selected from J$^3$).

Preferred compounds of the invention include those in which:

R$^1$ does not represent —N(R$^6$)— (e.g. R$^1$ is selected from —O—, —S—, —S(O)—, —S(O)$_2$— and —C(R$^6$)(R$^{6a}$)—), especially when R$^2$ represents —C(R$^6$)(R$^{6a}$)—;

when R$^3$ represents a substituted aryl (e.g. phenyl) group (i.e. substituted by one or more E$^3$ substituents), then that/those E$^3$ substituent(s) are preferably not located at the position ortho to the point of attachment of the R$^3$ group (to the requisite triazolopyridazine bicycle of formula I).

Preferred aryl groups and bicyclic heteroaryl groups (attached to the requisite triazolopyridazine of formula I via a fused benzene ring) that R$^3$ may represent include optionally substituted phenyl, naphthyl, indazolyl, indolyl, indolinyl, isoindolinyl, quinolinyl, isoquinolinyl, benzoxazolyl, benzofuranyl, isobenzofuranyl, chromanyl, benzothienyl, benzimidazolyl, quinazolinyl, quinoxalinyl, 1,3-benzodioxolyl, 1,3-dihydroisoindolyl, 3,4-dihydro-1H-isoquinolinyl, 1,3-dihydroisoindolyl, benzothiazolyl, and/or benzodioxanyl. Particularly preferred groups include optionally substituted aryl (e.g. naphthyl or, preferably, phenyl) or bicyclic heteroaryl (e.g. a bicyclic 10- or, preferably, 9-membered group, in which one ring of the bicycle is benzene and the other ring preferably contains one, two, three or four (e.g. one or two) heteroatoms preferably selected from nitrogen, oxygen and sulfur), in which the point of attachment of the bicyclic heteroaryl group to the requisite triazolopyridazine core of the compound of formula I is via a benzene ring of the bicyclic heteroaryl group.

Preferred monocyclic heteroaryl groups that R$^a$ or R$^b$ or Q$^1$, Q$^2$, Q$^4$ or Q$^5$ (if applicable) may independently represent include 5- or 6-membered rings, containing one to three (e.g. one or two) heteroatoms selected from sulfur, oxygen and nitrogen. Preferred bicyclic heteroaryl groups that R$^3$ (provided that it is attached to be requisite bicycle of formula I via a benzene ring of the bicycle), R$^a$ or R$^b$, or Q$^1$, Q$^2$, Q$^4$ or Q$^5$ may represent include 8- to 12- (e.g. 9- or 10-) membered rings containing one to four (e.g. one to three, or, preferably, one or two) heteroatoms selected from sulfur, oxygen and nitrogen (e.g. an indolyl group). Further, bicyclic rings may consist of benzene rings (and bicyclic heteroaryl groups that R$^3$ may represent must comprise a benzene ring) fused with a monocyclic heteroaryl group (as hereinbefore defined), e.g. a 6- or, preferably 5-membered monocyclic heteroaryl group optionally containing two, or, preferably, one heteroatom selected from sulfur, oxygen and nitrogen.

Preferred heterocycloalkyl groups that R$^a$ or R$^b$ or Q$^1$, Q$^2$, Q$^4$ or Q$^5$ may independently represent include 4- to 8-membered (e.g. 5- or 6-membered) heterocycloalkyl groups, which groups preferably contain one or two heteroatoms (e.g. sulfur or, preferably, nitrogen and/or oxygen heteroatoms), so forming for example, an optionally substituted pyrrolidinyl, piperidinyl, morpholinyl or tetrahydropyranyl group.

Preferred C$_{3-6}$ cycloalkyl groups that R$^a$ or R$^b$ or Q$^1$, Q$^2$, Q$^4$ or Q$^5$ may independently represent include optionally substituted C$_{3-8}$ (e.g. C$_{3-6}$) cycloalkyl groups, such as cyclohexyl, cyclopentyl, cyclobutyl and cyclopropyl.

Preferred compounds of the invention include those in which:

when R$^3$ represents aryl (e.g. phenyl), then that group may be unsubstituted but is preferably substituted by at least one (e.g. two or, preferably, one) substituent(s) selected from E$^3$, or, the aryl (e.g. phenyl) group may be substituted with two E$^3$ substituents that are linked together, so forming e.g. a bicyclic heteroaryl (e.g. a 8-, 9- or 10-membered heteroaryl group), consisting of a 6-membered benzene ring (which is attached to the requisite bicycle of formula I) fused to another 5- or 6-membered ring (in which the latter ring may contain one or more (e.g. four, or, preferably one to three) heteroatoms), and which bicyclic ring system is optionally substituted by one or more (e.g. two or, preferably, one) substituent(s) selected from E$^3$ or J$^1$ (as appropriate) (and, if there is a non-aromatic ring present in the bicyclic heteroaryl group, then such a group may also be substituted by one or more (e.g. one) =O groups). It may be more preferred that the R$^3$ group of compounds of the invention are not substituted with (at least) two E$^3$ substituents that are linked together to form a bicycle. It may be even more preferred that R$^3$ is an optionally substituted monocyclic aryl group.

Further preferred compounds of the invention include those in which:

each R$^{10a}$, R$^{11a}$ and R$^{12a}$ independently represent, on each occasion when used herein, hydrogen or C$_{1-12}$ (e.g. C$_{1-6}$) alkyl (which latter group is optionally substituted by one or more substituents selected from =O and E$^7$); or any relevant pair of R$^{10a}$, R$^{11a}$ and R$^{12a}$ may be linked together as defined herein (although they are preferably not linked);

each of E$^1$, E$^2$, E$^3$, E$^4$, E$^5$, E$^6$, E$^7$, E$^8$ and E$^9$ independently represent, on each occasion when used herein, Q$^4$ or C$_{1-6}$ alkyl (e.g. C$_{1-3}$) alkyl optionally substituted by one or more substituents selected from =O and Q$^5$;

each Q$^4$ and Q$^5$ independently represent halo, —CN, —NO$_2$, —N(R$^{20}$)R$^{21}$, —OR$^{20}$, —C(=Y)—R$^{20}$, —C(=Y)—OR$^{20}$, —C(=Y)N(R$^{20}$)R$^{21}$, —N(R$^{22}$)C(=Y)R$^{21}$, —N(R$^{22}$)C(=Y)OR$^{21}$, —N(R$^{22}$)C(=Y)N(R$^{20}$)R$^{21}$, —NR$^{22}$S(O)$_2$R$^{20}$, —NR$^{22}$S(O)$_2$N(R$^{20}$)R$^{21}$, —S(O)$_2$N(R$^{20}$)R$^{21}$, —S(O)$_2$R$^{20}$, —SR$^{20}$, —S(O)R$^{20}$ or C$_{1-6}$ alkyl optionally substituted by one or more fluoro atoms (and each Q$^5$ more preferably represents halo, such as fluoro);

any two E$^1$, E$^2$, E$^3$, E$^4$, E$^5$, E$^6$, E$^7$, E$^8$ and/or E$^9$ groups may be linked together (e.g. any two E$^3$ substituents may also be linked together as defined herein, for example when attached to the same or, preferably, adjacent carbon atoms), but (e.g. any two $E^1$, $E^2$, $E^4$, $E^5$, $E^6$, $E^7$, $E^8$ and/or $E^9$) are preferably not linked together;

each $R^{20}$, $R^{21}$, $R^{22}$ and $R^{23}$ independently represent, on each occasion when used herein, aryl (e.g. phenyl; preferably unsubstituted, but which may be substituted by one to three $J^5$ groups) or, more preferably, hydrogen or $C_{1-6}$ (e.g. $C_{1-3}$) alkyl optionally substituted by one or more substituents selected from =O and $J^4$; or any pair of $R^{20}$ and $R^{21}$, may, when attached to the same nitrogen atom, be linked together to form a 4- to 8-membered (e.g. 5- or 6-membered) ring, optionally containing one further heteroatom selected from nitrogen and oxygen, optionally containing one double bond, and which ring is optionally substituted by one or more substituents selected from $J^6$ and =O;

each $J^1$, $J^2$, $J^3$, $J^4$, $J^5$ and $J^6$ independently represents $C_{1-6}$ alkyl (e.g. acyclic $C_{1-4}$ alkyl or $C_{3-6}$ cycloalkyl) optionally substituted by one or more substituents selected from =O and $Q^8$, or, such groups independently represent a substituent selected from $Q^7$;

each $Q^7$ and $Q^8$ independently represents a substituent selected from halo (e.g. fluoro), —N($R^{50}$)$R^{51}$, —O$R^{50}$, —C(=$Y^a$)—$R^5$, —C(=$Y^a$)—O$R^{50}$, —C(=$Y^a$)N($R^{50}$)$R^{51}$, —N($R^{52}$)C(=$Y^a$)$R^{51}$, —N$R^{52}$S(O)$_2R^{50}$, —S(O)$_2R^{50}$ or $C_{1-6}$ alkyl optionally substituted by one or more fluoro atoms;

each $R^{50}$, $R^{51}$, $R^{52}$ and $R^{53}$ substituent independently represents, on each occasion when used herein, hydrogen or $C_{1-8}$ (e.g. $C_{1-3}$) alkyl optionally substituted by one or more substituents selected from fluoro;

when any relevant pair of $R^{50}$, $R^{51}$ and $R^{52}$ are linked together, then those pairs that are attached to the same nitrogen atom may be linked together (i.e. any pair of $R^{50}$ and $R^{51}$), and the ring so formed is preferably a 5- or 6-membered ring, optionally containing one further nitrogen or oxygen heteroatom, and which ring is optionally substituted by one or more selected from =O and $C_{1-3}$ alkyl (e.g. methyl);

$R^{60}$, $R^{61}$ and $R^{62}$ independently represent hydrogen or $C_{1-3}$ (e.g. $C_{1-2}$) alkyl optionally substituted by one or more fluoro atoms.

Preferred optional substituents on $R^3$ (or on any bicyclic group that $R^3$, together with two $E^3$ substituents that are linked together, may form), $R^4$ and the $R^1$, $R^2$ and X-containing ring (if applicable) include:

=O (unless the group is aromatic);
—CN;
halo (e.g. fluoro, chloro or bromo);
$C_{1-6}$ (e.g. $C_{1-4}$) alkyl, which alkyl group may be cyclic, part-cyclic, unsaturated or, preferably, linear or branched (e.g. $C_{1-4}$ alkyl (such as ethyl, n-propyl, isopropyl, t-butyl or, preferably, n-butyl or methyl), all of which are optionally substituted with one or more halo (e.g. fluoro) groups (so forming, for example, fluoromethyl, difluoromethyl or, preferably, trifluoromethyl) or substituted with an aryl, heteroaryl or heterocycloalkyl group (which themselves may be substituted with one or more —O$R^{z1}$, —C(O)$R^{z2}$, —C(O)O$R^{z3}$, —N($R^{z4}$)$R^{z5}$, —S(O)$_2R^{z6}$, —S(O)$_2$N($R^{z7}$)$R^{z8}$; —N($R^{z9}$)—C(O)—$R^{z10}$, —C(O)—N($R^{z11}$)$R^{z12}$ and/or —N($R^{z9}$)—C(O)—N($R^{z10}$) substituents; aryl (e.g. phenyl) (e.g. which substitutent may also be present on an alkyl group, thereby forming e.g. a benzyl group);
—O$R^{z1}$;
C(O)$R^{z2}$;
—C(O)O$R^{z3}$;
—N($R^{z4}$)$R^{z5}$;
—S(O)$_2R^{z6}$;
—S(O)$_2$N($R^{z7}$)$R^{z6}$;
—N($R^{z9}$)—C(O)—$R^{z10}$;
—C(O)—N($R^{z11}$)$R^{z12}$;
—N($R^{z9}$)—C(O)—N($R^{z10}$);
wherein each $R^{z1}$ to $R^{z12}$ independently represents, on each occasion when used herein, H or $C_{1-4}$ alkyl (e.g. ethyl, n-propyl, t-butyl or, preferably, n-butyl, methyl, isopropyl or cyclopropylmethyl (i.e. a part cyclic alkyl group)) optionally substituted by one or more halo (e.g. fluoro) groups (so forming e.g. a trifluoromethyl group). Further, any two $R^z$ groups (e.g. $R^{z4}$ and $R^{z5}$), when attached to the same nitrogen heteroatom may also be linked together to form a ring such as one hereinbefore defined in respect of corresponding linkage of $R^{10a}$ and $R^{11a}$ groups.

Preferred compounds of the invention include those in which:

each $R^{10a}$, $R^{11a}$ and $R^{12a}$ independently represent phenyl (optionally substituted by one or more $E^8$ substituents), preferably, heterocycloalkyl (optionally substituted by one or more =O and/or $E^7$ substituents) and, more preferably, hydrogen or $C_{1-12}$ (e.g. $C_{1-6}$) alkyl (optionally substituted by one or more =O and/or $E^7$ substituents), or any pair of $R^{10a}$, $R^{11a}$ and $R^{12a}$ (e.g. any pair of $R^{10a}$ and $R^{11a}$ when attached to the same nitrogen atom) may be linked together to form a 4- to 10-membered (e.g. a 4- to 6-membered monocyclic) ring, optionally substituted by one or more substituents selected from =O and $E^9$;

each $E^1$, $E^2$, $E^3$, $E^4$, $E^5$, $E^6$, $E^7$, $E^8$ and $E^9$ independently represents $C_{1-12}$ alkyl optionally substituted by one or more substituents selected from =O and $Q^5$, or, each $E^1$ to $E^9$ independently represent $Q^4$; or, any two $E^1$ to $E^9$ substituents (e.g. when attached to the same or adjacent atoms) may be linked together to form a 3- to 8-membered ring, optionally containing one to three double bonds, one to three heteroatoms, and which ring may be substituted by one or more substituents selected from =O and $J^1$;

each $R^{20}$, $R^{21}$, $R^{22}$ and $R^{23}$ (e.g. each $R^{20}$ and $R^{21}$) independently represents heteroaryl, preferably, aryl (e.g. phenyl) (which latter two groups are optionally substituted by one or more substituents selected from $J^5$), or, more preferably, hydrogen or $C_{1-6}$ (e.g. $C_{1-4}$) alkyl optionally substituted by one or more substituents selected from =O and $J^4$; or any relevant pair of $R^{20}$, $R^{21}$ and $R^{22}$ (e.g. $R^{20}$ and $R^{21}$) may (e.g. when both are attached to the same nitrogen atom) may be linked together to form a 3- to 8- (e.g. 4- to 8-) membered ring, optionally containing a further heteroatom, and optionally substituted by one or more substituents selected from =O and $J^6$;

each $J^1$, $J^2$, $J^3$, $J^4$, $J^5$ and $J^6$ independently represent $C_{1-6}$ alkyl (e.g. $C_{1-4}$ acyclic alkyl or $C_{3-5}$ cycloalkyl) optionally substituted by one or more substituents selected from $Q^8$, or, $J^1$ to $J^6$ more preferably represent a substituent selected from $Q^7$;

each $R^{50}$, $R^{51}$, $R^{52}$ and $R^{53}$ independently represents hydrogen or $C_{1-6}$ (e.g. $C_{1-4}$) alkyl optionally substituted by one or more fluoro atoms;

each $R^{60}$, $R^{61}$ and $R^{62}$ independently represents hydrogen or $C_{1-2}$ alkyl (e.g. methyl).

More preferred compounds of the invention include those in which:

$R^{d1}$, $R^{d2}$ and $R^{d3}$ independently represent $C_{1-6}$ (e.g. $C_{1-3}$) alkyl optionally substituted by one or more substituents selected from $E^1$, but which is preferably unsubstituted;

when $R^a$ and $R^b$ are linked together, they may represent a 3- to 6-membered ring (e.g. a 5- or, preferably, 6-membered ring), optionally containing one further heteroatom selected from nitrogen and oxygen, which ring may be: (a) fused to another saturated 5- or 6-membered carbocyclic or heterocyclic ring, in which the latter contains one to four heteroatoms preferably selected from nitrogen and oxygen; (b) comprises a —(CH$_2$)$_{n1}$—, —O— or —CH$_2$—O—CH$_2$— linker group linking any two non-adjacent atoms; or (c) comprises a further 4- to 6-membered saturated carbocyclic or heterocyclic ring, in which the latter contains one or two heteroatoms preferably selected from nitrogen and oxygen, which second ring is linked to the first via a single atom;

$Q^4$ and $Q^5$ independently represent halo (e.g. fluoro), —OR$^{20}$, —N(R$^{20}$)R$^{21}$, —C(=Y)R$^{20}$, —C(=Y)OR$^{20}$, —C(=Y)N(R$^{20}$)R$^{21}$, —N(R$^{22}$)C(=Y)R$^{21}$, —NR$^{22}$S(O)$_2$R$^{20}$ heterocycloalkyl, aryl, heteroaryl (which latter three groups are optionally substituted with one or more substitutents selected from $J^2$ or $J^3$, as appropriate) and/or C$_{1-6}$ alkyl (e.g. C$_{1-3}$ alkyl) optionally substituted by one or more fluoro atoms;

each Y represents, on each occasion when used herein, =S, or preferably =O;

each R$^{20}$, R$^{21}$, R$^{22}$ and R$^{23}$ (e.g. each R$^{20}$ and R$^{21}$) independently represents hydrogen or C$_{1-4}$ (e.g. C$_{1-3}$) alkyl (e.g. C$_{1-4}$ acyclic alkyl group or a part cyclic C$_4$ group) optionally substituted (but preferably unsubstituted) by one or more (e.g. one) $J^4$ substituent(s); or any relevant pair of R$^{20}$, R$^{21}$ and R$^{22}$ (e.g. R$^{20}$ and R$^{21}$) may (e.g. when both are attached to the same nitrogen atom) may be linked together to form a 5- or, preferably, a 6-membered ring, optionally containing a further heteroatom (preferably selected from nitrogen and oxygen), which ring is preferably saturated, and optionally substituted by one or more substituents selected from =O and $J^6$;

R$^{22}$ represents C$_{1-3}$ alkyl or hydrogen;

each $J^1$, $J^2$, $J^3$, $J^4$, $J^5$ and $J^6$ independently represent a substituent selected from $Q^7$, or $J^1$ to $J^6$ represents C$_{1-6}$ alkyl (e.g. C$_{1-4}$ alkyl);

each $Q^7$ and $Q^8$ independently represent halo (e.g. fluoro), —N(R$^{50}$)R$^{51}$, —OR$^{50}$,
—C(=Y$^a$)—R$^{50}$,
—C(=Y$^a$)—OR$^{50}$, —C(=Y$^a$)N(R$^{50}$)R$^{51}$, —N(R$^2$)C(=Y$^a$)R$^{51}$ or C$_{1-6}$ alkyl optionally substituted by one or more fluoro atoms;

each Y$^a$ independently represents =S or, preferably, =O;
each R$^{50}$, R$^{51}$, R$^{52}$ and R$^{53}$ independently represents H or C$_{1-4}$ alkyl (e.g. tBu, Me).

Preferred compounds of the invention include those in which:

R$^1$ and R$^2$ independently represent —C(R$^6$)(R$^{6a}$)—, preferably, —S(O)—, —S(O)$_2$—, and, more preferably, —O—, —S— or —N(R$^6$)—;

each R$^6$ and R$^{6a}$ independently represents, on each occasion when used herein, H or R$^{d3}$;

R$^{d3}$ represents C$_{1-6}$ (e.g. C$_{1-4}$) alkyl;

X represents optionally substituted (i.e. by E$^2$) C$_2$ alkylene (e.g. unsubstituted C$_2$ alkylene);

R$^3$ represents aryl (e.g. phenyl) optionally substituted by one or more (e.g. one to three) substituent(s) selected from E$^3$, in which the E$^3$ substituents are as herein defined, or, two E$^3$ substituents on the aryl (e.g. phenyl) ring may be linked together as defined herein;

R$^a$ and R$^b$ independently represents H, —C(O)C$_{1-2}$ alkyl (e.g. —C(O)CH$_3$), —S(O)$_2$C$_{1-2}$ alkyl (e.g. —S(O)$_2$CH$_3$), C$_{1-6}$ alkyl, heterocycloalkyl (which latter two groups are optionally substituted by one or more (one to three) substituent(s) selected from Q$^1$); or R$^a$ and R$^b$ may be linked together to form a 3- to 6-membered ring (e.g. a 5- or, preferably, 6-membered ring), preferably containing no further heteroatoms, which ring may be linked to a further 4- to 6-membered ring (e.g. 4-membered ring) via a single atom (i.e. forming a spiro cycle), all of which cyclic groups are optionally substituted by one or more substituents selected from E$^4$;

Q$^1$ and Q$^2$ independently represent halo, —N(R$^{10a}$)R$^a$, —OR$^{10a}$, —C(=Y)—R$^{10a}$, —C(=Y)—OR$^{10a}$, —C(=Y)N(R$^{10a}$)R$^{11a}$, —N(R$^{12a}$)C(=Y)R$^{11a}$, —N(R$^{12a}$)C(=Y)OR$^{11a}$, —N(R$^{12a}$)C(=Y)N(R$^{10a}$)R$^{11a}$, —NR$^{12a}$S(O)$_2$R$^{10a}$, —NR$^{12a}$S(O)$_2$N(R$^{10a}$)R$^{11a}$, —S(O)$_2$N(R$^{10a}$)R$^{11a}$, —S(O)$_2$R$^{10a}$, —SR$^{10a}$, —S(O)R$^{10a}$, C$_{1-6}$ alkyl, heterocycloalkyl (which latter two groups are optionally substituted by one or more substituents selected from =O, =S, =N(R$^{10a}$) and E$^5$), aryl or heteroaryl (which latter two groups are optionally substituted by one or more substituents selected from E$^6$);

R$^{10a}$, R$^{11a}$ and R$^{12a}$ independently represent H or C$_{1-6}$ (e.g. C$_{1-4}$) alkyl optionally substituted by one or more groups selected from =O and E$^7$;

E$^1$ to E$^9$ independently represent Q$^4$ or C$_{1-6}$ (e.g. C$_{1-3}$, such as methyl) alkyl optionally substituted by one or more Q$^5$ substituents; or any two E$^1$ to E$^9$ substituents (e.g. two E$^3$ substituents) when attached to adjacent carbon atoms may be linked together to form a 3- to 8-membered (e.g. 5- or 6-membered) ring (preferably containing one to three double bonds, e.g. forming an aromatic ring), preferably containing one to three (e.g. one) heteroatom(s), and which ring is optionally substituted by one or more substituents selected from =O and, preferably, $J^1$ (when the ring is aromatic, then it may only be substituted by one or more $J^1$ substituents);

Q$^4$ and Q$^5$ independently represent C$_{1-6}$ alkyl (optionally substituted by one or more =O and/or $J^2$ substituents, but preferably, unsubstituted) or, preferably, halo, —CN, —OR$^{20}$, —N(R$^{20}$)R$^{21}$, —C(=Y)R$^{20}$, —C(=Y)OR$^{20}$ or —N(R$^{22}$)C(=Y)R$^{21}$;

Y represents =S or, preferably, =O;

R$^{20}$ and R$^{21}$ independently represent hydrogen, C$_{1-4}$ alkyl, which latter group is optionally substituted by one or more (e.g. one) substituent(s) selected from $J^4$;

when there is a —N(R$^{20}$)R$^{21}$ moiety present, then one of R$^{20}$ and R$^{21}$ represents hydrogen, and the other represents hydrogen or C$_{1-4}$ alkyl (e.g. methyl, ethyl or isopropyl), which latter group is optionally substituted by one or more (e.g. one) substituent(s) selected from $J^4$;

R$^{22}$ represents hydrogen and C$_{1-3}$ alkyl (e.g. methyl);

$J^3$ represents Q$^7$;

$J^4$ represents Q$^7$ or C$_{1-6}$ (e.g. C$_{1-3}$) alkyl, which is preferably unsubstituted;

Q$^7$ represents halo (e.g. fluoro).

Preferred R$^1$, R$^2$ and X-containing rings of the compounds of the invention include:

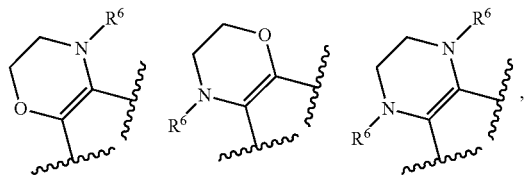

wherein the squiggly lines represent the point of attachment to the requisite triazolopyridazine of the compound of formula I, and R$^6$ is as defined herein.

Preferred R³ groups of the compounds of the invention include methoxyphenyl (e.g. 4-methoxyphenyl), trifluoromethoxyphenyl (e.g. 3-OCF₃-phenyl), trifluoromethylphenyl (e.g. 3-trifluoromethylphenyl) halophenyl (e.g. fluorophenyl, such as 4-fluorophenyl), cyanophenyl (e.g. 3-cyanophenyl), indolyl (attached to the requisite bicycle via the benzene ring, e.g. 4- or, preferably, 5-indolyl) and hydroxyphenyl (e.g. 4-hydroxyphenyl). The phenyl group attached to the requisite triazolopyridazine bicycle of formula I is preferably substituted.

Preferably substituents on such phenyl groups are in the meta and/or para position (or two substituents in the meta and para position may be linked together to form a further ring, e.g. an indolyl ring).

Preferred R⁴ groups of compounds of the invention include:

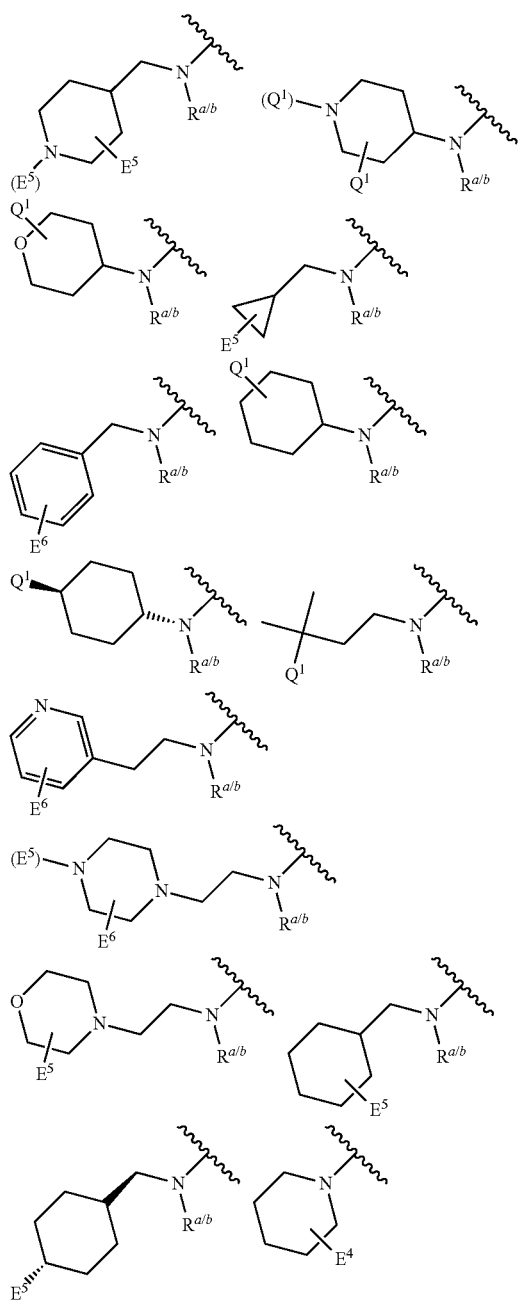

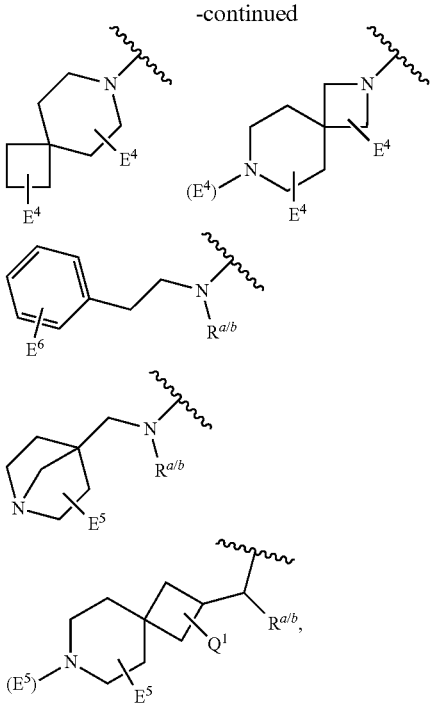

wherein the squiggly line represents the point of attachment to the requisite triazolopyridazine of the compound of formula I, $R^{a/b}$ represents $R^a$ or $R^b$, and the other integers (e.g. $E^4$, $E^5$, $Q^1$ and $E^6$; which are optional substituents that may be attached to specific atoms, or, may be depicted as 'floating', in which case the relevant group is optionally substituted by one or more of those $E^5/Q^1/E^6/E^4$ substituents) are as defined herein. The depiction of a substituent in brackets signifies that that substituent is optionally present, and may therefore be absent (i.e. N-($E^5$) may signify N-$E^5$ or N—H).

More preferred compounds of the invention include those in which:

one of R¹ and R² represents —N(R⁶)— and the other represents —O— or —N(R⁶)—;

R⁶ represents H or, more preferably, $R^{d3}$;

$R^{d3}$ represents $C_{1-3}$ alkyl (e.g. methyl or ethyl);

X represents $C_2$ alkylene, preferably unsubstituted (i.e. —CH₂—CH₂—);

R³ represents aryl (e.g. phenyl) optionally substituted (e.g. at the meta or para-position, when e.g. R³ represents phenyl) by one or more (e.g. one or two) substituent(s) selected from E³, or, any two E³ substituents, when attached to adjacent carbon atoms of the aryl (e.g. phenyl) group may be linked together to form a further 3- to 6- (e.g. 5-) membered ring containing one or preferably two double bonds, preferably containing one or two (e.g. one) heteroatom(s) (preferably selected from nitrogen) (and the further ring may therefore be thienyl, furanyl or, preferably, pyrrolyl), and which two E³ substituents are preferably attached meta and para, and hence R³ may form a fused bicyclic group (e.g. a benzothienyl, benzofuranyl or, preferably, an indolyl, e.g. 5-indolyl group);

one of $R^a$ and $R^b$ represents H, —C(O)$C_{1-2}$ alkyl (e.g. —C(O)CH₃), —S(O)₂$C_{1-2}$ alkyl (e.g. —S(O)₂CH₃) or $C_{1-3}$alkyl (e.g. methyl) and the other represents a substituent other than hydrogen (or the foregoing groups);

when either of $R^a$ and $R^b$ represents a substituent (see above), then it may be:

(i) $C_{1-6}$ alkyl (e.g. $C_{1-3}$ acyclic alkyl or $C_{3-6}$ cycloalkyl) (e.g. methyl, ethyl, n-propyl, cyclobutyl or cyclohexyl) optionally substituted by one or more substituents (and preferably substituted by at least one (e.g. one) substituent) selected from $Q^1$;

(ii) heterocycloalkyl (e.g. a 5- or, preferably 6-membered heterocycloalkyl group containing one or two (e.g. one) heteroatom(s) in which one is preferably nitrogen or oxygen, so forming e.g. piperidinyl or tetrahydropyranyl, such as 4-piperidinyl or 4-tetrahydropyranyl) and which heterocycloalkyl group is optionally substituted by one or more (e.g. one; which substituent(s) may be attached to a nitrogen heteroatom) selected from $Q^1$; or $R^a$ and $R^b$ may be linked together to form a 3- to 6-membered ring (e.g. a 5- or, preferably, a 4- or 6-membered ring), preferably containing no further heteroatoms, which ring may be linked to a further 4- to 6-membered ring (e.g. a 4- or 6-membered ring) via a single atom (i.e. forming a spiro cycle, which is preferably a [3.5] or [5.3] spiro-cycle), all of which cyclic groups are optionally substituted by one or more substituents selected from $E^4$;

$Q^1$ may represent (for instance, when it is attached to a heterocycloalkyl group) $C_{1-6}$ (e.g. $C_{1-3}$) alkyl (e.g. methyl), $-N(R^{10a})R^{11a}$ (e.g. $-N(CH_3)_2$) or $-OR^{10a}$ (e.g. $-OH$);

$Q^1$ may represent (for instance, when it is a substituent on an alkyl group): $C_{1-6}$ alkyl (e.g. $C_{3-6}$ cycloalkyl, such as cyclopropyl or cyclohexyl) optionally substituted by one or more (e.g. two or, preferably, one) substituents selected from $=O$ and, preferably $E^5$; heterocycloalkyl (e.g. a 5- or, preferably 6-membered heterocycloalkyl group containing one or more (e.g. one or two) heteroatom(s) in which one is preferably nitrogen, so forming e.g. a piperidinyl, morpholinyl or piperazinyl group, such as a 4-piperidinyl, 4-morpholinyl or 1-piperazinyl, which heterocycloalkyl groups may be attached to a single carbon atom of a $C_{3-6}$ cycloalkyl group, thereby forming a spiro-cycle) (which heterocycloalkyl group is optionally substituted by one or more (e.g. one) substituent (which may be on a nitrogen heteroatom) selected from $=O$ and, preferably, $E^5$, and which heterocyclalkyl group may further be bridged, i.e. two non-adjacent atoms (which may be in a 1,4-relationship) of the first ring may be linked together with $-(CH_2)_{n1}-$ (where n is 2 or, preferably, 1), so forming for example a 1-aza-bicyclo[2.2.1]hept-4-yl group); aryl (e.g. phenyl) (which is optionally substituted by one or more substituents selected from $E^6$) or heteroaryl (e.g. a 5- or, preferably, a 6-membered heteroaryl group preferably containing one nitrogen heteroatom, so forming e.g. pyridyl, such as 3-pyridyl), which group is preferably unsubstituted;

$E^3$ represents $Q^4$ or $C_{1-3}$ alkyl (e.g. methyl) optionally substituted by one or more $Q^5$ substituents (so forming e.g. a trifluoromethyl group); or two $E^3$ groups (e.g. when attached to adjacent carbon atoms of an aryl (e.g. phenyl) group) may be linked together to form an aromatic (e.g. 5-membered) ring, preferably containing one or two (e.g. one) heteroatom(s) (selected from sulfur, oxygen and, preferably nitrogen), and hence the linked $E^3$ groups preferably represent a thienyl, fuanyl or, more preferably, a pyrrolyl group;

$E^4$ represents $Q^4$, or, $C_{1-3}$ alkyl (e.g. methyl) optionally substituted by one or more (e.g. one) $Q^5$ substituent;

$E^5$ represents $Q^4$ or $C_{1-6}$ (e.g. $C_{1-4}$) alkyl (acyclic or part-cyclic; so forming e.g. methyl or cyclopropylmethyl, i.e. $C_{1-2}$ alkyl (e.g. methyl) substituted by $C_{3-6}$ cycloalkyl (e.g. cyclopropyl)), which is preferably unsubstituted;

$E^6$ represents $Q^4$;

$Q^4$ represents halo (e.g. fluoro), $-CN$, $-OR^{20}$, $-N(R^{20})R^{21}$, $-C(=Y)R^{20}$, $-C(=Y)OR^{20}$ or $-S(O)_2R^{20}$;

$Q^5$ represents $C_{1-6}$ alkyl (preferably unsubstituted) or, preferably, halo (e.g. fluoro), $-N(R^{20})R^{21}$ or $-N(R^{22})C(=Y)R^{21}$;

$R^{10a}$ and $R^{11a}$ independently represent H or, preferably, $C_{1-3}$ alkyl (e.g. methyl);

$R^{20}$ represents H or $C_{1-4}$ alkyl (e.g. ethyl or, preferably, methyl, isopropyl or tert-butyl) optionally substituted by one or more $J^4$ substituents (in particular $J^4$ may represent halo, such as fluoro, and hence $R^{20}$ may represent a trifluoromethyl group);

$R^{21}$ represents hydrogen or $C_{1-4}$ (e.g. $C_{1-3}$) alkyl (e.g. isopropyl or, preferably, methyl);

$R^{22}$ represents hydrogen;

Y represents $=O$;

$J^4$ represents $Q^7$;

$Q^7$ represents halo (e.g. fluoro).

Preferred $R^1$, $R^2$ and X-containing rings of the compounds of the invention include:

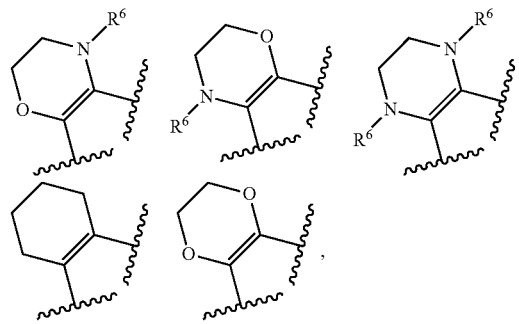

wherein the squiggly lines represent the point of attachment to the requisite triazolopyridazine of the compound of formula I, each of the relevant carbon atoms of the ring may be substituted by $R^6$ or $R^{6a}$ (as appropriate) in which the substituent is other than hydrogen, and each $R^6$ and $R^{6a}$ is/are as defined herein.

Preferred $R^a$ and $R^b$ groups of compounds of the invention include those in which:

$R^a$ and $R^b$ independently represent H, $C_{1-12}$ (e.g. $C_{1-8}$) alkyl, heterocycloalkyl (which latter two groups are optionally substituted by one or more substituents selected from $Q^1$), aryl or heteroaryl (which latter two groups are optionally substituted by one or more substituents selected from $Q^2$), or $R^a$ and $R^b$ are linked together; preferably $R^a$ and $R^b$ independently represent H, $C_{1-6}$ alkyl or heterocycloalkyl (which latter two groups are optionally substituted by one or more substituents selected from $Q^1$), or $R^a$ and $R^b$ are linked together; more preferably, one of $R^a$ and $R^b$ represents H or $C_{1-3}$ alkyl (e.g. methyl) and the other represents a substituent other than hydrogen;

when either of $R^a$ and $R^b$ represents a substituent (other than hydrogen), then it may be:

(i) $C_{1-6}$ alkyl (e.g. $C_{1-3}$ acyclic alkyl or $C_{3-6}$ cycloalkyl) optionally substituted by one or more substituents (and preferably substituted by at least one (e.g. one) substituent) selected from $Q^1$;

(ii) heterocycloalkyl (e.g. a 5- or, preferably, 6-membered heterocycloalkyl group containing one or two (e.g. one) heteroatom(s)) and which heterocycloalkyl group is optionally substituted by one or more (e.g. one; which substituent(s) may be attached to a nitrogen heteroatom) selected from $Q^1$; or $R^a$ and $R^b$ may be linked together to form a 3- to 7-membered ring (e.g. a 5- or, preferably, a 4-, 6- or 7-membered ring), preferably containing no further heteroatoms, which ring may be linked to a further 4- to 6-membered ring via a single atom, all of which cyclic groups are optionally substituted by one or more substituents selected from $E^4$.

Preferred $R^4$ groups of compounds of the invention include:

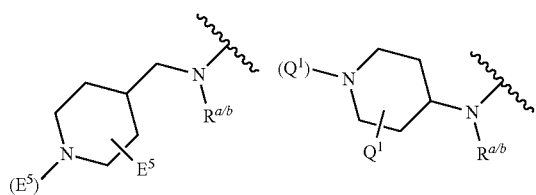
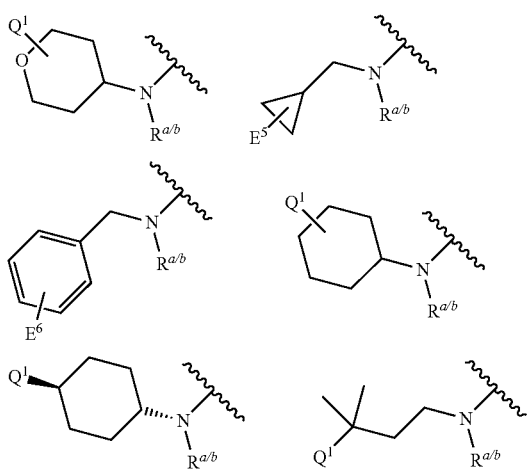
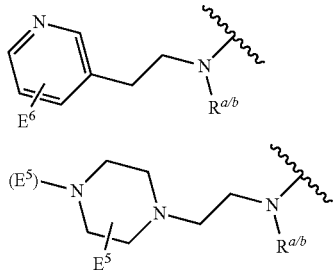
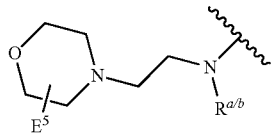
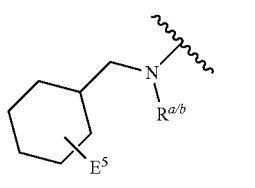
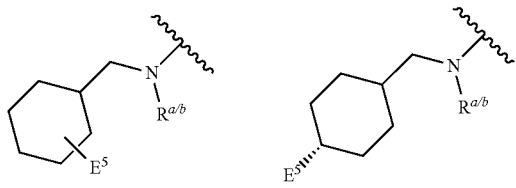
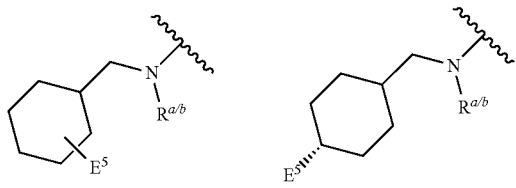
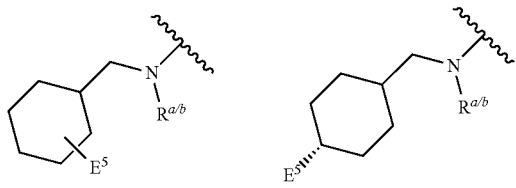
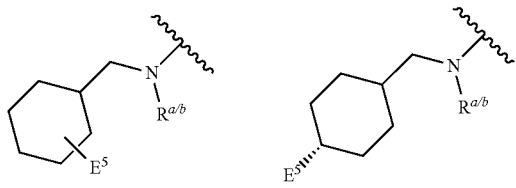
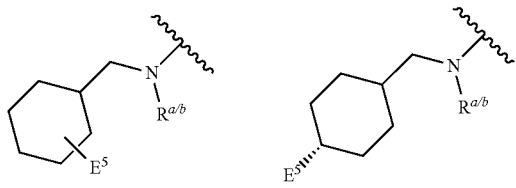
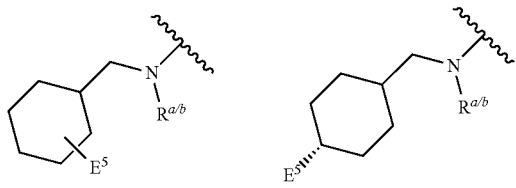
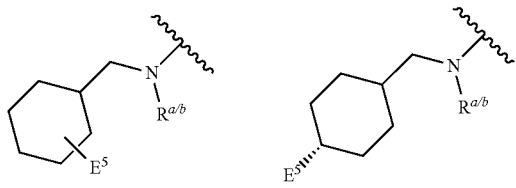

-continued

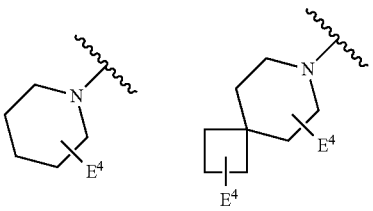
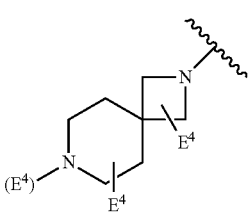
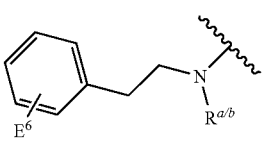
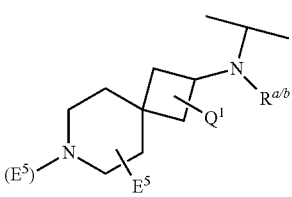
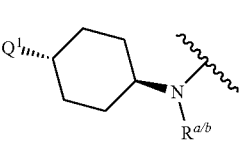
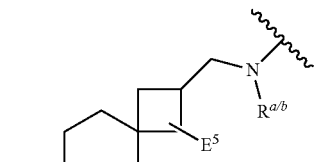
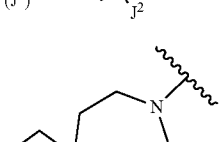
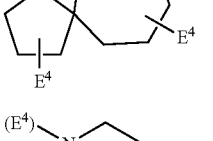
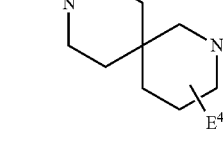
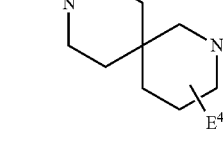
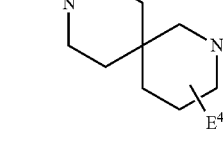
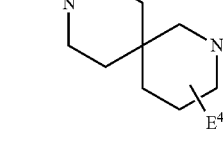

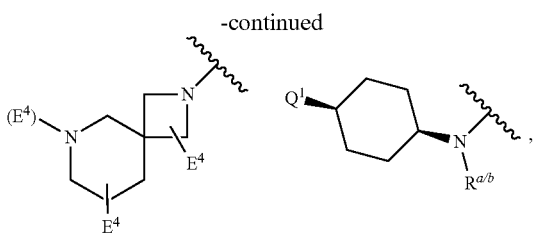

wherein the squiggly line represents the point of attachment to the requisite triazolopyridazine of the compound of formula I, $R^{a/b}$ represents $R^a$ or $R^b$, and the other integers (e.g. $E^4$, $E^5$, $Q^1$, $E^6$ and $J^2$; which are optional substituents that may be attached to specific atoms, or, may be depicted as 'floating', in which case the relevant group is optionally substituted by one or more of those $E^5/Q^1/E^6/E^4$ substituents) are as defined herein. The depiction of a substituent in brackets signifies that that substituent is optionally present, and may therefore be absent (i.e. N-($E^5$) may signify N-$E^5$ or N—H).

More preferred compounds of the invention include those in which:
$R^1$ and $R^2$ independently represent —N($R^6$)—, —O— or —C($R^6$)($R^{6a}$)—;
$R^6$ and $R^{6a}$ independently represent H or $R^{d3}$;
$R^{d3}$ represents $C_{1-3}$ alkyl (e.g. methyl or ethyl);
X represents $C_2$ alkylene optionally substituted by one or more (e.g. one or two) substituents selected from $E^2$;
$R^3$ represents aryl (e.g. phenyl) optionally substituted (e.g. at the meta or para-position, when e.g. $R^3$ represents phenyl) by one or more (e.g. one or two) substituent(s) selected from $E^3$, or, any two $E^3$ substituents, when attached to adjacent carbon atoms of the aryl (e.g. phenyl) group may be linked together to form a further 3- to 6- (e.g. 5-) membered ring containing one or preferably two double bonds, preferably containing one or two (e.g. one) heteroatom(s) (preferably selected from nitrogen) (and the further ring may therefore be thienyl, furanyl or, preferably, pyrrolyl), and which two $E^3$ substituents are preferably attached meta and para, and hence $R^3$ may form a fused bicyclic group (e.g. a benzothienyl, benzofuranyl or, preferably, an indolyl, e.g. 5-indolyl group); one of $R^a$ and $R^b$ represents H, —C(O)$C_{1-2}$ alkyl (e.g. —C(O)CH$_3$), —S(O)$_2$$C_{1-2}$ alkyl (e.g. —S(O)$_2$CH$_3$) or $C_{1-3}$ alkyl (e.g. methyl) and the other represents a substituent other than hydrogen (or the foregoing groups);
when either of $R^a$ and $R^b$ represents a substituent (see above), then it may be:
(i) $C_{1-6}$ alkyl (e.g. $C_{1-3}$ acyclic alkyl or $C_{3-6}$ cycloalkyl) (e.g. methyl, ethyl, n-propyl, cyclobutyl or cyclohexyl) optionally substituted by one or more substituents (and preferably substituted by at least one (e.g. one) substituent) selected from $Q^1$;
(ii) heterocycloalkyl (e.g. a 5- or, preferably 6-membered heterocycloalkyl group containing one or two (e.g. one) heteroatom(s) in which one is preferably nitrogen or oxygen, so forming e.g. piperidinyl or tetrahydropyranyl, such as 4-piperidinyl or 4-tetrahydropyranyl) and which heterocycloalkyl group is optionally substituted by one or more substituents (e.g. one; which substituent(s) may be attached to a nitrogen heteroatom) selected from $Q^1$; or
$R^a$ and $R^b$ may be linked together to form a 3- to 7-membered ring (e.g. a 5- or, preferably, a 4-, 6- or 7-membered ring), preferably containing no further heteroatoms, which ring may be linked to a further 4- to 6-membered ring (e.g. a 4-, 5- or 6-membered ring) via a single atom (i.e. forming a spiro cycle, which is preferably a [3.5], [5.3], [5.5], [6.4] or [4.6] spiro-cycle), all of which cyclic groups are optionally substituted by one or more substituents selected from $E^4$;
$Q^1$ may represent: —N($R^{10a}$)$R^{11a}$ (e.g. —N(CH$_3$)$_2$ or —NH$_2$); —O$R^{10a}$ (e.g. —OH); $C_{1-6}$ alkyl (e.g. $C_{3-6}$ cycloalkyl, such as cyclopropyl or cyclohexyl) optionally substituted by one or more (e.g. two or, preferably, one) substituents selected from =O and, preferably $E^5$ (in which $E^5$ may be a cyclic group, so forming a spiro-cyclic group when it is substituted on a cyclic alkyl group); heterocycloalkyl (e.g. a 5- or, preferably 6-membered heterocycloalkyl group containing one or more (e.g. one or two) heteroatom(s) in which one is preferably nitrogen, so forming e.g. a piperidinyl, morpholinyl or piperazinyl group, such as a 4-piperidinyl, 4-morpholinyl or 1-piperazinyl, which heterocycloalkyl groups may be attached to a single cabon atom of a $C_3$—S cycloalkyl group, thereby forming a spiro-cycle) (which heterocycloalkyl group is optionally substituted by one or more (e.g. one) substituent (which may be on a nitrogen heteroatom) selected from =O and, preferably, $E^5$, and which heterocyclalkyl group may further be bridged, i.e. two non-adjacent atoms (which may be in a 1,4-relationship) of the first ring may be linked together with —(CH$_2$)$_{n1}$— (where n is 2 or, preferably, 1), so forming for example a 1-aza-bicyclo[2.2.1]hept-4-yl group); aryl (e.g. phenyl) (which is optionally substituted by one or more substituents selected from $E^6$) or heteroaryl (e.g. a 5- or, preferably, a 6-membered heteroaryl group preferably containing one nitrogen heteroatom, so forming e.g. pyridyl, such as 3-pyridyl), which group is preferably unsubstituted;
$E^2$ represents $C_{1-3}$ alkyl (e.g. $C_{1-2}$ alkyl, such as methyl);
$E^3$ represents $Q^4$ or $C_{1-3}$ alkyl (e.g. methyl) optionally substituted by one or more
$Q^5$ substituents (so forming e.g. a trifluoromethyl group); or two $E^3$ groups (e.g. when attached to adjacent carbon atoms of an aryl (e.g. phenyl) group) may be linked together to form an aromatic (e.g. 5-membered) ring, preferably containing one or two (e.g. one) heteroatom(s) (selected from sulfur, oxygen and, preferably nitrogen), and hence the linked $E^3$ groups preferably represent a thienyl, fuanyl or, more preferably, a pyrrolyl group;
$E^4$ represents $Q^4$, or, $C_{1-3}$ alkyl (e.g. methyl) optionally substituted by one or more (e.g. one) $Q^5$ substituent;
$E^5$ represents $Q^4$ or $C_{1-6}$ (e.g. $C_{1-4}$) alkyl (acyclic or part-cyclic; so forming e.g. methyl or cyclopropylmethyl, i.e. $C_{1-2}$ alkyl (e.g. methyl) substituted by $C_{3-6}$ cycloalkyl (e.g. cyclopropyl)), which is preferably unsubstituted;
$E^6$ represents $Q^4$;
$Q^4$ represents halo (e.g. fluoro), —CN, —O$R^{20}$, —N($R^{20}$)$R^{21}$, —C(=Y)$R^{20}$, —C(=Y)O$R^{20}$, —S(O)$_2$$R^{20}$ or heterocycloalkyl (optionally substituted by one or more substituents selected from $J^2$, but preferably unsubstituted; and which heterocycloalkyl group may be substituted on a cyclic group via a single atom so forming a spiro-cycle);
when $E^3$ represents $Q^4$, then $Q^4$ preferably represents halo, —CN, —C(=Y)$R^{20}$, —C(=Y)O$R^{20}$, —S(O)$_2$$R^{20}$ or, more preferably, —O$R^{20}$ or —N($R^{20}$)$R^{21}$ (especially —O$R^{20}$);
when $E^4$ represents $Q^4$, then $Q^4$ preferably represents halo, —CN, —C(=Y)$R^{20}$, —C(=Y)O$R^{20}$, or, more preferably, —O$R^{20}$ or —N($R^{20}$)$R^{21}$;
when $E^5$ represents $Q^4$, then $Q^4$ preferably represents —O$R^{20}$, —C(=Y)$R^{20}$, —S(O)$_2$$R^{20}$, —C(=Y)O$R^{20}$ or heterocycloalkyl (e.g. a 5- or 6-membered group, e.g. piperidinyl, which may form a spiro-cycle through the substitution to a cyclic group via a single atom) (and wherein —C(=Y)R$^{20}$ and —S(O)$_2$R$^{20}$ are preferably substituted on a (nitrogen) heteroatom);

when E$^6$ represents Q$^4$, then Q$^4$ preferably represents halo or —OR$^{20}$;

Q$^5$ represents C$_{1-6}$ alkyl (preferably unsubstituted) or, preferably, halo (e.g. fluoro), —N(R$^{20}$)R$^{21}$ or —N(R$^{22}$)C(=Y)R$^{21}$;

R$^{10a}$ and R$^{11a}$ independently represent H or, preferably, C$_{1-3}$ alkyl (e.g. methyl);

R$^{20}$ represents H or C$_{1-4}$ alkyl (e.g. ethyl or, preferably, methyl, isopropyl or tert-butyl) optionally substituted by one or more J$^4$ substituents (in particular J$^4$ may represent halo, such as fluoro, and hence R$^{20}$ may represent a trifluoromethyl group);

R$^{21}$ represents hydrogen or C$_{1-4}$ (e.g. C$_{1-3}$) alkyl (e.g. isopropyl or, preferably, methyl);

R$^{22}$ represents hydrogen;

Y represents =O;

J$^4$ represents Q$^7$;

Q$^7$ represents halo (e.g. fluoro).

Particularly preferred compounds of the invention include those of the examples described hereinafter.

Compounds of the invention may be made in accordance with techniques that are well known to those skilled in the art, for example as described hereinafter.

According to a further aspect of the invention there is provided a process for the preparation of a compound of formula I which process comprises:

(i) reaction of a compound of formula II,

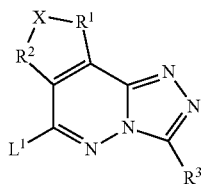

wherein L$^1$ represents a suitable leaving group, such as iodo, bromo, chloro or a sulfonate group (e.g. —OS(O)$_2$CF$_3$, —OS(O)$_2$CH$_3$ or —OS(O)$_2$PhMe), and R$^1$, R$^2$, R$^3$ and X are as hereinbefore defined, with a compound of formula III,

wherein R$^4$ is as hereinbefore defined, under standard conditions, for example optionally in the presence of an appropriate metal catalyst (or a salt or complex thereof) such as Cu, Cu(OAc)$_2$, CuI (or CuI/diamine complex), copper tris(triphenyl-phosphine)bromide, Pd(OAc)$_2$, tris(dibenzylideneacetone)-dipalladium(0) (Pd$_2$(dba)$_3$) or NiCl$_2$ and an optional additive such as Ph$_3$P, 2,2'-bis(diphenylphosphino)-1,1'-binaphthyl, xantphos, NaI or an appropriate crown ether such as 18-crown-6-benzene, in the presence of an appropriate base such as NaH, Et$_3$N, pyridine, N,N'-dimethylethylenediamine, Na$_2$CO$_3$, K$_2$CO$_3$, K$_3$PO$_4$, Cs$_2$CO$_3$, t-BuONa or t-BuOK (or a mixture thereof, optionally in the presence of 4 Å molecular sieves), in a suitable solvent (e.g. dichloromethane, dioxane, toluene, ethanol, isopropanol, dimethylformamide, ethylene glycol, ethylene glycol dimethyl ether, water, dimethylsulfoxide, acetonitrile, dimethylacetamide, N-methylpyrrolidinone, tetrahydrofuran or a mixture thereof). This reaction may be carried out under microwave irradiation reaction conditions or, alternatively, the reaction may be performed in the absence of other reagents such as catalyst, base and even solvent. Such a reaction may be accompanied by a rearrangement reaction, for instance if the compound of formula III is 2,7-diaza-spiro[3.5]nonane (or the 7-protected derivative thereof, e.g. the corresponding 7-carboxylic acid tert-butyl ester thereof), then such a spirocyclic amine may undergo ring-opening to form a 1-aza-bicyclo[2.2.1]hept-4-ylmethyl-amino moiety (i.e. a bridged amine) so forming a corresponding compound of formula I in which R$^4$ represents 1-aza-bicyclo[2.2.1]hept-4-ylmethyl-amino;

(ii) reaction of a compound of formula IV,

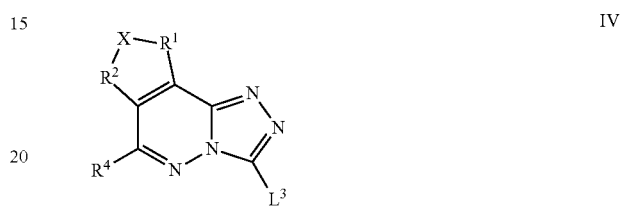

wherein L$^3$ represents a suitable leaving group such as one hereinbefore defined in respect of L$^1$ (e.g. halo, such as chloro or, preferably, bromo), and R$^1$, R$^2$, X and R$^4$ are as hereinbefore defined, with a compound of formula V,

wherein L$^4$ represents a suitable group, such as —B(OH)$_2$, —B(OR$^{wx}$)$_2$ or —Sn(R$^{wx}$)$_3$, in which each R$^{wx}$ independently represents a C$_{1-6}$ alkyl group, or, in the case of —B(OR$^{wx}$)$_2$, the respective R$^{wx}$ groups may be linked together to form a 4- to 6-membered cyclic group (such as a 4,4,5,5-tetramethyl-1,3,2-dioxaborolan-2-yl group), thereby forming e.g. a pinacolato boronate ester group, (or L$^4$ may represent iodo, bromo or chloro, provided that L$^3$ and L$^4$ are mutually compatible) and R$^3$ is as hereinbefore defined. The reaction may be performed, for example in the presence of a suitable catalyst system, e.g. a metal (or a salt or complex thereof) such as Pd, CuI, Pd/C, PdCl$_2$, Pd(OAc)$_2$, Pd(Ph$_3$P)$_2$Cl$_2$, Pd(Ph$_3$P)$_4$ (i.e. palladium tetrakistriphenylphosphine), Pd$_2$(dba)$_3$ and/or NiCl$_2$ (preferred catalysts include palladium) and a ligand such as PdCl$_2$(dppf).DCM, t-Bu$_3$P, (C$_6$H$_{11}$)$_3$P, Ph$_3$P, AsPh$_3$, P(o-Tol)$_3$, 1,2-bis(diphenylphosphino)ethane, 2,2'-bis(di-tert-butylphosphino)-1,1'-biphenyl, 2,2'-bis(diphenylphosphino)-1,1'-bi-naphthyl, 1,1'-bis(diphenyl-phosphino-ferrocene), 1,3-bis(diphenylphosphino)propane, xantphos, or a mixture thereof (preferred ligands include PdCl$_2$(dppf).DCM), together with a suitable base such as, Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof; preferred bases include Na$_2$CO$_3$ and K$_2$CO$_3$) in a suitable solvent such as dioxane, toluene, ethanol, dimethylformamide, dimethoxyethane, ethylene glycol dimethyl ether, water, dimethylsulfoxide, acetonitrile, dimethylacetamide, N-methylpyrrolidinone, tetrahydrofuran or mixtures thereof (preferred solvents include dimethylformamide and dimethoxyethane). The reaction may be carried out for example at room temperature or above (e.g. at a high temperature such as at about the reflux temperature of the solvent system). Alternative reaction conditions include microwave irradiation conditions, for example at elevated temperature of about 130° C.;

(iii) reaction of a compound of formula VI,

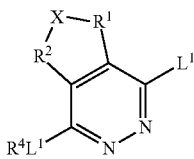

VI wherein $R^4L^1$ represents either $L^1$ or $R^4$, and $R^1$, $R^2$, $R^4$, X and each $L^1$ (which are independent of each other) are as hereinbefore defined, with a compound of formula VII,

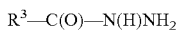

$R^3$—C(O)—N(H)NH$_2$    VII wherein $R^3$ is as hereinbefore defined, under standard reaction conditions to promote the formation of the requisite triazolopyridazine bicyclic core, for example, in the presence of base, such as an organic base (e.g. triethylamine or the like), and/or an acid, such as an organic acid (e.g. para-toluenesulfonic acid or the like), and the base and acid are preferably in a ratio of about 1:1. The reaction may also take place in the presence of a suitable solvent, such as a polar solvent (e.g. 1,4-dioxane and the like), which may be heated at room temperature, or, preferably, above room temperature, e.g. above 50° C., such as at about 100° C. In the case where reaction takes place with a compound of formula VI in which $R^4L^1$ represents either $L^1$, then the reaction may be proceeded by reaction with a compound of formula III, for example as defined in respect of process step (i) above;

(iv) for compounds of formula I in which $R^1$ and $R^2$ are independently selected from —O—, —S— and —NR$^6$—, reaction of a compound of formula VIII,

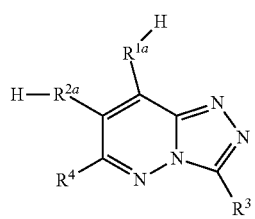

VIII wherein $R^{1a}$ and $R^{2a}$ independently represent —O—, —S— and —NR$^6$—, and $R^3$ and $R^4$ are as hereinbefore defined, with a compound of formula IX,

$L^5$-X-$L^6$    IX wherein $L^5$ and $L^6$ independently represent a suitable leaving group, such as one hereinbefore defined in respect of $L^1$ (e.g. halo, such as chloro), and X is as hereinbefore defined, under standard reaction conditions (to promote the nucleophilic substitution reactions), for example in the presence of a suitable base, such as Na$_2$CO$_3$, K$_3$PO$_4$, Cs$_2$CO$_3$, NaOH, KOH, K$_2$CO$_3$, CsF, Et$_3$N, (i-Pr)$_2$NEt, t-BuONa or t-BuOK (or mixtures thereof) in a suitable solvent such as dioxane, toluene, ethanol, tert-butanol, dimethylformamide, ethylene glycol dimethyl ether, water, dimethylsulfoxide, acetonitrile, dimethylacetamide, N-methylpyrrolidinone, tetrahydrofuran or mixtures thereof. Preferred bases include t-BuOK.

Compounds of formula II may be prepared by reaction of a compound of formula VI as hereinbefore defined but in which $R^4L^1$ represents $L^1$ and a compound of formula VII as hereinbefore defined, for example under reaction conditions such as those hereinbefore described in respect of preparation of compounds of formula I (process step (iii)).

Compounds of formula II may alternatively be prepared by reaction of a compound of formula X,

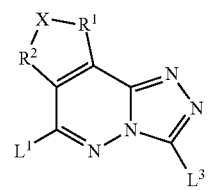

X wherein $L^1$, $L^3$, $R^1$, $R^2$ and X are as hereinbefore defined, with a compound of formula V as hereinbefore defined, under reaction conditions such as those described in respect of preparation of compounds of formula I (process step (ii) above).

Compounds of formula IV may be prepared by reaction of a compound of formula X as hereinbefore defined with a compound of formula III as hereinbefore defined, for example under reaction conditions such as those described in respect of preparation of compounds of formula I (process step (i) above).

Compounds of formula IV and compounds of formula X (in which $L^3$ represents halo, e.g. bromo) may be prepared by reaction of a compound of formula XI,

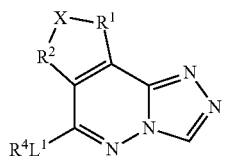

XI wherein $R^4L^1$, $R^1$, $R^2$ and X are as hereinbefore defined, for example by reaction in the presence of a source of halide (e.g. bromide) ions, for instance an electrophile that provides a source of iodide ions includes iodine, diiodoethane, diiodotetrachloroethane or, preferably, N-iodosuccinimide, a source of bromide ions includes N-bromosuccinimide and bromine, and a source of chloride ions includes N-chlorosuccinimide, chlorine and iodine monochloride, for instance in the presence of a suitable solvent, such as an alcohol (e.g. methanol) or, preferably a halogenated solvent (e.g. chloroform), and which reaction may take place under microwave irradiation conditions (e.g. at above 100° C., such as at about 120° C.) or may alternatively take place in the presence of a suitable base, such as a weak inorganic base, e.g. sodium bicarbonate.

Compounds of formula VI may be prepared by reaction of a compound of formula XII,

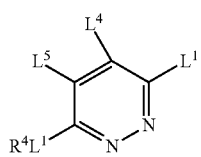

XII wherein $L^4$ and $L^5$ independently represent a suitable leaving group (e.g. chloro), and $R^4L^1$, $L^1$ are as hereinbefore defined, with a compound of formula XIII,

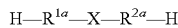　　　　　　　　　　　　　　　　XIII wherein $R^{1a}$, $R^{2a}$ and X are as hereinbefore defined, under standard aromatic nucleophilic reaction conditions, for example in the presence of a base and solvent (such as one hereinbefore described in respect of process step (iv) above, e.g. NaOt-Bu in the presence of a solvent such as acetonitrile) or under reaction conditions such as those described in respect of process step (ii) above.

Compounds of formula XI may be prepared by reaction of a compound of formula VI as hereinbefore defined, with a compound of formula XIV,

　　　　　　　　　　　　　　　　XIV for example under reaction conditions described herein (e.g. process step (iii) above).

Other specific transformation steps (including those that may be employed in order to form compounds of formula I) that may be mentioned include:
(i) reductions, for example of a carboxylic acid (or ester) to either an aldehyde or an alcohol, using appropriate reducing conditions (e.g. —C(O)OH (or an ester thereof), may be converted to a —C(O)H or —CH$_2$—OH group, using DIBAL and LiAlH$_4$, respectively (or similar chemoselective reducing agents));
(ii) reductions of an aldehyde (—C(O)H) group to an alcohol group (—CH$_2$OH), using appropriate reduction conditions such as those mentioned at point (i) above;
(iii) oxidations, for example of a moiety containing an alcohol group (e.g. —CH$_2$OH) to an aldehyde (e.g. —C(O)H), for example in the presence of a suitable oxidising agent, e.g. MnO$_2$ or the like;
(iv) reductive amination of an aldehyde and an amine, under appropriate reaction conditions, for example in "one-pot" procedure in the presence of an appropriate reducing agent, such as a chemoselective reducing agent such as sodium cyanoborohydride or, preferably, sodium triacetoxyborohydride, or the like. Alternatively, such reactions may be performed in two steps, for example a condensation step (in the presence of e.g. a dehydrating agent such as trimethyl orthoformate or MgSO$_4$ or molecular sieves, etc) followed by a reduction step (e.g. by reaction in the presence of a reducing agent such as a chemoselective one mentioned above or NaBH$_4$, AlH$_4$, or the like), for instance the conversion of —NH$_2$ to —N(H)-isopropyl by condensation in the presence of acetone (H$_3$C—C(O)—CH$_3$) followed by reduction in the presence of a reducing agent such as sodium cyanaoborohydride (i.e. overall a reductive amination);
(iv) amide coupling reactions, i.e. the formation of an amide from a carboxylic acid (or ester thereof), for example when $R^2$ represents —C(O)OH (or an ester thereof), it may be converted to a —C(O)N($R^{10b}$)$R^{11b}$ group (in which $R^{10b}$ and $R^{11b}$ are as hereinbefore defined, and may be linked together, e.g. as defined above), and which reaction may (e.g. when $R^2$ represents —C(O)OH) be performed in the presence of a suitable coupling reagent (e.g. 1,1'-carbonyldiimidazole, N,N'-dicyclohexylcarbodiimide, or the like) or, in the case when $R^2$ represents an ester (e.g. —C(O)OCH$_3$ or —C(O)OCH$_2$CH$_3$), in the presence of e.g. trimethylaluminium, or, alternatively the —C(O)OH group may first be activated to the corresponding acyl halide (e.g —C(O)Cl, by treatment with oxalyl chloride, thionyl chloride, phosphorous pentachloride, phosphorous oxychloride, or the like), and, in all cases, the relevant compound is reacted with a compound of formula HN($R^{10a}$)$R^{11a}$ (in which $R^{10a}$ and $R^{11a}$ are as hereinbefore defined), under standard conditions known to those skilled in the art (e.g. optionally in the presence of a suitable solvent, suitable base and/or in an inert atmosphere);

(v) amide coupling reactions, i.e. the formation of an amide from a carboxylic acid (or ester thereof), for example when $R^2$ represents —C(O)OH (or an ester thereof), it may be converted to a —C(O)N($R^{10b}$)$R^{11b}$ group (in which $R^{10b}$ and $R^{11b}$ are as hereinbefore defined, and may be linked together, e.g. as defined above), and which reaction may (e.g. when $R^2$ represents —C(O)OH) be performed in the presence of a suitable coupling reagent (e.g. 1,1'-carbonyldiimidazole, N,N'-dicyclohexylcarbodiimide, or the like) or, in the case when $R^2$ represents an ester (e.g. —C(O)OCH$_3$ or —C(O)OCH$_2$CH$_3$), in the presence of e.g. trimethylaluminium, or, alternatively the —C(O)OH group may first be activated to the corresponding acyl halide (e.g —C(O)Cl, by treatment with oxalyl chloride, thionyl chloride, phosphorous pentachloride, phosphorous oxychloride, or the like), and, in all cases, the relevant compound is reacted with a compound of formula HN($R^{10a}$)$R^{11a}$ (in which $R^{10a}$ and $R^{11a}$ are as hereinbefore defined), under standard conditions known to those skilled in the art (e.g. optionally in the presence of a suitable solvent, suitable base and/or in an inert atmosphere);
(vi) conversion of a primary amide to a nitrile functional group, for example under dehydration reaction conditions, e.g. in the presence of POCl$_3$, or the like;
(vii) nucleophilic substitution reactions, where any nucleophile replaces a leaving group, e.g. methylsulfonylpiperazine may replace a chloro leaving group;
(viii) transformation of a methoxy group to a hydroxy group, by reaction in the presence of an appropriate reagent, such as boron fluoride-dimethyl sulfide complex or BBr$_3$ (e.g. in the presence of a suitable solvent such as dichloromethane);
(ix) alkylation, acylation or sulfonylation reactions, which may be performed in the presence of base and solvent (such as those described hereinbefore in respect of preparation of compounds of formula I, process step (iv) above, for instance, a —N(H)— or —OH or —NH$_2$ (or a protected version of the latter) moiety may be alkylated, acylated or sulfonylated by employing a reactant that is an alkyl, acyl or sulfonyl moiety attached to a leaving group (e.g. C$_{1-6}$ alkyl-halide (e.g. ethylbromide), C$_{1-6}$ alkyl-C(O)-halide (e.g. H$_3$C—C(O)Cl), an anhydride (e.g. H$_3$C—C(O)—O—C(O)—CH$_3$, i.e. "—O—C(O)—CH$_3$" is the leaving group), dimethylformamide (i.e. —N(CH$_3$)$_2$ is the leaving group) or a sulfonyl halide (e.g. H$_3$C—S(O)$_2$Cl) and the like);
(x) specific deprotection steps, such as deprotection of an N-Boc protecting group by reaction in the presence of an acid, or, a hydroxy group protected as a silyl ether (e.g. a tert-butyl-dimethylsilyl protecting group) may be deprotected by reaction with a source of fluoride ions, e.g. by employing the reagent tetrabutylammonium fluoride (TBAF).

Intermediate compounds described herein are either commercially available, are known in the literature, or may be obtained either by analogy with the processes described herein, or by conventional synthetic procedures, in accordance with standard techniques, from available starting materials using appropriate reagents and reaction conditions. Further, processes to prepare compounds of formula I may be described in the literature, for example in:

Werber, G. et al.; *J. Heterocycl. Chem.; EN;* 14; 1977; 823-827;
Andanappa K. Gadad et al. *Bioorg. Med. Chem.* 2004, 12, 5651-5659;
Paul Heinz et al. *Monatshefte für Chemie,* 1977, 108, 665-680;
M. A. El-Sherbeny et al. *Boll. Chim. Farm.* 1997, 136, 253-256;
Nicolaou, K. C.; Bulger, P. G.; Sarlah, D. *Angew. Chem. Int. Ed.* 2005, 44, 2-49;
Bretonnet et al. *J. Med. Chem.* 2007, 50, 1872;
Asunción Marin et al. *Farmaco* 1992, 47 (1), 63-75;
Severinsen, R. et al. *Tetrahedron* 2005, 61, 5565-5575;

Nicolaou, K. C.; Bulger, P. G.; Sarlah, D. *Angew. Chem. Int. Ed.* 2005, 44, 2-49;
M. Kuwahara et al., *Chem. Pharm Bull.*, 1996, 44, 122;
Wipf, P.; Jung, J.-K. *J. Org. Chem.* 2000, 65(20), 6319-6337;
Shintani, R.; Okamoto, K. *Org. Lett.* 2005, 7 (21), 4757-4759;
Nicolaou, K. C.; Bulger, P. G.; Sarlah, D. *Angew. Chem. Int. Ed.* 2005, 44, 2-49;
J. Kobe et al., *Tetrahedron*, 1968, 24, 239;
P. F. Fabio, A. F. Lanzilotti and S. A. Lang, *Journal of Labelled Compounds and Pharmaceuticals*, 1978, 15, 407;
F. D. Bellamy and K. Ou, *Tetrahedron Lett.*, 1985, 25, 839;
M. Kuwahara et al., *Chem. Pharm Bull.*, 1996, 44, 122;
A. F. Abdel-Magid and C. A Maryanoff. *Synthesis*, 1990, 537;
M. Schlosser et al. *Organometallics in Synthesis. A Manual*, (M. Schlosser, Ed.),
Wiley &Sons Ltd: Chichester, UK, 2002, and references cited therein;
L. Wengwei et al., *Tetrahedron Lett.*, 2006, 47, 1941;
M. Plotkin et al. *Tetrahedron Lett.*, 2000, 41, 2269;
Seyden-Penne, *J. Reductions by the Alumino and Borohydrides*, VCH, NY, 1991;
O. C. Dermer, *Chem. Rev.*, 1934, 14, 385;
N. Defacqz, et al., *Tetrahedron Lett.*, 2003, 44, 9111;
S. J. Gregson et al., *J. Med. Chem.*, 2004, 47, 1161;
A. M. Abdel Magib, et al., *J. Org. Chem.*, 1996, 61, 3849;
A. F. Abdel-Magid and C. A Maryanoff. *Synthesis*, 1990, 537;
T. Ikemoto and M. Wakimasu, *Heterocycles*, 2001, 55, 99;
E. Abignente et al., *Il Farmaco*, 1990, 45, 1075;
T. Ikemoto et al., *Tetrahedron*, 2000, 56, 7915;
T. W. Greene and P. G. M. Wuts, *Protective Groups in Organic Synthesis*, Wiley, N.Y., 1999;
S. Y. Han and Y.-A. Kim. *Tetrahedron*, 2004, 60, 2447;
J. A. H. Lainton et al., *J. Comb. Chem.*, 2003, 5, 400; or
Wiggins, J. M. *Synth. Commun.*, 1988, 18, 741.

The substituents $R^1$, $R^2$, $R^3$, $R^4$ and X in final compounds of the invention or relevant intermediates may be modified one or more times, after or during the processes described above by way of methods that are well known to those skilled in the art. Examples of such methods include substitutions, reductions, oxidations, alkylations, acylations, hydrolyses, esterifications, etherifications, halogenations or nitrations. Such reactions may result in the formation of a symmetric or asymmetric final compound of the invention or intermediate. The precursor groups can be changed to a different such group, or to the groups defined in formula I, at any time during the reaction sequence.

For example, when substituents in the compounds of the invention such as $CO_2Et$, CHO, CN and/or $CH_2Cl$, are present, these groups can be further derivatized to other fragments described (e.g. by those integers mentioned above) in compounds of the invention, following synthetic protocols very well know to the person skilled in the art and/or according to the experimental part described in the patent. Other specific transformation steps that may be mentioned include: the reduction of a nitro or azido group to an amino group; the hydrolysis of a nitrile group to a carboxylic acid group; and standard nucleophilic aromatic substitution reactions, for example in which an iodo-, preferably, fluoro- or bromo-phenyl group is converted into a cyanophenyl group by employing a source of cyanide ions (e.g. by reaction with a compound which is a source of cyano anions, e.g. sodium, copper (I), zinc or potassium cyanide, optionally in the presence of a palladium catalyst) as a reagent (alternatively, in this case, palladium catalysed cyanation reaction conditions may also be employed).

Other transformations that may be mentioned include: the conversion of a halo group (preferably iodo or bromo) to a 1-alkynyl group (e.g. by reaction with a 1-alkyne), which latter reaction may be performed in the presence of a suitable coupling catalyst (e.g. a palladium and/or a copper based catalyst) and a suitable base (e.g. a tri-($C_{1-6}$ alkyl)amine such as triethylamine, tributylamine or ethyldiisopropylamine); the introduction of amino groups and hydroxy groups in accordance with standard conditions using reagents known to those skilled in the art; the conversion of an amino group to a halo, azido or a cyano group, for example via diazotisation (e.g. generated in situ by reaction with $NaNO_2$ and a strong acid, such as HCl or $H_2SO_4$, at low temperature such as at 0° C. or below, e.g. at about −5° C.) followed by reaction with the appropriate nucleophile e.g. a source of the relevant anions, for example by reaction in the presence of a halogen gas (e.g. bromine, iodine or chlorine), or a reagent that is a source of azido or cyanide anions, such as $NaN_3$ or NaCN; the conversion of —C(O)OH to a —$NH_2$ group, under Schmidt reaction conditions, or variants thereof, for example in the presence of $HN_3$ (which may be formed in by contacting $NaN_3$ with a strong acid such as $H_2SO_4$), or, for variants, by reaction with diphenyl phosphoryl azide (($PhO)_2$ $P(O)N_3$) in the presence of an alcohol, such as tert-butanol, which may result in the formation of a carbamate intermediate; the conversion of —$C(O)NH_2$ to —$NH_2$, for example under Hofmann rearrangement reaction conditions, for example in the presence of NaOBr (which may be formed by contacting NaOH and $Br_2$) which may result in the formation of a carbamate intermediate; the conversion of —$C(O)N_3$ (which compound itself may be prepared from the corresponding acyl hydrazide under standard diazotisation reaction conditions, e.g. in the presence of $NaNO_2$ and a strong acid such as $H_2SO_4$ or HCl) to —$NH_2$, for example under Curtius rearrangement reaction conditions, which may result in the formation of an intermediate isocyanate (or a carbamate if treated with an alcohol); the conversion of an alkyl carbamate to —$NH_2$, by hydrolysis, for example in the presence of water and base or under acidic conditions, or, when a benzyl carbamate intermediate is formed, under hydrogenation reaction conditions (e.g. catalytic hydrogenation reaction conditions in the presence of a precious metal catalyst such as Pd); halogenation of an aromatic ring, for example by an electrophilic aromatic substitution reaction in the presence of halogen atoms (e.g. chlorine, bromine, etc, or an equivalent source thereof) and, if necessary an appropriate catalyst/Lewis acid (e.g. $AlCl_3$ or $FeCl_3$).

Compounds of the invention bearing a carboxyester functional group may be converted into a variety of derivatives according to methods well known in the art to convert carboxyester groups into carboxamides, N-substituted carboxamides, N,N-disubstituted carboxamides, carboxylic acids, and the like. The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or a mixture thereof; preferably the reaction is carried out with ammonium hydroxide in a methanol/dimethylformamide mixture, at a temperature ranging from about 50° C. to about 100° C.

Analogous operative conditions apply in the preparation of N-substituted or N,N-disubstituted carboxamides wherein a suitable primary or secondary amine is used in place of ammonia or ammonium hydroxide. Likewise, carboxyester groups may be converted into carboxylic acid derivatives through basic or acidic hydrolysis conditions, widely known in the art. Further, amino derivatives of compounds of the invention may easily be converted into the corresponding carbamate, carboxamido or ureido derivatives.

Compounds of the invention may be isolated from their reaction mixtures using conventional techniques (e.g. recrystallisations).

It will be appreciated by those skilled in the art that, in the processes described above and hereinafter, the functional groups of intermediate compounds may need to be protected by protecting groups.

The need for such protection will vary depending on the nature of the remote functionality and the conditions of the preparation methods (and the need can be readily determined by one skilled in the art). Suitable amino-protecting groups include acetyl, trifluoroacetyl, t-butoxycarbonyl (BOC), benzyloxycarbonyl (CBz), 9-fluorenylmethylene-oxycarbonyl (Fmoc) and 2,4,4-trimethylpentan-2-yl (which may be deprotected by reaction in the presence of an acid, e.g. HCl in water/alcohol (e.g. MeOH)) or the like. The need for such protection is readily determined by one skilled in the art.

The protection and deprotection of functional groups may take place before or after a reaction in the above-mentioned schemes.

Protecting groups may be removed in accordance with techniques that are well known to those skilled in the art and as described hereinafter. For example, protected compounds/intermediates described herein may be converted chemically to unprotected compounds using standard deprotection techniques.

The type of chemistry involved will dictate the need, and type, of protecting groups as well as the sequence for accomplishing the synthesis.

The use of protecting groups is fully described in "*Protective Groups in Organic Synthesis*", 3$^{rd}$ edition, T. W. Greene & P. G. M. Wutz, Wiley-Interscience (1999).

Medical and Pharmaceutical Uses

Compounds of the invention are indicated as pharmaceuticals. According to a further aspect of the invention there is provided a compound of the invention, as hereinbefore defined, for use as a pharmaceutical.

Compounds of the invention may inhibit protein or lipid kinases, such as a PIM family kinase such as PIM-1, PIM-2 and/or PIM-3, for example as may be shown in the tests described below and/or in tests known to the skilled person. Thus, the compounds of the invention may be useful in the treatment of those disorders in an individual in which the inhibition of such protein or lipid kinases (e.g. a PIM family kinase such as PIM-1, PIM-2 and/or PIM-3) is desired and/or required.

The term "inhibit" may refer to any measurable reduction and/or prevention of catalytic kinase (e.g. a PIM family kinase such as PIM-1, PIM-2 and/or PIM-3) activity. The reduction and/or prevention of kinase activity may be measured by comparing the kinase activity in a sample containing a compound of the invention and an equivalent sample of kinase (e.g. a PIM family kinase such as PIM-1, PIM-2 and/or PIM-3) in the absence of a compound of the invention, as would be apparent to those skilled in the art. The measurable change may be objective (e.g. measurable by some test or marker, for example in an in vitro or in vivo assay or test, such as one described hereinafter, or otherwise another suitable assay or test known to those skilled in the art) or subjective (e.g. the subject gives an indication of or feels an effect).

Compounds of the invention may be found to exhibit 50% inhibition of a protein or lipid kinase (e.g. a PIM family kinase such as PIM-1, PIM-2 and/or PIM-3) at a concentration of 100 µM or below (for example at a concentration of below 50 µM, or even below 10 µM, such as below 1 µM), when tested in an assay (or other test), for example as described hereinafter, or otherwise another suitable assay or test known to the skilled person.

Compounds of the invention are thus expected to be useful in the treatment of a disorder in which a protein or lipid kinase (e.g. a PIM family kinase such as PIM-1, PIM-2 and/or PIM-3) is known to play a role and which are characterised by or associated with an overall elevated activity of that protein kinase (due to, for example, increased amount of the kinase or increased catalytic activity of the kinase). Compounds of the invention (alone or in combination with another active) may be shown to be active e.g. in the biochemical assays described herein, may be shown to have predictive activity based on e.g. the phosphorylation assay described herein, and/or may reduce the rate of cell proliferation e.g. as may be shown in the cell proliferation assays described herein (for instance using cancer cell lines (e.g. known commercially available ones), such as those described herein).

Hence, compounds of the invention are expected to be useful in the treatment of a disease/disorder arising from abnormal cell growth, function or behaviour associated with the protein or lipid kinase (e.g. a PIM family kinase such as PIM-1, PIM-2 and/or PIM-3). Such conditions/disorders include cancer, immune disorders, cardiovascular diseases, viral infections, inflammation, metabolism/endocrine function disorders and neurological disorders.

The disorders/conditions that the compounds of the invention may be useful in treating hence includes cancer (such as lymphomas, solid tumours or a cancer as described hereinafter), obstructive airways diseases, allergic diseases, inflammatory diseases (such as asthma, allergy and Chrohn's disease), immunosuppression (such as transplantation rejection and autoimmune diseases), disorders commonly connected with organ transplantation, AIDS-related diseases and other associated diseases. Other associated diseases that may be mentioned (particularly due to the key role of kinases in the regulation of cellular proliferation) include other cell proliferative disorders and/or non-malignant diseases, such as benign prostate hyperplasia, familial adenomatosis, polyposis, neuro-fibromatosis, psoriasis, bone disorders, atherosclerosis, vascular smooth cell proliferation associated with atherosclerosis, pulmonary fibrosis, arthritis glomerulonephritis and post-surgical stenosis and restenosis. Other disease states that may be mentioned include cardiovascular disease, stroke, diabetes, hepatomegaly, Alzheimer's disease, cystic fibrosis, hormone-related diseases, immunodeficiency disorders, destructive bone disorders, infectious diseases, conditions associated with cell death, thrombin-induced platelet aggregation, chronic myelogenous leukaemia, liver disease, pathologic immune conditions involving T cell activation and CNS disorders.

As stated above, the compounds of the invention may be useful in the treatment of cancer. More, specifically, the compounds of the invention may therefore be useful in the treatment of a variety of cancer including, but not limited to: carcinoma such as cancer of the bladder, breast, colon, kidney, liver, lung (including non-small cell cancer and small cell lung cancer), esophagus, gall-bladder, ovary, pancreas, stomach, cervix, thyroid, prostate, skin, squamous cell carcinoma, testis, genitourinary tract, larynx, glioblastoma, neuroblastoma, keratoacanthoma, epidermoid carcinoma, large cell carcinoma, non-small cell lung carcinoma, small cell lung carcinoma, lung adenocarcinoma, bone, adenoma, adenocarcinoma, follicular carcinoma, undifferentiated carcinoma, papilliary carcinoma, seminona, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukaemia; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xeroderma pigmentosum, keratoxanthoma, thyroid follicular cancer and Kaposi's sarcoma.

Further, the protein or lipid kinases (e.g. a PIM family kinase such as PIM-1, PIM-2 and/or PIM-3) may also be implicated in the multiplication of viruses and parasites. They may also play a major role in the pathogenesis and development of neurodegenerative disorders. Hence, compounds of the invention may also be useful in the treatment of viral conditions, parasitic conditions, as well as neurodegenerative disorders.

Compounds of the invention are indicated both in the therapeutic and/or prophylactic treatment of the above-mentioned conditions.

According to a further aspect of the present invention, there is provided a method of treatment of a disease (e.g. cancer or another disease as mentioned herein) which is associated with the inhibition of protein or lipid kinase (e.g. a PIM family kinase such as PIM-1, PIM-2 and/or PIM-3) is desired and/or required (for example, a method of treatment of a disease/disorder arising from abnormal cell growth, function or behaviour associated with protein or lipid kinases, e.g. a PIM family kinase such as PIM-1, PIM-2 and/or PIM-3), which method comprises administration of a therapeutically effective amount of a compound of the invention, as hereinbefore defined, to a patient suffering from, or susceptible to, such a condition.

"Patients" include mammalian (including human) patients. Hence, the method of treatment discussed above may include the treatment of a human or animal body.

The term "effective amount" refers to an amount of a compound, which confers a therapeutic effect on the treated patient. The effect may be objective (e.g. measurable by some test or marker) or subjective (e.g. the subject gives an indication of or feels an effect).

Compounds of the invention may be administered orally, intravenously, subcutaneously, buccally, rectally, dermally, nasally, tracheally, bronchially, sublingually, by any other parenteral route or via inhalation, in a pharmaceutically acceptable dosage form.

Compounds of the invention may be administered alone, but are preferably administered by way of known pharmaceutical formulations, including tablets, capsules or elixirs for oral administration, suppositories for rectal administration, sterile solutions or suspensions for parenteral or intramuscular administration, and the like. The type of pharmaceutical formulation may be selected with due regard to the intended route of administration and standard pharmaceutical practice. Such pharmaceutically acceptable carriers may be chemically inert to the active compounds and may have no detrimental side effects or toxicity under the conditions of use.

Such formulations may be prepared in accordance with standard and/or accepted pharmaceutical practice. Otherwise, the preparation of suitable formulations may be achieved non-inventively by the skilled person using routine techniques and/or in accordance with standard and/or accepted pharmaceutical practice.

According to a further aspect of the invention there is thus provided a pharmaceutical formulation including a compound of the invention, as hereinbefore defined, in admixture with a pharmaceutically acceptable adjuvant, diluent and/or carrier.

Depending on e.g. potency and physical characteristics of the compound of the invention (i.e. active ingredient), pharmaceutical formulations that may be mentioned include those in which the active ingredient is present in at least 1% (or at least 10%, at least 30% or at least 50%) by weight. That is, the ratio of active ingredient to the other components (i.e. the addition of adjuvant, diluent and carrier) of the pharmaceutical composition is at least 1:99 (or at least 10:90, at least 30:70 or at least 50:50) by weight.

The amount of compound of the invention in the formulation will depend on the severity of the condition, and on the patient, to be treated, as well as the compound(s) which is/are employed, but may be determined non-inventively by the skilled person.

The invention further provides a process for the preparation of a pharmaceutical formulation, as hereinbefore defined, which process comprises bringing into association a compound of the invention, as hereinbefore defined, or a pharmaceutically acceptable ester, amide, solvate or salt thereof with a pharmaceutically-acceptable adjuvant, diluent or carrier.

Compounds of the invention may also be combined with other therapeutic agents that are inhibitors of protein or lipid kinases (e.g. a PIM family kinase such as PIM-1, PIM-2 and/or PIM-3) and/or useful in the treatment of a cancer and/or a proliferative disease. Compounds of the invention may also be combined with other therapies (e.g. radiation).

For instance, compounds of the invention may be combined with one or more treatments independently selected from surgery, one or more anti-cancer/anti-neoplastic/anti-tumoral agent, one or more hormone therapies, one or more antibodies, one or more immunotherapies, radioactive iodine therapy, and radiation.

More specifically, compounds of the invention may be combined with an agent that modulates the Ras/Raf/Mek pathway (e.g. an inhibitor of MEK), the Jak/Stat pathway (e.g. an inhibitor of Jak), the PI3K/Akt pathway (e.g. an inhibitor of Akt), the DNA damage response mechanism (e.g. an inhibitor of ATM or ATR) or the stress signaling pathway (an inhibitor of p38 or NF-KB).

For instance, compounds of the invention may be combined with:
 (i) a targeted kinase inhibitor;
 (ii) a receptor tyrosine kinase (RTK) inhibitor;
 (iii) an Akt or PI3-K inhibitor, such as GDC-0941;
 (iv) an Flt-3 inhibitor;
 (v) an EGFR or HER2 inhibitor, such as lapatanib;
 (vi) a therapeutic monoclonal antibody, such as the HER2 inhibitor trastuzumab;
 (vii) a MEK inhibitor, such as PD-0325901;
 (vii) a BRaf inhibitor, such as GDC-0879;
 (viii) an anthracyclin, such as doxorubicin;
 (ix) a taxane, such as paclitaxel or, particularly, docetaxel (Taxotere);
 (x) a platin, such as carboplatin or, particularly, cisplatin;
 (xi) a nucleotide analog, such as 5-fluorouracil (5-FU) or gemcitabine);
 (xii) an alkylating agent, such as temozolomide;
 (xiii) a hormone therapeutic agent, such as an estrogen receptor antagonist e.g. tamoxifen;
 (xiv) an anti-tumour compound that has potential radio-sensitising and/or chemosensitising effects, such as chloroquine;
 (xv) an mTOR inhibitor, such as rapamycin;
 (xvi) a JAK inhibitor;
 (xvii) a cyclin dependent kinase inhibitor (e.g. a CDK6 or CDK4 inhibitor, such as PD-0332991); and/or
 (xviii) an agent that modulates the DNA damage response mechanism and/or the stress signaling pathway, e.g. an inhibitor of ATM or ATR, an inhibitor of p38 and/or NF-KB.

According to a further aspect of the invention, there is provided a combination product comprising:
(A) a compound of the invention, as hereinbefore defined; and
(B) another therapeutic agent that is useful in the treatment of cancer and/or a proliferative disease, wherein each of components (A) and (B) is formulated in admixture with a pharmaceutically-acceptable adjuvant, diluent or carrier.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e. presented as a single formulation including a compound of the invention and the other therapeutic agent).

Thus, there is further provided:
(1) a pharmaceutical formulation including a compound of the invention, as hereinbefore defined, another therapeutic agent that is useful in the treatment of cancer and/or a proliferative disease, and a pharmaceutically-acceptable adjuvant, diluent or carrier; and
(2) a kit of parts comprising components:
(a) a pharmaceutical formulation including a compound of the invention, as hereinbefore defined, in admixture with a pharmaceutically-acceptable adjuvant, diluent or carrier; and
(b) a pharmaceutical formulation including another therapeutic agent that is useful in the treatment of cancer and/or a proliferative disease in admixture with a pharmaceutically-acceptable adjuvant, diluent or carrier,
which components (a) and (b) are each provided in a form that is suitable for administration in conjunction with the other.

In a particularly preferred aspect of the invention, compounds of the invention may be combined with other therapeutic agents (e.g. chemotherapeutic agents) for use as medicaments (e.g. for use in the treatment of a disease or condition as mentioned herein, such as one in which the inhibition of growth of cancer cells are required and/or desired e.g. for treating hyperproliferative disorders such as cancer (e.g. specific cancers that may be mentioned herein, e.g. in the examples) in mammals, especially humans). Such active ingredients in combinations may act in synergy.

In particular, compounds of the invention may be combined with known chemotherapeutic agents (as may be demonstrated by the examples, for instance where a compound of the examples is employed in combination and inhibits cellular proliferative in vitro), for instance:
(i) a PI3K inhibitor, such as GDC-0941;
(ii) an EGFR inhibitor, such as Lapatinib;
(iii) a BRaf inhibitor such as GDC-0879;
(iv) docetaxel (Taxotere®, Sanofi-Aventis);
(v) a MEK inhibitor, such as PD-0325901; and/or
(vi) a CDK4 inhibitor, such as PD-0332991.

The MEK inhibitor PD-0325901 (CAS RN 391210-10-9, Pfizer) is a second-generation, non-ATP competitive, allosteric MEK inhibitor for the potential oral tablet treatment of cancer (U.S. Pat. No. 6,960,614; U.S. Pat. No. 6,972,298; US 2004/1147478; US 2005/085550). Phase II clinical trials have been conducted for the potential treatment of breast tumors, colon tumors, and melanoma. PD-0325901 is named (R)—N-(2,3-dihydroxypropoxy)-3,4-difluoro-2-(2-fluoro-4-iodophenylamino)benz-amide, and has the structure:

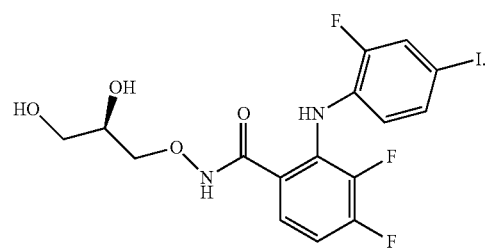 [SMILES: O=C(NOC[C@H](O)CO)c1ccc(F)c(F)c1Nc1ccc(I)cc1F]

Docetaxel (TAXOTERE®, Sanofi-Aventis) is used to treat breast, ovarian, and NSCLC cancers (U.S. Pat. No. 4,814,470; U.S. Pat. No. 5,438,072; U.S. Pat. No. 5,698,582; U.S. Pat. No. 5,714,512; U.S. Pat. No. 5,750,561; Mangatal et al (1989) Tetrahedron 45:4177; Ringel et at (1991) J. Natl. Cancer Inst. 83:288; Bissery et al (1991) Cancer Res. 51:4845; Herbst et al (2003) Cancer Treat. Rev. 29:407-415; Davies et al (2003) Expert. Opin. Pharmacother. 4:553-565). Docetaxel is named as (2R,3S)—N-carboxy-3-phenylisoserine, N-tert-butyl ester, 13-ester with 5,20-epoxy-1,2,4,7,10,13-hexahydroxytax-11-en-9-one 4-acetate 2-benzoate, trihydrate (U.S. Pat. No. 4,814,470; EP 253738; CAS Reg. No. 114977-28-5) (or named as 1,7β,10β-trihydroxy-9-oxo-5β,20-epoxytax-11-ene-2α,4,13α-triyl 4-acetate 2-benzoate 13-{(2R,3S)-3-[(tert-butoxycarbonyl)amino]-2-hydroxy-3-phenylpropanoate}) and has the structure:

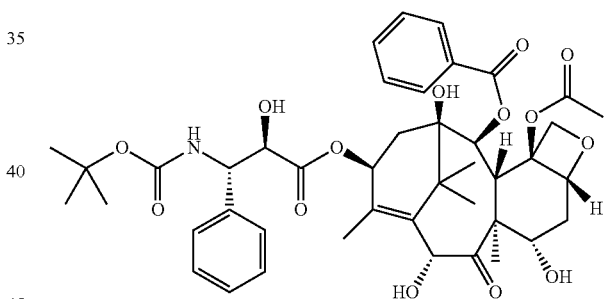

Lapatinib (TYKERB®, GW572016, Glaxo SmithKline) has been approved for use in combination with capecitabine (XELODA®, Roche) for the treatment of patients with advanced or metastatic breast cancer whose tumors over-express HER2 (ErbB2) and who have received prior therapy including an anthracycline, a taxane and trastuzumab. Lapatinib is an ATP-competitive epidermal growth factor (EGFR) and HER2/neu (ErbB-2) dual tyrosine kinase inhibitor (U.S. Pat. No. 6,727,256; U.S. Pat. No. 6,713,485; U.S. Pat. No. 7,109,333; U.S. Pat. No. 6,933,299; U.S. Pat. No. 7,084,147; U.S. Pat. No. 7,157,466; U.S. Pat. No. 7,141,576) which inhibits receptor autophosphorylation and activation by binding to the ATPbinding pocket of the EGFRIHER2 protein kinase domain. Lapatinib is named as N-(3-chloro-4-(3-fluorobenzyloxy)phenyl)-6-(5-((2-(methylsulfonyl)ethylamino)-methyl)furan-2-yl)quinazolin-4-amine (or alternatively named as N-[3-chloro-4-[(3-fluorophenyl)methoxy]phenyl]-6-[5-[(2-methylsulfonylethylamino)methyl]-2-furyl]quinazolin-4-amine), and has the structure:

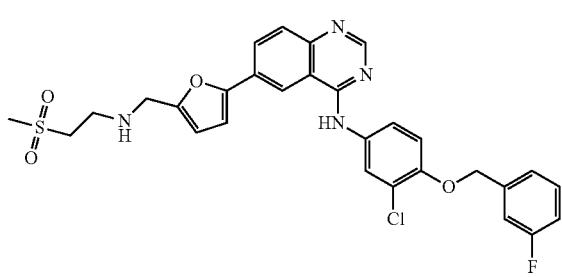 [SMILES: CS(=O)(=O)CCNCc1ccc(-c2ccc3ncnc(Nc4ccc(OCc5cccc(F)c5)c(Cl)c4)c3c2)o1]

The invention further provides a process for the preparation of a combination product as hereinbefore defined, which process comprises bringing into association a compound of the invention, as hereinbefore defined, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

By "bringing into association", we mean that the two components are rendered suitable for administration in conjunction with each other.

Thus, in relation to the process for the preparation of a kit of parts as hereinbefore defined, by bringing the two components "into association with" each other, we include that the two components of the kit of parts may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Depending on the disorder, and the patient, to be treated, as well as the route of administration, compounds of the invention may be administered at varying therapeutically effective doses to a patient in need thereof. However, the dose administered to a mammal, particularly a human, in the context of the present invention should be sufficient to effect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the potency of the specific compound, the age, condition, body weight, sex and response of the patient to be treated, and the stage/severity of the disease.

Administration may be continuous or intermittent (e.g. by bolus injection). The dosage may also be determined by the timing and frequency of administration. In the case of oral or parenteral administration the dosage can vary from about 0.01 mg to about 1000 mg per day of a compound of the invention.

In any event, the medical practitioner, or other skilled person, will be able to determine routinely the actual dosage, which will be most suitable for an individual patient. The above-mentioned dosages are exemplary of the average case; there can, of course, be individual instances where higher or lower dosage ranges are merited, and such are within the scope of this invention.

Compounds of the invention may have the advantage that they are effective inhibitors of protein or lipid kinases (e.g. a PIM family kinase such as PIM-1, PIM-2 and/or PIM-3). Advantageously, when compounds of the invention are employed in combination with known chemotherapeutic agents (such as those described herein), the components of the combinations may act in a synergistic manner.

Compounds of the invention may also have the advantage that they may be more efficacious than, be less toxic than, be longer acting than, be more potent than, produce fewer side effects than, be more easily absorbed than, and/or have a better pharmacokinetic profile (e.g. higher oral bioavailability and/or lower clearance) than, and/or have other useful pharmacological, physical, or chemical properties over, compounds known in the prior art, whether for use in the above-stated indications or otherwise.

EXAMPLES/BIOLOGICAL TESTS

PIM-1 Biochemical Assay

The biochemical assay to measure PIM-1 activity relies on the ADP Hunter assay kit (DiscoveRx Corp., Cat. #90-0077), that determines the amount of ADP as direct product of the kinase enzyme activity.

The enzyme has been expressed and purified in-house as a recombinant human protein with a C-terminal histidine tag. The protein is active and stable.

Assay conditions were as indicated by the kit manufacturers with the following adaptations for the kinase activity step:
  Kinase assay buffer and assay volume stay as recommended (15 mM HEPES, pH 7.4, 20 mM NaCl, 1 mM EGTA, 0.02% Tween 20, 10 mM MgCl$_2$ and 0.1 mg/ml bovine γ-globulins/75 μl assay volume)
  Incubation time and temperature: 60 min at 30° C.
  PIM-1 concentration: 50 pg/μl
  ATP concentration: 100 μM
  PIM-1 substrate peptide: PIMtide (ARKRRRHPSGPPTA)
  Peptide concentration: 60 μM
  Positive control for kinase activity inhibition: 1-10 μM Staurosporine
  DMSO concentration have to stay below 2% during the kinase reaction Assays were performed in either 96 or 384-well plates. The final outcome of the coupled reactions provided by the kit is the release of the fluorescent product Resorufin and has been measured with a multilabel HTS counter VICTOR V (PerkinElmer) using an excitation filter at 544 nm and an emission filter at 580 nm.

PIM-2 Biochemical Assay

The biochemical assay to measure PIM-2 activity relies on the ADP Hunter assay kit (DiscoveRx Corp., Cat. #90-0077), that determines the amount of ADP as direct product of the kinase enzyme activity.

The enzyme has been expressed and purified in-house as a recombinant human protein with a N-terminal histidine tag. The protein is active and stable.

Assay conditions were as indicated by the kit manufacturers with the following adaptations for the kinase activity step:
  Kinase assay buffer and assay volume stay as recommended (15 mM HEPES, pH 7.4, 20 mM NaCl, 1 mM EGTA, 0.02% Tween 20, 10 mM MgCl$_2$ and 0.1 mg/ml bovine γ-globulins/20 μl assay volume)
  Incubation time and temperature: 30 min at 30° C.
  PIM-2 concentration: 350 pg/μl
  ATP concentration: 100 μM
  PIM-1 substrate peptide: PIMtide (ARKRRRHPSGPPTA)
  Peptide concentration: 100 μM
  Positive control for kinase activity inhibition: 1-10 μM Staurosporine
  DMSO concentration have to stay below 2% during the kinase reaction Assays were performed in either 96 or 384-well plates. The final outcome of the coupled reactions provided by the kit is the release of the fluorescent product Resorufin and has been measured with a multilabel HTS counter VICTOR V (PerkinElmer) using an excitation filter at 544 nm and an emission filter at 580 nm.

PIM-3 Biochemical Assay

The biochemical assay to measure PIM-3 activity relies on the ADP Hunter assay kit (DiscoveRx Corp., Cat. #90-0077), that determines the amount of ADP as direct product of the kinase enzyme activity.

The enzyme has been bought from Millipore (#14-738). The protein is active and stable.

Assay conditions were as indicated by the kit manufacturers with the following adaptations for the kinase activity step:
  Kinase assay buffer and assay volume stay as recommended (15 mM HEPES, pH 7.4, 20 mM NaCl, 1 mM EGTA, 0.02% Tween 20, 10 mM $MgCl_2$ and 0.1 mg/ml bovine γ-globulins/20 µl assay volume)
  Incubation time and temperature: 30 min at 30° C.
  PIM-3 concentration: 250 pg/µl
  ATP concentration: 100 µM
  PIM-1 substrate peptide: PIMtide (ARKRRRHPS-GPPTA)
  Peptide concentration: 60 µM
  Positive control for kinase activity inhibition: 1-10 µM Staurosporine
  DMSO concentration have to stay below 2% during the kinase reaction Assays were performed in either 96 or 384-well plates. The final outcome of the coupled reactions provided by the kit is the release of the fluorescent product Resorufin and has been measured with a multilabel HTS counter VICTOR V (PerkinElmer) using an excitation filter at 544 nm and an emission filter at 580 nm.

Bad S112 Phosphorilation Inhibition Assay

Efficacy of compounds of the invention on the inhibition of Bad phosphorylation was measured by an In Cell ELISA. EC50 values were established for the tested compounds.
Assay Conditions:
Cells: H1299 cells overexpressing Pim1 (H1299Pim1)
DMSO Plates: 96-well-Polystyrene, Untreated, Round-Bottom plates from Costar (Cat #3797)
Cell Plates: 96-Flat bottom biocoated with Poly-D-Lysin plates with lid from Becton Dickinson (Cat#354651)
Cell Culture Medium: DMEM high glucose, 10% Fetal Bovine Serum, 2 mM L-Glutamine, P/S
Antibodies: phosphor Bad S112 antibody from Cell Signaling (cat. #9291S), anti rabbit conjugated with peroxidise from Amersham (cat.#3619)
Reagent: SuperSignal ELISA femto from Pierce (cat.#1001110)

Procedure:
Cells were seeded in 15000 cells per 200 µl per well into 96-well plates and incubated for 16 h at 37° C., 5% $CO_2$. On day two, nine serial 1:2 compound dilutions were made in DMSO in a 96-well plate. The compounds were added to duplicate wells in 96-well cell plates using a FX BECKMAN robot (Beckman Coulter) and incubated at 37° C. with $CO_2$ atmosphere. After 4 hours, relative levels of Bad S112 phosphorylation were measured in Cell ELISA using SuperSignal ELISA Femto substrate (Pierce) and read on VICTOR (Perkin Elmer). EC50 values were calculated using ActivityBase from IDBS.

MTT In Vitro Cell Proliferation Assay

Proliferation assays (MTT) were performed as described in:

"Chemical interrogation of FOXO3a nuclear translocation identifies potent and selective inhibitors of phosphoinositide 3-kinases", W. Link, J. Oyarzabal, B. G. Serelde, M. I. Albarran, O. Rabal, A. Cebria, P. Alfonso, J. Fominaya, O. Renner, S. Peregrina, D. Soilan, P. A. Ceballos, A. I. Hernandez, M. Lorenzo, P. Pevarello, T. G. Granda, G. Kurz, A. Carnero, J. R. Bischoff, *J. Biol. Chem.* 284 (2009) 28392-28400.

Combination Assay

Example 106 shows the combination index (CI) of combinations of certain example compounds and various chemotherapeutic agents in the MTT in vitro cell proliferarion assays. A combination index score is calculated by the Chou and Talalay method (CalcuSyn software, Biosoft). The strength of synergy is scored using the ranking system Chou and Talalay: CI less than 0.8 indicates synergy, CI between 0.8 and 1.2 indicates additivity and CI greater than 1.2 indicates antagonism.

The EC50 values of representative combinations were also calculated. The individually measured EC50 values of the chemotherapeutic agent and the example compounds are compared to the EC50 value of the combination. The cell lines are characterised by tumor type.

Combination assays were performed as described in:
"Pim 1 kinase inhibitor ETP-45299 suppresses cellular proliferation and synergizes with PI3K inhibition". Blanco-Aparicio, Carmen; Collazo, Ana Maria Garcia; Oyarzabal, Julen; Leal, Juan F.; Albaran, Maria Isabel; Lima, Francisco Ramos; Pequeno, Belen; Ajenjo, Nuria; Becerra, Mercedes; Alfonso, Patricia; Reymundo, Maria Isabel; Palacios, Irene; Mateos, Genoveva; Quinones, Helena; Corrionero, Ana; Carnero, Amancio; Pevarello, Paolo; Lopez, Ana Rodriguez; Fominaya, Jesus; Pastor, Joaquin; Bischoff, James R. *Cancer Letters* (Shannon, Ireland) 2011, 300(2), 145-153.

The invention is illustrated by way of the following examples.

The compound names given herein were generated with MDL ISIS/DRAW 2.5 SP 2, Autonom 2000.

General scheme:
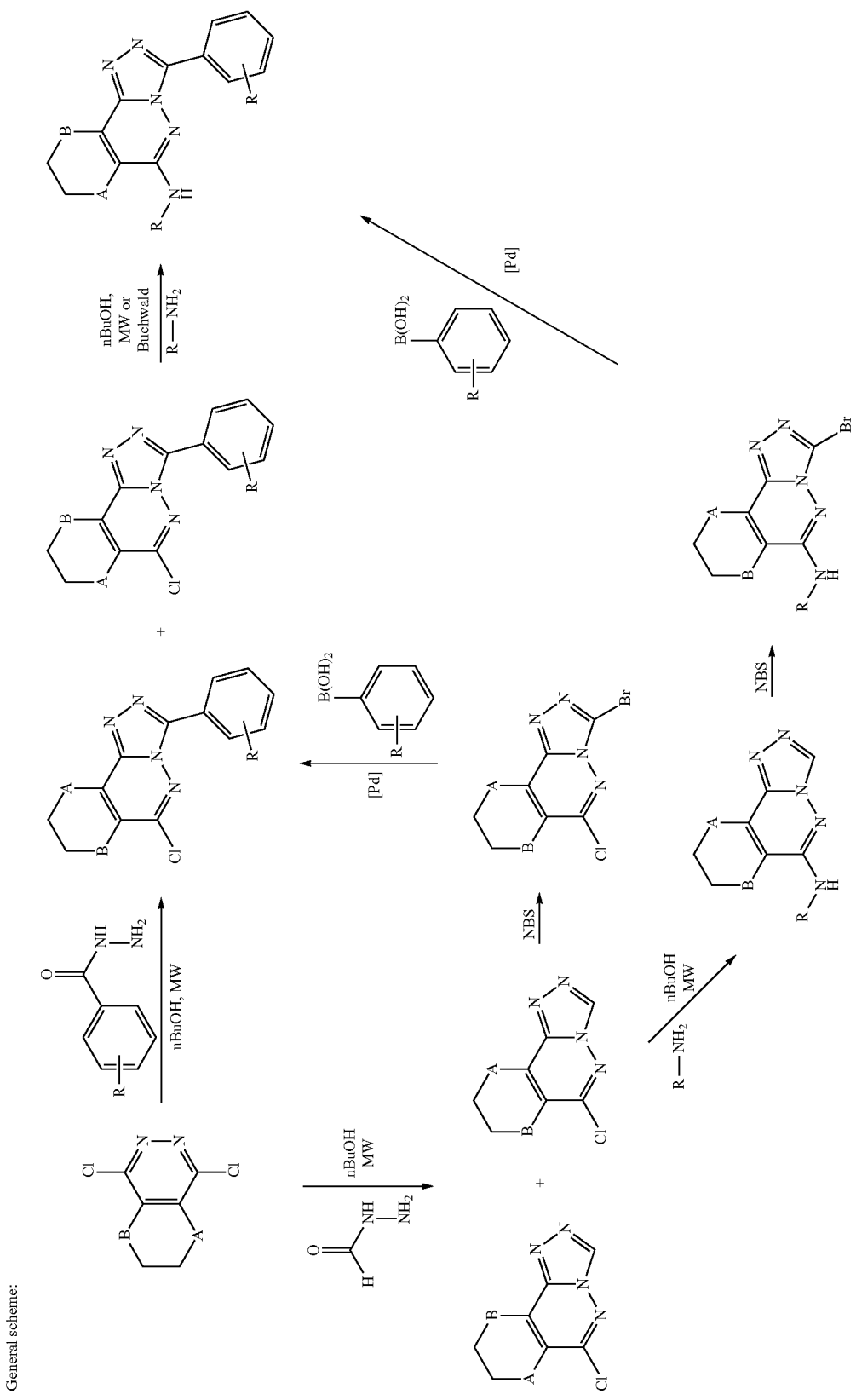

Experimental

Hereinafter, the term "DCM" means dichloromethane, "Et$_2$O" means diethyl ether, "MeOH" means methanol, "THF" means tetrahydrofuran, "DMF" means dimethylformamide, "DME" means 1,2-dimethoxyethane, "EtOAc" means ethyl acetate, "Pd(PPh$_3$)$_4$" means tetrakis(triphenylphosphine)palladium, "DIPEA" means diisopropylethylamine, "BINAP" means (R)/(+)-2,2'-bis(diphenylphosphino)-1,1'-binaphtyl, "min" means minutes, "h" means hours, "Pd$_2$(dba)$_3$" means tris(dibenzylideneacetone)-dipalladium (0), "eq" means equivalents, "nBuOH" means n-butanol, "Pd(dppf)Cl$_2$." means 1,1'-bis(diphenylphosphino)ferrocenepalladium(II) dichloride, "LDA" means lithium diisopropylamine.

NMR spectra were recorded in a Bruker Avance II 300 spectrometer and Bruker Avance II 700 spectrometer fitted with 5 mm QXI 700 S4 inverse phase, Z-gradient unit and variable temperature controller.

The HPLC measurements were performed using a HP 1100 from Agilent Technologies comprising a pump (binary) with degasser, an autosampler, a column oven, a diode-array detector (DAD) and a column as specified in the respective methods below. Flow from the column was split to a MS spectrometer. The MS detector was configured with an electrospray ionization source or API/APCI. Nitrogen was used as the nebulizer gas. Data acquisition was performed with ChemStation LC/MSD quad, software.

Method 1
Reversed phase HPLC was carried out on a Gemini-NX C18 (100×2.0 mm; 5 um), Solvent A: water with 0.1% formic acid; Solvent B: acetonitrile with 0.1% formic acid. Gradient: 5% of B to 100% of B within 8 min at 50° C., DAD.

Method 2
Reversed phase HPLC was carried out on a Gemini-NX C18 (100×2.0 mm; 5 um), Solvent A: water with 0.1% formic acid; Solvent B: acetonitrile with 0.1% formic acid. Gradient: 50% of B to 100% of B within 8 min at 50° C., DAD.

Method 3
Reversed phase HPLC was carried out on a Gemini-NX C18 (100×2.0 mm; Sum), Solvent A: water with 0.1% formic acid; Solvent B: acetonitrile with 0.1% formic acid. Gradient: 5% of B to 40% of B within 8 min at 50° C., DAD.

Method 4
Reversed phase HPLC was carried out on a Gemini C18 column (50×2 mm, 3 um). Solvent A: water with 0.1% formic acid; Solvent B: acetonitrile with 0.1% formic acid. Gradient: 10% to 95% of B within 4 min at 50° C., DAD.
"Found mass" refers to the most abundant isotope detected in the HPLC-MS.

Bicyclic Intermediates
General Procedure A: Bicycle Formation from 3,4,5,6-tetrachloropyridazine To a solution of 3,4,5,6-tetrachloropyridazine (1 eq) in acetonitrile (2 mL/mmol), magnetically stirred at −2° C.-0° C., a solution of the appropiate aminoalcohol (ex: 2-(methylamino)-ethanol) (1 eq) or diamine (see intermediate 4 below) in acetonitrile (1 mL/mmol) was added dropwise. The reaction was allowed to reach room temperature and it was stirred at this temperature for 16 h. Sodium tertbutoxide was then added at room temperature (4 portions, up to a total of 2 eq) and the reaction mixture left stirring at room temperature (in some cases it was needed to heat it up to 40° C.) for 20 h. Then, the solvent was removed under vacuum, the dry residue was dissolved in DCM, washed with water brine (2×) and the organic layer dried over magnesium sulphate. The obtained crude mixture was used as such in the next step or purified by column chromatography (Biotage/Flash, silica, 0% to 60% EtOAc in cyclohexane to 0% to 30% MeOH in DCM) to give the desired product (ex: 5,8-dichloro-3,4-dihydro-4-methyl-2H-pyridazino[4,5-b][1,4]oxazine).

Intermediate 1

5,8-Dichloro-3,4-dihydro-4-methyl-2H-pyridazino[4,5-b][1,4]oxazine

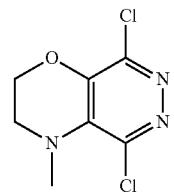

HPLC-MS (method 1): Rt=2.80 min, [M+H]$^+$ m/z 222.0, $^1$H NMR (300 MHz, CDCl$_3$) δ 4.34-4.25 (m, 2H), 3.32-3.21 (m, 2H), 3.08 (s, 3H).
Yield: 36%

Intermediate 2

5,8-Dichloro-4-ethyl-3,4-dihydro-2H-pyridazino[4,5-b][1,4]oxazine

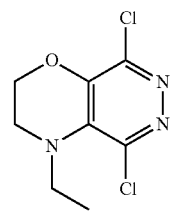

HPLC-MS (method 4): Rt=3.7 min, [M+H]$^+$ m/z 234.2.
Yield: 95% of the crude mixture.

Intermediate 3

5,8-Dichloro-4-isopropyl-3,4-dihydro-2H-pyridazino[4,5-b][1,4]oxazine

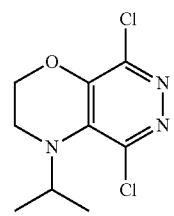

HPLC-MS (method 4): Rt=3.9 min, [M+H]⁺ m/z 248.
Yield: 95% of the crude mixture.

Intermediate 4

5,8-Dichloro-1,4-dimethyl-1,2,3,4-tetrahydro-pyrazino[2,3-d]pyridazine

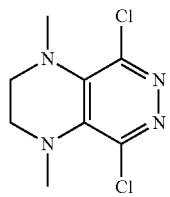

$^1$H NMR (300 MHz, CDCl$_3$) δ 3.05 (s, 4H), 3.04 (s, 6H).
Yield: 53%.

Intermediate 5

5,8-Dichloro-3,4-dimethyl-3,4-dihydro-2H-pyridazino[4,5-b][1,4]oxazine

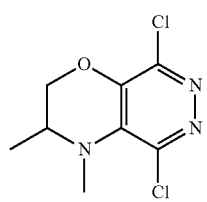

HPLC-MS (method 4): Rt=3.44 min, [M+H]⁺ m/z 234.1.
$^1$H NMR (300 MHz, CDCl$_3$) δ 4.25 (dd, J=10.9, 3.3 Hz, 1H), 4.13 (dd, J=10.8, 2.6 Hz, 1H), 3.47-3.33 (m, 1H), 3.11 (s, 3H), 1.17 (d, J=6.9 Hz, 3H).
Yield: 16%.

Intermediate 6

5,8-Dichloro-2,4-dimethyl-3,4-dihydro-2H-pyridazino[4,5-b][1,4]oxazine

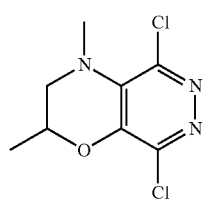

HPLC-MS (method 4): Rt=3.44 min, [M+H]⁺ m/z 234.1.

$^1$H NMR (300 MHz, CDCl$_3$) δ 4.27-4.15 (m, 1H), 3.25 (dd, J=13.9, 2.3 Hz, 1H), 3.13 (s, 3H), 2.94 (dd, J=13.8, 8.9 Hz, 1H), 1.49 (d, J=6.3 Hz, 3H)
Yield: 8%.

Intermediate 7

5,8-Dichloro-2,3-dihydro-[1,4]dioxino[2,3-d]pyridazine

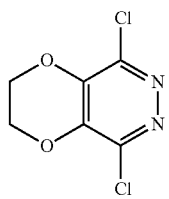

A mixture of 3,4,5,6-tetrachloropyridazine (5.0 g, 22.9 mmol), ethylene glycol (1.49 mL) and sodium hydride (60% in mineral oil, 1.1 g) in dry DMF (250 mL) was stirred for 18 h at room temperature. Then, more sodium hydride (60% in mineral oil, 1.1 g) was added and the mixture was stirred for 3 h at 60° C. and 18 h at room temperature. The solvents were removed under vacuum and the residue purified by flash chromatography (EtOAc/hexanes 1:10 to 1:1) to give compound 5,8-dichloro-2,3-dihydro-[1,4]dioxino[2,3-d]pyridazine as a yellow solid (758 mg, 16% yield). HPLC-MS (method 4): Rt=2.52 min, [M+H]⁺ m/z 206.9.
$^1$H NMR (300 MHz, CDCl$_3$) δ 4.54 (s, 4H).

Intermediate 8

1,4-Dichloro-5,6,7,8-tetrahydro-phthalazine)

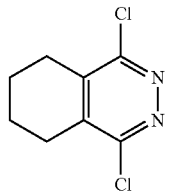

A mixture of 3,4,5,6-tetrahydrophthalic anhydride (1 g, 6.5 mmol), hydrazine hydrate (0.57 mL, 11.83 mmol), sodium acetate (4.3 g, 52.5 mmol) in acetic acid (29 mL) was heated at 100° C. for 16 h. The reaction was cooled to room temperature and a white solid precipitated. The solid was filtered and washed with water and 855 mg of the expected compound 2,3,5,6,7,8-Hexahydro-phthalazine-1,4-dione were obtained (78.3% yield).

A mixture of 2,3,5,6,7,8-Hexahydro-phthalazine-1,4-dione (855 mg, 5.14 mmol) and phosphorus oxychloride (5 mL) was heated under reflux conditions for 16 h. The reaction was poured into ice, and neutralized very carefully with solid sodium carbonate. The water layer was extrated with EtOAc (×2), and the combined organic layers were dried (sodium sulphate), filtered and concentrated. The crude was purified by trituration with Et$_2$O to give the expected compound 1,4-dichloro-5,6,7,8-tetrahydro-phthalazine (876 mg, 83.8% yield).

HPLC-MS (method 4): Rt=4.16 min, [M+H]⁺ m/z 203.0.
$^1$H NMR (300 MHz, CDCl$_3$) δ 2.71 (m, 4H), 1.87 (m, 4H).

General Procedure B: Bicycle Formation from 3,4,5-trichloropyridazine

To a solution of 3,4,5-trichloropyridazine (1 eq) in MeOH (1 mL/mmol) was added dropwise a solution of the appropiate aminoalcohol (ex: 2-methylamino-ethanol) (3 eq) in MeOH (1 mL/mmol)(acetonitrile can be also used). The reaction mixture was stirred at room temperature from 1 h to 2 days depending on the amine. The solvent was removed under vacuum to give a brown oil which was purified by biotage flash column chromatography (70% EtOAc in cyclohexane to 100% EtOAc) to give the desired product (ex: 2-[(5,6-dichloro-pyridazin-4-yl)-methyl-amino]-ethanol).

The appropriate dichloropyridazine (ex: 2-[(5,6-dichloro-pyridazin-4-yl)-methyl-amino]-ethanol) (1 eq) was dissolved in THF (20 mL/mmol). When the solution started refluxing, potassium tert-butoxide (1.2 eq) was added portionwise. The reaction mixture was refluxed for 2 h. On cooling, a saturated aqueous solution of amonium chloride was added and the layers were separated. The aqueous phase was extracted with EtOAc (×2). The combined organic layers were dried (sodium sulphate), filtered and evaporated. The residue was triturated with Et$_2$O-DCM 9:1 and filtered off to afford the desired product (ex: 8-chloro-4-methyl-3,4-dihydro-2H-pyridazino[4,5-b]-1,4-oxazine).

Intermediate 9

8-Chloro-4-methyl-3,4-dihydro-2H-pyridazino[4,5-b]-1,4-oxazine

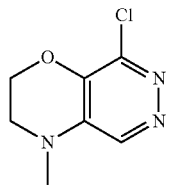

HPLC-MS (method 4): Rt=0.98 min, [M+H]$^+$ 186.1.
$^1$H NMR (300 MHz, CDCl$_3$) δ 8.47 (s, 1H), 4.42 (m, 2H), 3.46 (m, 2H), 3.06 (s, 3H).
Yield: 77% for two steps Intermediate 10

(S)-8-Chloro-3,4-dimethyl-3,4-dihydro-2H-pyridazino[4,5-b][1,4]oxazine

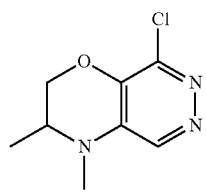

HPLC-MS (method 4): Rt=1.305 min, [M+H]$^+$ 200.1.
$^1$H NMR (300 MHz, CDCl$_3$) δ 8.46 (s, 1H), 4.24-4.20 (m, 2H), 3.54 (dt, J=6.6, 2.6 Hz, 1H), 3.02 (s, 3H), 1.26 (d, J=6.6 Hz, 4H).
Yield: 20% for two steps Intermediate 11

8-Chloro-3,3,4-trimethyl-3,4-dihydro-2H-pyridazino[4,5-b][1,4]oxazine

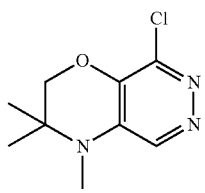

2-Amino-2-methyl-1-propanol (14.5 g, 163.5 mmol, 3 eq) was added to a stirred mixture of 3,4,5-trichloropyridazine (10 g, 54.5 mmol, 1 eq) in acetonitrile (250 mL). The reaction was stirred at room temperature overnight then at 100° C. for 3 days. The solvents were removed under reduced pressure. The residue was purified by biotage flash column chromatography (cyclohexane/EtOAc 50 to 100% EtOAc) to afford two fractions. The more polar fraction of the two in the silica flash column contained the desired product 2-(5,6-dichloro-pyridazin-4-ylamino)-2-methyl-propan-1-ol (3.23 g, 25% yield).
HPLC-MS (method 4): Rt=3.12 min, [M+H]$^+$ 236.1.
$^1$H NMR (300 MHz, DMSO-d$_6$) δ 9.02 (s, 1H), 5.88 (s, 1H), 5.47 (t, J=5.5 Hz, 1H), 3.45 (d, J=5.5 Hz, 2H), 1.37 (s, 6H).

Potassium tert-butoxide (1.84 g, 16.4 mmol, 1.2 eq) was added to a stirred solution of 2-(5,6-dichloro-pyridazin-4-ylamino)-2-methyl-propan-1-ol (3.227 g, 13.668 mmol, 1 eq) in THF (250 mL). The reaction was stirred at 100° C. for 44 h.

The solvents were evaporated to dryness. The resulting residue was purified by biotage flash column chromatography (A=DCM, B=9:1 DCM/MeOH, 10-100% B) to afford the desired product 8-chloro-3,3-dimethyl-3,4-dihydro-2H-pyridazino[4,5-b][1,4]oxazine (843 mg, 31% yield).
HPLC-MS (method 4): Rt=4.60 min, [M+H]$^+$ 200.1.
$^1$H NMR (300 MHz, CDCl$_3$) δ 8.40 (s, 1H), 3.98 (s, 2H), 1.30 (s, 6H).

Sodium bis(trimethylsilyl)amide (1M in THF) (4.22 mL, 4.22 mmol, 1 eq) was added to a stirred room temperature mixture of 8-chloro-3,3-dimethyl-3,4-dihydro-2H-pyridazino[4,5-b][1,4]oxazine (0.843 g, 4.22 mmol, 1 eq) in THF (21 mL). The reaction was stirred at room temperature for 1 h then iodomethane (0.315 mL, 5.07 mmol, 1.2 eq) was added and stirring continued for 1 h 15 min. The reaction was quenched with brine, stirred for 5 min then diluted with EtOAc. Layers were separated and the aqueous layer was extracted with EtOAc (×2). The combined organic layers were dried and evaporated. The residue was purified on silica gel (A=DCM, B=9:1 DCM/MeOH, 10-100% B) to afford 8-chloro-3,3,4-trimethyl-3,4-dihydro-2H-pyridazino[4,5-b][1,4]oxazine (216 mg, 24%).
HPLC-MS (method 4): Rt=4.60 min, [M+H]$^+$ 200.1.
$^1$H NMR (300 MHz, CDCl$_3$) δ 8.47 (s, 1H), 4.01 (s, 2H), 2.91 (s, 3H), 1.26 (s, 6H).

General Procedure C: Bicycle Chlorination

A mixture of the appropiate bicyclic chloropyridazines (ex: 8-chloro-4-methyl-3,4-dihydro-2H-pyridazino[4,5-b]-1,4-oxazine) (1 eq) in acetonitrile (5 mL/mmol) was heated at 50° C. Then, NCS (1.2 eq) was added and the reaction mixture was heated at 50° C. for 3 h. The solvent was removed under vacuum. The residue was taken up into DMC and washed with a saturated solution of sodium bicarbonate. The organic layer was dried (Na$_2$SO$_4$), filtered and evaporated to give a residue which was purified by biotage flash column chromatography (DCM/EtOAc 20%) to afford the desired product (ex: 5,8-dichloro-4-methyl-3,4-dihydro-2H-pyridazino[4,5-b]-1,4-oxazine).

Intermediate 12

5,8-Dichloro-4-methyl-3,4-dihydro-2H-pyridazino[4,5-b]-1,4-oxazine

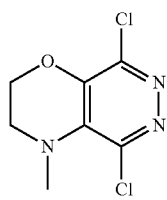

HPLC-MS (method 4): Rt=3.1 min, [M+H]$^+$ 220.0, 222.0.
$^1$H NMR (300 MHz, CDCl$_3$) δ 4.36 (m, 2H), 3.31 (m, 2H), 3.14 (s, 3H).
Yield: 60%

Intermediate 13

(3S)-5,8-Dichloro-3,4-dimethyl-3,4-dihydro-2H-pyridazino[4,5-b][1,4]oxazine

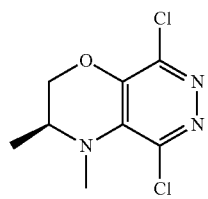

HPLC-MS (method 4): Rt=4.40 min, [M+H]$^+$ m/z 234.0.
$^1$H NMR (300 MHz, CDCl$_3$) δ 4.25 (dd, J=10.8, 3.2 Hz, 1H), 4.14 (dd, J=11.0, 2.6 Hz, 1H), 3.40 (m, 1H), 3.11 (s, 3H), 1.18 (d, J=6.8 Hz, 3H).
Yield: 71%.

Intermediate 14

5,8-Dichloro-3,3,4-trimethyl-3,4-dihydro-2H-pyridazino[4,5-b][1,4]oxazine

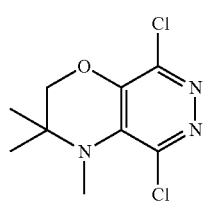

HPLC-MS (method 4): Rt=4.54 min, [M+H]$^+$ m/z 248.1.
$^1$H NMR (300 MHz, CDCl$_3$) δ 3.94 (s, 2H), 2.91 (s, 3H), 1.18 (s, 6H).
Yield: 97%.

Tricyclic Intermediates

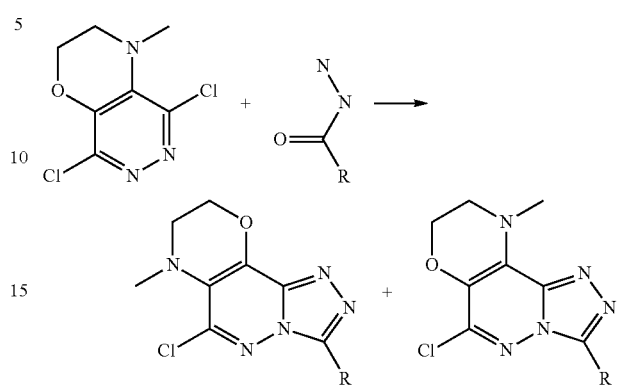

General Procedure D: Tricycle Formation

A solution of the appropiate bicyclic dichloropyridazines (1 eq), appropiate hydrazide (3.5 eq), triethylamine (1.1 eq) and p-toluenesulfonic acid (1.1 eq) in 1,4-dioxane (6.6 mL/mmol) was heated at 100° C. for ~18 h (sand bath). Prolonged reaction time and additional amounts of base, acid and hydrazide could be needed in order to drive the reaction to completion. The reaction was worked up by removing the 1,4-dioxane and the dry residue was dissolved in DCM, washed with water (3×) and brine (2×). The organic layers were dried over magnesium sulphate, filtered and the solvent removed under vacuum. The crude was purified by reversed phase column chromatography or by flash column chromatography (Isolute/Flash, Sill) to give both regioisomers.

Intermediate 15 and 16

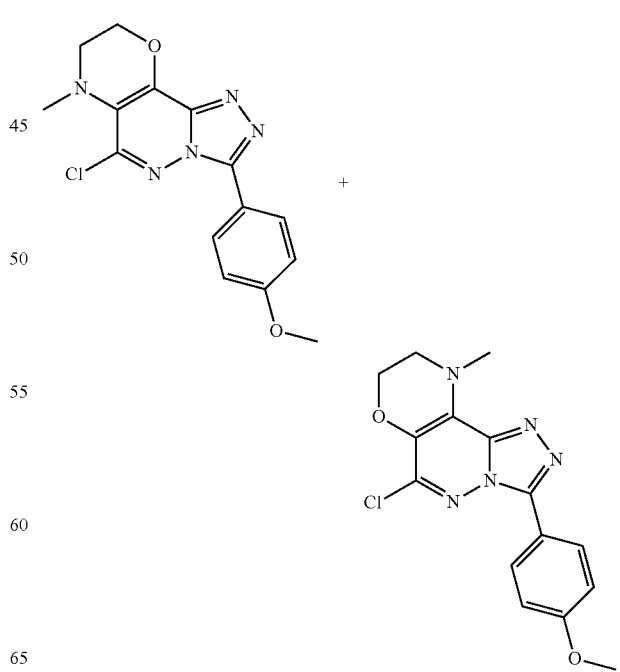

Intermediate 15

5-Chloro-3-(4-methoxy-phenyl)-6-methyl-7,8-dihydro-6H-9-oxa-1,2,3a,4,6-pentaaza-cyclopenta[a]naphthalene HPLC-MS (method 1): Rt=4.1 min, [M+H]+ m/z 332.2.
1H NMR (300 MHz, CDCl3) δ 8.31-8.24 (m, 2H), 7.04-6.96 (m, 2H), 4.44 (dd, J=6.1, 3.6, 2H), 3.86 (d, J=10.7, 3H), 3.49 (dd, J=10.0, 5.2, 2H), 3.37 (s, 3H).

Intermediate 16

5-Chloro-3-(4-methoxy-phenyl)-9-methyl-8,9-dihydro-7H-6-oxa-1,2,3a,4,9-pentaaza-cyclopenta[a]naphthalene HPLC-MS (method 1): Rt=5.2 min, [M+H]+ m/z 332.2.
1H NMR (300 MHz, CDCl3) δ 8.44-8.31 (m, 2H), 6.99 (dd, J=27.1, 8.9, 2H), 4.40-4.31 (m, 2H), 3.87 (2 s, J=6.9, 6H), 3.61-3.54 (m, 2H).
Yield: 50% of the mixture General Procedure E: Tricycle Formation A mixture of the appropiate bicyclic dichloropyridazines (ex: 5,8-dichloro-3,4-dihydro-4-methyl-2H-pyridazino[4,5-b][1,4]oxazine) and the appropiate hydrazide (ex: 3-(trifluoromethoxy)benzohydrazide) (1.5 eq) in nBuOH (9 mL/mmol) was heated under microwave irradiation for 1.5 h at 185° C. (or 18 h at 160-180° C. in a silicon bath). The solvent was evaporated under vacuum and the obtained residue was purified either by reversed phase chromatographic purification or by flash column chromatography (Isolute/Flash, Sill) to yield two compounds (regioisomers formed in the reaction) (ex: 5-chloro-9-methyl-3-(3-trifluoromethoxy-phenyl)-8,9-dihydro-7H-6-oxa-1,2,3a,4,9-pentaaza-cyclopenta[a]naphthalene and 5-chloro-6-methyl-3-(3-trifluoromethoxy-phenyl)-7,8-dihydro-6H-9-oxa-1,2,3a,4,6-pentaaza-cyclopenta[a]naphthalene). In some cases, the regioisomers were used as a mixture and separated in the final step by semi-preparative HPLC.

Intermediate 17

5-Chloro-9-methyl-3-(3-trifluoromethoxy-phenyl)-8,9-dihydro-7H-6-oxa-1,2,3a,4,9-pentaaza-cyclopenta[a]naphthalene

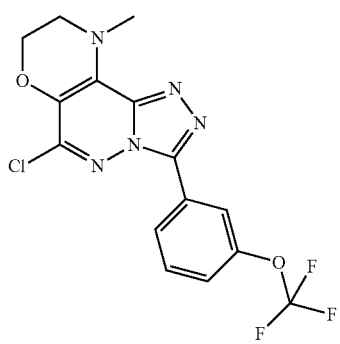 [SMILES: CN1CCOc2c(Cl)nn3c(-c4cccc(OC(F)(F)F)c4)nnc3c21]

HPLC-MS (method 4): Rt=4.78 min, [M+H]+ m/z 386.1.
1H NMR (300 MHz, CDCl3) δ 8.48-8.34 (m, 2H), 7.56 (dd, J=14.1, 6.0 Hz, 1H), 7.34-7.28 (m, 1H), 4.41-4.33 (m, 2H), 3.91 (s, 3H), 3.62-3.57 (m, 2H).
Yield: 22%

Intermediate 18

5-Chloro-6-methyl-3-(3-trifluoromethoxy-phenyl)-7,8-dihydro-6H-9-oxa-1,2,3a,4,6-pentaaza-cyclopenta[a]naphthalene

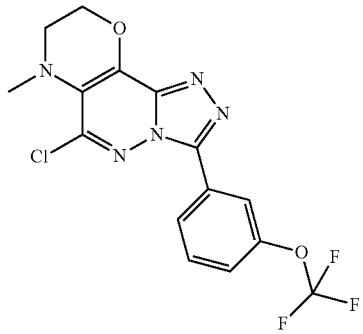 [SMILES: CN1CCOc2c1c(Cl)nn1c(-c3cccc(OC(F)(F)F)c3)nnc21]

HPLC-MS (method 4): Rt=4.57 min, [M+H]+ m/z 386.1
1H NMR (300 MHz, CDCl3) d 8.47-8.36 (m, 2H), 7.63-7.54 (m, 1H), 7.36 (d, J=8.2, 1H), 4.58-4.48 (m, 2H), 3.34-3.29 (m, 2H), 2.95 (s, 3H).
Yield: 13%

Intermediate 19

5-Chloro-6-ethyl-3-(3-Trifluoromethoxy-phenyl)-7,8-dihydro-6H-9-oxa-1,2,3a,4,6-pentaaza-cyclopenta[a]naphthalene

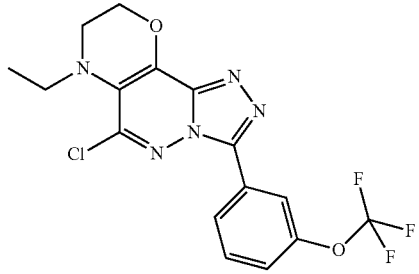 [SMILES: CCN1CCOc2c1c(Cl)nn1c(-c3cccc(OC(F)(F)F)c3)nnc21]

HPLC-MS (method 2): Rt=5.52 min, [M+H]+ m/z 400.1.
1H NMR (300 MHz, DMSO-d6) δ 10.79 (s, 1H), 8.38-8.20 (m, 2H), 7.98 (d, J=7.5 Hz, 1H), 7.86 (s, 1H), 7.79-7.59 (m, 4H), 7.52 (d, J=8.0 Hz, 1H), 4.58-4.45 (m, 2H), 3.66 (dd, J=14.0, 7.0 Hz, 2H), 3.52 (d, J=4.4 Hz, 2H), 2.07 (s, 1H), 1.27 (t, J=7.0 Hz, 3H).
Yield: 26.3%.

Intermediate 20

5-Chloro-3-(4-methoxy-phenyl)-6,9-dimethyl-6,7,8,9-tetrahydro-1,2,3a,4,6,9-hexaaza-cyclopenta[a]naphthalene

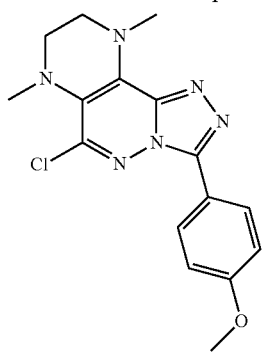

HPLC-MS (method 1): Rt=4.46 min, [M+H]⁺ m/z 345.
¹H NMR (300 MHz, CDCl₃) δ 8.46-8.34 (m, 2H), 7.10-6.97 (m, 2H), 4.00 (s, 3H), 3.86 (s, 3H), 3.51-3.41 (m, 2H), 3.13-3.02 (m, 2H), 2.72 (s, 3H).
Yield: 59%.

Intermediate 21

5-Chloro-3-(3-trifluoromethoxy-phenyl)-7,8-dihydro-6,9-dioxa-1,2,3a,4-tetraaza-cyclopenta[a]naphthalene

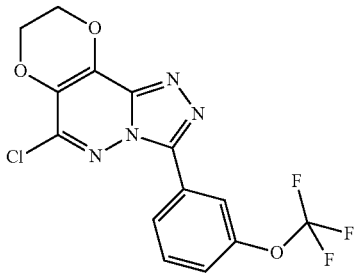 [SMILES: FC(F)(F)Oc1cccc(-c2nnc3c4c(c(Cl)nn23)OCCO4)c1]

HPLC-MS (method 4): Rt=4.52 min, [M+H]⁺ m/z 372.8.
¹H NMR (300 MHz, CDCl₃) δ 8.44 (m, 1H), 8.39 (s, 1H), 7.60 (m, 1H), 7.38 (m, 1H), 4.69 (m, 2H), 4.60 (m, 2H).
Yield: 31%.

Intermediate 22

5-Chloro-6,7-dimethyl-3-(3-trifluoromethoxy-phenyl)-7,8-dihydro-6H-9-oxa-1,2,3a,4,6-pentaaza-cyclopenta[a]naphthalene

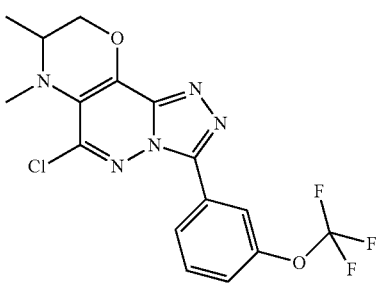 [SMILES: CC1COc2c(c(Cl)nn3c(-c4cccc(OC(F)(F)F)c4)nnc23)N1C]

HPLC-MS (method 4): Rt=4.86 min, [M+H]⁺ m/z 400.2.
¹H NMR (300 MHz, CDCl₃) δ 8.40 (m, 1H), 8.36 (s, 1H), 7.55 (m, 1H), 7.33 (m, 1H), 4.37 (dd, J=10.8, 3.2 Hz, 1H), 4.29 (dd, J=11.0, 2.6 Hz, 1H), 3.33 (m, 1H), 2.86 (s, 3H), 1.16 (d, J=7.2 Hz, 3H).
Yield: 34%.

Intermediate 23

5-Chloro-8,9-dimethyl-3-(3-trifluoromethoxy-phenyl)-8,9-dihydro-7H-6-oxa-1,2,3a,4,9-pentaaza-cyclopenta[a]naphthalene

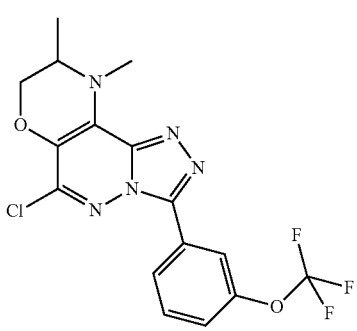 [SMILES: CC1COc2c(Cl)nn3c(-c4cccc(OC(F)(F)F)c4)nnc3c2N1C]

HPLC-MS (method 4): Rt=4.68 min, [M+H]⁺ m/z 400.2.
¹H NMR (300 MHz, CDCl₃) δ 8.44 (m, 1H), 8.39 (s, 1H), 7.55 (m, 1H), 7.32 (m, 1H), 4.26 (dd, J=11.0, 2.3 Hz, 1H), 4.11 (dd, J=11.0, 2.3 Hz, 1H), 3.91 (s, 3H), 3.65 (m, 1H).
Yield: 29%.

Intermediate 24

5-Chloro-6,7,7-trimethyl-3-(3-trifluoromethoxy-phenyl)-7,8-dihydro-6H-9-oxa-1,2,3a,4,6-pentaaza-cyclopenta[a]naphthalene

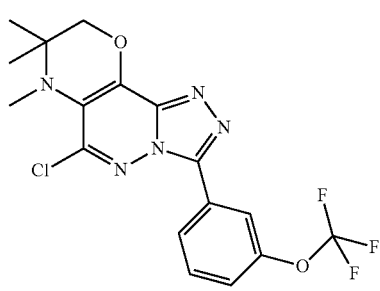 [SMILES: CN1c2c(Cl)nn3c(-c4cccc(OC(F)(F)F)c4)nnc3c2OCC1(C)C]

HPLC-MS (method 4): Rt=4.79 min, [M+H]⁺ m/z 413.9.
¹H NMR (300 MHz, CDCl₃) δ 8.41 (m, 1H), 8.38 (s, 1H), 7.56 (m, 1H), 7.34 (m, 1H), 4.15 (s, 2H), 2.73 (s, 3H), 1.24 (s, 6H).
Yield: 16%.

Intermediate 25

5-Chloro-8,8,9-trimethyl-3-(3-trifluoromethoxy-phenyl)-8,9-dihydro-7H-6-oxa-1,2,3a,4,9-pentaaza-cyclopenta[a]naphthalene

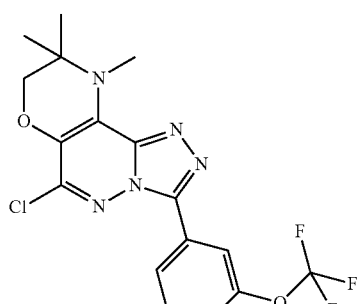

HPLC-MS (method 4): Rt=5.00 min, [M+H]⁺ m/z 414.0.
¹H NMR (300 MHz, CDCl₃) δ 8.43 (m, 1H), 8.39 (s, 1H), 7.55 (m, 1H), 7.32 (m, 1H), 4.00 (s, 2H), 3.87 (s, 3H), 1.40 (s, 6H).
Yield: 15%.

Intermediate 26

(7S)-5-Chloro-6,7-dimethyl-3-(3-trifluoromethoxy-phenyl)-7,8-dihydro-6H-9-oxa-1,2,3a,4,6-pentaaza-cyclopenta[a]naphthalene

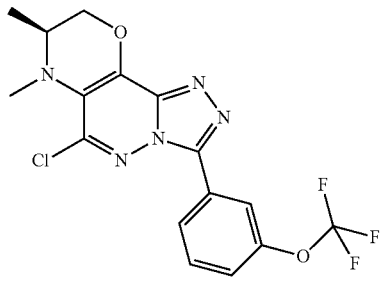 [SMILES: C[C@H]1COc2c(c(Cl)nn3c(-c4cccc(OC(F)(F)F)c4)nnc23)N1C]

HPLC-MS (method 4): Rt=4.73 min, [M+H]⁺ m/z 400.0.
¹H NMR (300 MHz, CDCl₃) δ 8.36 (m, 1H), 8.32 (s, 1H), 7.52 (m, 1H), 7.29 (m, 1H), 4.34 (dd, J=11.0, 3.4 Hz, 1H), 4.27 (dd, J=11.0, 2.6 Hz, 1H), 3.31 (m, 1H), 2.84 (s, 3H), 1.13 (d, J=7.2 Hz, 3H).
Yield: 25%.

Intermediate 27

(8S)-5-Chloro-8,9-dimethyl-3-(3-trifluoromethoxy-phenyl)-8,9-dihydro-7H-6-oxa-1,2,3a,4,9-pentaaza-cyclopenta[a]naphthalene

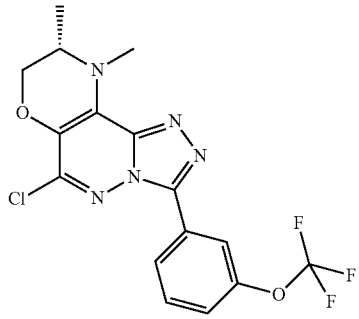 [SMILES: C[C@H]1COc2c(Cl)nn3c(-c4cccc(OC(F)(F)F)c4)nnc3c2N1C]

HPLC-MS (method 4): Rt=4.68 min, [M+H]⁺ m/z 400.2.
¹H NMR (300 MHz, CDCl₃) δ 8.42 (m, 1H), 8.38 (s, 1H), 7.54 (m, 1H), 7.31 (m, 1H), 4.26 (dd, J=11.0, 1.9 Hz, 1H), 4.10 (dd, J=10.8, 2.1 Hz, 1H), 3.89 (s, 3H), 3.64 (m, 1H), 1.38 (d, J=6.4 Hz, 3H).
Yield: 16%.

Intermediate 28

5-Chloro-6,8-dimethyl-3-(3-trifluoromethoxy-phenyl)-7,8-dihydro-6H-9-oxa-1,2,3a,4,6-pentaaza-cyclopenta[a]naphthalene

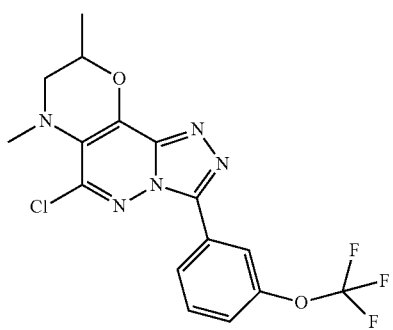 [SMILES: CC1CN(C)c2c(Cl)nn3c(-c4cccc(OC(F)(F)F)c4)nnc3c2O1]

HPLC-MS (method 4): Rt=4.93 min, [M+H]⁺ m/z 399.9.
¹H NMR (300 MHz, CDCl₃) δ 8.40 (m, 1H), 8.36 (s, 1H), 7.55 (m, 1H), 7.33 (m, 1H), 4.42 (m, 1H), 3.23 (dd, J=14.4, 2.3 Hz, 1H), 2.93 (s, 3H), 2.87 (dd, J=14.5, 9.6 Hz, 1H), 1.60 (d, J=6.4 Hz, 3H).
Yield: 17.6%.

Intermediate 29

5-Chloro-7,9-dimethyl-3-(3-trifluoromethoxy-phenyl)-8,9-dihydro-7H-6-oxa-1,2,3a,4,9-entaaza-cyclopenta[a]naphthalene

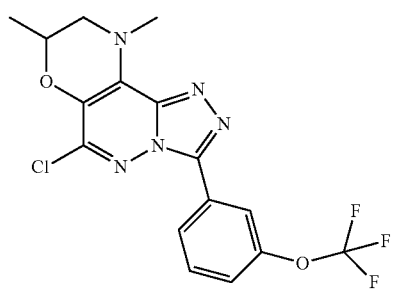 [SMILES: CC1CN(C)c2c(c(Cl)nn3c(-c4cccc(OC(F)(F)F)c4)nnc23)O1]

HPLC-MS (method 4): Rt=4.72 min, [M+H]⁺ m/z 400.0.
¹H NMR (300 MHz, CDCl₃) δ 8.44 (d, J=7.9 Hz, 1H), 8.40 (s, 1H), 7.55 (m, 1H), 7.31 (m, 1H), 4.24 (m, 1H), 3.87 (s, 3H), 3.45 (dd, J=12.8, 2.6 Hz, 1H), 3.32 (dd, J=12.8, 7.6 Hz, 1H), 1.47 (d, J=6.4 Hz, 3H).
Yield: 13%.

Intermediate 30

6-Chloro-3-(3-trifluoromethoxy-phenyl)-7,8,9,10-tetrahydro-[1,2,4]triazolo[3,4-a]phthalazine

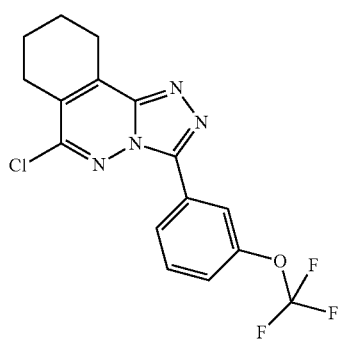 [SMILES: FC(F)(F)Oc1cccc(-c2nnc3c4c(c(Cl)nn23)CCCC4)c1]

HPLC-MS (method 4): Rt=4.85 min, [M+H]⁺ m/z 368.9.
Yield: 78.8%.

Intermediate 31

5-Chloro-6-methyl-7,8-dihydro-6H-9-oxa-1,2,3a,4,6-pentaaza-cyclopenta[a]naphthalene

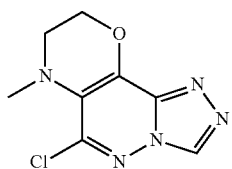

$^1$H NMR (300 MHz, CDCl$_3$) δ 8.87 (s, 1H), 4.51-4.44 (m, 2H), 3.26-3.21 (m, 2H), 2.89 (s, 3H).
Yield: 30%.

Intermediate 32

5-Chloro-9-methyl-8,9-dihydro-7H-6-oxa-1,2,3a,4,9-pentaaza-cyclopenta[a]naphthalene

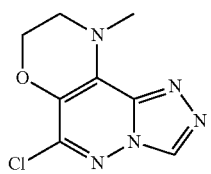

$^1$H NMR (300 MHz, CDCl$_3$) δ 8.83 (s, 1H), 4.41-4.34 (m, 2H), 3.90 (s, 3H), 3.64-3.57 (m, 2H).
Yield: 8%

Intermediate 33

3-bromo-5-chloro-6-methyl-7,8-dihydro-6H-9-oxa-1,2,3a,4,6-pentaaza cyclopenta[a]naphthalene

A mixture of 5-chloro-6-methyl-7,8-dihydro-6H-9-oxa-1,2,3a,4,6-pentaaza-cyclopenta[a]naphthalene (200 mg, 0.886 mmol) and N-bromosuccinimide (189 mg, 1.064 mmol) in chloroform (2.33 mL) The reaction mixture was stirred at RT for 20 h. The reaction was diluted with DCM and the organic layer was washed with Na$_2$S$_2$O$_3$ (10% sat solution). The combined organic layers were separated, dried (sodium sulphate), filtered and concentrated. The residue was purified by biotage flash chromatography (eluent: DCM-EtOAc 0-100%) to yield 3-bromo-5-chloro-6-methyl-7,8-dihydro-6H-9-oxa-1,2,3a,4,6-pentaaza-cyclopenta[a]naphthalene (170 mg, Yield: 64%).
HPLC-MS (method 4): Rt=3.3 min, [M+H]$^+$ 304.0, 306.0.
$^1$H NMR (300 MHz, CDCl$_3$) δ 3.77 (m, 2H), 3.48 (m, 2H), 3.03 (s, 3H).

General Procedure F: Suzuki Coupling

A mixture of 3-bromo-5-chloro-6-methyl-7,8-dihydro-6H-9-oxa-1,2,3a,4,6-pentaaza-cyclopenta[a]naphthalene (1 eq), the appropriate boronic acid (ex: 3-cyanophenylboronic acid) (1 eq), PdCl$_2$(dppf) (30%) and a saturated sodium carbonate solution (5.6 mL/mmol) in DME (13.5 mL/mmol) was heated under microwave irradiation at 80° C. for 2 h and 30 min. The reaction mixture was diluted with DCM and washed with water. The combined organic layers were dried (sodium sulphate), filtered and concentrated.

The residue was purified by column chromatography (Isolute/Flash, Sill, 0% to 30% MeOH in DCM) to give the desired product (ex: 3-(5-chloro-6-methyl-7,8-dihydro-6H-9-oxa-1,2,3a,4,6-pentaaza-cyclopenta[a]naphthalen-3-yl)-benzonitrile).

Intermediate 34

3-(5-Chloro-6-methyl-7,8-dihydro-6H-9-oxa-1,2,3a,4,6-pentaaza-cyclopenta[a]naphthalen-3-yl)-benzonitrile

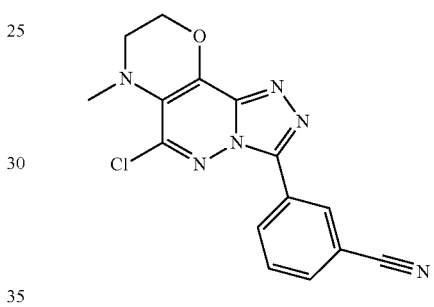

HPLC-MS (method 1): Rt=4.062 min, [M+H]$^+$ m/z 327.1.
$^1$H NMR (300 MHz, CDCl$_3$) δ 8.82 (t, J=1.4, 1H), 8.76-8.69 (m, 1H), 7.78 (dt, J=7.7, 1.4, 1H), 7.68 (d, J=7.9, 1H), 4.60-4.49 (m, 2H), 3.33-3.27 (m, 2H), 2.96 (s, 3H).
Yield: 31%.

Intermediate 35

5-Chloro-6-methyl-3-(3-trifluoromethyl-phenyl)-7,8-dihydro-6H-9-oxa-1,2,3a,4,6-pentaaza-cyclopenta[a]naphthalene

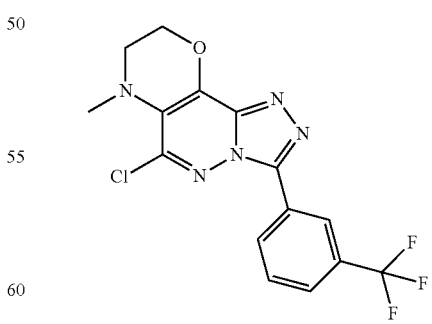

HPLC-MS (method 1): Rt=4.57 min, [M+H]$^+$ m/z 370.1.
$^1$H NMR (300 MHz, CDCl$_3$) δ 8.76 (s, 1H), 8.66 (d, J=7.8, 1H), 7.76 (d, J=7.8, 1H), 7.68 (t, J=7.9, 2H), 4.51 (t, J=4.3, 2H), 3.33-3.25 (m, 2H), 2.94 (s, 3H).
Yield: 99%

Intermediate 36

5-Chloro-3-(1H-indol-5-yl)-6-methyl-7,8-dihydro-6H-9-oxa-1,2,3a,4,6-pentaaza-cyclopenta[a]naphthalene

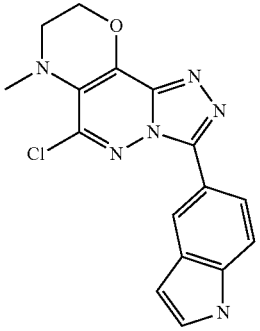 [SMILES: CN1CCOc2c1c(Cl)nn1c(-c3ccc4[nH]ccc4c3)nnc21]

HPLC-MS (method 1): Rt=3.95 min, [M+H]$^+$ m/z 341.1.
$^1$H NMR (300 MHz, CDCl$_3$) d 8.78 (s, 1H), 8.47 (s, 1H), 8.27 (dd, J=8.6, 1.6, 1H), 7.56 (d, J=8.6, 1H), 7.34-7.29 (m, 1H), 6.72 (brs, 1H), 4.59-4.46 (m, 2H), 3.35-3.23 (m, 2H), 2.94 (s, 3H).
Yield: 48%.

Intermediate 37

[3-(5-Chloro-6-methyl-7,8-dihydro-6H-9-oxa-1,2,3a,4,6-pentaaza-cyclopenta[a]naphthalen-3-yl)-phenyl]-dimethyl-amine

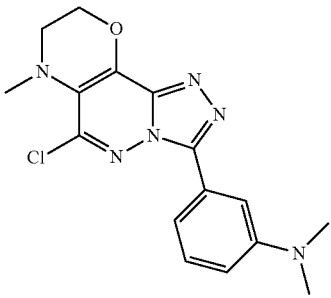

HPLC-MS (method 4): Rt=4.64 min, [M+H]$^+$ m/z 345.1.
Yield: 65%.

Intermediate 38

4-(5-Chloro-6-methyl-7,8-dihydro-6H-9-oxa-1,2,3a,4,6-pentaaza-cyclopenta[a]naphthalen-3-yl)-phenol

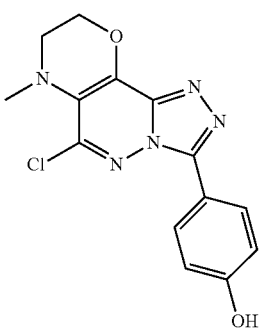 [SMILES: CN1CCOc2c1c(Cl)nn1c(-c3ccc(O)cc3)nnc21]

A solution of 5-chloro-3-(4-methoxy-phenyl)-6-methyl-7,8-dihydro-6H-9-oxa-1,2,3a,4,6-pentaaza-cyclopenta[a]naphthalene in DCM was cooled to −78° C. under argon. Then, borontribromide (solution in DCM) was added and the mixture was kept at −20° C. overnight. Once finished, reaction was cooled down to −20° C., borontribromide excess quenched with MeOH and neutralized with aq. sodium hydroxide solution. After solvent removal, the crude was used as such for next step.

HPLC-MS (method 4): Rt=3.6 min, [M+H]$^+$ m/z 317.7.
Yield: 99%.

Intermediate 39

4-(5-Chloro-9-methyl-8,9-dihydro-7H-6-oxa-1,2,3a,4,9-pentaaza-cyclopenta[a]naphthalen-3-yl)-phenol

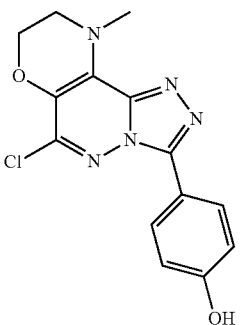 [SMILES: CN1CCOc2c(Cl)nn3c(-c4ccc(O)cc4)nnc3c21]

A solution of 5-chloro-3-(4-methoxy-phenyl)-9-methyl-8,9-dihydro-7H-6-oxa-1,2,3a,4,9-pentaaza-cyclopenta[a]naphthalene in dichloromethane was cooled down to −78° C. under argon. Then, borontribromide (solution in DCM) was added and the mixture was kept at −20° C. overnight. Once finished, reaction was cooled down to −20° C., borontribromide excess quenched with MeOH and neutralized with aq. sodium hydroxide solution. After solvent removal, the crude was used as such for next step.

HPLC-MS (method 4): Rt=3.9 min, [M+H]$^+$ m/z 317.7.
Yield: 99%.

EXAMPLES

General Method I

A solution of the appropriate chloride (1 eq) (ex: 5-chloro-6-methyl-3-(3-trifluoromethoxy-phenyl)-7,8-dihydro-6H-9-oxa-1,2,3a,4,6-pentaaza-cyclopenta-[a]naphthalene) and the appropriate amine (3 to 5 eq) (ex: 1-methyl-piperidin-4-ylamine) in nBuOH (15 mL/mmol) was heated up to 180-185° C. under microwave irradiation for 5 h-10 h (or 24 h at 160-180° C. in a silicon bath). The solvent was evaporated under vacuum and the residue was purified by flash chromatography (Isolute/Flash, Sill, 2.5% MeOH with 7N ammonia in DCM) or by semi-preparative HPLC (Gemini C18 (150 10 mm; 5 m), Solvent A: water with 0.1% formic acid; Solvent B: acetonitrile with 0.1% formic acid. Gradient: 40% of A to 0% of A).

The NH-BOC-protected amines got deprotected in the reaction conditions and reacted giving a mixture of regioisomers.

Example 1

[3-(4-Methoxy-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine

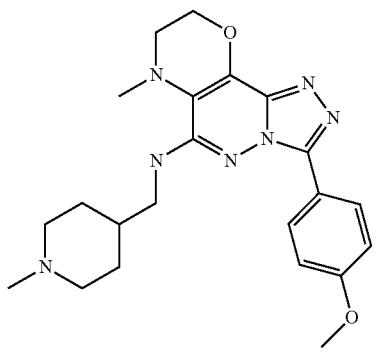 [SMILES: COc1ccc(-c2nnc3c4c(c(NCC5CCN(C)CC5)nn23)N(C)CCO4)cc1]

Amine: (1-methyl-4-piperidinyl)methylamine

HPLC-MS (method 3): Rt=3.59 min, [M+H]$^+$=424.1.

$^1$H NMR (300 MHz, MeOD) δ 8.34 (d, J=8.4, 2H), 7.10 (d, J=8.4, 2H), 4.50 (s, 2H), 3.90 (s, 3H), 3.42 (d, J=6.1, 3H), 2.75 (d, J=19.5, 8H), 2.17 (s, 1H), 2.04 (d, J=13.5, 2H), 1.57 (s, 2H).

Example 2

(1-Methyl-piperidin-4-yl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

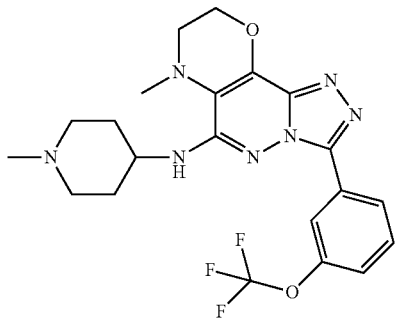 [SMILES: CN1CCC(Nc2nn3c(-c4cccc(OC(F)(F)F)c4)nnc3c3c2N(C)CCO3)CC1]

Amine: 4-amino-1-methylpiperidine

HPLC-MS (method 1): Rt=3.101 min, [M+H]$^+$ m/z 464.3.

$^1$H NMR (300 MHz, CDCl$_3$) δ 8.56 (s, 1H), 8.41 (d, J=8.0 Hz, 1H), 7.51 (t, J=8.1 Hz, 1H), 7.28 (d, J=8.3 Hz, 1H), 5.01 (d, J=7.3 Hz, 1H), 4.54-4.38 (m, 2H), 4.05-3.84 (m, 1H), 3.20 (dd, J=11.7, 7.3 Hz, 4H), 2.71 (s, 3H), 2.51 (m, 5H), 2.27 (d, J=10.9 Hz, 2H), 1.95 (td, J=14.8, 3.7 Hz, 2H),

Example 3

(1-Methyl-piperidin-4-yl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

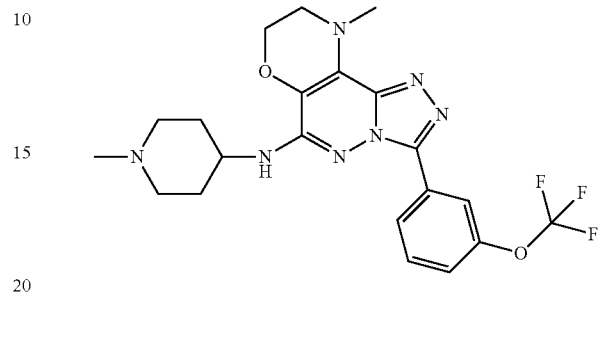

Amine: 4-amino-1-methylpiperidine

HPLC-MS (method 1): Rt=3.17 min, [M+H]$^+$ m/z 464.3.

$^1$H NMR (300 MHz, CDC$_3$) δ 8.58 (s, 1H), 8.39 (d, J=8.0 Hz, 1H), 7.50 (t, J=8.1 Hz, 1H), 7.26 (dd, J=4.1, 3.0 Hz, 1H), 4.83 (d, J=7.7 Hz, 1H), 4.35-4.26 (m, 2H), 4.00-3.82 (m, 1H), 3.70 (s, 3H), 3.46 (t, J=4.3 Hz, 2H), 3.27 (d, J=11.8 Hz, 2H), 2.64-2.43 (m, 5H), 2.24 (d, J=11.2 Hz, 2H), 1.91 (td, J=14.6, 3.6 Hz, 2H).

Example 4

[3-(4-Methoxy-phenyl)-6-methyl-7,8-dihydro-6H-9-oxa-1,2,3a,4,6-pentaaza-cyclopenta[a]naphthalen-5-yl]-(2-morpholin-4-yl-ethyl)-amine

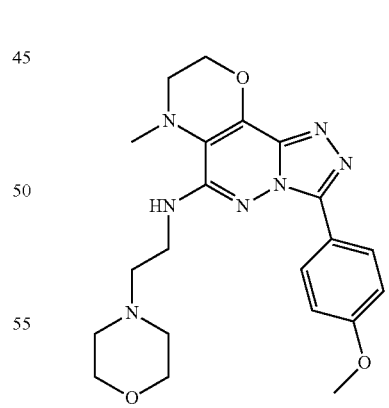

Amine: 4-(2-aminoethyl)morpholine

HPLC-MS (method 1): Rt=2.47 min, [M+H]$^+$ m/z 426.2.

$^1$H NMR (300 MHz, CDCl$_3$) δ 8.54-8.37 (m, 2H), 7.06-6.90 (m, 2H), 5.63 (t, J=4.4 Hz, 1H), 4.46-4.35 (m, 2H), 3.84 (s, 3H), 3.70 (dd, J=12.7, 8.2 Hz, 4H), 3.49 (dd, J=10.9, 5.5 Hz, 2H), 3.24-3.14 (m, 2H), 2.79-2.65 (m, 5H), 2.57-2.47 (m, 4H).

Example 5

Dimethyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-amine

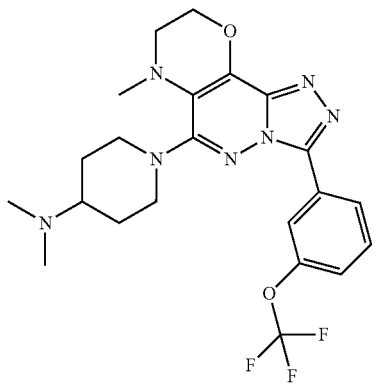 [SMILES: CN1CCOc2c1c(N1CCC(N(C)C)CC1)nn1c(-c3cccc(OC(F)(F)F)c3)nnc21]

Amine: 4-(dimethylamino)piperidine
HPLC-MS (method 1): Rt=3.15 min, [M+H]$^+$ m/z 479.3.
$^1$H NMR (300 MHz, CDCl$_3$) δ 8.47 (s, 1H), 8.43-8.36 (m, 1H), 7.51 (t, J=8.1 Hz, 1H), 7.31-7.19 (m, 1H), 4.35-4.25 (m, 4H), 3.31-3.18 (m, 3H), 2.88 (s, 3H), 2.84-2.58 (m, 5H), 2.51 (s, 6H), 2.12 (d, J=12.6 Hz, 2H), 1.89-1.68 (m, 2H).

Example 6

Dimethyl-{1-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl}-amine

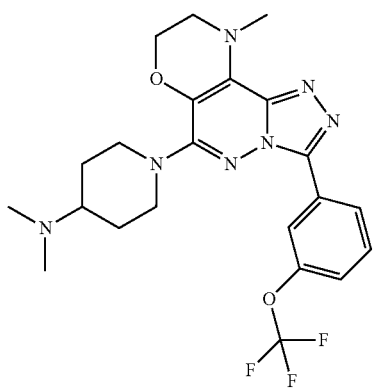 [SMILES: CN1CCOc2c(N3CCC(N(C)C)CC3)nn3c(-c4cccc(OC(F)(F)F)c4)nnc3c21]

Amine: 4-(dimethylamino)piperidine
HPLC-MS (method 1): Rt=3.32 min, [M+H]$^+$ m/z 479.3.
$^1$H NMR (300 MHz, CDC$_3$) δ 8.56 (s, 1H), 8.51-8.40 (m, 1H), 7.54 (t, J=8.1 Hz, 1H), 7.32-7.28 (m, 1H), 4.40-4.26 (m, 2H), 4.05 (d, J=12.9 Hz, 2H), 3.79 (s, 3H), 3.62-3.43 (m, 2H), 2.86 (t, J=11.7 Hz, 2H), 2.50 (d, J=11.4 Hz, 1H), 2.40 (s, 6H), 1.99 (d, J=11.7 Hz, 2H), 1.76 (tt, J=12.0, 6.2 Hz, 2H).

Example 7

Cyclopropylmethyl-[6-methyl-3-(3-trifluoromethoxy-phenyl)-7,8-dihydro-6H-9-oxa-1,2,3a,4,6-pentaaza-cyclopenta[a]naphthalen-5-yl]-amine

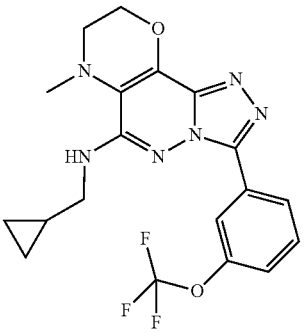 [SMILES: CN1CCOc2c1c(NCC1CC1)nn1c(-c3cccc(OC(F)(F)F)c3)nnc21]

Amine: cyclopropanemethylamine
HPLC-MS (method 2): Rt=1.84 min, [M+H]$^+$ m/z 421.
$^1$H NMR (300 MHz, CDCl$_3$) δ 8.59 (s, 1H), 8.43 (d, J=7.9, 1H), 7.50 (t, J=8.1, 1H), 7.29-7.21 (m, 1H), 5.11 (t, J=4.9, 1H), 4.52-4.39 (m, 2H), 3.32-3.15 (m, 4H), 2.75 (s, 3H), 1.27-1.09 (m, 1H), 0.65-0.55 (m, 2H), 0.30 (q, J=4.8, 2H).

Example 8

Cyclopropylmethyl-[9-methyl-3-(3-trifluoromethoxy-phenyl)-8,9-dihydro-7H-6-oxa-1,2,3a,4,9-pentaaza-cyclopenta[a]naphthalen-5-yl]-amine

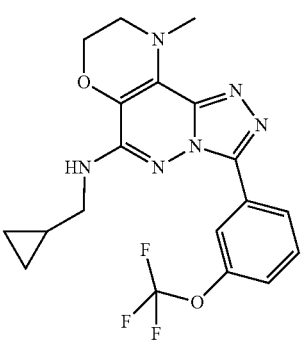 [SMILES: CN1CCOc2c(NCC3CC3)nn3c(-c4cccc(OC(F)(F)F)c4)nnc3c21]

Amine: cyclopropanemethylamine
HPLC-MS (method 2): Rt=2.64 min, [M+H]$^+$ m/z 421.
$^1$H NMR (300 MHz, CDCl$_3$) δ 8.66-8.58 (m, 1H), 8.48-8.39 (m, 1H), 7.49 (t, J=8.1, 1H), 7.28-7.18 (m, 1H), 4.95 (t, J=5.0, 1H), 4.34 (dd, J=11.3, 7.1, 2H), 3.69 (s, 3H), 3.46 (dd, J=9.4, 5.0, 2H), 3.23 (dd, J=7.1, 5.3, 2H), 1.14 (qdd, J=12.1, 7.5, 4.8, 1H), 0.64-0.52 (m, 2H), 0.34-0.23 (m, 2H).

Example 9

(4-Fluoro-benzyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

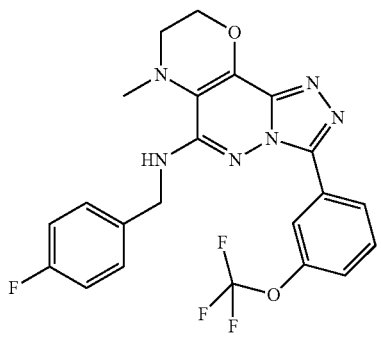 [SMILES: CN1CCOc2c1c(NCc1ccc(F)cc1)nn1c(-c3cccc(OC(F)(F)F)c3)nnc21]

Amine: 4-fluorobenzylamine

HPLC-MS (method 2): Rt=2 min, [M+H]$^+$ m/z 475.

$^1$H NMR (300 MHz, CDCl$_3$) δ 8.45 (s, 1H), 8.33 (d, J=7.9, 1H), 8.23 (s), 7.47 (t, J=8.1, 1H), 7.41-7.32 (m, 2H), 7.31-7.21 (m, 1H), 7.11-6.99 (m, 2H), 5.36 (t, J=5.2, 1H), 4.56 (d, J=5.5, 2H), 4.51-4.43 (m, 2H), 3.24-3.16 (m, 2H), 2.75 (s, 3H).

Example 10

(4-Fluoro-benzyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

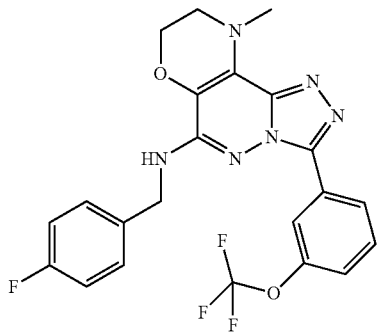 [SMILES: CN1CCOc2c(NCc3ccc(F)cc3)nn3c(-c4cccc(OC(F)(F)F)c4)nnc3c21]

Amine: 4-fluorobenzylamine

HPLC-MS (method 2): Rt-2 min, [M+H]$^+$ m/z 475.

$^1$H NMR (300 MHz, CDCl$_3$) δ 8.48 (s, 1H), 8.39-8.31 (m, 1H), 7.51-7.41 (m, 1H), 7.40-7.31 (m, 2H), 7.28-7.19 (m, 1H), 7.09-6.97 (m, 2H), 5.17 (t, J=5.5, 1H), 4.55 (d, J=5.6, 2H), 4.33 (dd, J=10.5, 6.3, 2H), 3.71 (s, 3H), 3.52-3.40 (m, 2H).

Example 11

Cyclopropylmethyl-[6-ethyl-3-(3-trifluoromethoxy-phenyl)-7,8-dihydro-6H-9-oxa-1,2,3a,4,6-pentaaza-cyclopenta[a]naphthalen-5-yl]-amine

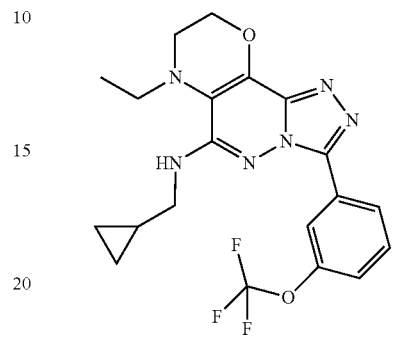

Amine: cyclopropanemethylamine

HPLC-MS (method 2): Rt=2.63 min, [M+H]$^+$ m/z 435.

$^1$H NMR (300 MHz, CDCl$_3$) δ 8.63-8.55 (m, 1H), 8.47-8.38 (m, 1H), 7.50 (t, J=8.1 Hz, 1H), 7.30-7.19 (m, 1H), 5.00 (t, J=4.9 Hz, 1H), 4.45-4.35 (m, 2H), 3.31-3.14 (m, 4H), 2.86 (q, J=7.1 Hz, 2H), 1.30 (t, J=7.1 Hz, 3H), 1.18 (qdd, J=12.2, 7.4, 4.9 Hz, 1H), 0.66-0.57 (m, 2H), 0.31 (q, J=4.7 Hz, 2H).

Example 12

[6-Ethyl-3-(3-trifluoromethoxy-phenyl)-7,8-dihydro-6H-9-oxa-1,2,3a,4,6-pentaaza-cyclopenta[a]naphthalen-5-yl]-(1-methyl-piperidin-4-ylmethyl)-amine

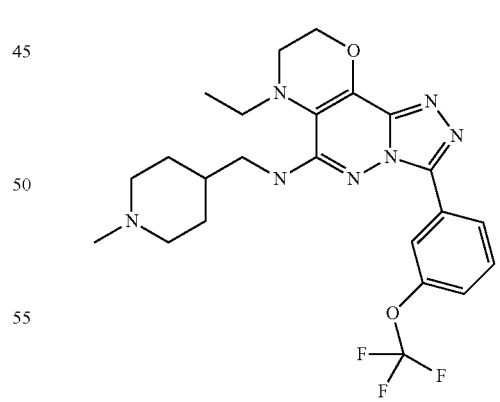

Amine: (1-methyl-4-piperidinyl)methanamine

HPLC-MS (method 1): Rt=3.32 min, [M+H]$^+$ m/z 492.3.

$^1$H NMR (300 MHz, CDCl$_3$) δ 8.61 (s, 1H), 8.46 (d, J=8.0 Hz, 1H), 7.52 (m, 1H), 7.28 (m, 1H), 5.00 (t, J=5.6 Hz, 1H), 4.43 (m, 2H), 3.36 (t, J=5.9 Hz, 2H), 3.21 (m, 2H), 2.93 (m, 2H), 2.86 (q, J=7.2 Hz, 3H), 2.28 (s, 3H), 1.97 (m, 2H), 1.79 (m, 3H), 1.45 (m, 2H), 1.30 (t, J=7.1 Hz, 3H).

Example 13

[8-Ethyl-3-(3-trifluoromethoxy-phenyl)-7,8-dihydro-6H-5-oxa-1,2,3a,4,8-pentaaza-cyclopenta[b]naphthalen-9-yl]-(1-methyl-piperidin-4-ylmethyl)-amine

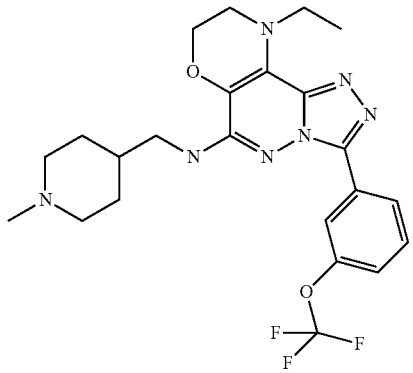 [SMILES: CCN1CCOc2c(NCC3CCN(C)CC3)nn3c(-c4cccc(OC(F)(F)F)c4)nnc3c21]

Amine: (1-methyl-4-piperidinyl)methanamine

HPLC-MS (method 1): Rt=3.32 min, [M+H]$^+$ m/z 492.3.

$^1$H NMR (300 MHz, CDCl$_3$) δ 8.64 (s, 1H), 8.47 (d, J=8.0 Hz, 1H), 7.51 (m, 1H), 7.26 (m, 1H), 4.97 (t, J=5.7 Hz, 1H), 4.29 (m, 4H), 3.53 (m, 2H), 3.34 (t, J=6.0 Hz, 2H), 2.92 (m, 2H), 2.29 (s, 3H), 1.97 (m, 2H), 1.79 (m, 3H), 1.42 (m, 2H), 1.26 (t, J=7.0 Hz, 3H).

Example 14

[9-Ethyl-3-(3-trifluoromethoxy-phenyl)-8,9-dihydro-7H-6-oxa-1,2,3a,4,9-pentaaza-cyclopenta[a]naphthalen-5-yl]-(tetrahydro-pyran-4-yl)-amine

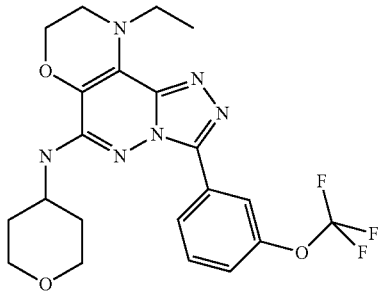 [SMILES: CCN1CCOc2c(NC3CCOCC3)nn3c(-c4cccc(OC(F)(F)F)c4)nnc3c21]

Amine: 4-aminotetrahydropyran hydrochloride

HPLC-MS (method 1): Rt=6.06 min, [M+H]$^+$ m/z 465.3.

$^1$H NMR (300 MHz, CDCl$_3$) δ 8.61 (s, 1H), 8.43 (d, J=8.0 Hz, 1H), 7.50 (m, 1H), 7.26 (m, 1H), 4.75 (d, J=7.3 Hz, 1H), 4.28 (m, 4H), 4.03 (m, 3H), 3.55 (m, 4H), 2.13 (m, 2H), 1.59 (m, 2H), 1.25 (t, J=7.0 Hz, 3H).

Example 15

(4-Fluoro-benzyl)-[3-(4-methoxy-phenyl)-6,9-dimethyl-6,7,8,9-tetrahydro-1,2,3a,4,6,9-hexaaza-cyclopenta[a]naphthalen-5-yl]-amine

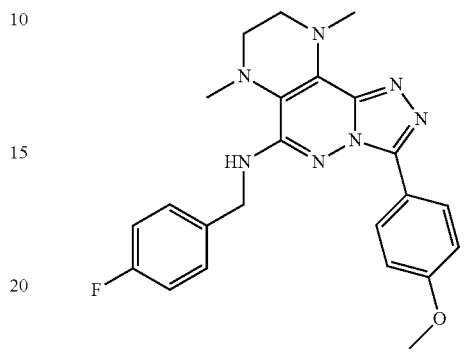

Amine: 4-fluorobenzylamine

HPLC-MS (method 1): Rt=5.90 min, [M+H]$^+$ m/z 434

$^1$H NMR (300 MHz, CDCl$_3$) δ 8.40-8.30 (m, 2H), 7.37 (dd, J=8.6, 5.4, 2H), 7.09-6.99 (m, 2H), 6.98-6.90 (m, 2H), 5.44 (t, J=5.5, 1H), 4.52 (d, J=5.5, 2H), 3.86 (s, 3H), 3.85 (s, 3H), 3.45-3.34 (m, 2H), 3.07-2.96 (m, 2H), 2.59 (s, 3H).

Example 16

(1-Methyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

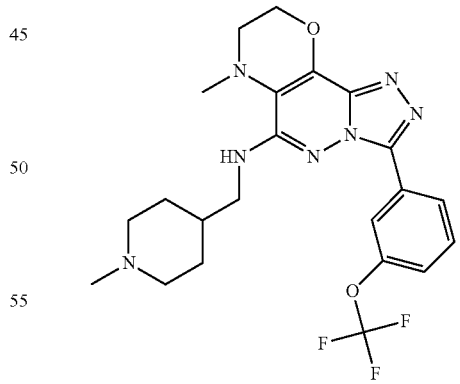

Amine: (1-methyl-4-piperidinyl)methanamine

HPLC-MS (method 1): Rt=3.157, [M+H]$^+$ m/z 478.3.

$^1$H NMR (300 MHz, CDCl$_3$) δ 8.49 (s, 1H), 8.38 (d, J=8.0, 1H), 7.51 (t, J=8.1, 1H), 7.29 (t, J=3.6, 1H), 5.53 (s, 1H), 4.51-4.41 (m, 2H), 3.55 (d, J=10.9, 2H), 3.42 (t, J=5.7, 2H), 3.25-3.13 (m, 2H), 2.74 (s, 3H), 2.72 (s, 3H), 2.20 (brs, 1H), 2.07-1.72 (m, 4H). Yield: 48%.

Example 17

(1-Methyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

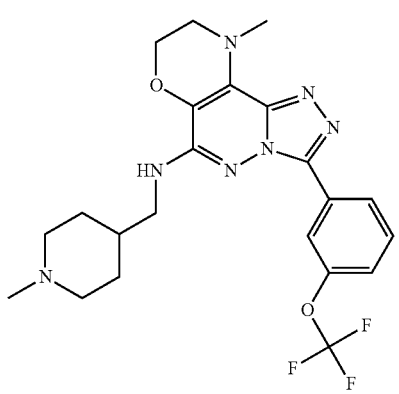 [SMILES: CN1CCC(CNc2nn3c(-c4cccc(OC(F)(F)F)c4)nnc3c3c2OCCN3C)CC1]

Amine: (1-methyl-4-piperidinyl)methanamine

HPLC-MS (method 1): Rt=3.333 min, [M+H]⁺ m/z 478.3.

$^1$H NMR (300 MHz, CDCl$_3$) δ 8.55 (s, 1H), 8.40 (d, J=8.0, 1H), 7.51 (t, J=8.1, 1H), 7.27 (d, J=8.1, 1H), 5.22 (t, J=5.7, 1H), 4.38-4.25 (m, 2H), 3.70 (s, 3H), 3.49 (dd, J=13.5, 9.3, 4H), 3.37 (t, J=6.3, 2H), 2.69 (s, 3H), 2.65 (s, 1H), 2.13 (s, 1H), 1.95 (s, 1H), 1.78 (t, J=12.2, 2H).

Example 18

Methyl-(1-methyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

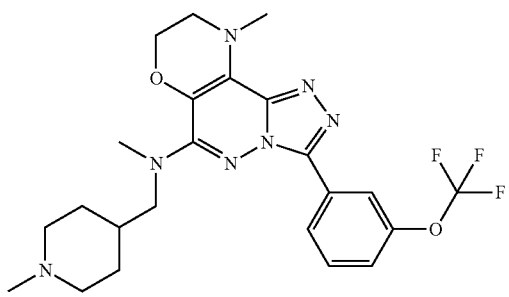 [SMILES: CN1CCC(CN(C)c2nn3c(-c4cccc(OC(F)(F)F)c4)nnc3c3c2OCCN3C)CC1]

Amine: 1-Methyl-4-(methylaminomethyl)-piperidine

HPLC-MS (method 1): Rt=3.54 min, [M+H]⁺ m/z 492.4.

$^1$H NMR (300 MHz, CDCl$_3$) δ 8.58 (s, 1H), 8.46 (d, J=8.0 Hz, 1H), 7.52 (t, J=8.1 Hz, 1H), 7.27 (d, J=4.0 Hz, 1H), 4.32-4.23 (m, 2H), 3.76 (s, 3H), 3.50 (m, J=6.5 Hz, 7H), 3.36 (d, J=7.0 Hz, 2H), 3.03 (s, 3H), 2.84 (d, J=11.4 Hz, 2H), 2.26 (s, 3H), 1.89 (t, J=10.9 Hz, 2H), 1.69 (d, J=13.4 Hz, 2H), 1.53 (s, 1H), 1.41-1.18 (m, 2H).

Example 19

4-[6-Methyl-3-(3-trifluoromethoxy-phenyl)-7,8-dihydro-6H-9-oxa-1,2,3a,4,6-pentaaza-cyclopenta[a]naphthalen-5-ylamino]-cyclohexanol

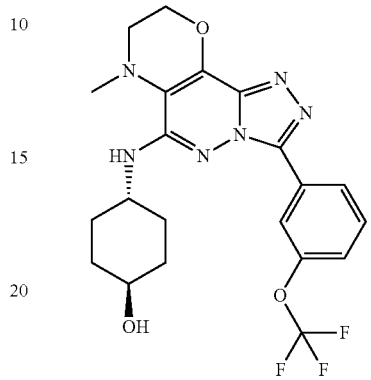

Amine: (trans-4-aminocyclohexanol hydrochloride

HPLC-MS (method 1): Rt=4.897 min, [M+H]⁺ m/z 465.2.

$^1$H NMR (300 MHz, CDCl$_3$) δ 8.58 (s, 1H), 8.49-8.44 (m, 1H), 7.53 (t, J=8.1, 1H), 7.34-7.27 (m, 1H), 4.89 (d, J=6.9, 1H), 4.53-4.42 (m, 2H), 3.88-3.70 (m, 2H), 3.23-3.18 (m, 2H), 2.73 (s, 3H), 2.30 (d, J=11.3, 2H), 2.10 (d, J=11.3, 2H), 1.46 (ddd, J=23.7, 13.3, 3.0, 4H).

Example 20

4-[9-Methyl-3-(3-trifluoromethoxy-phenyl)-8,9-dihydro-7H-6-oxa-1,2,3a,4,9-pentaaza-cyclopenta[a]naphthalen-5-ylamino]-cyclohexanol

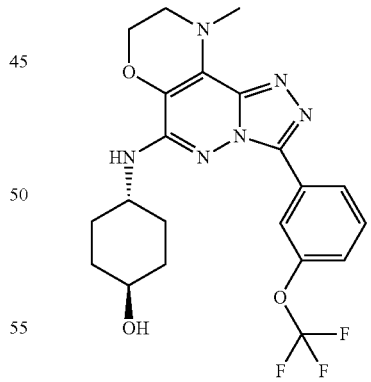

Amine: (trans-4-aminocyclohexanol hydrochloride

HPLC-MS (method 1): Rt=5.25 min, [M+H]⁺ m/z 465.2.

$^1$H NMR (300 MHz, CDCl$_3$) δ 8.60 (s, 1H), 8.46 (d, J=8.0, 1H), 7.52 (t, J=8.1, 1 H), 7.32-7.28 (m, 1H), 4.71 (d, J=7.3, 1 H), 4.39-4.28 (m, 2H), 3.71 (s, 3H), 3.52-3.41 (m, 2H), 2.27 (d, J=11.6, 2H), 2.08 (d, J=10.5, 2H), 1.63-1.23 (m, 5H).

Yield: 18%.

Example 21

3-[6-Methyl-3-(3-trifluoromethoxy-phenyl)-7,8-dihydro-6H-9-oxa-1,2,3a,4,6-pentaaza-cyclopenta[a]naphthalen-5-ylamino]-propan-1-ol

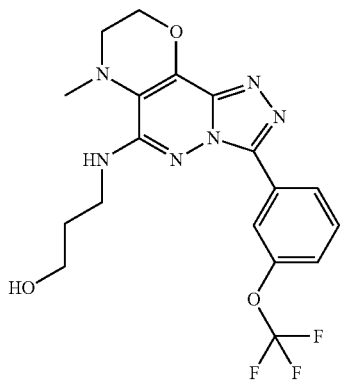 [SMILES: CN1CCOc2c1c(NCCCO)nn1c(-c3cccc(OC(F)(F)F)c3)nnc21]

Amine: 3-amino-1-propanol
HPLC-MS (method 1): Rt=4.775 min, [M+H]$^+$ m/z 425.0.
$^1$H NMR (300 MHz, CDCl$_3$) δ 8.59 (s, 1H), 8.45 (d, J=8.0, 1H), 7.52 (t, J=8.1, 1H), 7.28 (d, J=6.9, 1H), 5.64 (brs, 1H), 4.53-4.38 (m, 2H), 3.88 (t, J=5.6, 2H), 3.62 (dd, J=12.0, 6.1, 2H), 3.27-3.10 (m, 2H), 2.75 (s, 3H), 2.09-1.93 (m, 2H).

Example 22

3-[9-Methyl-3-(3-trifluoromethoxy-phenyl)-8,9-dihydro-7H-6-oxa-1,2,3a,4,9-pentaaza-cyclopenta[a]naphthalen-5-ylamino]-propan-1-ol

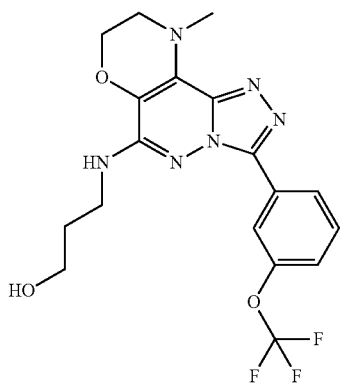 [SMILES: CN1CCOc2c(NCCCO)nn3c(-c4cccc(OC(F)(F)F)c4)nnc3c21]

Amine: 3-amino-1-propanol
HPLC-MS (method 1): Rt=6.06 min, [M+H]$^+$ m/z 425.0.
$^1$H NMR (300 MHz, CDCl$_3$) δ 8.56 (d, J=1.1, 1H), 8.46-8.39 (m, 1H), 7.51 (t, J=8.1, 1H), 7.31-7.23 (m, 1H), 5.25 (t, J=5.5, 1H), 4.32-4.24 (m, 2H), 3.81 (t, J=5.8, 2H), 3.69 (s, 3H), 3.58 (dd, J=12.4, 6.1, 2H), 3.47-3.37 (m, 2H), 1.94 (dt, J=12.0, 6.1, 2H).

Example 23

[6-Methyl-3-(3-trifluoromethoxy-phenyl)-7,8-dihydro-6H-9-oxa-1,2,3a,4,6-pentaaza-cyclopenta[a]naphthalen-5-yl]-(tetrahydro-pyran-4-yl)-amine

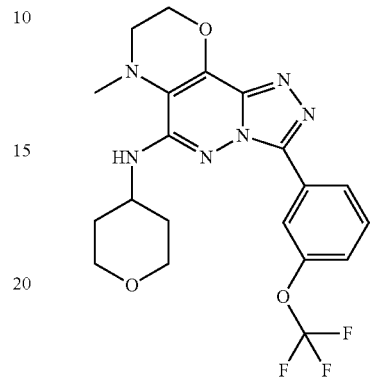

Amine: 4-aminotetrahydropyran hydrochloride
HPLC-MS (method 1): Rt=5.42 min, [M+H]$^+$ m/z 451.2.
$^1$H NMR (300 MHz, CDCl$_3$) δ 8.58 (s, 1H), 8.47-8.41 (m, 1H), 7.53 (t, J=8.1, 1H), 7.34-7.28 (m, 1H), 4.96 (d, J=6.9, 1H), 4.53-4.43 (m, 2H), 4.05 (dt, J=7.1, 3.8, 3H), 3.60 (td, J=11.7, 2.1, 2H), 3.27-3.18 (m, 2H), 2.76 (s, 3H), 2.18 (dd, J=12.3, 2.2, 2H), 1.73-1.55 (m, 2H).

Example 24

(3,4-Dimethoxy-benzyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

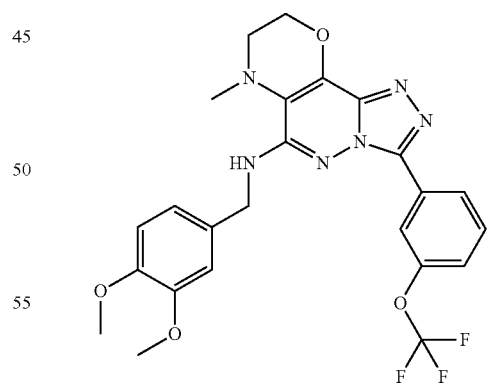

Amine: 3,4-dimethoxybenzylamine
HPLC-MS (method 1): Rt=5.736 min, [M+H]$^+$ m/z 517.3.
$^1$H NMR (300 MHz, CDCl$_3$) δ 8.56 (s, 1H), 8.41 (d, J=7.9, 1H), 7.51 (t, J=8.1, 1H), 7.28 (d, J=7.1, 1H), 7.00-6.92 (m, 2H), 6.87 (d, J=8.0, 1H), 5.33 (t, J=5.2, 1H), 4.54 (d, J=5.3, 2H), 4.50-4.43 (m, 2H), 3.88 (s, 3H), 3.82 (s, 3H), 3.24-3.16 (m, 2H), 2.76 (s, 3H).

Example 25

(3,4-Dimethoxy-benzyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

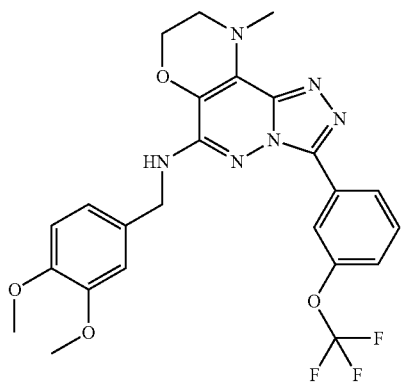 [SMILES: COc1ccc(CNc2nn3c(-c4cccc(OC(F)(F)F)c4)nnc3c3c2OCCN3C)cc1OC]

HPLC-MS (method 1): Rt=6.11 min, [M+H]+ m/z 517.3.

$^1$H NMR (300 MHz, CDCl$_3$) δ 8.58 (s, 1H), 8.43 (d, J=7.9, 1H), 7.50 (t, J=8.1, 1H), 7.26 (t, J=4.1, 1H), 6.96 (d, J=7.6, 2H), 6.86 (d, J=7.8, 1H), 5.13 (t, J=5.3, 1H), 4.52 (d, J=5.4, 2H), 4.32 (t, J=4.2, 2H), 3.87 (s, 3H), 3.82 (s, 3H), 3.72 (s, 3H), 3.51-3.44 (m, 2H).

Example 26

[6-Methyl-3-(3-trifluoromethoxy-phenyl)-7,8-dihydro-6H-9-oxa-1,2,3a,4,6-pentaaza-cyclopenta[a]naphthalen-5-yl]-(2-pyridin-3-yl-ethyl)-amine

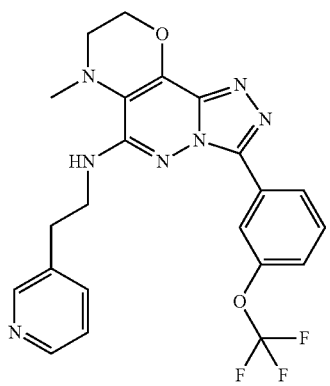 [SMILES: CN1CCOc2c1c(NCCc1cccnc1)nn1c(-c3cccc(OC(F)(F)F)c3)nnc21]

Amine: 2-pyridin-3-yl-ethylamine

HPLC-MS (method 1): Rt=3.85 min, [M+H]+ m/z 473.2.

$^1$H NMR (300 MHz, CDCl$_3$) δ 8.52 (dd, J=25.8, 13.5, 4H), 7.64-7.50 (m, 2H), 7.35-7.26 (m, 2H), 5.13 (t, J=5.5, 1H), 4.53-4.42 (m, 2H), 3.76 (dd, J=12.8, 6.8, 2H), 3.23-3.15 (m, 2H), 3.08 (t, J=6.9, 2H), 2.63 (s, 3H).

Example 27

[2-(4-Methyl-piperazin-1-yl)-ethyl]-[6-methyl-3-(3-trifluoromethoxy-phenyl)-5,6,7,8-tetrahydro-9-oxa-1,2,3a,4,6-pentaaza-cyclopenta[a]naphthalen-5-yl]-amine

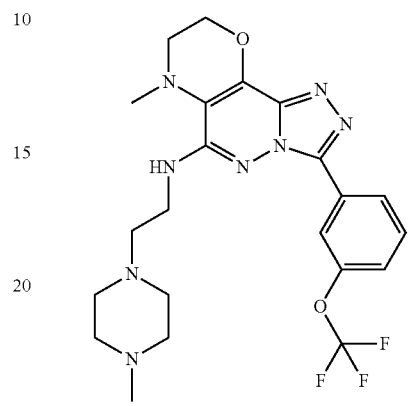

Amine: 2-(4-methyl-piperazin-1-yl)-ethylamine

HPLC-MS (method 1): Rt=3.10 min, [M+H]+ m/z 494.3.

$^1$H NMR (300 MHz, CDCl$_3$) δ 8.60 (s, 1H), 8.50-8.43 (m, 1H), 7.53 (t, J=8.1, 1H), 7.32-7.26 (m, 1H), 5.77 (t, J=4.5, 1H), 4.54-4.42 (m, 2H), 3.52 (dd, J=11.0, 5.7, 2H), 3.28-3.19 (m, 2H), 2.78 (s, 3H), 2.78-2.76 (m, 2H), 2.68-2.58 (s, 4H), 2.57-2.48 (s, 4H), 2.35 (s, 3H).

Example 28

[2-(4-Methyl-piperazin-1-yl)-ethyl]-[9-methyl-3-(3-trifluoromethoxy-phenyl)-5,7,8,9-tetrahydro-6-oxa-1,2,3a,4,9-pentaaza-cyclopenta[a]naphthalen-5-yl]-amine

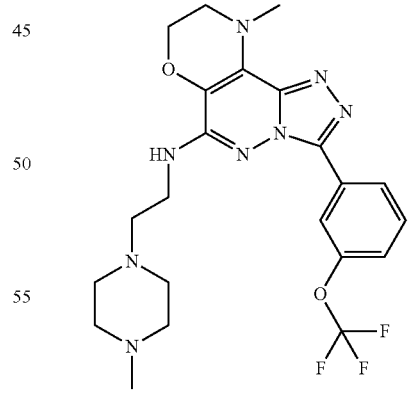

Amine: 2-(4-Methyl-piperazin-1-yl)-ethylamine

HPLC-MS (method 1): Rt=3.28 min, [M+H]+ m/z 494.3.

$^1$H NMR (300 MHz, CDCl$_3$) δ 8.60 (s, 1H), 8.48-8.39 (m, 1H), 7.54 (t, J=8.1, 1H), 7.33-7.26 (m, 1H), 5.42 (t, J=4.9, 1H), 4.41-4.32 (m, 2H), 3.74 (s, 3H), 3.57 (dd, J=11.5, 5.8, 2H), 3.52-3.47 (m, 2H), 2.83 (dd, J=14.7, 8.6, 10H), 2.54 (s, 3H).

Example 29

[6-Methyl-3-(3-trifluoromethoxy-phenyl)-5,6,7,8-tetrahydro-9-oxa-1,2,3a,4,6-pentaaza-cyclopenta[a]naphthalen-5-yl]-(2-morpholin-4-yl-ethyl)-amine

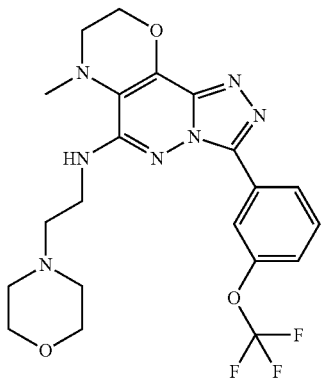 [SMILES: CN1CCOc2c1c(NCCN1CCOCC1)nn1c(-c3cccc(OC(F)(F)F)c3)nnc21]

Amine: 4-(2-aminoethyl)morpholine

HPLC-MS (method 1): Rt=3.06 min, [M+H]$^+$ m/z 481.2.

$^1$H NMR (300 MHz, CDCl$_3$) δ 8.61 (d, J=1.1, 1H), 8.53-8.41 (m, 1H), 7.53 (t, J=8.1, 1H), 7.34-7.23 (m, 1H), 5.78 (brs, 1H), 4.52-4.45 (m, 2H), 3.81-3.73 (m, 4H), 3.54 (dd, J=10.6, 5.2, 2H), 3.28-3.21 (m, 2H), 2.79 (s, 3H), 2.75 (d, J=5.8, 2H), 2.58 (brs, 4H).

Example 30

[9-Methyl-3-(3-Trifluoromethoxy-phenyl)-5,7,8,9-tetrahydro-6-oxa-1,2,3a,4,9-pentaaza-cyclopenta[a]naphthalen-5-yl]-(2-morpholin-4-yl-ethyl)-amine

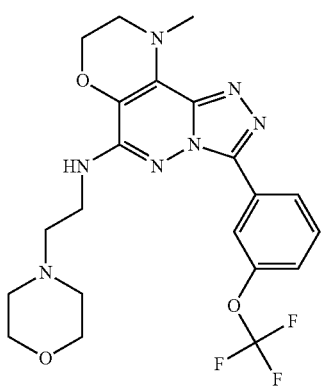 [SMILES: CN1CCOc2c(NCCN3CCOCC3)nn3c(-c4cccc(OC(F)(F)F)c4)nnc3c21]

Amine: 4-(2-aminoethyl)morpholine

HPLC-MS (method 1): Rt=3.22 min, [M+H]$^+$ m/z 481.2.

$^1$H NMR (300 MHz, CDCl$_3$) δ 8.63 (s, 1H), 8.50-8.45 (m, 1H), 7.53 (t, J=8.1, 1H), 7.31-7.24 (m, 1H), 5.49 (brs, 1H), 4.41-4.33 (m, 2H), 3.80-3.75 (m, 4H), 3.74 (s, 3H), 3.55-3.49 (m, 4H), 2.73-2.69 (m, 2H), 2.59-2.51 (m, 4H).

Example 31

3-{6-Methyl-5-[(1-methyl-piperidin-4-ylmethyl)-amino]-7,8-dihydro-6H-9-oxa-1,2,3a,4,6-pentaaza-cyclopenta[a]naphthalen-3-yl}-benzonitrile

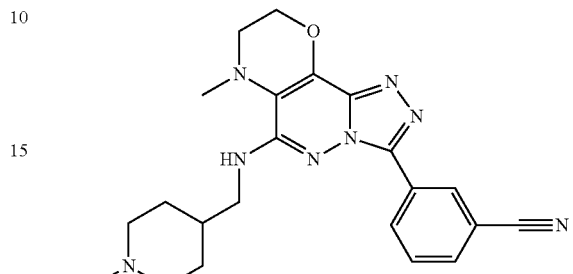

Amine: (1-methyl-4-piperidinyl)methanamine

HPLC-MS (method 1): Rt=2.74 min, [M+H]$^+$ m/z 419.2.

$^1$H NMR (300 MHz, MeOD) δ 8.80 (s, 1H), 8.46 (d, J=8.1, 1H), 8.34 (s, 1H), 7.73 (d, J=7.7, 1H), 7.60 (t, J=7.9, 1H), 4.43-4.35 (m, 2H), 3.44 (d, J=12.1, 2H), 3.28 (d, J=6.9, 2H), 3.19-3.14 (m, 2H), 3.00 (t, J=11.5, 2H), 2.76 (s, 3H), 2.68 (s, 3H), 2.24 (s, 1H), 2.08 (d, J=10.8, 2H), 1.51 (d, J=11.7, 2H).

Example 32

(1-Methyl-piperidin-4-ylmethyl)-[6-methyl-3-(3-trifluoromethyl-phenyl)-7,8-dihydro-6H-9-oxa-1,2,3a,4,6-pentaaza-cyclopenta[a]naphthalen-5-yl]-amine

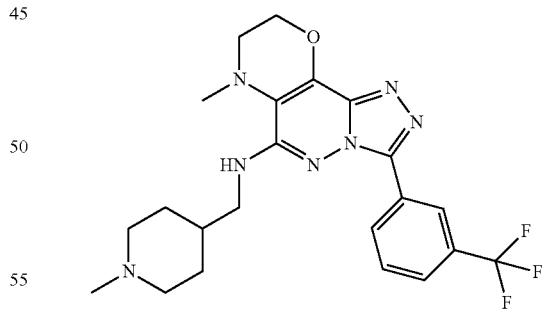

Amine: (1-methyl-4-piperidinyl)methanamine

HPLC-MS (method 1): Rt=3.20 min, [M+H]$^+$ m/z 462.2.

$^1$H NMR (300 MHz, MeOD) δ 8.88 (s, 1H), 8.59 (d, J=7.8 Hz, 1H), 7.71 (dt, J=15.6, 7.8 Hz, 2H), 4.52-4.42 (m, 2H), 3.27 (dd, J=9.7, 5.6 Hz, 4H), 2.88 (d, J=11.6 Hz, 2H), 2.76 (s, 3H), 2.24 (s, 3H), 1.98 (t, J=11.1 Hz, 2H), 1.89-1.74 (m, 3H), 1.33 (dt, J=15.0, 7.5 Hz, 2H).

Example 33

[3-(1H-Indol-5-yl)-6-methyl-7,8-dihydro-6H-9-oxa-1,2,3a,4,6-pentaaza-cyclopenta[a]naphthalen-5-yl]-(1-methyl-piperidin-4-ylmethyl)-amine

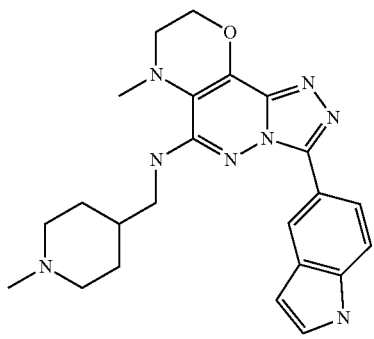 [SMILES: CN1CCC(CNc2nn3c(-c4ccc5[nH]ccc5c4)nnc3c3c2N(C)CCO3)CC1]

Amine: (1-methyl-4-piperidinyl)methylamine

HPLC-MS (method 1): Rt=2.337 min, [M+H]$^+$ m/z 433.2.

$^1$H NMR (300 MHz, MeOD) δ 8.60 (d, J=1.1, 1H), 8.46 (s, 1H), 7.98 (dd, J=8.6, 1.5, 1H), 7.49 (d, J=8.6, 1H), 7.35 (d, J=3.1, 1H), 6.65 (t, J=5.6, 1H), 6.50 (d, J=3.2, 1H), 4.48-4.35 (m, 2H), 3.48 (d, J=11.3, 2H), 3.36 (dd, J=8.4, 4.0, 2H), 3.26-3.14 (m, 2H), 2.99 (t, J=11.5, 2H), 2.79 (s, 3H), 2.70 (s, 3H), 2.22 (d, J=10.5, 1H), 2.06 (d, J=13.5, 2H), 1.59 (dd, J=23.2, 11.5, 2H).

Example 34

[3-(3-Dimethylamino-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine

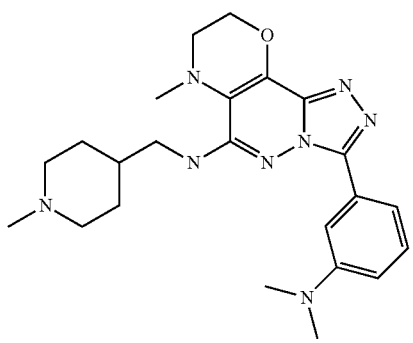 [SMILES: CN1CCC(CNc2nn3c(-c4cccc(N(C)C)c4)nnc3c3c2N(C)CCO3)CC1]

Amine: (1-methyl-4-piperidinyl)methylamine

HPLC-MS (method 1): Rt=0.32, 2.29 min, [M+H]$^+$ m/z 437.4.

$^1$H NMR (300 MHz, CDCl$_3$) δ 7.94 (m, 1H), 7.89 (d, J=7.8 Hz, 1H), 7.34 (m, 1H), 6.83 (m, 1H), 5.07 (t, J=5.6 Hz, 1H), 4.47 (m, 2H), 3.38 (t, J=6.0 Hz, 2H), 3.20 (m, 2H), 3.09 (d, J=11.6 Hz, 2H), 3.03 (s, 6H), 2.74 (s, 3H), 2.40 (s, 3H), 2.16 (m, 2H), 1.84 (m, 3H), 1.57 (m, 2H).

Example 35

4-{Methyl-[6-methyl-3-(3-trifluoromethoxy-phenyl)-7,8-dihydro-6H-9-oxa-1,2,3a,4,6-pentaaza-cyclopenta[a]naphthalen-5-yl]-amino}-cyclohexanol

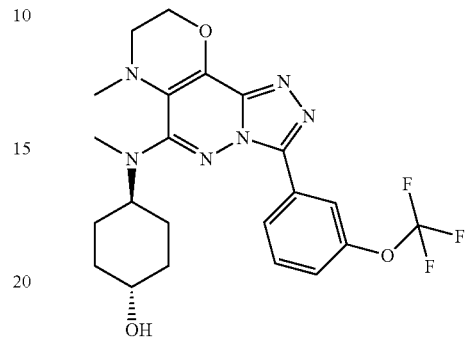

Amine: Trans-4-(methylamino)cyclohexanol

HPLC-MS (method 1): Rt=5.35 min, [M+H]$^+$ m/z 479.3.

$^1$H NMR (300 MHz, MeOD) δ 8.41 (m, 2H), 7.65 (m, 1H), 7.42 (d, J=8.3 Hz, 1H), 4.42 (m, 2H), 4.25 (m, 1H), 3.56 (m, 1H), 3.35 (m, 2H), 2.99 (s, 3H), 2.87 (s, 3H), 2.05 (m, 2H), 1.80 (m, 4H), 1.41 (m, 2H).

Example 36

Methyl-(1-methyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

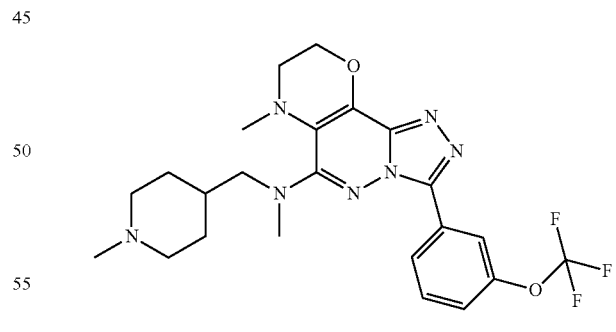

Amine: 1-Methyl-4-(methylaminomethyl)-piperidine

HPLC-MS (method 1): Rt=3.45 min, [M+H]$^+$ m/z 492.4.

$^1$H NMR (300 MHz, MeOD) δ 8.48 (s, 1H), 8.39 (d, J=7.9 Hz, 1H), 7.66 (m, 1H), 7.43 (d, J=8.3 Hz, 1H), 4.43 (m, 2H), 3.60 (d, J=7.1 Hz, 2H), 3.35 (m, 3H), 3.16 (s, 3H), 2.88 (m, 2H), 2.85 (s, 3H), 2.28 (s, 3H), 2.06 (m, 2H), 1.88 (m, 1H), 1.70 (d, J=12.8 Hz, 2H), 1.27 (m, 2H).

Example 37

(1-Methyl-piperidin-4-ylmethyl)-[3-(3-trifluoromethoxy-phenyl)-7,8,9,10-tetrahydro-[1,2,4]triazolo[3,4-a]phthalazin-6-yl]-amine

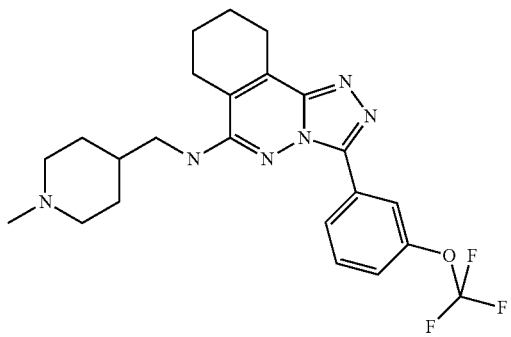 [SMILES: CN1CCC(CNc2nn3c(-c4cccc(OC(F)(F)F)c4)nnc3c3c2CCCC3)CC1]

Amine: (1-methyl-4-piperidinyl)methylamine

HPLC-MS (method 1): Rt=3.30 min, [M+H]$^+$ m/z 461.2.

$^1$H NMR (300 MHz, DMSO) δ 8.57 (s, 1H), 8.44 (m, 1H), 7.69 (m, 1H), 7.49 (m, 1H), 6.92 (t, J=5.3 Hz, 1H), 3.23 (t, J=6.0 Hz, 2H), 2.92 (m, 2H), 2.84 (m, 2H), 2.46 (m, 2H), 2.20 (s, 3H), 1.84 (m, 9H), 1.25 (m, 2H).

Example 38

[8,9-Dimethyl-3-(3-trifluoromethoxy-phenyl)-8,9-dihydro-7H-6-oxa-1,2,3a,4,9-pentaaza-cyclopenta[a]naphthalen-5-yl]-(1-methyl-piperidin-4-ylmethyl)-amine; HCOOH salt

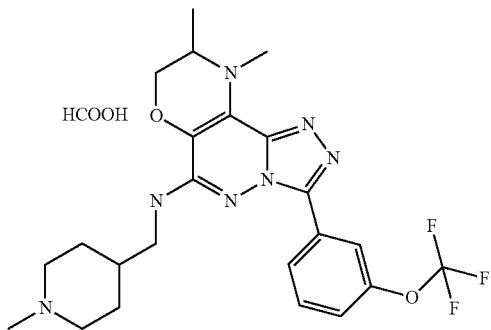 [SMILES: CC1COc2c(NCC3CCN(C)CC3)nn3c(-c4cccc(OC(F)(F)F)c4)nnc3c2N1C ; "HCOOH"]

Amine: (1-methyl-4-piperidinyl)methylamine

HPLC-MS (method 1): Rt=3.34, 3.45 min, [M+H]$^+$ m/z 492.3.

$^1$H NMR (300 MHz, DMSO-d$_6$) δ 8.59 (s, 1H), 8.42 (d, J=8.0 Hz, 1H), 8.23 (s, 1H), 7.68 (m, 1H), 7.48 (d, J=8.3 Hz, 1H), 6.76 (t, J=5.8 Hz, 1H), 4.23 (dd, J=10.6, 2.6 Hz, 1H), 4.09 (dd, J=10.6, 2.0 Hz, 1H), 3.60 (m, 4H), 3.19 (m, 2H), 2.84 (m, 2H), 2.21 (s, 3H), 1.96 (m, 2H), 1.74 (m, 3H), 1.24 (m, 5H).

Example 39

[6,7-Dimethyl-3-(3-trifluoromethoxy-phenyl)-7,8-dihydro-6H-9-oxa-1,2,3a,4,6-pentaaza-cyclopenta[a]naphthalen-5-yl]-(1-methyl-piperidin-4-ylmethyl)-amine

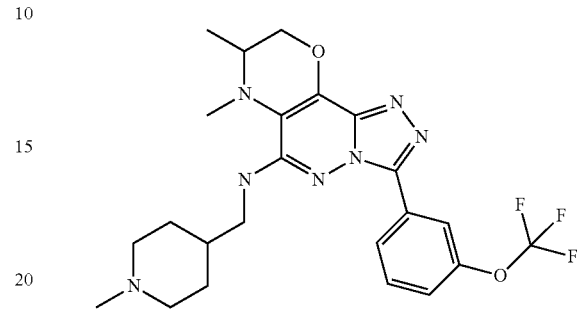

Amine: (1-methyl-4-piperidinyl)methylamine

HPLC-MS (method 1): Rt=5.12 min, [M+H]$^+$ m/z 492.3.

$^1$H NMR (300 MHz, DMSO) δ 8.58 (s, 1H), 8.42 (d, J=8.0 Hz, 1H), 7.69 (t, J=8.1 Hz, 1H), 7.49 (d, J=8.2 Hz, 1H), 6.87 (t, J=5.6 Hz, 1H), 4.29 (d, J=2.6 Hz, 2H), 3.41-3.24 (m, 1H), 3.18 (m, 2H), 2.78 (d, J=11.0 Hz, 2H), 2.64 (s, 3H), 2.14 (s, 3H), 1.84 (m, 3H), 1.70 (d, J=12.6 Hz, 2H), 1.36-1.14 (m, 2H), 1.07 (d, J=6.9 Hz, 3H).

Example 40

[6,8-Dimethyl-3-(3-trifluoromethoxy-phenyl)-7,8-dihydro-6H-9-oxa-1,2,3a,4,6-pentaaza-cyclopenta[a]naphthalen-5-yl]-(1-methyl-piperidin-4-ylmethyl)-amine; HCOOH salt

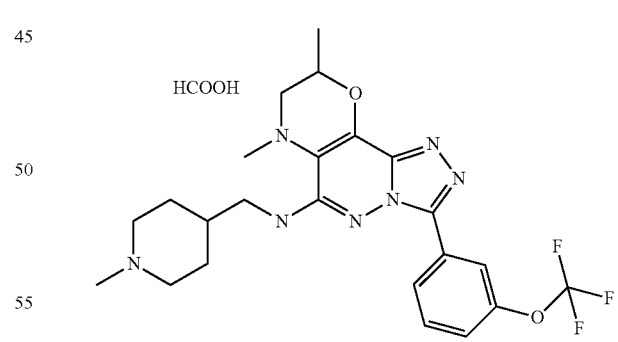

Amine: (1-methyl-4-piperidinyl)methylamine

HPLC-MS (method 1): Rt=3.28 min, [M+H]$^+$ m/z 492.1.

$^1$H NMR (300 MHz, DMSO-d$_6$) δ 8.58 (s, 1H), 8.43 (d, J=7.9 Hz, 1H), 8.20 (s, 1H), 7.69 (m, 1H), 7.49 (m, 1H), 6.91 (s, 1H), 4.46 (m, 1H), 3.20 (m, 4H), 2.80 (m, 2H), 2.70 (s, 3H), 2.17 (s, 3H), 1.89 (m, 3H), 1.72 (m, 2H), 1.46 (d, J=6.2 Hz, 3H), 1.25 (m, 2H).

Example 41

(1-Methyl-piperidin-4-ylmethyl)-[3-(3-trifluoromethoxy-phenyl)-7,8-dihydro-6,9-dioxa-1,2,3a,4-tetraaza-cyclopenta[a]naphthalen-5-yl]-amine; HCOOH salt

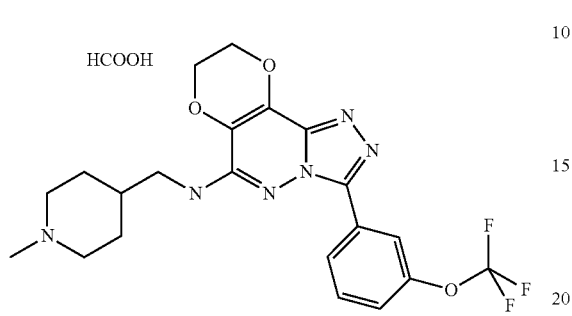

Amine: (1-methyl-4-piperidinyl)methylamine
HPLC-MS (method 1): Rt=2.92, 3.01 min, [M+H]⁺ m/z 465.0.
¹H NMR (300 MHz, DMSO-d₆) δ 8.54 (s, 1H), 8.40 (d, J=8.0 Hz, 1H), 8.26 (s, 1H), 7.69 (m, 1H), 7.50 (d, J=8.3 Hz, 1H), 7.23 (t, J=5.7 Hz, 1H), 4.55 (m, 4H), 3.22 (m, 2H), 2.77 (d, J=11.3 Hz, 2H), 2.14 (s, 3H), 1.84 (m, 3H), 1.70 (m, 2H), 1.23 (m, 2H).

Example 42

[9-Methyl-3-(3-trifluoromethoxy-phenyl)-8,9-dihydro-7H-6-oxa-1,2,3a,4,9-pentaaza-cyclopenta[a]naphthalen-5-yl]-(2-piperazin-1-yl-ethyl)-amine

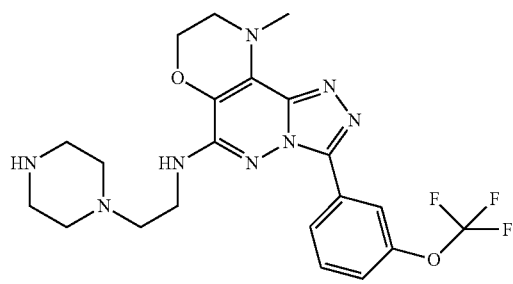 [SMILES: CN1CCOc2c(NCCN3CCNCC3)nn3c(-c4cccc(OC(F)(F)F)c4)nnc3c21]

Amine: 4-N-(2-aminoethyl)-1-N-BOC-piperazine

HPLC-MS (method 1): Rt=3.04 min, [M+H]⁺ m/z 480.2.
¹H NMR (300 MHz, CDCl₃) δ 8.62-8.57 (m, 1H), 8.47-8.41 (m, 1H), 7.53 (t, J=8.1, 1H), 7.31-7.24 (m, 1H), 5.28 (t, J=4.8, 1H), 4.41-4.32 (m, 2H), 3.74 (s, 3H), 3.53-3.48 (m, 4H), 3.30-3.27 (m, 4H), 2.88-2.84 (m, 4H), 2.79 (t, J=5.8, 2H).

Example 43

4-{[6-Methyl-3-(3-trifluoromethoxy-phenyl)-7,8-dihydro-6H-9-oxa-1,2,3a,4,6-pentaaza-cyclopenta[a]naphthalen-5-ylamino]-methyl}-cyclohexanol

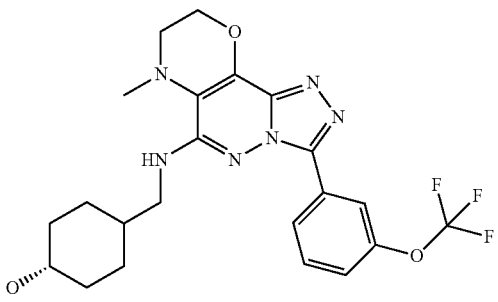

Amine: trans-N-BOC-4-aminomethyl-cyclohexanol
HPLC-MS (method 1): Rt=5.09 min, [M+H]⁺ m/z 479.2.
¹H NMR (300 MHz, MeOD) δ 8.57 (s, 1H), 8.43-8.32 (m, 1H), 7.62 (t, J=8.1 Hz, 1H), 7.45-7.34 (m, 1H), 4.52-4.42 (m, 2H), 3.50 (td, J=10.7, 5.4 Hz, 1H), 3.29-3.21 (m, 4H), 2.77 (s, 3H), 1.95 (m, 5H), 1.38-0.99 (m, 5H).

Example 44 and 45

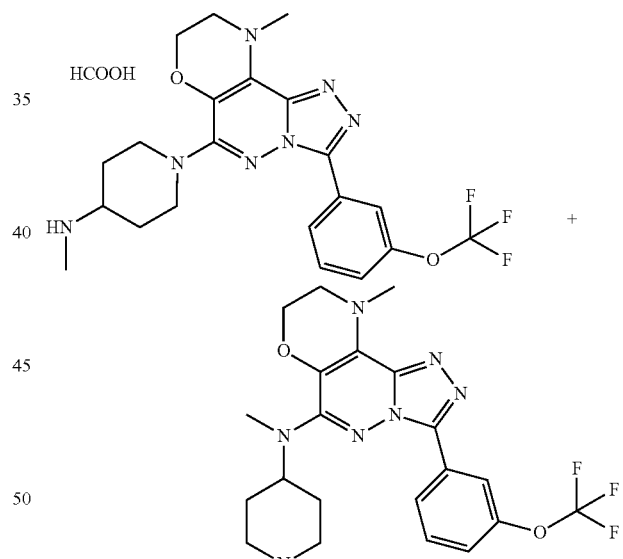

Amine: 4-N-BOC-4-N-methyl-aminopiperidine

Example 44

Methyl-{1-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl}-amine; HCOOH salt HPLC-MS (method 1): Rt=3.22 min, [M+H]⁺ m/z 464.2.
¹H NMR (300 MHz, CDCl₃) δ 8.54 (s, 1H), 8.43 (d, J=7.5 Hz, 1H), 7.62-7.42 (m, 1H), 7.25 (d, J=4.7 Hz, 1H), 4.31 (d, J=3.9 Hz, 2H), 3.92 (d, J=12.6 Hz, 2H), 3.76 (s, 3H), 3.50

(d, J=3.9 Hz, 2H), 2.91 (t, J=12.1 Hz, 2H), 2.74-2.54 (m, 1H), 2.47 (s, 6H), 2.01 (d, J=12.2 Hz, 2H), 1.55 (d, J=11.1 Hz, 2H).

Example 45

Methyl-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl-amine HPLC-MS (method 1): Rt=3.21 min, [M+H]+ m/z 464.2.
1H NMR (300 MHz, MeOD) δ 8.44-8.29 (m, 2H), 7.63 (t, J=8.1 Hz, 1H), 7.44-7.34 (m, 1H), 4.33 (t, J=4.2 Hz, 2H), 4.15 (d, J=13.2 Hz, 2H), 3.67 (s, 3H), 3.55 (t, J=4.2 Hz, 2H), 2.95 (t, J=11.8 Hz, 2H), 2.75 (s, 3H), 2.19 (t, J=10.1 Hz, 2H), 1.85 (tt, J=12.2, 6.1 Hz, 2H).

Example 46 and 47

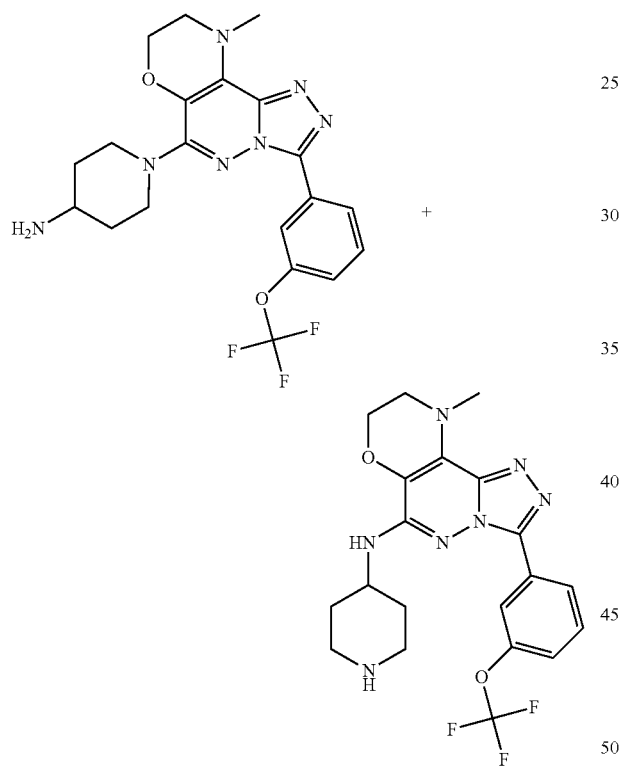

Amine: 4-amino-1-BOC-piperidine

Example 46

1-[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-ylamine HPLC-MS (method 1): Rt=3.20 min, [M+H]+ m/z 450.2.
1H NMR (300 MHz, CDCl3) δ 8.53 (s, 1H), 8.42 (d, J=8.0 Hz, 1H), 7.49 (t, J=8.1 Hz, 1H), 7.28-7.18 (m, 1H), 4.34-4.23 (m, 2H), 4.06 (dt, J=8.2, 5.1 Hz, 1H), 3.89 (d, J=13.0 Hz, 2H), 3.74 (s, 3H), 3.53-3.44 (m, 2H), 2.97-2.80 (m, 2H), 1.91 (d, J=10.3 Hz, 2H), 1.52 (d, J=10.6 Hz, 2H).

Example 47

[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl-amine HPLC-MS (method 1): Rt=3.10 min, [M+H]+ m/z 450.2.
1H NMR (300 MHz, CDCl3) δ 8.60 (s, 1H), 8.50-8.36 (m, 1H), 7.99 (s, 1H), 7.49 (t, J=8.1 Hz, 1H), 7.31-7.19 (m, 1H), 4.76 (d, J=7.5 Hz, 1H), 4.40-4.26 (m, 2H), 3.96-3.81 (m, 1H), 3.69 (s, 3H), 3.45 (t, J=4.3 Hz, 2H), 3.15 (dd, J=9.2, 3.4 Hz, 2H), 2.85-2.70 (m, 2H), 2.16 (d, J=9.3 Hz, 2H), 1.56-1.35 (m, 2H).

Example 48 and 49

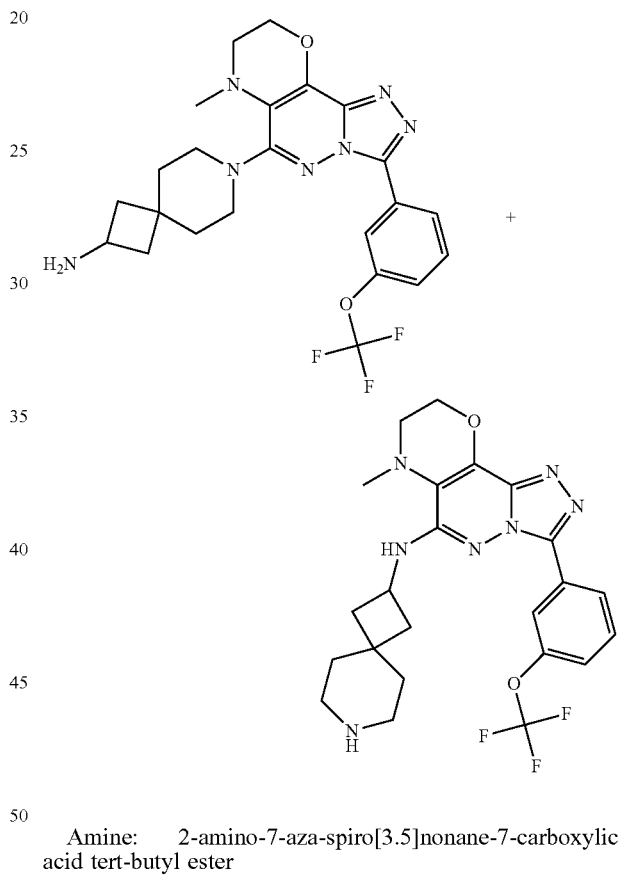

Amine: 2-amino-7-aza-spiro[3.5]nonane-7-carboxylic acid tert-butyl ester

Example 48

7-[6-Methyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-ylamine HPLC-MS (method 1): Rt=3.37 min, [M+H]+ m/z 490.2.
1H NMR (700 MHz, MeOD) δ 8.49 (s, 1H), 8.42-8.36 (m, 1H), 7.66 (td, J=8.1, 2.2 Hz, 1H), 7.42 (d, J=8.2 Hz, 1H), 4.45-4.39 (m, 2H), 3.47 (ddd, J=30.1, 20.6, 10.2 Hz, 4H), 2.96 (d, J=4.9 Hz, 3H), 2.37 (s, 1H), 2.34-2.27 (m, 2H), 1.90 (dd, J=12.6, 7.5 Hz, 3H), 1.81 (ddd, J=22.6, 10.9, 5.6 Hz, 4H), 1.65 (dd, J=12.3, 8.3 Hz, 2H).

Example 49

(7-Aza-spiro[3.5]non-2-yl)-[6-methyl-3-(3-trifluoromethoxy-phenyl)-7,8-dihydro-6H-9-oxa-1,2,3a,4,6-pentaaza-cyclopenta[a]naphthalen-5-yl]-amine HPLC-MS (method 1): Rt=3.21 min, [M+H]+ m/z 490.2.

$^1$H NMR (300 MHz, MeOD) δ 8.60 (s, 1H), 8.37 (d, J=8.0 Hz, 1H), 7.66 (t, J=8.1 Hz, 1H), 7.44 (d, J=8.3 Hz, 1H), 4.56-4.44 (m, 2H), 4.38 (dd, J=16.0, 8.0 Hz, 1H), 3.28 (dd, J=6.9, 2.5 Hz, 2H), 3.25-3.15 (m, 2H), 3.16-3.05 (m, 2H), 2.79 (s, 3H), 2.59-2.44 (m, 2H), 2.07-1.92 (m, 4H), 1.92-1.81 (m, 2H).

Example 50

7-[6,7-Dimethyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-ylamine; HCOOH salt

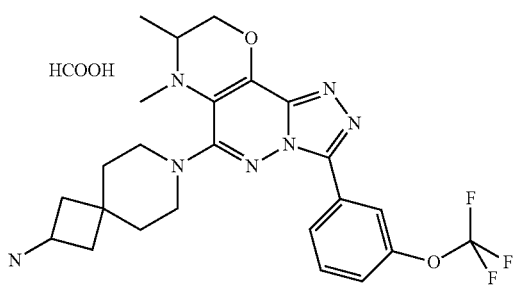 [SMILES: CC1COc2c(c(N3CCC4(CC3)CC(N)C4)nn3c(-c4cccc(OC(F)(F)F)c4)nnc23)N1C ; "HCOOH"]

Amine: 2-amino-7-aza-spiro[3.5]nonane-7-carboxylic acid tert-butyl ester

HPLC-MS (method 1): Rt=7.00 min, [M+H]+ m/z 504.3.

$^1$H NMR (300 MHz, DMSO-d$_6$) δ 8.46 (s, 1H), 8.42 (m, 1H), 8.38 (d, J=8.0 Hz, 1H), 7.72 (t, J=8.1 Hz, 1H), 7.51 (d, J=8.2 Hz, 1H), 4.29 (dd, J=10.5, 2.0 Hz, 1H), 4.17 (dd, J=10.6, 1.7 Hz, 1H), 3.69 (m, 1H), 3.52 (m, 2H), 3.41 (m, 1H), 3.20 (s, 2H), 2.81 (s, 3H), 2.16 (m, 2H), 1.72 (m, 6H), 1.09 (d, J=6.8 Hz, 3H).

Example 51 and 52

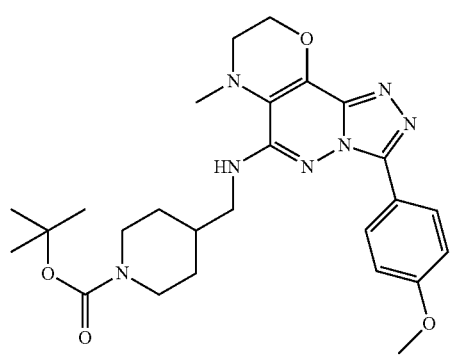

+

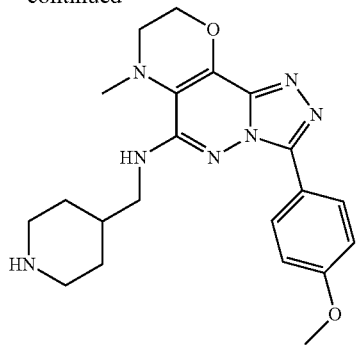

Amine: 1-BOC-4-(aminomethyl)piperidine

Example 51

4-{[3-(4-Methoxy-phenyl)-6-methyl-7,8-dihydro-6H-9-oxa-1,2,3a,4,6-pentaaza-cyclopenta[a]naphthalen-5-ylamino]-methyl}-piperidine-1-carboxylic acid tert-butyl ester HPLC-MS (method 1): Rt=5.6 min, [M+H]+ m/z 510.3.

$^1$H NMR (300 MHz, CDCl$_3$) d 8.44 (d, J=9.0 Hz, 2H), 6.99 (d, J=9.0 Hz, 2H), 5.07 (s, 1H), 4.50-4.40 (m, 2H), 4.14 (s, 2H), 3.86 (s, 3H), 3.32 (t, J=6.1 Hz, 2H), 3.25-3.13 (m, 2H), 2.70 (d, J=14.6 Hz, 5H), 2.00 (m, 1H), 1.77 (d, J=12.8 Hz, 2H), 1.44 (s, 9H).

Example 52

C-{1-[3-(4-Methoxy-phenyl)-6-methyl-7,8-dihydro-6H-9-oxa-1,2,3a,4,6-pentaaza-cyclopenta[a]naphthalen-5-yl]-piperidin-4-yl}-methylamine HPLC-MS (method 1): Rt=2.85 min, [M+H]+ m/z 410.3.

$^1$H NMR (300 MHz, CDCl$_3$) δ 8.47-8.38 (m, 2H), 7.07-6.94 (m, 2H), 4.41-4.28 (m, 2H), 4.18 (d, J=12.8 Hz, 2H), 3.86 (s, 3H), 3.28-3.14 (m, 2H), 2.88 (s, 3H), 2.78 (t, J=11.5 Hz, 2H), 2.66 (d, J=6.2 Hz, 2H), 1.90 (d, J=10.7 Hz, 2H), 1.71-1.27 (m, 2H).

Example 53

(1-Aza-bicyclo[2.2.1]hept-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

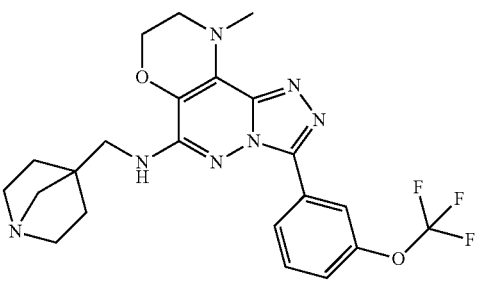 [SMILES: CN1CCOc2c(NCC34CCN(CC3)C4)nn3c(-c4cccc(OC(F)(F)F)c4)nnc3c21]

Amine: 2,7-diaza-spiro[3.5]nonane-7-carboxylic acid tert-butyl ester, hydrochloride HPLC-MS (method 1): Rt=3.34 min, [M+H]+ m/z 476.2.

¹H NMR (300 MHz, CDCl₃) δ 8.63 (d, J=1.0 Hz, 1H), 8.46-8.32 (m, 1H), 7.54-7.42 (m, 1H), 7.27-7.12 (m, 1H), 4.90 (t, J=5.9 Hz, 1H), 4.33-4.26 (m, 2H), 3.74 (d, J=6.0 Hz, 2H), 3.66 (d, J=7.8 Hz, 3H), 3.48-3.37 (m, 2H), 2.94 (td, J=11.0, 5.1 Hz, 2H), 2.61 (dt, J=12.1, 5.6 Hz, 2H), 2.38-2.28 (m, 2H), 1.71-1.53 (m, 2H), 1.37-1.24 (m, 2H).

Example 54

(1-Aza-bicyclo[2.2.1]hept-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

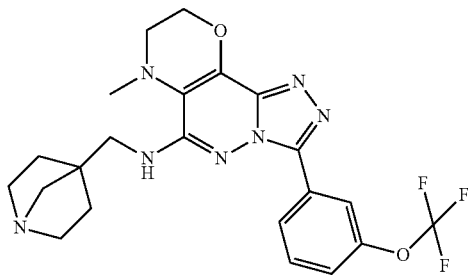 [SMILES: CN1CCOc2c1c(NCC13CCN(CC1)C3)nn1c(-c3cccc(OC(F)(F)F)c3)nnc21]

Amine: 2,7-diaza-spiro[3.5]nonane-7-carboxylic acid tert-butyl ester, hydrochloride HPLC-MS (method 1): Rt=3.18 min, [M+H]⁺ m/z 475.4.
¹H NMR ((300 MHz, CDCl₃) δ 8.60 (s, 1H), 8.40 (d, J=8.0 Hz, 1H), 7.50 (t, J=8.1 Hz, 1H), 7.30-7.25 (m, 1H), 5.13 (t, J=5.8 Hz, 1H), 4.54-4.40 (m, 2H), 3.78 (d, J=5.9 Hz, 2H), 3.26-3.13 (m, 2H), 3.01 (td, J=10.7, 4.9 Hz, 2H), 2.77-2.59 (m, 5H), 2.41 (s, 2H), 1.69 (qd, J=8.0, 3.5 Hz, 2H), 1.47-1.30 (m, 2H).

Example 55 and 56

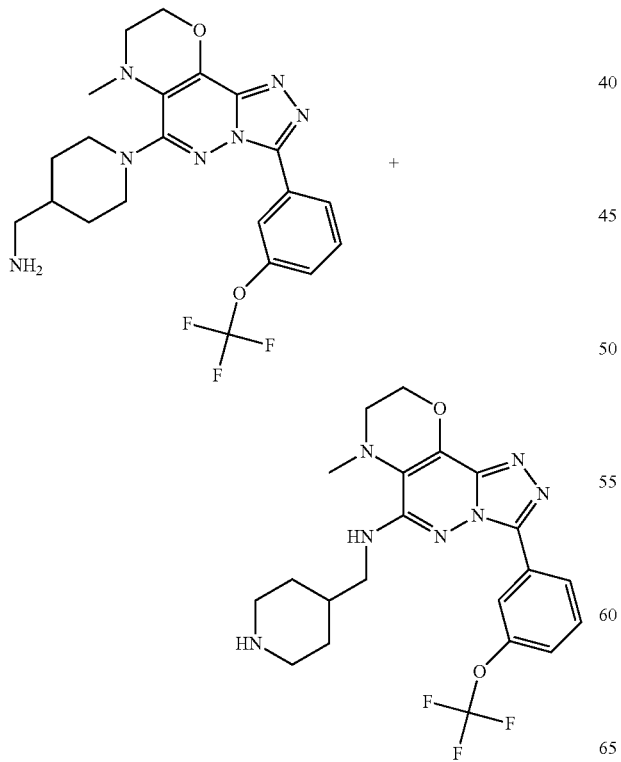

Amine: 1-BOC-4-(aminomethyl)piperidine

Example 55

C-{1-[6-Methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-methylamine HPLC-MS (method 1): Rt=3.46 min, [M+H]⁺ m/z 464.3.
¹H NMR (300 MHz, MeOD) δ 8.55 (s, 1H), 8.47 (s, 1H), 8.38 (d, J=8.0 Hz, 1H), 7.64 (t, J=8.1 Hz, 1H), 7.41 (d, J=6.0 Hz, 1H), 4.46-4.37 (m, 2H), 4.30 (d, J=12.8 Hz, 2H), 3.34-3.30 (m, 2H), 2.95 (s, 3H), 2.84 (t, J=12.4 Hz, 2H), 2.71 (m, 2H), 1.92 (dd, J=11.9, 5.9 Hz, 2H), 1.72 (m, 1H), 1.59-1.39 (m, 2H).

Example 56

[6-Methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl-amine HPLC-MS (method 1): Rt=3.19 min, [M+H]⁺ m/z 464.3.
¹H NMR (700 MHz, MeOD) δ 8.51 (s, 1H), 8.39 (d, J=7.9 Hz, 1H), 7.66 (t, J=8.1 Hz, 1H), 7.44 (d, J=8.2 Hz, 1H), 4.59-4.42 (m, 2H), 3.46 (d, J=12.8 Hz, 2H), 3.42 (d, J=6.9 Hz, 2H), 3.31-3.27 (m, 2H), 3.02 (td, J=12.9, 2.6 Hz, 2H), 2.81 (s, 3H), 2.32-2.24 (m, 1H), 2.09 (d, J=13.7 Hz, 2H), 1.56 (td, J=15.5, 4.0 Hz, 2H).

Example 57 and 58

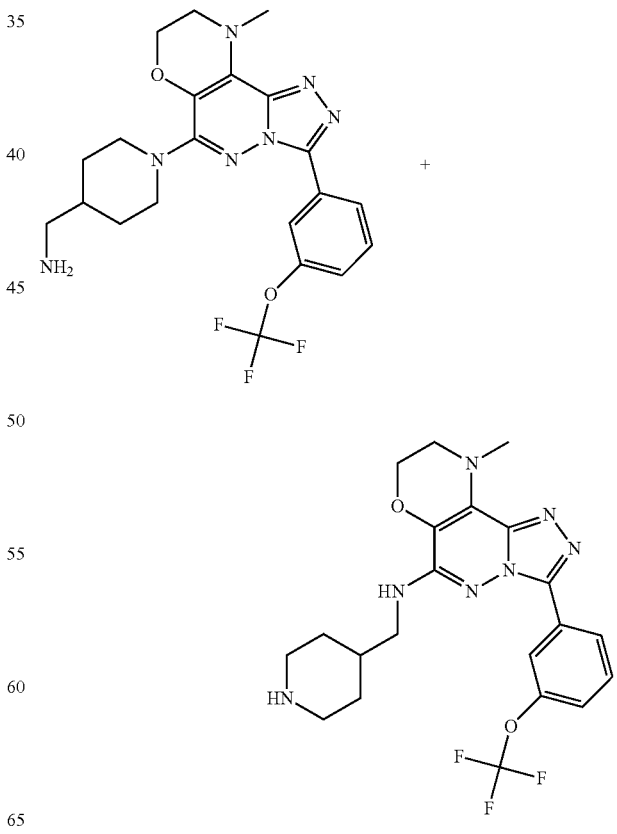

Amine: 1-BOC-4-(aminomethyl)piperidine

Example 57

C-{1-[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl}-methylamine HPLC-MS (method 1): Rt=3.54 min, [M+H]⁺ m/z 464.3.
¹H NMR (300 MHz, MeOD) δ 8.57 (s, 1H), 8.49 (s, 1H), 8.38 (dd, J=8.0, 1.0 Hz, 1H), 7.62 (t, J=8.1 Hz, 1H), 7.43-7.35 (m, 1H), 4.36-4.25 (m, 2H), 4.03 (d, J=12.7 Hz, 2H), 3.65 (s, 3H), 3.57-3.48 (m, 2H), 2.83 (t, J=11.6 Hz, 2H), 2.71-2.62 (m, 2H), 1.93-1.80 (m, 2H), 1.68 (d, J=3.8 Hz, 1H), 1.42 (td, J=12.1, 3.1 Hz, 2H).

Example 58

[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-ylmethyl-amine HPLC-MS (method 1): Rt=3.32 min, [M+H]⁺ m/z 464.3.
¹H NMR (300 MHz, MeOD) δ 8.54 (s, 1H), 8.38 (d, J=8.0 Hz, 1H), 7.63 (t, J=8.1 Hz, 1H), 7.40 (dd, J=8.3, 1.1 Hz, 1H), 4.44-4.30 (m, 2H), 3.58 (s, 3H), 3.54-3.44 (m, 2H), 3.36 (t, J=3.3 Hz, 2H), 2.93 (dd, J=12.9, 10.4 Hz, 2H), 2.16 (dd, J=9.0, 5.6 Hz, 1H), 2.10-1.96 (m, 2H), 1.58-1.35 (m, 2H).

Example 59

C-{7-[6-Methyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-yl}-methyl-amine

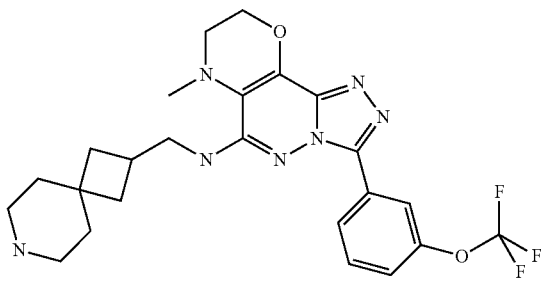 [SMILES: CN1CCOc2c1c(NCC1CC3(CCNCC3)C1)nn1c(-c3cccc(OC(F)(F)F)c3)nnc21]

Amine: 2-Aminomethyl-7-aza-spiro[3.5]nonane-7-carboxylic acid tery-butyl ester
HPLC-MS (method 1): Rt=3.38 min, [M+H]⁺ m/z 504.2.
¹H NMR (300 MHz, CDCl₃) δ 8.63 (s, 1H), 8.44 (d, J=8.0 Hz, 1H), 7.53 (m, 1H), 7.28 (m, 1H), 4.99 (t, J=5.4 Hz, 1H), 4.48 (m, 2H), 3.48 (m, 2H), 3.21 (m, 2H), 2.97 (m, 2H), 2.89 (m, 2H), 2.73 (m, 4H), 2.08 (m, 2H), 1.82 (m, 2H), 1.72 (m, 2H), 1.62 (m, 2H).

Example 60 and 61

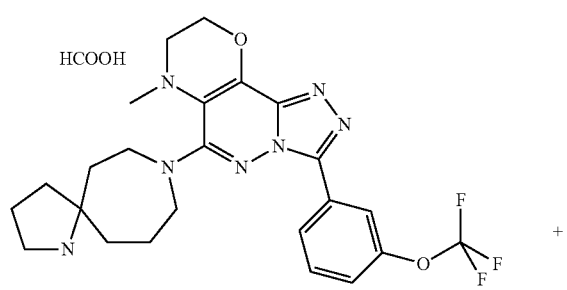

+

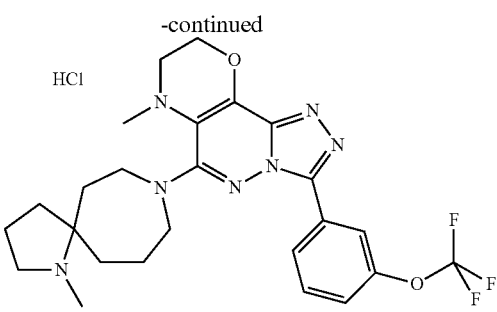

Amine: 2 1,8-diaza-spiro[4.6]undecane-1-carboxylic acid tert-butyl ester

Example 60

5-(1,8-Diaza-spiro[4.6]undec-8-yl)-6-methyl-3-(3-trifluoromethoxy-phenyl)-7,8-dihydro-6H-9-oxa-1,2,3a,4,6-pentaaza-cyclopenta[a]naphthalene; HCOOH salt HPLC-MS (method 1): Rt=4.28 min, [M+H]⁺ m/z 504.3.
¹H NMR (300 MHz, CDCl₃) δ 8.53 (s, 1H), 8.41 (m, 1H), 7.53 (t, J=7.6 Hz, 1H), 7.28 (m, 1H), 4.37 (m, 2H), 3.86 (m, 1H), 3.71 (m, 3H), 3.26 (m, 4H), 2.75 (s, 3H), 2.35 (m, 1H), 2.24 (m, 1H), 2.05 (m, 4H), 1.90 (m, 4H).

Example 61

6-Methyl-5-(1-methyl-1,8-diaza-spiro[4.6]undec-8-yl)-3-(3-trifluoromethoxy-phenyl)-7,8-dihydro-6H-9-oxa-1,2,3a,4,6-pentaaza-cyclopenta[a]naphthalene; HCl salt HPLC-MS (method 1): Rt=3.48 min, [M+H]⁺ m/z 518.3.
¹H NMR (300 MHz, MeOD) δ 8.37 (m, 2H), 7.67 (m, 1H), 7.45 (d, J=7.4 Hz, 1H), 4.45 (m, 2H), 4.24 (m, 1H), 3.80 (m, 2H), 3.64 (m, 1H), 3.38 (m, 4H), 2.82 (s, 3H), 2.76 (s, 3H), 2.13 (m, 10H).

Secondary product obtained due to an impurity in the amine used as starting material.

Example 62

Methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-amine; HCOOH salt

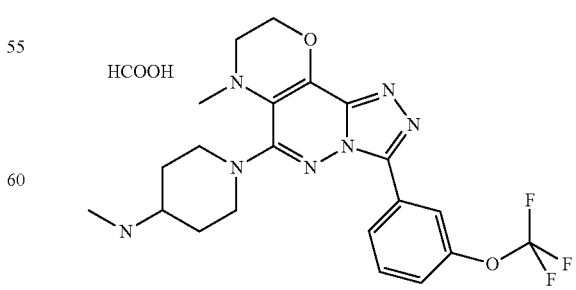

Amine: 4-N-BOC-4-N-methyl-aminopiperidine
HPLC-MS (method 1): Rt=3.15 min, [M+H]⁺ m/z 464.3.

¹H NMR (300 MHz, MeOD) δ 8.55 (s, 1H), 8.39 (s, 1H), 8.33 (d, J=7.9 Hz, 1H), 7.63 (t, J=7.9 Hz, 1H), 7.40 (d, J=7.9 Hz, 1H), 4.39 (m, 4H), 3.33 (m, 2H), 3.16 (m, 1H), 2.95 (m, 5H), 2.68 (s, 3H), 2.20 (d, J=11.3 Hz, 2H), 1.82 (m, 2H).

Example 63

Methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine

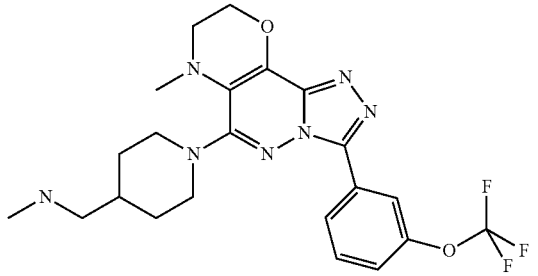 [SMILES: CNCC1CCN(c2nn3c(-c4cccc(OC(F)(F)F)c4)nnc3c3c2N(C)CCO3)CC1]

Amine: 4-[(methylamino)methyl]piperidine-1-carboxylic acid tert-butyl ester

HPLC-MS (method 1): Rt=3.40 min, [M+H]⁺ m/z 478.1.

¹H NMR (300 MHz, MeOD) δ 8.48 (s, 1H), 8.39 (d, J=7.6 Hz, 1H), 7.67 (m, 1H), 7.44 (d, J=7.8 Hz, 1H), 4.44 (m, 2H), 4.36 (m, 2H), 3.36 (m, 2H), 2.95 (m, 7H), 2.76 (s, 3H), 1.96 (m, 3H), 1.61 (m, 2H).

Example 64

Methyl-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl-amine

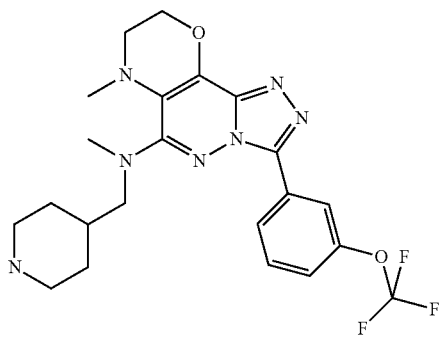 [SMILES: CN(CC1CCNCC1)c1nn2c(-c3cccc(OC(F)(F)F)c3)nnc2c2c1N(C)CCO2]

Amine: 4-[(methylamino)methyl]piperidine-1-carboxylic acid tert-butyl ester

HPLC-MS (method 1): Rt=3.49 min, [M+H]⁺ m/z 478.3.

¹H NMR (300 MHz, MeOD) δ 8.47 (s, 1H), 8.39 (d, J=8.0 Hz, 1H), 7.67 (m, 1H), 7.44 (d, J=8.3 Hz, 1H), 4.45 (m, 2H), 3.64 (d, J=7.1 Hz, 2H), 3.36 (m, 4H), 3.19 (s, 3H), 2.95 (m, 2H), 2.85 (s, 3H), 2.17 (m, 1H), 1.90 (m, 2H), 1.39 (m, 2H).

Example 65

(7-Aza-spiro[3.5]non-2-yl)-[9-methyl-3-(3-trifluoromethoxy-phenyl)-8,9-dihydro-7H-6-oxa-1,2,3a,4,9-pentaaza-cyclopenta[a]naphthalen-5-yl]-amine; HCl salt

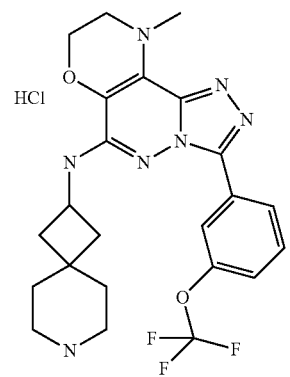 [SMILES: Cl ; CN1CCOc2c(NC3CC4(CCNCC4)C3)nn3c(-c4cccc(OC(F)(F)F)c4)nnc3c21]

Amine: 2-amino-7-aza-spiro[3.5]nonane-7-carboxylic acid tert-butyl ester

HPLC-MS (method 1): Rt=3.51 min, [M+H]⁺ m/z 490.1.

¹H NMR (300 MHz, MeOD) δ 8.52 (s, 1H), 8.38 (d, J=8.0 Hz, 1H), 7.71 (m, 1H), 7.49 (d, J=8.3 Hz, 1H), 4.37 (m, 2H), 3.85 (m, 1H), 3.63 (s, 3H), 3.58 (m, 2H), 3.49 (m, 2H), 3.42 (m, 2H), 2.39 (m, 2H), 2.00 (m, 2H), 1.84 (m, 4H).

Example 66

7-[9-Methyl-3-(3-trifluoromethoxy-phenyl)-8,9-dihydro-7H-6-oxa-1,2,3a,4,9-pentaaza-cyclopenta[a]naphthalen-5-yl]-7-aza-spiro[3.5]non-2-ylamine; HCl salt

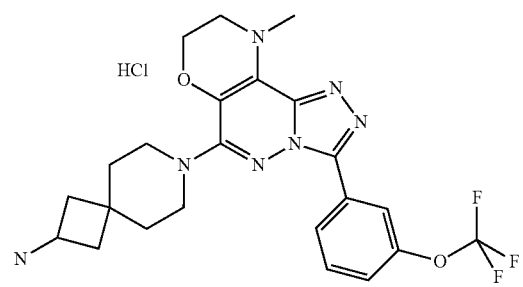 [SMILES: CN1CCOc2c(N3CCC4(CC3)CC(N)C4)nn3c(-c4cccc(OC(F)(F)F)c4)nnc3c21 ; Cl]

Amine: 2-amino-7-aza-spiro[3.5]nonane-7-carboxylic acid tert-butyl ester

HPLC-MS (method 1): Rt=3.53 min, [M+H]⁺ m/z 490.2.

¹H NMR (300 MHz, MeOD) δ 8.49 (s, 1H), 8.36 (m, 1H), 7.72 (m, 1H), 7.52 (m, 1H), 4.39 (m, 2H), 3.84 (m, 1H), 3.51 (m, 9H), 2.39 (m, 2H), 2.00 (m, 2H), 1.83 (m, 4H).

Example 67

5-(2,9-Diaza-spiro[5.5]undec-9-yl)-6-methyl-3-(3-trifluoromethoxy-phenyl)-7,8-dihydro-6H-9-oxa-1,2,3a,4,6-pentaaza-cyclopenta[a]naphthalene; HCl salt

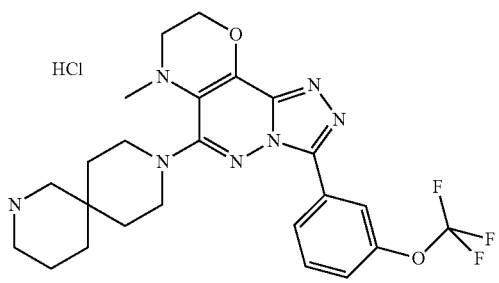 [SMILES: CN1CCOc2c1c(N1CCC3(CCCNC3)CC1)nn1c(-c3cccc(OC(F)(F)F)c3)nnc21 ; Cl]

Amine: 2,9-diaza-spiro[5.5]undecane-9-carboxylic acid tert-butyl ester

HPLC-MS (method 1): Rt=3.44 min, [M+H]⁺ m/z 504.3.

¹H NMR (300 MHz, MeOD) δ 8.40 (m, 2H), 7.71 (m, 1H), 7.50 (d, J=7.8 Hz, 1H), 4.46 (m, 2H), 3.70 (m, 2H), 3.54 (m, 2H), 3.41 (m, 2H), 3.15 (m, 4H), 3.02 (s, 3H), 1.82 (m, 8H).

Example 68

5-(2,9-Diaza-spiro[S5.5]undec-2-yl)-6-methyl-3-(3-trifluoromethoxy-phenyl)-7,8-dihydro-6H-9-oxa-1,2,3a,4,6-pentaaza-cyclopenta[a]naphthalene; HCl salt

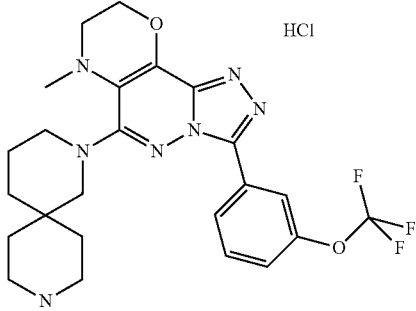 [SMILES: CN1CCOc2c1c(N1CCCC3(CCNCC3)C1)nn1c(-c3cccc(OC(F)(F)F)c3)nnc21 ; Cl]

Amine: 2,9-diaza-spiro[5.5]undecane-9-carboxylic acid tert-butyl ester

HPLC-MS (method 1): Rt=4.50 min, [M+H]⁺ m/z 504.3.

¹H NMR (300 MHz, MeOD) δ 8.52 (s, 1H), 8.38 (d, J=7.5 Hz, 1H), 7.74 (m, 1H), 7.54 (d, J=8.3 Hz, 1H), 4.49 (m, 2H), 3.54 (m, 2H), 3.43 (m, 4H), 3.21 (m, 4H), 3.02 (s, 3H), 1.83 (m, 8H).

Example 69

5-(2,6-Diaza-spiro[3.5]non-2-yl)-6-methyl-3-(3-trifluoromethoxy-phenyl)-7,8-dihydro-6H-9-oxa-1,2,3a,4,6-pentaaza-cyclopenta[a]naphthalene; HCl salt

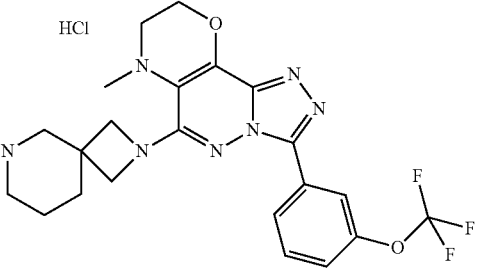 [SMILES: CN1CCOc2c1c(N1CC3(CCCNC3)C1)nn1c(-c3cccc(OC(F)(F)F)c3)nnc21 ; Cl]

Amine: 2,6-diaza-spiro[3.5]nonane-6-carboxylic acid tert-butyl ester; hydrochloride HPLC-MS (method 1): Rt=3.37 min, [M+H]⁺ m/z 476.2.

¹H NMR (300 MHz, MeOD) δ 8.43 (m, 2H), 7.74 (m, 1H), 7.56 (d, J=7.8 Hz, 1H), 4.51 (m, 2H), 4.24 (m, 2H), 4.11 (m, 2H), 3.67 (s, 2H), 3.49 (m, 2H), 3.18 (m, 2H), 2.91 (s, 3H), 2.05 (m, 2H), 1.91 (m, 2H).

Example 70

N-[6-Methyl-3-(3-trifluoromethoxy-phenyl)-7,8-dihydro-6H-9-oxa-1,2,3a,4,6-pentaaza-cyclopenta[a]naphthalen-5-yl]-cyclohexane-1,4-diamine; HCOOH salt

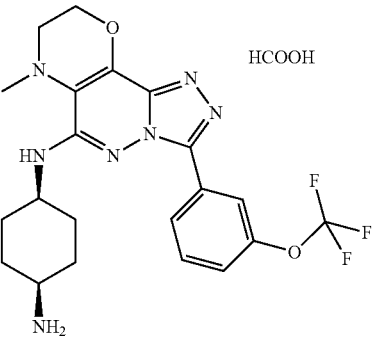 [SMILES: CN1CCOc2c1c(N[C@H]1CC[C@@H](N)CC1)nn1c(-c3cccc(OC(F)(F)F)c3)nnc21 ; "HCOOH"]

Amine: 1-N-BOC-cis-1,4-cyclohexyldiamine

HPLC-MS (method 1): Rt=3.22 min, [M+H]⁺ m/z 464.3.

¹H NMR (300 MHz, MeOD) δ 8.55 (s, 1H), 8.48 (s, 1H), 8.36 (d, J=7.9 Hz, 1H), 7.63 (m, 1H), 7.41 (d, J=8.0 Hz, 1H), 4.51 (m, 2H), 4.03 (m, 1H), 3.30 (m, 3H), 2.84 (s, 3H), 2.15 (m, 2H), 1.87 (m, 6H).

Example 71

N-[6-Methyl-3-(3-trifluoromethoxy-phenyl)-7,8-dihydro-6H-9-oxa-1,2,3a,4,6-pentaaza-cyclopenta[a]naphthalen-5-yl]-cyclohexane-1,4-diamine

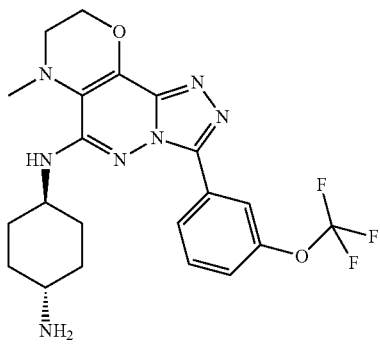 [SMILES: CN1CCOc2c1c(N[C@H]1CC[C@H](N)CC1)nn1c(-c3cccc(OC(F)(F)F)c3)nnc21]

Amine: 1-N-BOC-trans-1,4-cyclohexyldiamine

HPLC-MS (method 1): Rt=4.00 min, [M+H]⁺ m/z 464.3.

$^1$H NMR (300 MHz, MeOD) δ8.49 (s, 1H), 8.41 (d, J=7.9 Hz, 1H), 7.63 (m, 1H), 7.41 (d, J=8.1 Hz, 1H), 4.48 (m, 2H), 3.77 (m, 1H), 3.26 (m, 2H), 2.75 (s, 3H), 2.70 (m, 1H), 2.21 (d, J=11.2 Hz, 2H), 1.99 (d, J=12.1 Hz, 2H), 1.49 (m, 2H), 1.33 (m, 2H).

Example 72

(1-Methyl-piperidin-4-ylmethyl)-[8,8,9-trimethyl-3-(3-trifluoromethoxy-phenyl)-8,9-dihydro-7H-6-oxa-1,2,3a,4,9-pentaaza-cyclopenta[a]naphthalen-5-yl]-amine

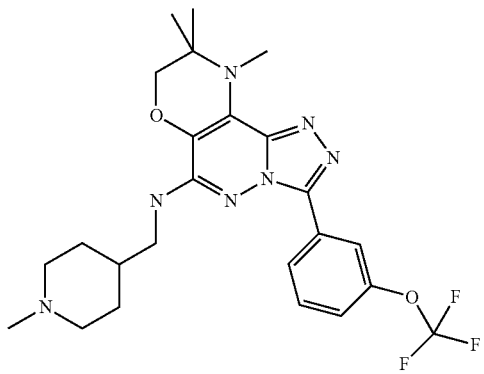 [SMILES: CN1CCC(CNc2nn3c(-c4cccc(OC(F)(F)F)c4)nnc3c3c2OCC(C)(C)N3C)CC1]

Amine: (1-methyl-4-piperidinyl)methylamine

HPLC-MS (method 1): Rt=3.62 min, [M+H]⁺ m/z 506.5.

$^1$H NMR (300 MHz, DMSO) δ 8.58 (s, 1H), 8.43 (d, J=8.0 Hz, 1H), 7.70 (m, 1H), 7.49 (d, J=8.6 Hz, 1H), 6.83 (t, J=5.4 Hz, 1H), 4.04 (s, 2H), 3.60 (s, 3H), 3.22 (m, 2H), 3.13 (m, 2H), 2.52 (m, 3H, not clearly seen), 1.93 (m, 1H), 1.81 (m, 2H), 1.30 (m, 10H).

Example 73

(1-Methyl-piperidin-4-ylmethyl)-[6,7,7-trimethyl-3-(3-trifluoromethoxy-phenyl)-7,8-dihydro-6H-9-oxa-1,2,3a,4,6-pentaaza-cyclopenta[a]naphthalen-5-yl]-amine

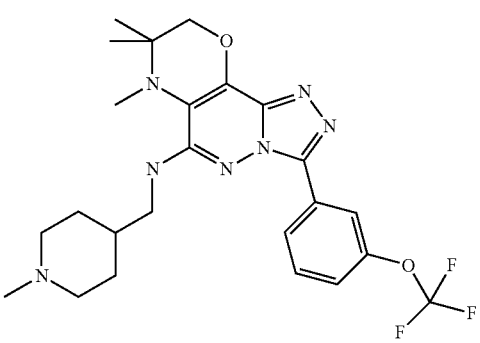 [SMILES: CN1CCC(CNc2nn3c(-c4cccc(OC(F)(F)F)c4)nnc3c3c2N(C)C(C)(C)CO3)CC1]

Amine: (1-methyl-4-piperidinyl)methylamine

HPLC-MS (method 1): Rt=3.33 min, [M+H]⁺ m/z 506.3.

$^1$H NMR (300 MHz, DMSO) b 8.58 (s, 1H), 8.42 (d, J=7.7 Hz, 1H), 7.70 (m, 1H), 7.50 (m, 1H), 6.86 (t, J=5.3 Hz, 1H), 4.14 (s, 2H), 3.25 (m, 2H), 2.84 (m, 2H), 2.54 (s, 3H), 2.20 (broad s, 3H), 1.90 (m, 1H), 1.72 (m, 2H), 1.26 (m, 4H), 1.17 (m, 6H).

Example 74

N—[(S)-6,7-Dimethyl-3-(3-trifluoromethoxy-phenyl)-7,8-dihydro-6H-9-oxa-1,2,3a,4,6-pentaaza-cyclopenta[a]naphthalen-5-yl]-cyclohexane-1,4-diamine

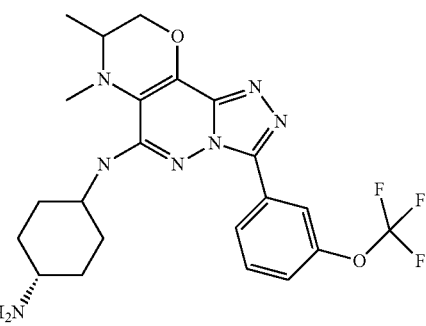

Amine: 1-N-BOC-trans-1,4-cyclohexyldiamine

HPLC-MS (method 1): Rt=3.17 min, [M+H]⁺ m/z 478.3.

$^1$H NMR (300 MHz, MeOD) δ 8.50 (s, 1H), 8.42 (m, 1H), 7.64 (m, 1H), 7.42 (m, 1H), 4.33 (m, 2H), 3.80 (m, 1H), 3.36 (m, 1H), 2.75 (m, 1H), 2.71 (s, 3H), 2.19 (m, 2H), 2.01 (m, 2H), 1.42 (m, 4H), 1.16 (d, J=7.0 Hz, 3H).

Example 77

7-[(S)-6,7-Dimethyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-ylamine

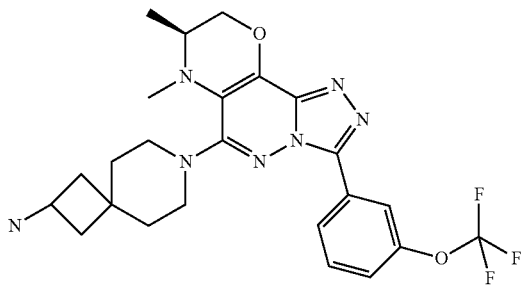 [SMILES: C[C@H]1COc2c(c(N3CCC4(CC3)CC(N)C4)nn3c(-c4cccc(OC(F)(F)F)c4)nnc23)N1C]

Amine: 2-amino-7-aza-spiro[3.5]nonane-7-carboxylic acid tert-butyl ester
HPLC-MS (method 1): Rt=3.51 min, [M+H]$^+$ m/z 504.3.
$^1$H NMR (300 MHz, MeOD) δ 8.44 (s, 1H), 8.35 (m, 1H), 7.61 (m, 1H), 7.37 (m, 1H), 4.30 (dd, J=10.6, 2.6 Hz, 1H), 4.30 (dd, J=10.6, 2.1 Hz, 1H), 3.64 (m, 2H), 3.42 (m, 2H), 3.22 (m, 2H), 2.91 (s, 3H), 2.26 (m, 2H), 1.78 (m, 4H), 1.62 (m, 2H), 1.18 (d, J=6.9 Hz, 3H).

Example 78

(7-Aza-spiro[3.5]non-2-yl)-[(S)-6,7-dimethyl-3-(3-trifluoromethoxy-phenyl)-7,8-dihydro-6H-9-oxa-1,2,3a,4,6-pentaaza-cyclopenta[a]naphthalen-5-yl]-amine

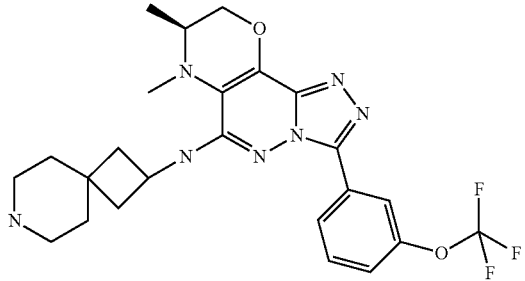 [SMILES: C[C@H]1COc2c(c(NC3CC4(CCNCC4)C3)nn3c(-c4cccc(OC(F)(F)F)c4)nnc23)N1C]

Amine: 2-amino-7-aza-spiro[3.5]nonane-7-carboxylic acid tert-butyl ester
HPLC-MS (method 1): Rt=3.41 min, [M+H]$^+$ m/z 504.4.
$^1$H NMR (300 MHz, MeOD) δ $^1$H 8.62 (s, 1H), 8.37 (m, 1H), 7.64 (m, 1H), 7.42 (m, 1H), 4.33 (m, 3H), 3.36 (m, 1H), 2.86 (m, 2H), 2.78 (m, 2H), 2.75 (s, 3H), 2.46 (m, 2H), 1.94 (m, 1H), 1.87 (m, 1H), 1.74 (m, 2H), 1.64 (m, 2H), 1.17 (d, J=7.0 Hz, 3H).

General Method II

To a solution of the appropriate chloride (ex: 5-chloro-6-methyl-3-(3-trifluoromethoxy-phenyl)-7,8-dihydro-6H-9-oxa-1,2,3a,4,6-pentaaza-cyclopenta-[a]naphthalene) in degassed dry 1,4-dioxane, sodium tert-butoxide (1.7 eq), BINAP (0.09 eq), Pd$_2$(dba)$_3$ (0.05 equiv) and the appropriate amine (ex: 1-BOC-4-(aminomethyl)piperidine) were added at room temperature. The mixture was refluxed for 6 h to 8 h (110° C.). The reaction mixture was filtered through a Celite pad and washed with DCM. The solvent was removed under vacuum to yield the crude mixture. The residue was purified by flash chromatography (Isolute/Flash, Sill, 2.5% MeOH with 7N ammonia in DCM) or by semi-preparative HPLC (Gemini C18 (150 10 mm; 5 m), Solvent A: water with 0.1% formic acid; Solvent B: acetonitrile with 0.1% formic acid. Gradient: 40% of A to 0% of A).

Example 79

4-{[6-Methyl-3-(3-trifluoromethoxy-phenyl)-7,8-dihydro-6H-9-oxa-1,2,3a,4,6-pentaaza-cyclopenta[a]naphthalen-5-ylamino]-methyl}-piperidine-1-carboxylic acid tert-butyl ester

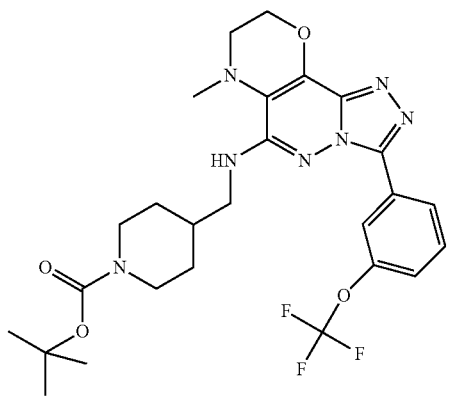 [SMILES: CN1CCOc2c1c(NCC1CCN(C(=O)OC(C)(C)C)CC1)nn1c(-c3cccc(OC(F)(F)F)c3)nnc21]

Amine: 1-BOC-4-(aminomethyl)piperidine
HPLC-MS (method 1): Rt=6.50 min, [M+H]$^+$ m/z 564.3.
$^1$H NMR ((300 MHz, CDCl$_3$) δ 8.60 (s, 1H), 8.49-8.39 (m, 1H), 7.58-7.45 (m, 1H), 7.29 (dd, J=4.6, 3.4 Hz, 1H), 5.16 (t, J=5.7 Hz, 1H), 4.52-4.40 (m, 2H), 4.29-4.05 (m, 2H), 3.43-3.28 (m, 2H), 3.27-3.15 (m, 2H), 2.72 (s, 3H), 2.10-1.89 (m, 1H), 1.86-1.60 (m, 2H), 1.46 (s, 9H), 1.36-1.12 (m, 2H).

Example 80

(4-Fluoro-benzyl)-[3-(4-methoxy-phenyl)-9-methyl-8,9-dihydro-7H-6-oxa-1,2,3a,4,9-pentaaza-cyclopenta[a]naphthalen-5-yl]-amine

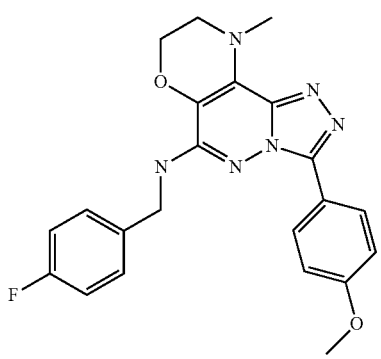 [SMILES: COc1ccc(-c2nnc3c4c(c(NCc5ccc(F)cc5)nn23)OCCN4C)cc1]

Amine: 4-fluorobenzylamine
(4-Fluoro-benzyl)-[3-(4-methoxy-phenyl)-9-methyl-8,9-dihydro-7H-6-oxa-1,2,3a,4,9-pentaaza-cyclopenta[a]naphthalen-5-yl]-amine HPLC-MS (method 1): Rt=7.21 min, [M+H]+ m/z 421.2.

1H NMR (300 MHz, CDCl3) δ 8.31 (d, J=8.7, 2H), 7.35 (dd, J=8.0, 5.7, 2H), 7.02 (t, J=8.6, 2H), 6.95 (d, J=8.7, 2H), 5.13 (s, 1H), 4.53 (d, J=5.4, 2H), 4.29 (t, J=3.9, 2H), 3.84 (s, 3H), 3.69 (s, 3H), 3.51-3.37 (m, 2H).

Example 81

(4-Fluoro-benzyl)-[3-(4-methoxy-phenyl)-6-methyl-7,8-dihydro-6H-9-oxa-1,2,3a,4,6-pentaaza-cyclopenta[a]naphthalen-5-yl]-amine

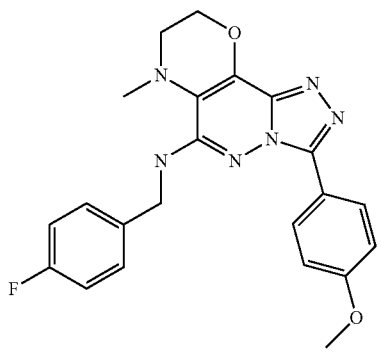 [SMILES: COc1ccc(-c2nnc3c4c(c(NCc5ccc(F)cc5)nn23)N(C)CCO4)cc1]

Amine: 4-fluorobenzylamine

HPLC-MS (method 1): Rt=6.82 min, [M+H]+ m/z 421.2.

1H NMR (300 MHz, CDCl3) δ 8.31 (d, J=8.7, 2H), 7.43-7.31 (m, 2H), 7.05 (t, J=8.5, 2H), 6.95 (d, J=8.7, 2H), 5.31 (t, J=5.0, 1H), 4.54 (d, J=5.2, 2H), 4.49-4.38 (m, 2H), 3.85 (s, 3H), 3.23-3.10 (m, 2H), 2.73 (s, 3H).

Example 82

[2-(4-Fluoro-phenyl)-ethyl]-[3-(4-methoxy-phenyl)-9-methyl-8,9-dihydro-7H-6-oxa-1,2,3a,4,9-pentaaza-cyclopenta[a]naphthalen-5-yl]-amine

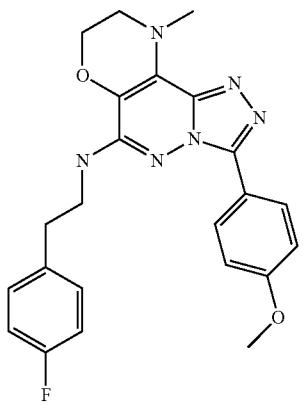 [SMILES: COc1ccc(-c2nnc3c4c(c(NCCc5ccc(F)cc5)nn23)OCCN4C)cc1]

Amine: 2-(4-fluoro-phenyl)-ethylamine

1H NMR (300 MHz, CDCl3) δ 8.52-8.43 (m, 2H), 8.07-8.01 (m, 4H), 7.05-6.98 (m, 10H), 4.87 (s, 1H), 4.31-4.23 (m, 2H), 3.87 (s, 3H), 3.70 (s, 3H), 3.63 (dd, J=14.1, 6.4, 2H), 3.48-3.40 (m, 2H), 2.96 (t, J=7.2, 2H).

Intermediate 40

2-[9-Methyl-3-(3-trifluoromethoxy-phenyl)-8,9-dihydro-7H-6-oxa-1,2,3a,4,9-pentaaza-cyclopenta[a]naphthalen-5-yl]-2,7-diaza-spiro[3.5]nonane-7-carboxylic acid tert-butyl ester

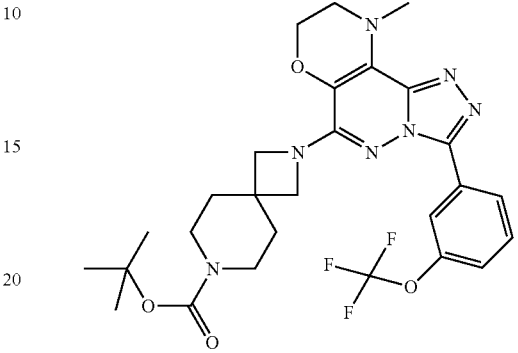

Amine: 2,7-diaza-spiro[3.5]nonane-7-carboxylic acid tert-butyl ester

HPLC-MS (method 1): Rt=7.22 min, [M+H]+ m/z 576.3.

1H NMR (300 MHz, CDCl3) δ 8.59 (s, 1H), 8.45 (d, J=8.0 Hz, 1H), 7.52 (t, J=8.1 Hz, 1H), 7.26 (d, J=2.4 Hz, 1H), 4.32-4.22 (m, 2H), 3.93 (s, 4H), 3.72 (s, 3H), 3.47 (d, J=6.7 Hz, 2H), 3.44-3.35 (m, 4H), 2.04-1.94 (s, 9H), 1.84-1.73 (m, 4H).

Example 83

5-(2,7-Diaza-spiro[3.5]non-2-yl)-9-methyl-3-(3-trifluoromethoxy-phenyl)-8,9-dihydro-7H-6-oxa-1,2,3a,4,9-pentaaza-cyclopenta[a]naphthalene

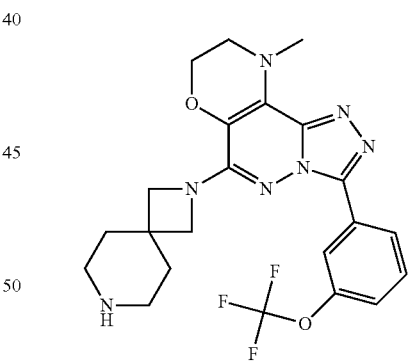

To a solution of 2-[9-methyl-3-(3-trifluoromethoxy-phenyl)-8,9-dihydro-7H-6-oxa-1,2,3a,4,9-pentaaza-cyclopenta[a]naphthalen-5-yl]-2,7-diaza-spiro[3.5]nonane-7-carboxylic acid tert-butyl ester in dry MeOH (3 mL), HCl (10 eq) (4M in dioxane, 0.5 mL) was added. The mixture was stirred at room temperature overnight. The reaction mixture was concentrated under vacuum. The residue was washed with MeOH (7N NH3). The residue was purified using semi-preparative HPLC (Gemini C18 (150 10 mm; 5 m), Solvent A: water with 0.1% formic acid; Solvent B: acetonitrile with 0.1% formic acid. Gradient: 40% of A to 0% of A) to give 5-(2,7-diaza-spiro[3.5]non-2-yl)-9-methyl-3-(3-trifluoromethoxy-phenyl)-8,9-dihydro-7H-6-oxa-1,2,3a,4,9-pentaaza-cyclopenta[a]naphthalene.

HPLC-MS (method 1): Rt=3.27 min, [M+H]+ m/z 476.2.
1H NMR ((300 MHz, MeOD) δ 8.48 (m, 1H), 8.37-8.26 (m, 1H), 7.55 (t, J=8.1 Hz, 1H), 7.31 (ddd, J=8.2, 1.5, 0.8 Hz, 1H), 4.17 (t, J=4.1 Hz, 2H), 3.80 (s, 2H), 3.53 (s, 3H), 3.36 (dd, J=5.3, 2.8 Hz, 2H), 2.84-2.71 (m, 4H), 1.85-1.69 (m, 4H).

Example 84

4-{6-Methyl-5-[(1-methyl-piperidin-4-ylmethyl)-amino]-7,8-dihydro-6H-9-oxa-1,2,3a,4,6-pentaaza-cyclopenta[a]naphthalen-3-yl}-phenol

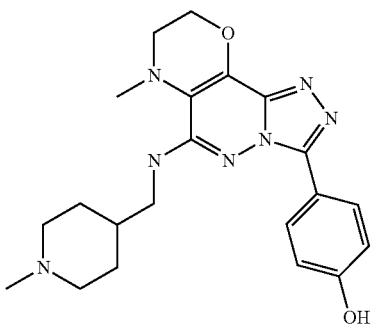 [SMILES: CN1CCC(CNc2nn3c(-c4ccc(O)cc4)nnc3c3c2N(C)CCO3)CC1]

A solution of [3-(4-methoxy-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine in DCM was cooled down to −78° C. under argon. Then, borontribromide (solution in DCM) was added dropwise and the mixture kept at −20° C. for two days. Additional amounts of borontribromide (~5 eq) and extended reaction times were needed in order to drive the reaction to completion. Once finished, the excess of borontribromide was quenched at −78° C. by adding MeOH (~0.5 mL). The pH was checked and brought up to ~9 by adding MeOH(NH₃ 7N) at room temperature. The solvent was removed under vacuum at low temperature and the sample was purified first by reversed phase chromatography followed by semi-preparative HPLC (Gemini C18 (150 10 mm; 5 m), Solvent A: water with 0.1% formic acid; Solvent B: acetonitrile with 0.1% formic acid. Gradient: 40% of A to 0% of A) to give 4-{6-methyl-5-[(1-methyl-piperidin-4-ylmethyl)-amino]-7,8-dihydro-6H-9-oxa-1,2,3a,4,6-pentaaza-cyclopenta[a]naphthalen-3-yl}-phenol (6 mg, 61% yield).
HPLC-MS (method 3): Rt=2.67 min, [M+H]+ m/z 410.5.
1H NMR (700 MHz, DMSO-d₆) δ 8.27-8.25 (m, ArH, OH; 3H), 6.90 (m, J=9.0 Hz, 2H), 6.78 (m, 1H), 4.40 (t, J=4.2 Hz, 2H), 3.2 (t, 2H), 3.18 (t, 2H), 3.17 (s, 3H), 2.8 (m, 2H), 2.66 (s, 3H), 2.5 (m, 2H), 1.9 (m, 2H), 1.7 (m, 1H), 1.27-1.23 (m, 2H).

General Method III

A mixture of the appropriate amine (ex: C-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-methylamine in acetone (2 mL) was treated with potassium carbonate (1 eq) and stirred at room temperature for 4 h. Sodium cyanoborohydride (1.2 eq) was added and the reaction mixture was stirred overnight at room temperature. The solvent was evaporated under vacuum and the residue was purified by semi-preparative HPLC (Gemini C18 (150 10 mm; 5 m), Solvent A: water with 0.1% formic acid; Solvent B: acetonitrile with 0.1% formic acid. Gradient: 40% of A to 0% of A) to give the desidered product (ex: isopropyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine).

Example 85

Isopropyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine

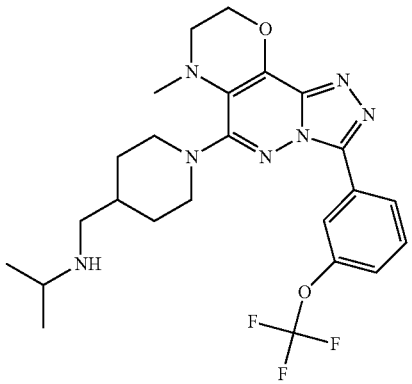 [SMILES: CC(C)NCC1CCN(c2nn3c(-c4cccc(OC(F)(F)F)c4)nnc3c3c2N(C)CCO3)CC1]

HPLC-MS (method 1): Rt=3.34 min, [M+H]+ m/z 506.3.
1H NMR (300 MHz, CDCl₃) δ 8.56 (s, 0.5H), 8.49 (s, 1H), 8.42 (d, J=8.0 Hz, 1H), 7.51 (t, J=8.1 Hz, 1H), 7.31-7.25 (m, 1H), 4.41-4.27 (m, 2H), 4.21 (d, J=12.7 Hz, 2H), 3.29-3.16 (m, 2H), 3.07-2.92 (m, 1H), 2.87 (s, 3H), 2.81 (m, 2H), 2.68 (d, J=6.6 Hz, 2H), 1.85 (m, 1H), 1.55-1.32 (m, 2H), 1.20 (2 s, 6H).

Example 86

Isopropyl-{1-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-ylmethyl}-amine

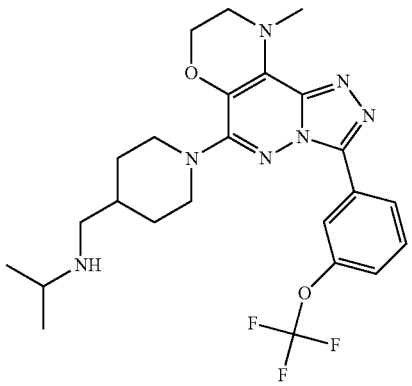 [SMILES: CC(C)NCC1CCN(c2nn3c(-c4cccc(OC(F)(F)F)c4)nnc3c3c2OCCN3C)CC1]

HPLC-MS (5-100% B in 8 min, 0.6 mU/min): Rt=3.41 min, [M+H]+ m/z 506.3.
1H NMR ((300 MHz, CDCl₃) δ 8.59 (s, 0.5H), 8.54 (s, 1H), 8.43 (d, J=8.0 Hz, 1H), 7.50 (t, J=8.1 Hz, 1H), 7.25 (d, J=5.2 Hz, 1H), 4.30 (dd, J=15.1, 11.0 Hz, 2H), 3.94 (d, J=12.8 Hz, 2H), 3.72 (s, 3H), 3.47 (dd, J=5.3, 3.1 Hz, 2H), 2.86 (dt, J=22.8, 9.3 Hz, 3H), 2.59 (d, J=6.6 Hz, 2H), 1.88 (d, J=13.8 Hz, 2H), 1.75 (s, 1H), 1.44 (dt, J=20.4, 10.4 Hz, 2H), 1.14 (t, J=5.9 Hz, 6H).

Example 87

Isopropyl-{7-[6-methyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-yl}-amine

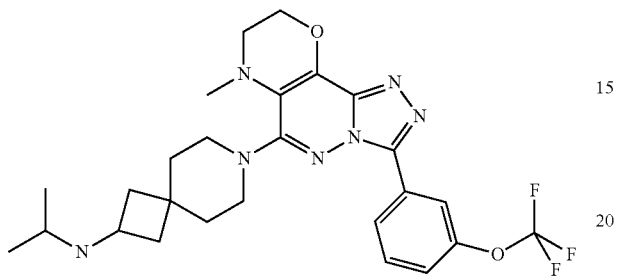

HPLC-MS (method 1): Rt=3.61 min, [M+H]⁺ m/z 532.4.
¹H NMR (300 MHz, CDCl₃) δ 8.62 (s, 1H), 8.50 (s, 1H), 8.44 (d, J=8.0 Hz, 1H), 7.54 (m, 1H), 7.28 (d, J=7.5 Hz, 1H), 4.37 (m, 2H), 3.59 (m, 1H), 3.42 (m, 4H), 3.24 (m, 2H), 3.07 (m, 1H), 2.87 (s, 3H), 2.28 (m, 2H), 2.01 (m, 2H), 1.81 (m, 4H), 1.24 (d, J=6.3 Hz, 6H).

General Method IV

A mixture of the appropriate amine (ex: [6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl-amine), the appropriate alkyl halide (ex: cyclopropylmethylbromide) (1 eq) and Et₃N (1 eq) in acetonitrile (and one drop of DMF) was heated up to 100° C. under microwave irradiation for 6 h. The reaction mixture was evaporated and the residue redissolved in DCM and washed with HCl (2N aq.sol). The residue was purified by flash chromatography (Isolute/Flash, Sill, 5% MeOH-7N ammonia in DCM) to yield the final product (ex: 1-cyclopropylmethyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine).

Example 88

(1-Cyclopropylmethyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine

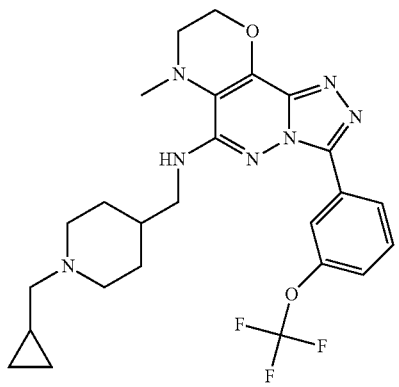 [SMILES: CN1CCOc2c1c(NCC1CCN(CC3CC3)CC1)nn1c(-c3cccc(OC(F)(F)F)c3)nnc21]

HPLC-MS (method 1): Rt=3.53 min, [M+H]⁺ m/z 518.3.
¹H NMR (300 MHz, CDCl₃) δ 8.58 (s, 1H), 8.44 (dd, J=8.0, 1.1 Hz, 1H), 7.49 (t, J=8.1 Hz, 1H), 7.30-7.26 (m, 1H), 5.12 (t, J=5.5 Hz, 1H), 4.52-4.37 (m, 2H), 3.34 (q, J=6.2 Hz, 2H), 3.18 (dd, J=9.8, 5.5 Hz, 2H), 3.11 (d, J=11.6 Hz, 2H), 2.73 (s, 3H), 2.23 (t, J=6.0 Hz, 2H), 1.97 (t, J=11.6 Hz, 2H), 1.80 (dd, J=9.1, 3.0 Hz, 3H), 1.55-1.32 (m, 3H), 0.97-0.68 (m, 2H), 0.56-0.35 (m, 2H), 0.15-0.03 (m, 2H).

Example 89

(1-Cyclopropylmethyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

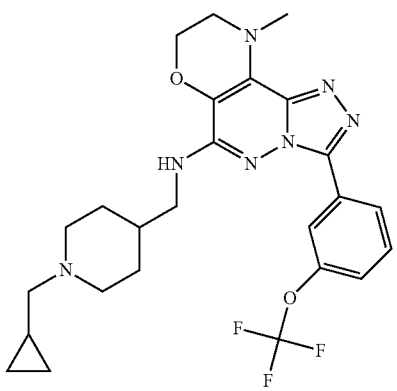 [SMILES: CN1CCOc2c(NCC3CCN(CC4CC4)CC3)nn3c(-c4cccc(OC(F)(F)F)c4)nnc3c21]

HPLC-MS (method 1): Rt=5.03 min, [M+H]⁺ m/z 492.3.
¹H NMR (300 MHz, CDCl₃) δ 8.61 (s, 1H), 8.42 (d, J=8.0 Hz, 1H), 8.01 (s, 1H), 7.50 (t, J=8.1 Hz, 1H), 7.26 (d, J=8.7 Hz, 1H), 4.98 (s, 1H), 4.45 (d, J=13.6 Hz, 2H), 4.38-4.26 (m, 2H), 3.67 (s, 3H), 3.65 (d, J=13.2 Hz, 1H), 3.51-3.43 (m, 2H), 3.43-3.22 (m, 2H), 3.06 (dd, J=18.0, 7.8 Hz, 1H), 2.61 (td, J=12.9, 3.1 Hz, 2H), 1.88 (t, J=12.6 Hz, 2H).

General Method V

To a solution of the appropriate amine (ex: methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine) (1 eq) in dry DMF (47 mL/mmol), Et₃N (3 eq) was added and the mixture was stirred at room temperature for 10 min. The reaction mixture was cooled down to 0° C. and the appropriate alkyl halide (0.99 eq) (ex: ethyl bromide) was added. The mixture was allowed to reach RT and stirred overnight. To the reaction mixture drops of NaOH aq. solution (2M) were added. The solvent was removed under vacuum. The resulting residue was purified by semi-preparative HPLC (Gemini C18 (150 10 mm; 5 m), Solvent A: water with 0.1% formic acid; Solvent B: acetonitrile with 0.1% formic acid. Gradient: 40% of A to 0% of A) to yield the desired product (ex: ethyl-methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine).

Example 90

Ethyl-methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine; HCOOH salt

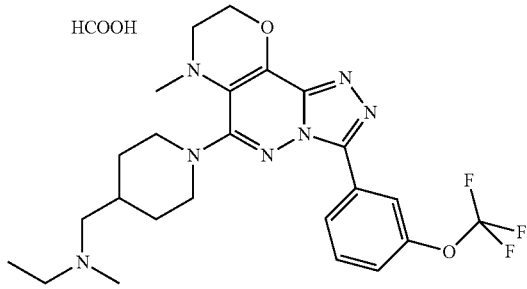 [SMILES: CCN(C)CC1CCN(c2nn3c(-c4cccc(OC(F)(F)F)c4)nnc3c3c2N(C)CCO3)CC1 ; "HCOOH"]

HPLC-MS (method 1): Rt=3.46 min, [M+H]$^+$ m/z 506.3.
$^1$H NMR (300 MHz, MeOD) δ 8.54 (s, 1H), 8.49 (s, 1H), 8.41 (d, J=7.9 Hz, 1H), 7.68 (m, 1H), 7.45 (d, J=8.5 Hz, 1H), 4.44 (m, 2H), 4.36 (m, 2H), 3.36 (m, 2H), 3.08 (m, 2H), 2.97 (s, 3H), 2.91 (m, 4H), 2.76 (s, 3H), 2.07 (m, 1H), 1.97 (m, 2H), 1.60 (m, 2H), 1.32 (t, J=7.2 Hz, 3H).
Yield: 17%

Example 91

(1-Ethyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine; compound with formic acid

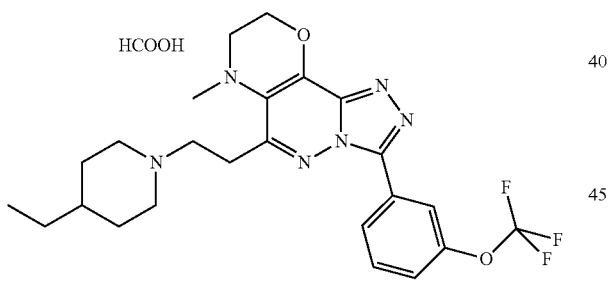

HPLC-MS (method 1): Rt=3.20 min, [M+H]$^+$ m/z 492.3.
$^1$H NMR (300 MHz, MeOD) δ 8.49 (s, 1H), 8.46 (s, 1H), 8.36 (d, J=7.9 Hz, 1H), 7.63 (m, 1H), 7.41 (d, J=8.1 Hz, 1H), 4.49 (m, 2H), 3.58 (d, J=12.1 Hz, 2H), 3.41 (d, J=6.4 Hz, 2H), 3.26 (m, 2H), 3.14 (m, 2H), 2.95 (m, 2H), 2.78 (s, 3H), 2.26 (m, 1H), 2.10 (m, 2H), 1.62 (m, 2H), 1.33 (t, J=7.1 Hz, 3H).

General Method VI

To a THF solution of the appropriate amine (ex: C-{1-[3-(4-methoxy-phenyl)-6-methyl-7,8-dihydro-6H-9-oxa-1,2,3a,4,6-pentaaza-cyclopenta[a]naphthalen-5-yl]-piperidin-4-yl}-methylamine) at room tempearture, DMAP (1.5 eq) and acetic anhydride (1 eq) were added. The mixture was stirred at room temperature for 48 h. Then, DCM was added to the reaction mixture. The organic phase was washed with sodium bicarbonate (aq. solution) and dried with magnesium sulphate. The obtained residue was filtered through silica flash to eliminate part of the impurities. The residue was purified by semi-preparative HPLC (Gemini C18 (150 mm; 5 m), Solvent A: water with 0.1% formic acid; Solvent B: acetonitrile with 0.1% formic acid. Gradient: 40% of A to 0% of A) to give the desired product (ex: N-{1-[3-(4-methoxy-phenyl)-6-methyl-7,8-dihydro-6H-9-oxa-1,2,3a,4,6-pentaaza-cyclopenta[a]naphthalen-5-yl]-piperidin-4-ylmethyl}-acetamide).

Example 92

N-{1-[3-(4-Methoxy-phenyl)-6-methyl-7,8-dihydro-6H-9-oxa-1,2,3a,4,6-pentaaza-cyclopenta[a]naphthalen-5-yl]-piperidin-4-ylmeth I}-acetamide

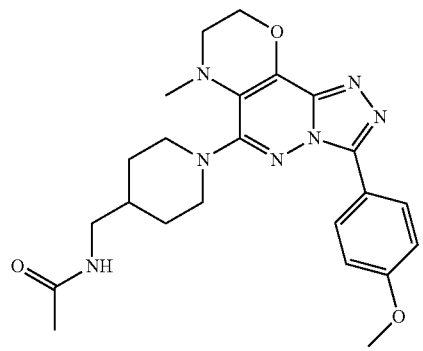 [SMILES: COc1ccc(-c2nnc3c4c(c(N5CCC(CNC(C)=O)CC5)nn23)N(C)CCO4)cc1]

HPLC-MS (method 1): Rt=4.31 min, [M+H]$^+$ m/z 452.3.
$^1$H NMR (300 MHz, CDCl$_3$) δ 8.40 (d, J=9.0 Hz, 2H), 7.00 (d, J=9.0 Hz, 2H), 5.72 (m, 1H), 4.42-4.26 (m, 2H), 4.16 (d, J=12.7 Hz, 2H), 3.85 (s, 3H), 3.29-3.13 (m, 4H), 2.87 (s, 3H), 2.75 (t, J=11.6 Hz, 2H), 2.00 (s, 3H), 1.85 (d, J=11.8 Hz, 2H), 1.76-1.58 (m, 1H), 1.51-1.31 (m, 2H).

Example 93

N-{1-[6-Methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-acetamide

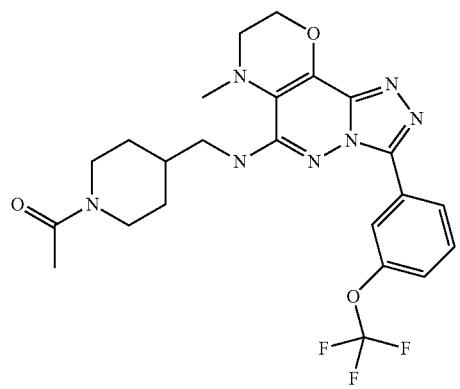 [SMILES: CC(=O)N1CCC(CNc2nn3c(-c4cccc(OC(F)(F)F)c4)nnc3c3c2N(C)CCO3)CC1]

HPLC-MS (method 1): Rt=4.91 min, [M+H]$^+$ m/z 506.2.
$^1$H NMR (300 MHz, MeOD) δ8.57 (s, 1H), 8.40 (d, J=7.4 Hz, 1H), 7.65 (m, 1H), 7.43 (d, J=7.7 Hz, 1H), 4.58 (s, 2H), 3.96 (d, J=13.5 Hz, 1H), 3.33 (m, 4H), 3.12 (t, J=12.6 Hz, 1H), 2.80 (s, 3H), 2.64 (t, J=12.2 Hz, 1H), 2.19 (m, 1H), 2.10 (s, 3H), 1.91 (m, 2H), 1.26 (m, 3H).

Example 94

4-[5-(4-Fluoro-benzylamino)-6,9-dimethyl-6,7,8,9-tetrahydro-1,2,3a,4,6,9-hexaaza-cyclopenta[a]naphthalen-3-yl]-phenol

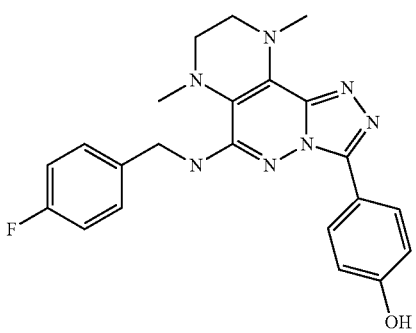 [SMILES: CN1CCN(C)c2c1c(NCc1ccc(F)cc1)nn1c(-c3ccc(O)cc3)nnc21]

To a DCM (10 mL) solution of (4-fluoro-benzyl)-[3-(4-methoxy-phenyl)-6,9-dimethyl-6,7,8,9-tetrahydro-1,2,3a,4,6,9-hexaaza-cyclopenta[a]naphthalen-5-yl]-amine (0.05 g, 0.115 mmol, 1.0 eq) under argon at −78° C., borontribromide (1.15 mL, 1.15 mmol, 10.0 eq) was added. Then, the reaction mixture was kept at −20° C. overnight. Additional amounts of borontribromide (2×1.0 mL) were added at −78° C. and stirred for 2×6 h. Cooled down at −78° C., MeOH was added (5 mL) and stirred for 1 h. Solvent was removed under vacuum. The crude solid was triturated from water and cooled down 0° C. Ammonia solution (32%) was added until pH=8 and the solid was filtered off, washed with cold water and dried with diethyl ether to afford 4-[5-(4-fluoro-benzylamino)-6,9-dimethyl-6,7,8,9-tetrahydro-1,2,3a,4,6,9-hexaaza-cyclopenta[a]naphthalen-3-yl]-phenol (0.045 g)

HPLC-MS (method 1): Rt=4.99 min, [M+H]$^+$ m/z 420.2.
$^1$H NMR (300 MHz, DMSO-ds) δ: 9.77 (s, 1H), 8.01 (d, J=8.7, 2H), 7.42 (dd, J=8.4, 5.7, 2H), 7.14 (t, J=8.8, 2H), 6.99 (t, J=5.8, 1H), 6.80 (d, J=8.8, 2H), 4.46 (d, J=5.7, 2H), 3.73 (s, 3H), 3.39 (m, 2H), 3.03 (m, 2H), 2.61 (s, 3H).

Example 95

1-(4-{2-[9-Methyl-3-(3-trifluoromethoxy-phenyl)-8,9-dihydro-7H-6-oxa-1,2,3a,4,9-pentaaza-cyclopenta[a]naphthalen-5-ylamino]-ethyl}-piperazin-1-yl)-ethanone

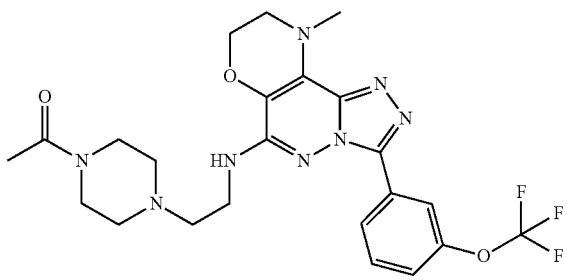 [SMILES: CC(=O)N1CCN(CCNc2nn3c(-c4cccc(OC(F)(F)F)c4)nnc3c3c2OCCN3C)CC1]

Dimethylaminopyridine (13 mg, 0.103 mmol) was added to a mixture of [9-Methyl-3-(3-trifluoromethoxy-phenyl)-8,9-dihydro-7H-6-oxa-1,2,3a,4,9-pentaaza-cyclopenta[a]naphthalen-5-yl]-(2-piperazin-1-yl-ethyl)-amine (33 mg, 0.069 mmol) in THF (1 mL) at room temperature followed by the addition of acetic anhydride (0.01 mL, 0.103 mmol). The reaction was stirred at room temperature for 24 h. The reaction was diluted with DCM and washed with a saturated sodium bicarbonate solution. The combined organic layers were dried (sodium sulphate), filtered and concentrated. The residue was purified by column chromatography (Isolute/Flash, Sill, 0% to 20% MeOH in DCM) followed by semi-preparative HPLC to give 1-(4-{2-[9-Methyl-3-(3-trifluoromethoxy-phenyl)-8,9-dihydro-7H-6-oxa-1,2,3a,4,9-pentaaza-cyclopenta[a]naphthalen-5-ylamino]-ethyl}-piperazin-1-yl)-ethanone.

HPLC-MS (method 1): Rt=3.19 min, [M+H]$^+$ m/z 521.3.
$^1$H NMR (300 MHz, CDCl$_3$) δ 8.54 (s, 1H), 8.48-8.43 (m, 1H), 7.56 (t, J=8.1 Hz, 1H), 7.31 (dt, J=6.2, 2.2 Hz, 1H), 4.37-4.32 (m, 2H), 3.82 (s, 3H), 3.59-3.51 (m, 6H), 3.47 (dd, J=11.0, 5.3 Hz, 2H), 2.73 (d, J=28.8 Hz, 6H), 2.04 (s, 3H).

Example 95A

N-[9-Methyl-3-(3-trifluoromethoxy-phenyl)-8,9-dihydro-7H-6-oxa-1,2,3a,4,9-pentaaza-cyclopenta[a]naphthalen-5-yl]-N-(2-piperazin-1-yl-ethyl)-acetamide

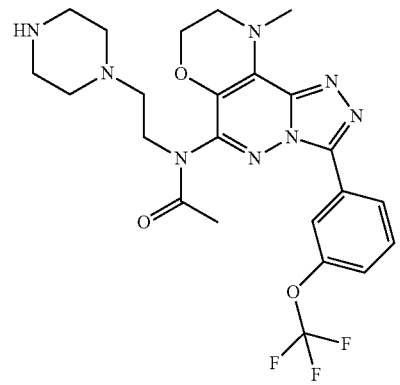 [SMILES: CC(=O)N(CCN1CCNCC1)c1nn2c(-c3cccc(OC(F)(F)F)c3)nnc2c2c1OCCN2C]

N-[9-Methyl-3-(3-trifluoromethoxy-phenyl)-8,9-dihydro-7H-6-oxa-1,2,3a,4,9-pentaaza-cyclopenta[a]naphthalen-5-yl]-N-(2-piperazin-1-yl-ethyl)-acetamide was obtained as a secondary product in the synthesis of 1-(4-{2-[9-methyl-3-(3-trifluoromethoxy-phenyl)-8,9-dihydro-7H-6-oxa-1,2,3a,4,9-pentaaza-cyclopenta[a]naphthalen-5-ylamino]-ethyl}-piperazin-1-yl)-ethanone.

HPLC-MS (method 1): Rt=3.175 min, [M+H]$^+$ m/z 521.3.
$^1$H NMR (300 MHz, CDCl$_3$) δ 8.60 (s, 1H), 8.45 (d, J=7.9 Hz, 1H), 7.53 (t, J=8.1 Hz, 1H), 7.29 (t, J=2.7 Hz, 1H), 5.45 (brs, 1H), 4.40-4.33 (m, 2H), 3.74 (s, 3H), 3.70-3.48 (m, 8H), 2.82-2.48 (m, 6H), 2.11 (s, 3H).

Yield: 28%.

Example 96

[2-(4-Methanesulfonyl-piperazin-1-yl)-ethyl]-[9-methyl-3-(3-trifluoromethoxy-phenyl)-8,9-dihydro-7H-6-oxa-1,2,3a,4,9-pentaaza-cyclopenta[a]naphthalen-5-yl]-amine

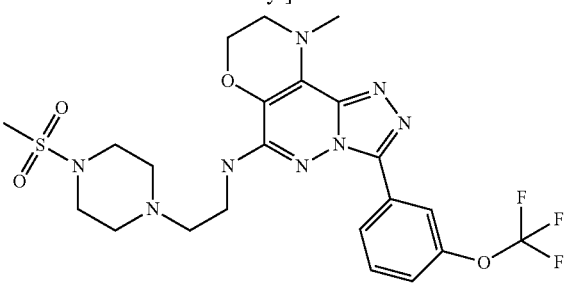

To a mixture of [9-methyl-3-(3-trifluoromethoxy-phenyl)-8,9-dihydro-7H-6-oxa-1,2,3a,4,9-pentaaza-cyclopenta[a]naphthalen-5-yl]-(2-piperazin-1-yl-ethyl)-amine (38 mg, 0.079 mmol) in acetonitrile (1.22 mL) at 0° C. was added triethylamine (0.033 mL, 0.208 mmol) followed by the addition of methanesulfonyl chloride (0.008 mL, 0.103 mmol). The reaction was stirred at room temperature for 24 h. The reaction was diluted with DCM and washed with a saturated sodium bicarbonate solution. The combined organic layers were dried (sodium sulphate), filtered and concentrated. The residue was purified by column chromatography (Isolute/Flash, Sill, 0% to 10% MeOH in DCM) followed by semi-preparative HPLC to give [2-(4-Methanesulfonyl-piperazin-1-yl)-ethyl]-[9-methyl-3-(3-Trifluoromethoxy-phenyl)-8,9-dihydro-7H-6-oxa-1,2,3a,4,9-pentaaza-cyclopenta[a]naphthalen-5-yl]-amine.

HPLC-MS (method 1): Rt=3.47 min, [M+H]⁺ m/z 557.2.
¹H NMR (300 MHz, CDCl₃) δ 8.60 (s, 1H), 8.45 (d, J=8.0 Hz, 1H), 7.53 (t, J=8.1 Hz, 1H), 7.31-7.27 (m, 1H), 5.31 (brs, 1H), 4.39-4.33 (m, 2H), 3.74 (s, 3H), 3.62-3.47 (m, 4H), 3.40-3.24 (m, 4H), 2.83 (s, 3H), 2.80-2.58 (m, 6H).

Example 96A

N-[9-Methyl-3-(3-trifluoromethoxy-phenyl)-8,9-dihydro-7H-6-oxa-1,2,3a,4,9-pentaaza-cyclopenta[a]naphthalen-5-yl]-N-(2-piperazin-1-yl-ethyl)-methanesulfonamide

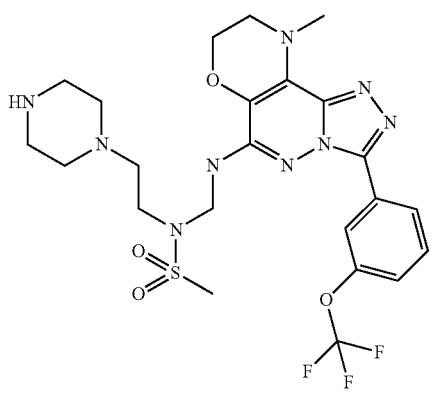 [SMILES: CN1CCOc2c(NCN(CCN3CCNCC3)S(C)(=O)=O)nn3c(-c4cccc(OC(F)(F)F)c4)nnc3c21]

N-[9-Methyl-3-(3-trifluoromethoxy-phenyl)-8,9-dihydro-7H-6-oxa-1,2,3a,4,9-pentaaza-cyclopenta[a]naphthalen-5-yl]-N-(2-piperazin-1-yl-ethyl)-methanesulfonamide was obtained as a secondary product in the synthesis of [2-(4-methanesulfonyl-piperazin-1-yl)-ethyl]-[9-methyl-3-(3-Trifluoromethoxy-phenyl)-8,9-dihydro-7H-6-oxa-1,2,3a,4,9-pentaaza-cyclopenta[a]naphthalen-5-yl]-amine.

HPLC-MS (method 1): Rt=3.09 min, [M+H]⁺ m/z 261.2.
¹H NMR (300 MHz, CDCl₃) δ 8.49 (s, 1H), 8.47-8.42 (m, 1H), 7.57 (t, J=8.1 Hz, 1H), 7.59-7.29 (m, 1H), 5.70 (brs, 1H), 4.36-4.30 (m, 2H), 3.83 (s, 3H), 3.70-3.61 (m, 4H), 3.59-3.53 (m, 2H), 3.43 (dt, J=5.7, 3.9 Hz, 2H), 3.02 (s, 3H), 2.89 (dd, J=16.0, 10.4 Hz, 6H).
Yield: 23%.
General Method VII To a DMF (75 mL/mmol) solution of an appropriate aniline (ex: [6-Methyl-3-(3-trifluoromethoxy-phenyl)-7,8-dihydro-6H-9-oxa-1,2,3a,4,6-pentaaza-cyclopenta[a]naphthalen-5-yl]-(tetrahydro-pyran-4-yl)-amine) (1 eq) at 0° C. was added in one portion NaH (10 eq). The colorless mixture turned to yellow, small bubbles were observed. The reaction mixture was stirred for 20 min at 0° C., then MeI was added dropwise (32 eq). The reaction mixture was stirred for 30 min at this temperature and 2 h more at room temperature. The reaction mixture was quenched with brine and extracted with EtOAc (×4). The combined organic layers were dried over Na₂SO₄ anhydrous and the solvent evaporated under vacuum. The obtained residue was purified by semi-preparative HPLC to yield the wanted final product (ex: methyl-[6-methyl-3-(3-trifluoromethoxy-phenyl)-7,8-dihydro-6H-9-oxa-1,2,3a,4,6-pentaaza-cyclopenta[a]naphthalen-5-yl]-(tetrahydro-pyran-4-yl)-amine).

Example 97

Methyl-[6-methyl-3-(3-trifluoromethoxy-phenyl)-7,8-dihydro-6H-9-oxa-1,2,3a,4,6-pentaaza-cyclopenta[a]naphthalen-5-yl]-(tetrahydro-pyran-4-yl)-amine

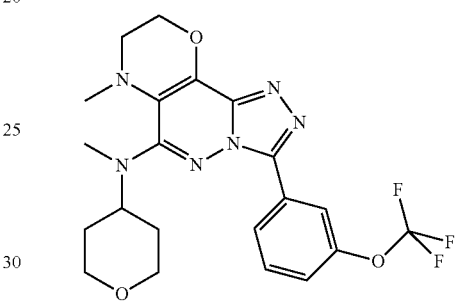

HPLC-MS (method 1): Rt=5.84 min, [M+H]⁺ m/z 465.2.
¹H NMR (300 MHz, CDCl₃) δ 8.49 (s, 1H), 8.45 (m, 1H), 7.53 (m, 1H), 7.31 (m, 1H), 4.40 (m, 2H), 4.34 (m, 1H), 4.09 (dd, J=11.3, 4.2 Hz, 2H), 3.50 (m, 2H), 3.30 (m, 2H), 2.99 (s, 3H), 2.84 (s, 3H), 1.98 (m, 2H), 1.78 (m, 2H).

Example 98

Methyl-[6-methyl-3-(3-trifluoromethoxy-phenyl)-7,8-dihydro-6H-9-oxa-1,2,3a,4,6-pentaaza-cyclopenta[a]naphthalen-5-yl]-(2-morpholin-4-yl-ethyl)-amine

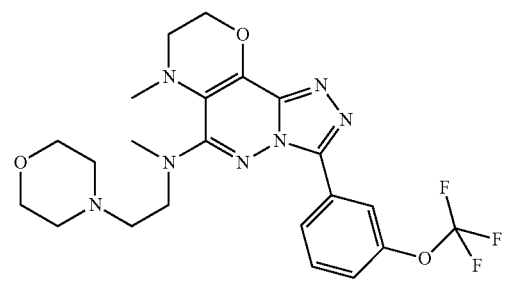 [SMILES: CN(CCN1CCOCC1)c1nn2c(-c3cccc(OC(F)(F)F)c3)nnc2c2c1N(C)CCO2]

HPLC-MS (method 1): Rt=4.14 min, [M+H]⁺ m/z 494.2.
¹H NMR (300 MHz, CDCl₃) G 8.43 (s, 1H), 8.36 (d, J=8.0 Hz, 1H), 8.22 (s, 1H), 7.47 (m, 1H), 7.23 (m, 1H), 4.32 (m, 2H), 3.73 (t, J=6.9 Hz, 2H), 3.56 (m, 4H), 3.21 (m, 2H), 3.04 (s, 3H), 2.77 (s, 3H), 2.60 (t, J=6.9 Hz, 2H), 2.47 (m, 4H).

Example 99

Cyclopropylmethyl-[3-(4-fluoro-phenyl)-6-methyl-7,8-dihydro-6H-9-oxa-1,2,3a,4,6-pentaaza-cyclopenta[a]naphthalen-5-yl]-amine

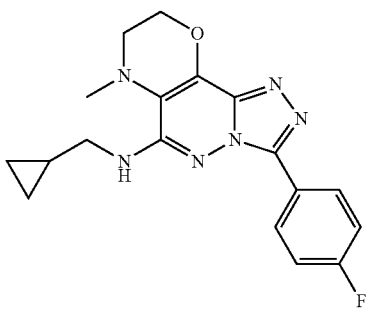 [SMILES: CN1CCOc2c1c(NCC1CC1)nn1c(-c3ccc(F)cc3)nnc21]

A mixture of 5-chloro-6-methyl-7,8-dihydro-6H-9-oxa-1,2,3a,4,6-pentaaza-cyclopenta[a]naphthalene (90 mg, 0.399 mmol) and cyclopropanemethylamine (0.17 mL, 1.994 mmol) in nBuOH (1.6 mL) was heated under microwave irradiation at 185° C. for 3 h. The solvent was evaporated under vacuum. The residue was purified by column chromatography (Isolute/Flash, Sill, 0% to 4% MeOH in DCM) to give a pale yellow solid which corresponds to cyclopropylmethyl-(6-methyl-7,8-dihydro-6H-9-oxa-1,2,3a,4,6-pentaaza-cyclopenta[a]naphthalen-5-yl)-amine (72 mg).

HPLC-MS ( ): Rt=3.09 min, [M+H]+ m/z 261.2.
$^1$H NMR (300 MHz, CDCl$_3$) δ 8.64 (s, 1H), 5.06 (brs, 1H), 4.47-4.38 (m, 2H), 3.26-3.12 (m, 4H), 2.73 (s, 3H), 1.22-1.06 (m, 1H), 0.66-0.51 (m, 2H), 0.34-0.23 (m, 2H).

A mixture of cyclopropylmethyl-(6-methyl-7,8-dihydro-6H-9-oxa-1,2,3a,4,6-pentaaza-cyclopenta[a]naphthalen-5-yl)-amine (72 mg, 0.277 mmol) and N-bromosuccinimide (59 mg, 0.332 mmol) in chloroform (0.73 mL) was stirred at room temperature for 24 h. The reaction was diluted with DCM and washed with a saturated sodium bicarbonate solution. The combined organic layers were dried (sodium sulphate), filtered and concentrated. The residue was purified by column chromatography (Isolute/Flash, Sill, 0% to 1% MeOH in DCM) to give (3-bromo-6-methyl-7,8-dihydro-6H-9-oxa-1,2,3a,4,6-pentaaza-cyclopenta[a]naphthalen-5-yl)-(2-methyl-butyl)-amine (13 mg, 14% yield).

The same intermediate was obtained by the following reaction:

A mixture of 3-Bromo-5-chloro-6-methyl-7,8-dihydro-6H-9-oxa-1,2,3a,4,6-pentaaza-cyclopenta[a]naphthalene (23 mg, 0.076 mmol) and cyclopropanemethylamine (6 mg, 0.091 mmol) in nBuOH (0.5 mL) was heated under microwave irradiation at 185° C. for 4 h. The solvent was evaporated under vacuum. The residue was purified by column chromatography (Isolute/Flash, Sill, 0% to 1% MeOH in DCM) to give (3-bromo-6-methyl-7,8-dihydro-6H-9-oxa-1,2,3a,4,6-pentaaza-cyclopenta[a]naphthalen-5-yl)-(2-methyl-butyl)-amine (10 mg, 39% yield).

A mixture of (3-bromo-6-methyl-7,8-dihydro-6H-9-oxa-1,2,3a,4,6-pentaaza-cyclopenta[a]naphthalen-5-yl)-(2-methyl-butyl)-amine (13 mg, 0.038 mmol), 4-fluorophenyl-boronic acid (6 mg, 0.046 mmol), Pd(PPh$_3$)$_4$ (1 mg, 0.00038 mmol) and cesium carbonate (37 mg, 0.115 mmol) in 1,4-dioxane (0.3 mL) and water (0.2 mL) was heated under microwave irradiation at 140° C. for 30 min. The reaction was diluted with DCM and water was added. The organic layer was separated, dried (sodium sulphate), filtered and concentrated. The residue was purified by column chromatography (Isolute/Flash, Sill, 0% to 1% MeOH in DCM) to give cyclopropylmethyl-[3-(4-fluoro-phenyl)-6-methyl-7,8-dihydro-6H-9-oxa-1,2,3a,4,6-pentaaza-cyclopenta[a]naphthalen-5-yl]-amine.

HPLC-MS (method 1): Rt=5.15 min, [M+H]+ m/z 356.2.
$^1$H NMR (300 MHz, CDCl$_3$) δ 8.54 (dd, J=9.0, 5.5, 2H), 7.20 (t, J=8.8, 2H), 5.12 (s, 1H), 4.52-4.43 (m, 2H), 3.28 (dd, J=7.1, 5.2, 2H), 3.25-3.20 (m, 2H), 2.78 (s, 3H), 1.24-1.17 (m, 1H), 0.69-0.57 (m, 2H), 0.34 (q, J=4.8, 2H).

Yield: 64%.

Example 100

[3-(4-Fluoro-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine

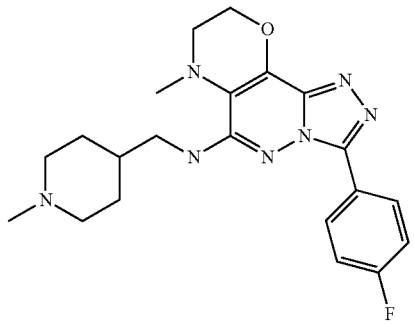 [SMILES: CN1CCC(CNc2nn3c(-c4ccc(F)cc4)nnc3c3c2N(C)CCO3)CC1]

Following the reaction sequence described for cyclopropylmethyl-[3-(4-fluoro-phenyl)-6-methyl-7,8-dihydro-6H-9-oxa-1,2,3a,4,6-pentaaza-cyclopenta[a]naph-thalen-5-yl]-amine starting from 3-bromo-5-chloro-6-methyl-7,8-dihydro-6H-9-oxa-1,2,3a,4,6-pentaaza-cyclopenta[a]naphthalene.

HPLC-MS (method 1): Rt=3.37 min, [M+H]+ m/z 412.2.
$^1$H NMR (300 MHz, MeOD) δ 8.26 (dd, J=9.0, 5.4, 2H), 8.23 (s, 1H), 7.15 (t, J=8.8, 2H), 4.43-4.32 (m, 2H), 3.43 (d, J=11.8, 2H), 3.28 (d, J=6.6, 2H), 3.19-3.11 (m, 2H), 2.94 (t, J=12.5, 2H), 2.75 (s, 3H), 2.67 (s, 3H), 2.19-2.02 (m, 1H), 1.97 (d, J=13.7, 2H), 1.61-1.39 (m, 2H).

Example 101

5-Piperidin-1-yl-3-(3-trifluoromethoxy-phenyl)-7,8-dihydro-6,9-dioxa-1,2,3a,4-tetraaza-cyclopenta[a]naphthalene

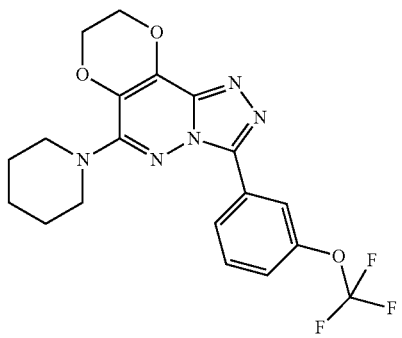 [SMILES: FC(F)(F)Oc1cccc(-c2nnc3c4c(c(N5CCCCC5)nn23)OCCO4)c1]

A mixture 5-chloro-2,3-dihydro-[1,4]dioxino[2,3-d]pyridazine (300 mg, 1.74 mmol) and piperidine (0.69 mL, 6.92 mmol) in n-BuOH (2 mL) was heated for 1.5 h at 150° C. under MW irradiation. On cooling, the mixture was taken up with EtOAc (200 mL), NaHCO$_3$ (sat aq) (25 mL) was added and the organic phase separated.

The combined organic phases were dried (Na$_2$SO$_4$) and the solvent removed under vacuum. The obtained residue was purified by recrystallization from cyclohexane/pentanes to give 5-piperidin-1-yl-2,3-dihydro-[1,4]dioxino[2,3-d] pyridazine as a yellow solid (342 g, 89% yield).

HPLC-MS (method 4): Rt=0.826 min, [M+H]$^+$ m/z 222.1.
$^1$H NMR (300 MHz, CDCl$_3$) δ 8.42 (s, 1H), 4.41 (m, 2H), 4.36 (m, 2H), 3.47 (dd, J=12.8, 8.1 Hz, 4H), 1.69 (m, 6H).

A solution of 5-piperidin-1-yl-2,3-dihydro-[1,4]dioxino [2,3-d]pyridazine (62 mg, 0.28 mmol) in THF (5 mL) was cooled to −78° C. Then, a solution of lithium diisopropylamide (1.3 N in THF/heptane/ethylbenzene) (0.46 mL, 0.6 mmol) was added dropwise and the mixture was stirred for 45 minutes at −78° C. Hexachloroethane (142 mg, 0.6 mmol) was added, the mixture was stirred for 1 h at −78° C. The reaction was quenched with aqueous saturated NH$_4$Cl (10 mL) at −78° C. and extracted with EtOAc (4×50 mL). The combined organic layers were dried (Na2SO4) and the solvent removed under vacuum. The obtained residue was purified by flash column chromatography (hexanes/EtOAc 7:3 to 1:1) to give 5-chloro-8-piperidin-1-yl-2,3-dihydro-[1, 4]dioxino[2,3-d]pyridazine as a yellow solid (49 mg, 70% yield).

HPLC-MS (method 4): Rt=3.81 min, [M+H]$^+$ m/z 256.2.
$^1$H NMR (300 MHz, CDCl$_3$) δ 4.43-4.30 (m, 4H), 3.41-3.31 (m, 4H), 1.62 (d, J=9.8 Hz, 6H).

A mixture of 5-chloro-8-piperidin-1-yl-2,3-dihydro-[1,4] dioxino[2,3-d]pyridazine (50 mg, 0.20 mmol) and 3-(trifluoromethoxy)benzohydrazide (67 mg, 0.30 mmol) in n-BuOH (2 mL) was heated for 1.5 h at 185° C. under MW irradiation. After cooling, the mixture was taken up with EtOAc (250 mL) and saturated aqueous NaHCO$_3$ (25 mL). After extraction with EtOAc, the combined organic phases were dried (Na$_2$SO$_4$) and the solvent removed under reduced pressure. The obtained residue was purified by flash column chromatography (EtOAc followed by EtOAc/MeOH 100:1) to give a white solid that was further purified by C-18 column chromatography (water to water/MeCN 1:1 mixtures) to give 28 mgs of 5-piperidin-1-yl-3-(3-trifluoromethoxy-phenyl)-7,8-dihydro-6,9-dioxa-1,2,3a,4-tetraazacyclopenta[a]naphthalene as a white solid (34% yield).

HPLC-MS (method 1): Rt=6.24 min, [M+H]$^+$ m/z 422.2.
$^1$H NMR (300 MHz, DMSO-d$_6$) δ 8.46 (s, 1H), 8.39 (d, J=7.9 Hz, 1H), 7.72 (m, 1H), 7.52 (m, 1H), 4.60 (m, 2H), 4.50 (m, 2H), 3.43 (m, 4H), 1.65 (m, 6H).

Example 102

Cyclopropylmethyl-[3-(3-trifluoromethoxy-phenyl)-7,8-dihydro-6,9-dioxa-1,2,3a,4-tetraaza-cyclopenta[a]naphthalen-5-yl]-amine

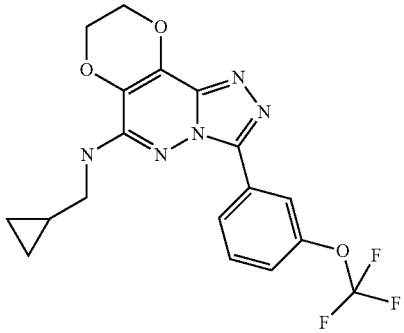 [SMILES: FC(F)(F)Oc1cccc(-c2nnc3c4c(c(NCC5CC5)nn23)OCCO4)c1]

A mixture 5-chloro-2,3-dihydro-[1,4]dioxino[2,3-d] pyridazine (300 mg, 1.74 mmol) and cyclopropanemethylamine (0.60 mL, 6.92 mmol) in n-BuOH (4 mL) was heated for 11 h at 150° C. under MW irradiation. On cooling, the solvents were removed under vacuum to give a residue that was purified by flash column chromatography (EtOAc as eluant) to give the desired compound cyclopropylmethyl-(2,3-dihydro-[1,4]dioxino[2,3-d]pyridazin-5-yl)-amine as a colourless oil (278 mg, 77% yield).

HPLC-MS (method 4): Rt=0.42 min, [M+H]$^+$ m/z 208.1.
$^1$H NMR (300 MHz, CDCl$_3$) δ 8.24 (s, 1H), 4.67 (bs, 1H), 4.40 (m, 2H), 4.34 (m, 2H), 3.42 (dd, J=7.1, 5.3 Hz, 2H), 1.14 (qd, J=7.3, 3.6 Hz, 1H), 0.55 (m, 2H), 0.28 (q, J=4.6 Hz, 2H).

A mixture cyclopropylmethyl-(2,3-dihydro-[1,4]dioxino [2,3-d]pyridazin-5-yl)-amine (150 mg, 0.72 mmol) and N-chlorosuccinimide (145 mg, 1.08 mmol) in acetonitrile (5 mL) was heated in a sealed tube for 18 h at 120° C. On cooling, the solvents were removed under vacuum to give a residue that was purified by flash column chromatography (hexane to hexane/EtOAc 1:1 mixtures) to afford (8-chloro-2,3-dihydro-[1,4]dioxino[2,3-d]pyridazin-5-yl)-cyclopropylmethyl-amine as a yellow solid (158 mg, 91% yield).

HPLC-MS (method 4): Rt=0.99 min, [M+H]$^+$ m/z 242.1.
$^1$H NMR (300 MHz, CDCl$_3$) δ 4.45 (bs, 4H), 3.40 (dd, J=7.1, 5.4 Hz, 2H), 1.13 (t, J=7.6 Hz, 1H), 0.56 (m, 2H), 0.29 (q, J=4.7 Hz, 2H).

A mixture of (8-chloro-2,3-dihydro-[1,4]dioxino[2,3-d] pyridazin-5-yl)-cyclopropylmethyl-amine (154 mg, 0.63 mmol) and 3-(trifluoromethoxy)benzohydrazide (210 mg, 0.95 mmol) in n-BuOH (5 mL) was heated for 2 h at 185° C. under MW irradiation. After cooling, the mixture was taken up with EtOAc (250 mL) and NaHCO$_3$ (saturated aqueous solution) (25 mL) was added. After extraction with EtOAc, the combined organic phases were dried (Na$_2$SO$_4$) and the solvent removed under reduced pressure. The obtained residue was purified by flash column chromatography (EtOAc and EtOAc/MeOH 100:1 mixtures) to give a white solid that was further purified by C-18 reverse-phase column chromatography (water to water/MeCN 1:1 mixtures as eluants) to yield cyclopropylmethyl-[3-(3-trifluoromethoxy-phenyl)-7,8-dihydro-6,9-dioxa-1,2,3a,4-tetraaza-cyclopenta[a]naphthalen-5-yl]-amine as a white solid (19 mg).

HPLC-MS (method 1): Rt=5.75 min, [M+H]$^+$ m/z 408.2.
$^1$H NMR (300 MHz, DMSO-d$_6$) δ 8.59 (s, 1H), 8.39 (d, J=7.5 Hz, 1H), 7.70 (m, 1H), 7.49 (m, 1H), 7.22 (t, J=5.5 Hz, 1H), 4.57 (m, 2H), 4.55 (m, 2H), 3.21 (m, 2H), 1.24 (m, 1H), 0.45 (m, 2H), 0.26 (m, 2H).

Example 103

(1-Methyl-1-oxy-pipe-din-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine

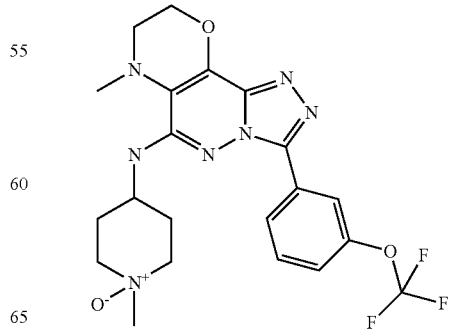

(1-methyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine (0.080 g, 0.168 mmol) was dissolved in dry DCM (8 mL). The solution was cooled to 0° C. and 3-chloroperoxybenzoic acid (0.094 g, 0.419 mmol) was added. The solution turned yellow. The ice bath was removed and the reaction was left stirring for 1 h. DCM (10 mL) was added and the solution was washed with saturated sodium bicarbonate (2×5 mL). The combined organic phases were dried over sodium sulphate and concentrated under reduced pressure. The obtained residue was purified on a biotage falsh column chromatography (100% DCM to 100% MeOH) to yield 6 mgs of (1-methyl-1-oxy-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine.

HPLC-MS (method 1): Rt=3.27 min, [M+H]$^+$ m/z 494.0.
$^1$H NMR (300 MHz, MeOD) δ 8.53 (s, 1H), 8.42 (m, 1H), 7.66 (m, 1H), 7.43 (m, 1H), 4.49 (m, 2H), 3.42 (d, J=5.7 Hz, 2H), 3.28 (m, 6H), 3.17 (s, 3H), 2.79 (s, 3H), 2.05 (m, 3H), 1.78 (m, 2H).

Example 104

PIM-1, PIM-2 and PIM-3 Biochemical Activity

Biological activity in PIM-1, PIM-2 and/or PIM-3 for selected compounds of the examples is represented in the following table:

| Example number | PIM1 IC50 (M) |
|---|---|
| 4 | 8.11E−07 |
| 5 | 1.72E−08 |
| 9 | 5.24E−08 |
| 7 | 2.52E−08 |
| 14 | 5.83E−07 |
| 15 | 4.35E−06 |
| 22 | 6.78E−07 |
| 100 | 1.81E−07 |

Example 105

Analytical Data and PIM-1, PIM-2 and PIM-3 Biochemical Activity

Biological activity in PIM-1, PIM-2 and/or PIM-3 for the example compounds is represented by semi-quantative results [IC50<100 nM (+++), 100 nM<IC50<1 μM (++), IC50>1 μM (+)] in the following table:

| Example number | PIM1 IC50 | PIM2 IC50 | PIM3 IC50 |
|---|---|---|---|
| 1 | ++ | + | |
| 2 | +++ | ++ | ++ |
| 3 | ++ | + | |
| 4 | ++ | + | |
| 5 | +++ | ++ | ++ |
| 6 | + | + | |
| 7 | +++ | ++ | +++ |
| 8 | ++ | + | |
| 9 | +++ | + | |
| 10 | + | + | |
| 11 | +++ | ++ | |
| 12 | +++ | | |
| 13 | ++ | + | |
| 14 | ++ | + | |
| 15 | + | + | |
| 16 | +++ | | |
| 17 | +++ | + | ++ |
| 18 | + | + | |
| 19 | +++ | | |
| 20 | ++ | + | ++ |
| 21 | +++ | ++ | ++ |
| 22 | ++ | + | |
| 23 | +++ | +++ | ++ |
| 24 | ++ | + | |
| 26 | +++ | ++ | ++ |
| 27 | +++ | + | + |
| 28 | + | + | |
| 29 | +++ | ++ | ++ |
| 30 | + | + | |
| 31 | ++ | + | ++ |
| 32 | +++ | ++ | +++ |
| 33 | ++ | + | |
| 34 | +++ | + | ++ |
| 35 | +++ | +++ | |
| 38 | ++ | | |
| 39 | +++ | ++ | |
| 40 | +++ | ++ | +++ |
| 41 | +++ | ++ | |
| 42 | ++ | + | |
| 43 | +++ | | +++ |
| 44 | ++ | + | |
| 45 | ++ | + | |
| 46 | ++ | + | |
| 47 | ++ | + | |
| 48 | +++ | | |
| 49 | +++ | | |
| 50 | +++ | | |
| 51 | + | + | |
| 52 | ++ | + | + |
| 53 | ++ | + | |
| 54 | +++ | + | |
| 55 | +++ | | +++ |
| 56 | +++ | | |
| 57 | +++ | + | + |
| 58 | +++ | + | ++ |
| 59 | +++ | | +++ |
| 60 | +++ | ++ | |
| 61 | +++ | ++ | |
| 62 | +++ | ++ | +++ |
| 63 | +++ | +++ | |
| 64 | +++ | | |
| 65 | +++ | | ++ |
| 66 | +++ | + | ++ |
| 67 | +++ | | |
| 68 | +++ | +++ | |
| 69 | +++ | ++ | |
| 70 | +++ | | |
| 71 | +++ | | |
| 72 | ++ | + | ++ |
| 73 | +++ | ++ | |
| 79 | ++ | + | |
| 80 | + | + | |
| 81 | +++ | + | ++ |
| 83 | ++ | + | |
| 84 | ++ | + | |
| 85 | +++ | ++ | ++ |
| 86 | ++ | + | ++ |
| 87 | +++ | | |
| 88 | +++ | + | + |
| 89 | ++ | + | + |
| 92 | + | + | |
| 93 | +++ | | +++ |
| 94 | +++ | | |
| 94 | ++ | + | |
| 95 | + | + | |
| 96 | ++ | + | |
| 97 | +++ | ++ | +++ |
| 98 | +++ | ++ | ++ |
| 100 | ++ | + | |
| 101 | +++ | ++ | ++ |

-continued

| Example number | PIM1 IC50 | PIM2 IC50 | PIM3 IC50 |
|---|---|---|---|
| 102 | +++ | +++ | |
| 103 | +++ | + | |

Example 106

Combination Assays

Combination index (CI) calculated for the combination of compounds of the invention and various chemotherapeutic agents in the MTT in vitro cell proliferation assays [CI<0.1 (++++), 0.1<CI<0.3 (+++), 0.3<CI<0.7 (++), 0.7<CI<1.2 (+)]:

| Cell line | Tumor type | Chemotherapeutic | Chemoth EC50 [μM] | Example number | Example EC50 [μM] | Combination Index (CI) | Synergy |
|---|---|---|---|---|---|---|---|
| MV4:11 | leukemia (AML) | GDC-0941 | 0.5 | 16 | 5 | 0.585 | ++ |
| | Mantle cell lymphoma | lapatinib | 5 | 16 | 10 | 0.289 | +++ |
| MV4:11 | leukemia (AML) | GDC-0941 | 0.5 | 56 | 0.5 | 0.024 | ++++ |
| MV4:11 | leukemia (AML) | PD-0332991 | 1 | 56 | 0.5 | 0.309 | ++ |
| MV4:11 | leukemia (AML) | GDC-0879 | 12.5 | 56 | 0.5 | 0.604 | ++ |
| SKMel19 | melanoma | GDC-0879 | 0.3 | 56 | 6 | 0.516 | ++ |
| SKMel19 | melanoma | PD-0332991 | 3 | 56 | 6 | 0.568 | ++ |
| MiaPaca-2 | pancreas | lapatinib | 20 | 48 | 5 | 0.57 | ++ |
| MV4:11 | leukemia (AML) | GDC-0941 | 0.5 | 48 | 1 | 0.3 | +++ |
| MV4:11 | leukemia (AML) | lapatinib | 10 | 48 | 1 | 0.548 | ++ |
| Jeko-1 | Mantle cell lymphoma | GDC-0941 | 2 | 48 | 2.5 | 0.718 | + |
| Jeko-1 | Mantle cell lymphoma | lapatinib | 5 | 48 | 2.5 | 0.244 | +++ |
| SKMel19 | melanoma | GDC-0879 | 0.3 | 48 | 3 | 0.319 | ++ |
| SKMel19 | melanoma | GDC-0941 | 4 | 48 | 4 | 0.571 | ++ |
| DU145 | prostate | Taxotere | 0.025 | 48 | 15 | 0.704 | + |
| A549 | lung adenocarcinoma | GDC-0941 | 12 | 48 | 6 | 0.12 | +++ |
| HTC116 | colon carcinoma | PD-0325901 | 1.25 | 48 | 10 | 0.759 | + |
| HTC116 | colon carcinoma | lapatinib | 10 | 48 | 10 | 0.608 | ++ |
| NCI H1975 | non small cell lung carcinoma | GDC-0941 | 10 | 48 | 5 | 0.038 | ++++ |

Example 107

Cell Data

BadP S112 Inhibition by Cell ELISA in H1299Pim1 Cells

Efficacy of compounds of the examples to inhibit the Bad phosphorylation is represented by semi-quantitative results [EC50<250 nM (+++), 250 nM<EC50<1 μM (++), 1 μM<EC50<10 μM (+)]:

| Example number | EC50 BadP ELISA H1299 Pim1 |
|---|---|
| 2 | ++ |
| 5 | ++ |
| 7 | + |
| 9 | + |
| 12 | +++ |
| 17 | + |
| 20 | ++ |
| 27 | +++ |
| 29 | +++ |
| 31 | + |
| 34 | + |
| 37 | + |
| 40 | ++ |
| 49 | ++ |
| 52 | + |
| 54 | ++ |
| 57 | + |
| 58 | + |
| 59 | ++ |
| 60 | +++ |
| 62 | +++ |
| 65 | + |
| 66 | + |
| 69 | +++ |
| 81 | + |
| 86 | + |
| 88 | + |
| 91 | ++ |
| 100 | + |
| 101 | + |

The invention claimed is:

1. A compound of formula I,

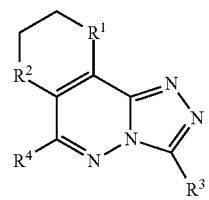

wherein:

$R^1$ and $R^2$ are independently selected from —O—, —C($R^6$)($R^{6a}$)— and —N($R^6$)—;

each $R^6$ and $R^{6a}$ independently represents, on each occasion when used herein, H or $R^{d3}$;

$R^{d3}$ represents $C_{1-3}$ alkynyl;

the —CH$_2$—CH$_2$— moiety between $R^1$ and $R^2$ is optionally substituted by one or more substituents selected from $E^2$;

$E^2$ represents $C_{1-3}$ alkyl;

$R^3$ represents phenyl, optionally substituted by one or more substituents selected from $E^3$ or any two $E^3$ substituents, when attached to adjacent carbons of the phenyl are linked together to form a further 3- to 6-membered ring containing one or two double bonds and containing one or two heteroatoms;

$R^4$ represents a group of the following formulae:

---

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthetic-PIM-1 substrate peptide: PIMtide

<400> SEQUENCE: 1

Ala Arg Lys Arg Arg Arg His Pro Ser Gly Pro Pro Thr Ala
1               5                   10

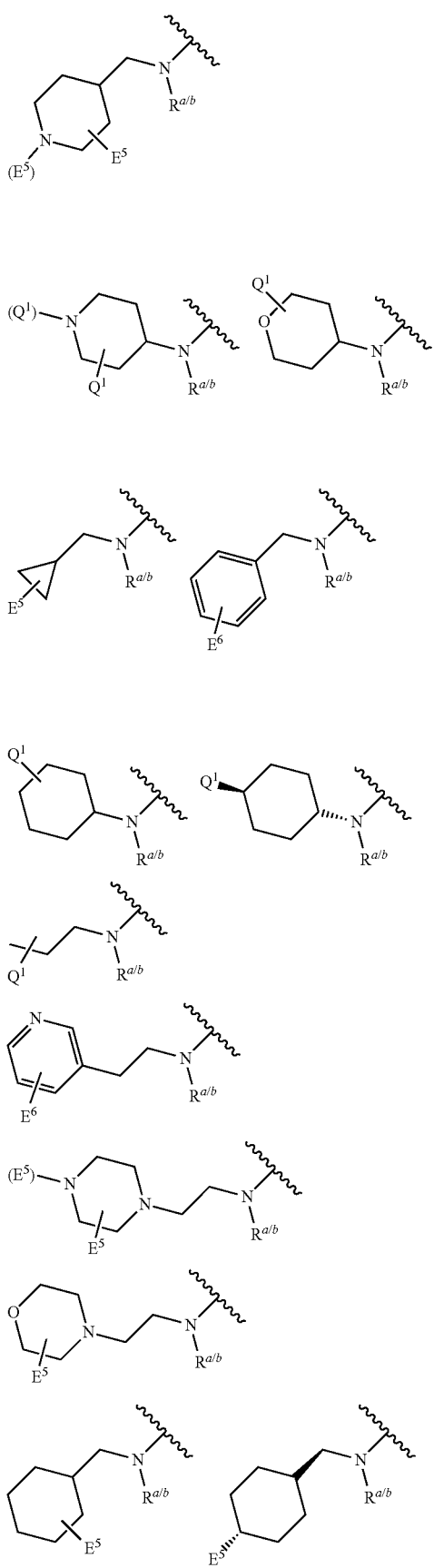
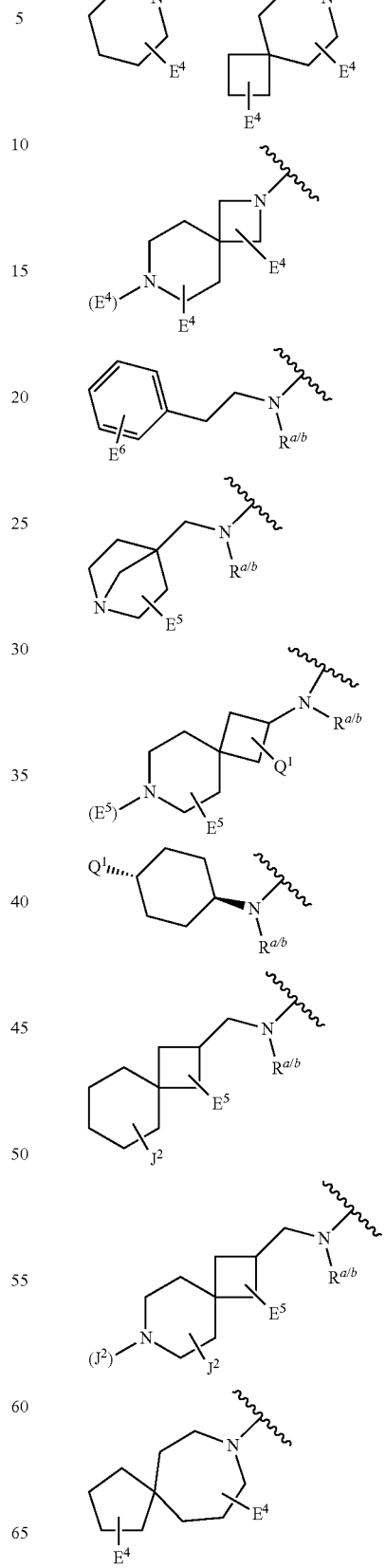

-continued

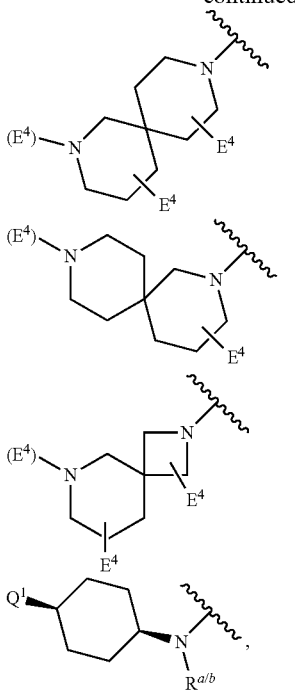

wherein the squiggly line represents the point of attachment to the requisite triazolopyridazine of the compound of formula I, $R^{a/b}$ represents $R^a$ or $R^b$;

$R^{a/b}$ represents H, —C(O)$C_{1-2}$alkyl, —S(O)$_2C_{1-2}$alkyl, or —$C_{1-3}$alkyl, and wherein $E^4$, $E^5$, $E^6$, $Q^1$ and $J^2$ are optionally substituted by one or more of the groups as defined below;

each $Q^1$ independently represents, on each occasion when used herein: $N(R^{10a})R^{11a}$, —$OR^{10a}$, or $C_{1-6}$ alkyl;

$R^{10a}$ and $R^{11a}$ independently represent hydrogen or $C_{1-3}$ alkyl;

$E^3$ represents $Q^4$ or $C_{1-3}$ alkyl optionally substituted by one or more substituents selected from $Q^5$;

$E^4$ represents $Q^4$ or $C_{1-3}$ alkyl optionally substituted by one or more substituents selected from $Q^5$;

$E^5$ represents $Q^4$ or $C_{1-6}$ alkyl, wherein $C_{1-6}$ alkyl is acyclic or part cyclic;

$E^6$ represents $Q^4$;

when $E^3$ represents $Q^4$, then $Q^4$ represents halo, —CN, —C(=Y)$R^{20}$, —C(=Y)O$R^{20}$, —S(O)$_2R^{20}$, —$OR^{20}$ or —N($R^{20}$)$R^{21}$;

when $E^4$ represents $Q^4$, then $Q^4$ represents halo, —CN, —C(=Y)$R^{20}$, —C(=Y)O$R^{20}$, —$OR^{20}$ or N($R^{20}$)$R^{21}$;

when $E^5$ represents $Q^4$, then $Q^4$ represents —$OR^{20}$, —C(=Y)$R^{20}$, —S(O)$_2R^{20}$ or —C(=Y)O$R^{20}$;

when $E^6$ represents $Q^4$, then $Q^4$ represents halo or —$OR^{20}$;

$Q^5$ represents $C_{1-6}$ alkyl, halo, —N($R^{20}$)$R^{21}$ or —N($R^{22}$)C(=Y)$R^{21}$;

each Y independently represents, on each occasion when used herein, =O;

each $R^{20}$ and $R^{21}$ independently represent, on each occasion when used herein, hydrogen or $C_{1-4}$ alkyl optionally substituted by one or more $J^4$;

$R^{22}$ represents hydrogen;

each $J^2$ and $J^4$ independently represents $Q^7$; $Q^7$ represents halo;

or a pharmaceutically acceptable ester, amide, solvate or salt thereof.

2. The compound as claimed in claim 1, wherein:
the $R^1$ and $R^2$ containing ring of the compounds represents a group of the following formulae:

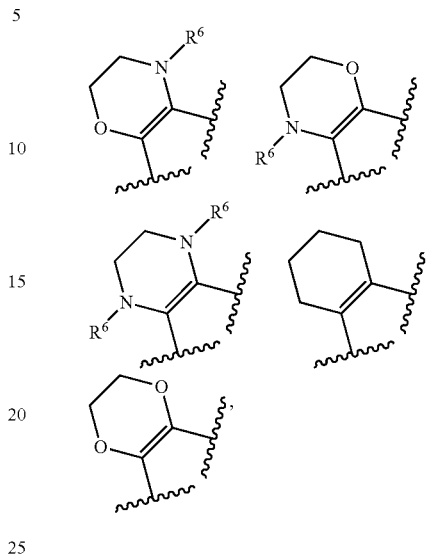

wherein the squiggly lines represent the point of attachment to the requisite triazolopyridazine of the compound of formula I, each of the relevant carbon atoms of the ring may be substituted by $R^6$ or $R^{6a}$ in which the substituent is other than hydrogen, and each $R^6$ and $R^{6a}$ is/are as defined in claim 1.

3. The compound as claimed in claim 1, wherein:
the —CH$_2$—CH$_2$— moiety between $R^1$ and $R^2$ is unsubstituted.

4. The compound as claimed in claim 1, wherein:
$R^{21}$ represents hydrogen or $C_{1-4}$ alkyl.

5. A compound of formula I as defined in claim 1, or a pharmaceutically acceptable ester, amide, solvate or salt thereof, for use as a pharmaceutical.

6. A pharmaceutical formulation comprising a compound of formula I, as defined in claim 1, or a pharmaceutically acceptable ester, amide, solvate or salt thereof, in admixture with a pharmaceutically acceptable adjuvant, diluent or carrier.

7. A combination product comprising:
(A) a compound of formula I as defined in claim 1, or a pharmaceutically-acceptable ester, amide, solvate or salt thereof; and
(B) another therapeutic agent that is useful in the treatment of cancer and/or a proliferative disease, wherein each of components (A) and (B) is formulated in admixture with a pharmaceutically-acceptable adjuvant, diluent or carrier.

8. A process for the preparation of a pharmaceutical formulation comprising a compound of formula I, as defined in claim 1, or a pharmaceutically acceptable ester, amide, solvate or salt thereof, in admixture with a pharmaceutically acceptable adjuvant, diluent or carrier, which process comprises bringing into association a compound of formula I, as defined in claim 1, or a pharmaceutically acceptable ester, amide, solvate or salt thereof with a pharmaceutically-acceptable adjuvant, diluent or carrier.

9. A process for the preparation of a combination product comprising
(A) a compound of formula I as defined in claim 1, or a pharmaceutically-acceptable ester, amide, solvate or salt thereof; and
(B) another therapeutic agent that is useful in the treatment of cancer and/or a proliferative disease, wherein each of components (A) and (B) is formulated in admixture with a pharmaceutically-acceptable adjuvant, diluent or carrier, which process comprises bringing into association a compound of formula I, as defined in claim 1, or a pharmaceutically acceptable ester, amide, solvate or salt thereof with the other therapeutic agent that is useful in the treatment of cancer and/or a proliferative disease, and at least one pharmaceutically-acceptable adjuvant, diluent or carrier.

10. A compound selected from

[3-(4-Methoxy-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine;

(1-Methyl-piperidin-4-yl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

(1-Methyl-piperidin-4-yl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

[3-(4-Methoxy-phenyl)-6-methyl-7,8-dihydro-6H-9-oxa-1,2,3a,4,6-pentaaza-cyclopenta[a]naphthalen-5-yl]-(2-morpholin-4-yl-ethyl)-amine;

Dimethyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-amine;

Dimethyl-{1-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl}-amine;

Cyclopropylmethyl-[6-methyl-3-(3-trifluoromethoxy-phenyl)-7,8-dihydro-6H-9-oxa-1,2,3a,4,6-pentaaza-cyclopenta[a]naphthalen-5-yl]-amine;

Cyclopropylmethyl-[9-methyl-3-(3-trifluoromethoxy-phenyl)-8,9-dihydro-7H-6-oxa-1,2,3a,4,9-pentaaza-cyclopenta[a]naphthalen-5-yl]-amine;

(4-Fluoro-benzyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

(4-Fluoro-benzyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

Cyclopropylmethyl-[6-ethyl-3-(3-trifluoromethoxy-phenyl)-7,8-dihydro-6H-9-oxa-1,2,3a,4,6-pentaaza-cyclopenta[a]naphthalen-5-yl]-amine;

[6-Ethyl-3-(3-trifluoromethoxy-phenyl)-7,8-dihydro-6H-9-oxa-1,2,3a,4,6-pentaaza-cyclopenta[a]naphthalen-5-yl]-(1-methyl-piperidin-4-ylmethyl)-amine;

[8-Ethyl-3-(3-trifluoromethoxy-phenyl)-7,8-dihydro-6H-5-oxa-1,2,3a,4,8-pentaaza-cyclopenta[b]naphthalen-9-yl]-(1-methyl-piperidin-4-ylmethyl)-amine;

[9-Ethyl-3-(3-trifluoromethoxy-phenyl)-8,9-dihydro-7H-6-oxa-1,2,3a,4,9-pentaaza-cyclopenta[a]naphthalen-5-yl]-(tetrahydro-pyran-4-yl)-amine;

(4-Fluoro-benzyl)-[3-(4-methoxy-phenyl)-6,9-dimethyl-6,7,8,9-tetrahydro-1,2,3a,4,6,9-hexaaza-cyclopenta[a]naphthalen-5-yl]-amine;

(1-Methyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

(1-Methyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

Methyl-(1-methyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

4-[6-Methyl-3-(3-trifluoromethoxy-phenyl)-7,8-dihydro-6H-9-oxa-1,2,3a,4,6-pentaaza-cyclopenta[a]naphthalen-5-ylamino]-cyclohexanol;

4-[9-Methyl-3-(3-trifluoromethoxy-phenyl)-8,9-dihydro-7H-6-oxa-1,2,3a,4,9-pentaaza-cyclopenta[a]naphthalen-5-ylamino]-cyclohexanol;

3-[6-Methyl-3-(3-trifluoromethoxy-phenyl)-7,8-dihydro-6H-9-oxa-1,2,3a,4,6-pentaaza-cyclopenta[a]naphthalen-5-ylamino]-propan-1-ol;

3-[9-Methyl-3-(3-trifluoromethoxy-phenyl)-8,9-dihydro-7H-6-oxa-1,2,3a,4,9-pentaaza-cyclopenta[a]naphthalen-5-ylamino]-propan-1-ol;

[6-Methyl-3-(3-trifluoromethoxy-phenyl)-7,8-dihydro-6H-9-oxa-1,2,3a,4,6-pentaaza-cyclopenta[a]naphthalen-5-yl]-(tetrahydro-pyran-4-yl)-amine;

(3,4-Dimethoxy-benzyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

(3,4-Dimethoxy-benzyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

[6-Methyl-3-(3-trifluoromethoxy-phenyl)-7,8-dihydro-6H-9-oxa-1,2,3a,4,6-pentaaza-cyclopenta[a]naphthalen-5-yl]-(2-pyridin-3-yl-ethyl)-amine;

[2-(4-Methyl-piperazin-1-yl)-ethyl]-[6-methyl-3-(3-trifluoromethoxy-phenyl)-5,6,7,8-tetrahydro-9-oxa-1,2,3a,4,6-pentaaza-cyclopenta[a]naphthalen-5-yl]-amine;

[2-(4-Methyl-piperazin-1-yl)-ethyl]-[9-methyl-3-(3-trifluoromethoxy-phenyl)-5,7,8,9-tetrahydro-6-oxa-1,2,3a,4,9-pentaaza-cyclopenta[a]naphthalen-5-yl]-amine;

[6-Methyl-3-(3-trifluoromethoxy-phenyl)-5,6,7,8-tetrahydro-9-oxa-1,2,3a,4,6-pentaaza-cyclopenta[a]naphthalen-5-yl]-(2-morpholin-4-yl-ethyl)-amine;

[9-Methyl-3-(3-Trifluoromethoxy-phenyl)-5,7,8,9-tetrahydro-6-oxa-1,2,3a,4,9-pentaaza-cyclopenta[a]naphthalen-5-yl]-(2-morpholin-4-yl-ethyl)-amine;

3-{6-Methyl-5-[(1-methyl-piperidin-4-ylmethyl)-amino]-7,8-dihydro-6H-9-oxa-1,2,3a,4,6-pentaaza-cyclopenta[a]naphthalen-3-yl}-benzonitrile;

(1-Methyl-piperidin-4-ylmethyl)-[6-methyl-3-(3-trifluoromethyl-phenyl)-7,8-dihydro-6H-9-oxa-1,2,3a,4,6-pentaaza-cyclopenta[a]naphthalen-5-yl]-amine;

[3-(1H-Indol-5-yl)-6-methyl-7,8-dihydro-6H-9-oxa-1,2,3a,4,6-pentaaza-cyclopenta[a]naphthalen-5-yl]-(1-methyl-piperidin-4-ylmethyl)-amine;

[3-(3-Dimethylamino-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine;

4-{Methyl-[6-methyl-3-(3-trifluoromethoxy-phenyl)-7,8-dihydro-6H-9-oxa-1,2,3a,4,6-pentaaza-cyclopenta[a]naphthalen-5-yl]-amino}-cyclohexanol;

Methyl-(1-methyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

(1-Methyl-piperidin-4-ylmethyl)-[3-(3-trifluoromethoxy-phenyl)-7,8,9,10-tetrahydro-[1,2,4]triazolo[3,4-a]phthalazin-6-yl]-amine;

[8,9-Dimethyl-3-(3-trifluoromethoxy-phenyl)-8,9-dihydro-7H-6-oxa-1,2,3a,4,9-pentaaza-cyclopenta[a]naphthalen-5-yl]-(1-methyl-piperidin-4-ylmethyl)-amine; HCOOH salt;

[6,7-Dimethyl-3-(3-trifluoromethoxy-phenyl)-7,8-dihydro-6H-9-oxa-1,2,3a,4,6-pentaaza-cyclopenta[a]naphthalen-5-yl]-(1-methyl-piperidin-4-ylmethyl)-amine;

[6,8-Dimethyl-3-(3-trifluoromethoxy-phenyl)-7,8-dihydro-6H-9-oxa-1,2,3a,4,6-pentaaza-cyclopenta[a]naphthalen-5-yl]-(1-methyl-piperidin-4-ylmethyl)-amine; HCOOH salt;

(1-Methyl-piperidin-4-ylmethyl)-[3-(3-trifluoromethoxy-phenyl)-7,8-dihydro-6,9-dioxa-1,2,3a,4-tetraaza-cyclopenta[a]naphthalen-5-yl]-amine; HCOOH salt;

[9-Methyl-3-(3-trifluoromethoxy-phenyl)-8,9-dihydro-7H-6-oxa-1,2,3a,4,9-pentaaza-cyclopenta[a]naphthalen-5-yl]-(2-piperazin-1-yl-ethyl)-amine;

4-{[6-Methyl-3-(3-trifluoromethoxy-phenyl)-7,8-dihydro-6H-9-oxa-1,2,3a,4,6-pentaaza-cyclopenta[a]naphthalen-5-ylamino]-methyl}-cyclohexanol;

Methyl-{1-[9-methyl-3-(3-trifluoromethoxy-phenyl)-8,9-dihydro-7H-6-oxa-1,2,3a,4,9pentaaza-cyclopenta[a]naphthalen-5-yl]-piperidin-4-yl}-amine; HCOOH salt;

Methyl-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl-amine;

1-[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-ylamine;

[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl-amine;

7-[6-Methyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-ylamine;

(7-Aza-spiro[3.5]non-2-yl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

7-[6,7-Dimethyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-ylamine; HCOOH salt;

4-{[3-(4-Methoxy-phenyl)-6-methyl-7,8-dihydro-6H-9-oxa-1,2,3a,4,6-pentaaza-cyclopenta[a]naphthalen-5-ylamino]-methyl}-piperidine-1-carboxylic acid tert-butyl ester;

C-{1-[3-(4-Methoxy-phenyl)-6-methyl-7,8-dihydro-6H-9-oxa-1,2,3a,4,6-pentaaza-cyclopenta[a]naphthalen-5-yl]-piperidin-4-yl}-methylamine;

(1-Aza-bicyclo[2.2.1]hept-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

(1-Aza-bicyclo[2.2.1]hept-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

C-{1-[6-Methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-methylamine;

[6-Methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl-amine;

C-{1-[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-yl}-methylamine;

[9-Methyl-3-(3-trifluoromethoxy-phenyl)-8,9-dihydro-7H-6-oxa-1,2,3a,4,9-pentaaza-cyclopenta[a]naphthalen-5-yl]-piperidin-4-ylmethyl-amine;

C-{7-[6-Methyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-yl}-methylamine;

5-(1,8-Diaza-spiro[4.6]undec-8-yl)-6-methyl-3-(3-trifluoromethoxy-phenyl)-7,8-dihydro-6H-9-oxa-1,2,3a,4,6-pentaaza-cyclopenta[a]naphthalene; HCOOH salt;

6-Methyl-5-(1-methyl-1,8-diaza-spiro[4.6]undec-8-yl)-3-(3-trifluoromethoxy-phenyl)-7,8-dihydro-6H-9-oxa-1,2,3a,4,6-pentaaza-cyclopenta[a]naphthalene; HCl salt;

Methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-yl}-amine; HCOOH salt;

Methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine;

Methyl-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl-amine;

(7-Aza-spiro[3.5]non-2-yl)-[9-methyl-3-(3-trifluoromethoxy-phenyl)-8,9-dihydro-7H-6-oxa-1,2,3a,4,9-pentaaza-cyclopenta[a]naphthalen-5-yl]-amine; HCl salt;

7-[9-Methyl-3-(3-trifluoromethoxy-phenyl)-8,9-dihydro-7H-6-oxa-1,2,3a,4,9-pentaaza-cyclopenta[a]naphthalen-5-yl]-7-aza-spiro[3.5]non-2-ylamine; HCl salt;

5-(2,9-Diaza-spiro[5.5]undec-9-yl)-6-methyl-3-(3-trifluoromethoxy-phenyl)-7,8-dihydro-6H-9-oxa-1,2,3a,4,6-pentaaza-cyclopenta[a]naphthalene; HCl salt;

5-(2,9-Diaza-spiro[5.5]undec-2-yl)-6-methyl-3-(3-trifluoromethoxy-phenyl)-7,8-dihydro-6H-9-oxa-1,2,3a,4,6-pentaaza-cyclopenta[a]naphthalene; HCl salt;

5-(2,6-Diaza-spiro[3.5]non-2-yl)-6-methyl-3-(3-trifluoromethoxy-phenyl)-7,8-dihydro-6H-9-oxa-1,2,3a,4,6-pentaaza-cyclopenta[a]naphthalene; HCl salt;

N-[6-Methyl-3-(3-trifluoromethoxy-phenyl)-7,8-dihydro-6H-9-oxa-1,2,3a,4,6-pentaaza-cyclopenta[a]naphthalen-5-yl]-cyclohexane-1,4-diamine; HCOOH salt;

N-[6-Methyl-3-(3-trifluoromethoxy-phenyl)-7,8-dihydro-6H-9-oxa-1,2,3a,4,6-pentaaza-cyclopenta[a]naphthalen-5-yl]-cyclohexane-1,4-diamine;

(1-Methyl-piperidin-4-ylmethyl)-[8,8,9-trimethyl-3-(3-trifluoromethoxy-phenyl)-8,9-dihydro-7H-6-oxa-1,2,3a,4,9-pentaaza-cyclopenta[a]naphthalen-5-yl]-amine;

(1-Methyl-piperidin-4-ylmethyl)-[6,7,7-trimethyl-3-(3-trifluoromethoxy-phenyl)-7,8-dihydro-6H-9-oxa-1,2,3a,4,6-pentaaza-cyclopenta[a]naphthalen-5-yl]-amine;

N—[(S)-6,7-Dimethyl-3-(3-trifluoromethoxy-phenyl)-7,8-dihydro-6H-9-oxa-1,2,3a,4,6-pentaaza-cyclopenta[a]naphthalen-5-yl]-cyclohexane-1,4-diamine;

7-[(S)-6,7-Dimethyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-ylamine;

(7-Aza-spiro[3.5]non-2-yl)-[(S)-6,7-dimethyl-3-(3-trifluoromethoxy-phenyl)-7,8-dihydro-6H-9-oxa-1,2,3a,4,6-pentaaza-cyclopenta[a]naphthalen-5-yl]-amine;

4-{[6-Methyl-3-(3-trifluoromethoxy-phenyl)-7,8-dihydro-6H-9-oxa-1,2,3a,4,6-pentaaza-cyclopenta[a]naphthalen-5-ylamino]-methyl}-piperidine-1-carboxylic acid tert-butyl ester;

(4-Fluoro-benzyl)-[3-(4-methoxy-phenyl)-9-methyl-8,9-dihydro-7H-6-oxa-1,2,3a,4,9-pentaaza-cyclopenta[a]naphthalen-5-yl]-amine;

(4-Fluoro-benzyl)-[3-(4-methoxy-phenyl)-6-methyl-7,8-dihydro-6H-9-oxa-1,2,3a,4,6-pentaaza-cyclopenta[a]naphthalen-5-yl]-amine;

[2-(4-Fluoro-phenyl)-ethyl]-[3-(4-methoxy-phenyl)-9-methyl-8,9-dihydro-7H-6-oxa-1,2,3a,4,9-pentaaza-cyclopenta[a]naphthalen-5-yl]-amine;

5-(2,7-Diaza-spiro[3.5]non-2-yl)-9-methyl-3-(3-trifluoromethoxy-phenyl)-8,9-dihydro-7H-6-oxa-1,2,3a,4,9-pentaaza-cyclopenta[a]naphthalene;

4-{6-Methyl-5-[(1-methyl-piperidin-4-ylmethyl)-amino]-7,8-dihydro-6H-9-oxa-1,2,3a,4,6-pentaaza-cyclopenta[a]naphthalen-3-yl}-phenol;

Isopropyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine;

Isopropyl-{1-[9-methyl-3-(3-trifluoromethoxy-phenyl)-8,9-dihydro-7H-6-oxa-1,2,3a,4,9-pentaaza-cyclopenta[a]naphthalen-5-yl]-piperidin-4-ylmethyl}-amine;

Isopropyl-{7-[6-methyl-3-(3-trifluoromethoxy-phenyl)-7,8-dihydro-6H-9-oxa-1,2,3a,4,6-pentaaza-cyclopenta[a]naphthalen-5-yl]-7-aza-spiro[3.5]non-2-yl}-amine;

(1-Cyclopropylmethyl-piperidin-4-ylmethyl)-[9-methyl-3-(3-trifluoromethoxy-phenyl)-8,9-dihydro-7H-6-oxa-1,2,3a,4,9-pentaaza-cyclopenta[a]naphthalen-5-yl]-amine;

(1-Cyclopropylmethyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;

Ethyl-methyl-{1-[6-methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-amine; HCOOH salt;
(1-Ethyl-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine; compound with formic acid;
N-{1-[3-(4-Methoxy-phenyl)-6-methyl-7,8-dihydro-6H-9-oxa-1,2,3a,4,6-pentaaza-cyclopenta[a]naphthalen-5-yl]-piperidin-4-ylmethyl}-acetamide;
N-{1-[6-Methyl-3-(3-trifluoromethoxy-phenyl)-7,8-dihydro-6H-9-oxa-1,2,3a,4,6-pentaaza-cyclopenta[a]naphthalen-5-yl]-piperidin-4-ylmethyl}-acetamide;
4-[5-(4-Fluoro-benzylamino)-6,9-dimethyl-6,7,8,9-tetrahydro-1,2,3a,4,6,9-hexaaza-cyclopenta[a]naphthalen-3-yl]-phenol;
1-(4-{2-[9-Methyl-3-(3-trifluoromethoxy-phenyl)-8,9-dihydro-7H-6-oxa-1,2,3a,4,9-pentaaza-cyclopenta[a]naphthalen-5-ylamino]-ethyl}-piperazin-1-yl)-ethanone;
N-[9-Methyl-3-(3-trifluoromethoxy-phenyl)-8,9-dihydro-7H-6-oxa-1,2,3a,4,9-pentaaza-cyclopenta[a]naphthalen-5-yl]-N-(2-piperazin-1-yl-ethyl)-acetamide;
[2-(4-Methanesulfonyl-piperazin-1-yl)-ethyl]-[9-methyl-3-(3-trifluoromethoxy-phenyl)-8,9-dihydro-7H-6-oxa-1,2,3a,4,9-pentaaza-cyclopenta[a]naphthalen-5-yl]-amine;
N-[9-Methyl-3-(3-trifluoromethoxy-phenyl)-8,9-dihydro-7H-6-oxa-1,2,3a,4,9-pentaaza-cyclopenta[a]naphthalen-5-yl]-N-(2-piperazin-1-yl-ethyl)-methanesulfonamide;
Methyl-[6-methyl-3-(3-trifluoromethoxy-phenyl)-7,8-dihydro-6H-9-oxa-1,2,3a,4,6-pentaaza-cyclopenta[a]naphthalen-5-yl]-(tetrahydro-pyran-4-yl)-amine;
Methyl-[6-methyl-3-(3-trifluoromethoxy-phenyl)-7,8-dihydro-6H-9-oxa-1,2,3a,4,6-pentaaza-cyclopenta[a]naphthalen-5-yl]-(2-morpholin-4-yl-ethyl)-amine;
Cyclopropylmethyl-[3-(4-fluoro-phenyl)-6-methyl-7,8-dihydro-6H-9-oxa-1,2,3a,4,6-pentaaza-cyclopenta[a]naphthalen-5-yl]-amine;
[3-(4-Fluoro-phenyl)-6-methyl-7,8-dihydro-6H-9-oxa-1,2,3a,4,6-pentaaza-cyclopenta[a]naphthalen-5-yl]-(1-methyl-piperidin-4-ylmethyl)-amine;
5-Piperidin-1-yl-3-(3-trifluoromethoxy-phenyl)-7,8-dihydro-6,9-dioxa-1,2,3a,4-tetraaza-cyclopenta[a]naphthalene;
Cyclopropylmethyl-[3-(3-trifluoromethoxy-phenyl)-7,8-dihydro-6,9-dioxa-1,2,3a,4-tetraaza-cyclopenta[a]naphthalen-5-yl]-amine;
(1-Methyl-1-oxy-piperidin-4-ylmethyl)-[6-methyl-3-(3-trifluoromethoxy-phenyl)-7,8-dihydro-6H-9-oxa-1,2,3a,4,6-pentaaza-cyclopenta[a]naphthalen-5-yl]-amine;
2-[9-Methyl-3-(3-trifluoromethoxy-phenyl)-8,9-dihydro-7H-6-oxa-1,2,3a,4,9-pentaaza-cyclopenta[a]naphthalen-5-yl]-2,7-diaza-spiro[3.5]nonane-7-carboxylic acid tert-butyl ester;
or a pharmaceutically acceptable ester, amide, solvate or salt thereof.

11. A process for the preparation of a compound of formula I as defined in claim 1, which process comprises:
(i) reacting a compound of formula II,

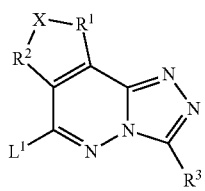

wherein $L^1$ represents a suitable leaving group, $R^1$, $R^2$, and $R^3$ are as defined in claim 1, and X is —$CH_2$—$CH_2$—, with a compound of formula III,
$R^4$—H  III
wherein $R^4$ is as defined in claim 1; or
(ii) reacting a compound of formula IV,

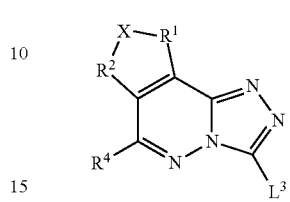

wherein $L^3$ represents a suitable leaving group, $R^1$, $R^2$, and $R^4$ are as defined in claim 1, and X is —$CH_2$—$CH_2$—, with a compound of formula V,
$R^3$—$L^4$  V
wherein $L^4$ represents a suitable group, and $R^3$ is as defined in claim 1; or
(iii) reacting a compound of formula VI,

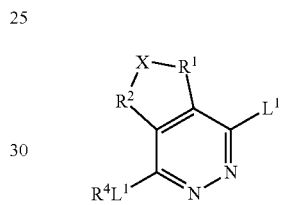

wherein $R^4L^1$ represents either $L^1$ or $R^4$; $R^1$, $R^2$, and $R^4$ are as defined in claim 1; X is —$CH_2$—$CH_2$, and each $L^1$ represents a suitable leaving group;
with a compound of formula VII,
$R^3$—C(O)—N(H)$NH_2$  VII
wherein $R^3$ is as defined in claim 1; or
(iv) for compounds of formula I in which $R^1$ and $R^2$ are independently selected from —O— and —$NR^6$—, reacting a compound of formula VIII,

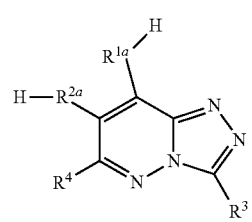

wherein $R^{1a}$ and $R^{2a}$ independently represent —O— and —$NR^6$—, and $R^3$ and $R^4$ are as defined in claim 1, with a compound of formula IX,
$L^5$—X—$L^6$  IX
wherein $L^5$ and $L^6$ independently represent a suitable leaving group and X is —$CH_2$—$CH_2$.

12. A process according to claim 11, wherein $L^1$, $L^3$, $L^5$ and $L^6$, each independently represents iodo, bromo, chloro or a sulfonate group; and $L^4$ represents —B(OH)$_2$, —B(OR$^{WX}$)$_2$ or —Sn(R$^{WX}$)$_3$, in which each $R^{WX}$ independently represents a $C_{1-6}$ alkyl group, or, in the case of —B(OR$^{WX}$)$_2$, the respective $R^{WX}$ groups may be linked together to form a 4- to 6-membered cyclic group.

* * * * *

UNITED STATES PATENT AND TRADEMARK OFFICE
CERTIFICATE OF CORRECTION

PATENT NO. : 9,682,991 B2  
APPLICATION NO. : 13/519872  
DATED : June 20, 2017  
INVENTOR(S) : Joaquín Pastor Fernández et al.

Page 1 of 1

It is certified that error appears in the above-identified patent and that said Letters Patent is hereby corrected as shown below:

In the Claims

Column 124, Claim 1, Line number 30, replace "$C_{1-3}$ alkynyl" with -- $C_{1-3}$ alkyl --;

Column 127, Claim 1, Line numbers 33-35, replace "wherein $E^4$, $E^5$, $E^6$, $Q^1$ and $J^2$ are optionally substituted by one or more groups as defined below" with
-- wherein when one or more $E^4$, $E^5$, $E^6$, $Q^1$ and $J^2$ are depicted in the structures, the substituted portions of those structures are optionally substituted by one or more of those groups as defined below --.

Signed and Sealed this  
Sixth Day of March, 2018

Andrei Iancu  
*Director of the United States Patent and Trademark Office*